United States Patent
Hu et al.

(10) Patent No.: US 6,525,202 B2
(45) Date of Patent: Feb. 25, 2003

(54) CYCLIC AMINE PHENYL BETA-3 ADRENERGIC RECEPTOR AGONISTS

(75) Inventors: Baihua Hu, Nanuet, NY (US); Fuk-Wah Sum, Pomona, NY (US); Michael S. Malamas, Jamison, PA (US)

(73) Assignee: Wyeth, Madison, NJ (US)

( * ) Notice: Subject to any disclaimer, the term of this patent is extended or adjusted under 35 U.S.C. 154(b) by 22 days.

(21) Appl. No.: 09/903,754

(22) Filed: Jul. 12, 2001

(65) Prior Publication Data

US 2002/0028835 A1 Mar. 7, 2002

Related U.S. Application Data

(60) Provisional application No. 60/218,627, filed on Jul. 17, 2000.

(51) Int. Cl.[7] ............... C07D 211/58; C07D 211/56; C07F 9/22; C07F 9/38
(52) U.S. Cl. .................. 546/223; 546/192; 546/22
(58) Field of Search .................. 546/192, 223, 546/22

(56) References Cited

U.S. PATENT DOCUMENTS

| | | | |
|---|---|---|---|
| 5,296,485 A | * 3/1994 | Lubisch et al. | 514/316 |
| 5,561,142 A | 10/1996 | Fisher et al. | |
| 5,578,620 A | 11/1996 | Fujita et al. | |
| 5,614,523 A | 3/1997 | Audia et al. | |
| 5,741,789 A | 4/1998 | Hibschman | |
| 5,786,356 A | 7/1998 | Bell et al. | |
| 5,789,402 A | 8/1998 | Audia et al. | |
| 6,069,176 A | 5/2000 | Tsuchiya et al. | |

FOREIGN PATENT DOCUMENTS

| | | |
|---|---|---|
| EP | 0 449 216 A1 | 10/1991 |
| EP | 0 659 737 A2 | 6/1995 |
| EP | 0 714 883 A1 | 6/1996 |
| EP | 0 764 640 A1 | 3/1997 |
| WO | WO 98/09625 | 3/1998 |
| WO | WO 99/65895 | 12/1999 |
| WO | WO 01/17989 A2 | 3/2001 |
| WO | WO 01/43744 A1 | 6/2001 |
| WO | WO 01/44227 A1 | 6/2001 |

OTHER PUBLICATIONS

Marc S. Berridge et al., Nucl. Med. Biol., 1992, 563–569, 19(5).
Joan M Caroon et al., J. Pharm. Sci., Jan. 1987, 32–34, 76(1).
A. Guy et al., Synthesis, Sep. 1992, 821–22.
Manabu HORI et al., J. Org. Chem., 1998, 889–894, 63.
Yunsheng Huang et al., J. Med.Chem., 1998, 2361–2370, 41.
Bernard Hulin et al., J. Med. Chem., 1992, 1853–1864, 35.
Carl Kaiser et al., J. Med. Chem., 1977, 687–692, 20(5).
Yutaka Kawashima et al., Chem. Pharm. Bull, 1995, 1132–1136, 43(7).
Kiyoto Koguro et al., Synthesis, 1998, 910–914.
Gerard Leclerc et al., J. Med. Chem., 1980, 738–744, 23(7).
D. Mauleon et al., II Farmaco,1989, 1109–1117, 44(11).
Alexander McKillop et al.,J. Am. Chem. Soc., Sep. 1971, 4919–4920, 93(19).
Ricardo Tapla et al., Synthetic Communications, 1986, 681–687, 16(6).
Edward C. Taylor et al., Synthesis, Aug. 1981, 606–608.
Michiaki Tominaga et al., Chem. Pharm. Bull, 1987, 3699–3704, 35(9).
R.H. Uloth et al., J. Med. Chem., 1966, 88–97, 9.
Paul C. Unangst et al., J. Med. Chem., 1994, 322–328, 37.
Sophie Vanwetswinkel et al., J. Anitbiotics, Sep. 1994, 1041–1051, 47(9).
S. Tamada et al., JP 01061468 A2 (English abstract), 1989.

* cited by examiner

*Primary Examiner*—Alan L. Rotman
*Assistant Examiner*—Rita Desai
(74) *Attorney, Agent, or Firm*—Arnold S. Milowsky

(57) ABSTRACT

This invention provides compounds of Formula I having the structure

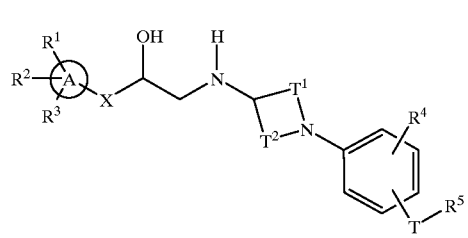

wherein, $R^1$, $R^2$, $R^3$, $R^4$, $R^5$, T, $T^1$, $T^2$, and X are as defined hereinbefore, or a pharmaceutically acceptable salt thereof, which are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension and frequent urination; and are particularly useful in the treatment or inhibition of type II diabetes.

3 Claims, No Drawings

CYCLIC AMINE PHENYL BETA-3 ADRENERGIC RECEPTOR AGONISTS

This application claims the benefit of U.S. Provisional Application No. 60/218,627, filed Jul. 17, 2000.

BACKGROUND OF THE INVENTION

This invention relates to cyclic amine phenyl $\beta_3$ adrenergic receptor agonists useful for the treatment of metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

The subdivision of $\beta$ adrenergic receptors ($\beta$-AR) into $\beta_1$- and $\beta_2$-AR has led to the development of $\beta_1$- and $\beta_2$-antagonists and/or agonists which have been useful for the treatment of cardiovascular disease and asthma. The recent discovery of "atypical" receptors, later called $\beta_3$-AR, has led to the development of $\beta_3$-AR agnoists which may be potentially useful as antiobesity and antidiabetic agents. For recent reviews on $\beta_3$-AR agnoists, see: 1. A. D. Strosberg, *Annu. Rev. Pharmacol. Toxicol.* 1997, 37, 421; 2. A. E. Weber, *Ann. Rep. Med. Chem.* 1998, 33, 193; 3. C. P. Kordik and A. B. Reitz, *J. Med. Chem.* 1999, 42, 181; 4. C. Weyer, J. F. Gautier and E. Danforth, *Diabetes and Metabolism,* 1999, 25, 11.

Compounds that are potent and selective $\beta_3$ agonists, may be potentially useful antiobesity agents. Low levels or lack of $\beta_1$ and $\beta_2$-agonistic properties will minimize or eliminate the adverse side effects that are associated with $\beta_1$ and $\beta_2$ agonistic activities, i.e. increased heart rate, and muscle tremor, respectively. Early developments in the $\beta_3$-agonist field are described in European patent 427480, U.S. Pat. Nos. 4,396,627, 4,478,849, 4,999,377, and 5,153,210. These early patents purport to claim compounds with greater selectivity for the $\beta_3$-AR than for the $\beta_1$- and $\beta_2$-AR's. However, clinical trials in humans with such compounds have not been successful to date.

More recently, potent and selective human $\beta_3$ agonists have been described in several patents and published applications: WO 98/32753, WO 97/46556, WO 97/37646, WO 97/15549, WO 97/25311, WO 96/16938, WO 95/29159, European Patents 659737, 801060, 714883, 764640, 827746, and U.S. Pat. Nos. 5,561,142, 5,705,515, 5,436, 257, and 5,578,620. These compounds were evaluated in Chinese hamster ovary (CHO) cells test procedures which predicts the effects that can be expected in humans. These assays utilize cloned human β3 receptors, expressed in CHO cells (see refs. Granneman et al., *Mol Pharmacol.,* 1992, 42, 964; Emorine et al., *Science,* 1989, 245, 1118; Liggett *Mol. Pharmacol.,* 1992, 42, 634).

$\beta_3$-Adrenergic agonists also are useful in controlling the frequent urge of urination. It has been known that relaxation of the bladder detrusor is under beta adrenergic control (Li J, Yasay G and Kau S. Beta-adrenoceptor subtypes in the detrusor of guinea-pig urinary bladder. *Pharmacology* 1992; 44: 13–18). Recently, a number of laboratories have provided experimental evidence in a number of animal species including human (Yamazaki Y, Takeda H, Akahane M, Igawa Y, et al. Species differences in the distribution of the beta-adrenoceptor subtypes in bladder smooth muscle. *Br. J. Pharmacol.* 1998; 124: 593–599) that activation of the $\beta_3$ receptor subtype by norepinephrine is responsible for relaxation of the urinary bladder. Urge urinary incontinence is characterized by abnormal spontaneous bladder contractions that can be unrelated to bladder urine volume. Urge urinary incontinence is often referred to hyperactive or unstable bladder. Several etiologies exist and fall into two major categories, myogenic and neurogenic. The myogenic bladder is usually associated with detrusor hypertrophy secondary to bladder outlet obstruction, or with chronic urinary tract infection. Neurogenic bladders are associated with an uninhibited micturition reflex. An upper motor neuron disease is usually the underlying cause. In either case, the disease is characterized by abnormal spontaneous contractions that result in an abnormal sense of urinary urgency and involuntary urine loss. At present, the most common therapy for hyperactive bladder includes the use of antimuscarinic agents to block the action of the excitatory neurotransmitter acetylcholine. While effective in neurogenic bladders, their utility in myogenic bladders is questionable. In addition, due to severe dry mouth side-effects associated with antimuscarinic therapy, the patient compliance with these agents is only approximately 30%.

In the bladder, $\beta_3$ adrenergic receptor agonists activate adenylyl cyclase and generate cAMP through the G-protein coupled $\beta_3$ receptor. The resulting phosphorylation of phospholamban/calcium ATPase enhances uptake of calcium into the sarcoplasmic reticulum. The decrease in intracellular calcium inhibits bladder smooth muscle contractility.

It is suggested therefore, that activation of the $\beta_3$ adrenergic receptor in the urinary bladder will inhibit abnormal spontaneous bladder contractions and be useful for the treatment of bladder hyperactivity. Note, that unlike the antimuscarinics, $\beta_3$ adrenergic receptor agonists would be expected to be active against both neurogenic and myogenic etiologies.

Despite all these recent developments there is still no single therapy available for the treatment of type II diabetes (NIDDM), obesity, atherosclerosis, gastrointestinal disorders, neurogenetic inflammation, frequent urination and related diseases. A potent and selective $\beta_3$ adrenergic receptor agonist is therefore highly desirable for the potential treatment of such disease states.

DESCRIPTION OF THE INVENTION

This invention provides compounds of Formula I having the structure

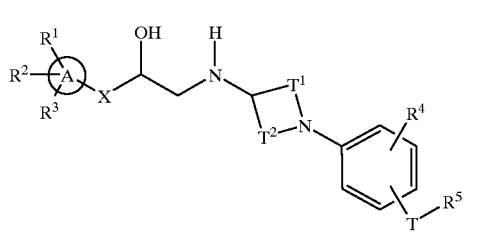

wherein
  A is Ar or Het;
  X is —OCH$_2$—, —SCH$_2$—, or a bond;
  T$^1$ is (CH$_2$)$_m$;
  T$^2$ is (CH$_2$)$_n$;
  T is a bond, alkyl of 1–6 carbon atoms optionally substituted with R$^{11}$, alkenyl of 2–7 carbon atoms optionally substituted with R$^{11}$, alkynyl of 2–7 carbon atoms, alkylthio of 1–6 carbon atoms, alkylamino of 1–6 carbon atoms, alkoxyalkyl of 1–6 carbon atoms per alkyl moiety, alkylthioalkyl of 1–6 carbon atoms per alkyl moiety, alkoxy of 1–6 carbon atoms, alkoxyalkyl of 1–6 carbon atoms per alkyl moiety, alkyloxoalkyl of 1–6 carbon atoms per alkyl moiety, acyl of 2–7 carbon atoms, or alkenylcarbonyl of 3–8 carbon atoms;

$R^1$, $R^2$, and $R^3$ are each, independently, hydrogen, alkyl of 1–6 carbon atoms, cycloalkyl of 3–8 carbon atoms, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, dihydroxyphosphorylamino, —$CO_2$-alkyl of 1–6 carbon atoms, or Ar optionally substituted with $R^{11}$;

$R^4$ is hydrogen, alkyl of 1–6 carbon atoms, halogen, hydroxy, alkyoxy of 1–6 carbon atoms, alkylthio of 1–6 carbon atoms, amino, alkylamino of 1–6 carbon atoms, carboxy, acyl of 2–7 carbon atoms, ArCO-, alkoxycarbonyl of 2–7 carbon atoms, aminocarbonyl, alkylaminocarbonyl of 2–7 carbon atoms, alkylsulfonyl of 1–6 carbon atoms, or alkylsulfonylamino of 1–6 carbon atoms, $R^5$ is

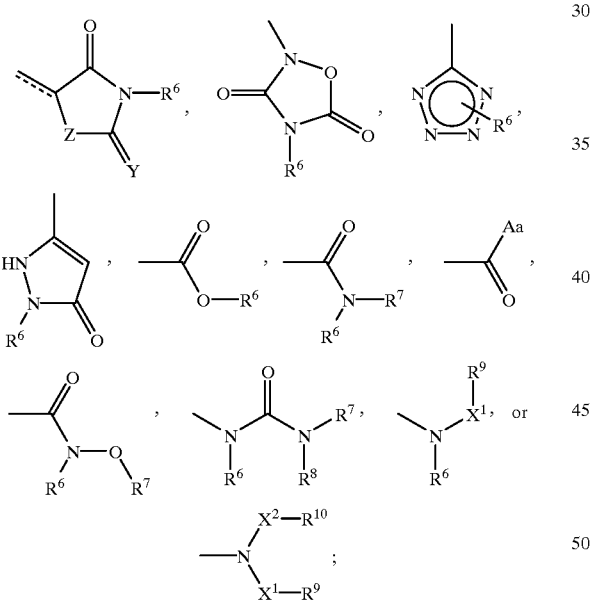

Aa is (i) an amino acid, wherein the nitrogen of amino acid attached to the adjacent carbonyl of $R^5$; or (ii) an alkyl ester of an amino acid, wherein the nitrogen of amino acid attached to the adjacent carbonyl of $R^5$, and the alkyl moiety of the alkyl ester contains 1–6 carbon atoms;

Y and Z are each, independently, $NR^7$, O, or S;

$X^1$ and $X^2$ are each, independently, CO or $SO_2$;

a dotted line represents and optional double bond;

$R^6$, $R^7$, and $R^8$ are each, independently, hydrogen; alkyl of 1–6 carbon atoms optionally substituted by $R^{11}$, $R^{12}$, and $R^{13}$; alkenyl of 2–7 carbon atoms op tionally substituted by $R^{11}$, $R^{12}$, and $R^{13}$; alkynyl of 2–7 carbon atoms optionally substituted with $R^{11}$; cycloalkyl of 3–8 carbon atoms optionally substituted by $R^{11}$, $R^{12}$, and $R^{13}$; bicycloalkyl of 7–11 carbon atoms optionally substituted by $R^{11}$, $R^{12}$, and $R^{13}$; —$CO_2$-alkyl of 1–6 carbon atoms; Het optionally substituted by $R^{11}$, $R^{12}$, or $R^{13}$; or Ar optionally substituted by $R^{11}$, $R^{12}$, and $R^{13}$; or when $R^6$ and $R^7$ are contained on a common nitrogen, they may be taken together to form a saturated 5–7 membered heterocycle that is optionally substituted with $R^{11}$;

$R^9$ and $R^{10}$ are each, independently, alkyl optionally substituted by $R^{11}$, $R^{12}$, and $R^{13}$; Ar optionally mono-, di-, or tri-substituted by $R^{15}$; Ar fused to a cycloalkyl ring of 3–8 carbon atoms, and optionally mono-, di-, or tri-substituted by $R^{15}$; Het optionally mono-, di-, or tri-substituted by $R^{15}$;

$R^{11}$, $R^{12}$, or $R^{13}$ are each, independently, alkyl of 1–6 carbon atoms, halogen, alkenyl of 2–7 carbon atoms, alkynyl of 2–7 carbon atoms, cycloalkyl of 3–8 carbon atoms, Ar-alkyl having 1–6 carbon atoms in the alkyl moiety, Ar optionally substituted with $R^{14}$, Het optionally substituted with $R^{14}$, hydroxy, alkoxy of 1–6 carbon atoms, Ar-oxy, oxo, —CN, —CHO, —$CO_2H$, —$OCO_2$-alkyl of 1–6 carbon atoms, —$CO_2$-alkyl of 1–6 carbon atoms, —$CO_2$—Ar, —$CO_2$-alkyl-Ar wherein the alkyl moiety has 1–6 carbon atoms, —$OCO_2$—Ar, —$CONH_2$, —CONHOH, amino, alkylamino of 1–6 carbon atoms, dialkylamino of 1–6 carbon atoms per alkyl moiety, —NHCONH-alkyl of 1–6 carbon atoms, —$NHSO_2$-alkyl of 1–6 carbon atoms, —$NHSO_2$—Ar, or —$NHSO_2$-Het; or when $R^{11}$ and $R^{12}$ are contained on a common carbon atom of an alkyl moiety, they may be taken together to form a spiro cycloalkyl ring of 3–8 carbon atoms;

$R^{14}$ is halogen, alkoxy of 1–6 carbon atoms, alkyl of 1–6 carbon atoms, alkenyl of 2–7 carbon atoms, alkynyl of 2–7 carbon atoms, hydroxy, acyl of 2–7 carbon atoms, —$SO_2$-alkyl of 1–6 carbon atoms, —$CO_2$-alkyl of 1–6 carbon atoms, or alkoxycarbonylalkyl of 3–13 carbon atoms;

$R^{15}$ is
(a) hydroxy, halogen, —CN, —$NR^{16}R^{16}$, —$OR^{16}$, —$SR^{16}$, triflouromethyl, alkyl of 1–6 carbon atoms, —$SO_2R^{17}$, —O-alkyl-$CO_2R^{17}$ wherein the alkyl moiety contains 1–6 carbon atoms, —$CO_2R^{17}$, —$OCOR^{17}$, —$NR^{16}COR^{17}$, —$COR^{17}$, —$NR^{16}SO_2R^{17}$, or —$NR^{16}CO_2R^{16}$; or
(b) alkyl of 1–6 carbon atoms mono-, or di-substituted with hydroxy; halogen; —CN; —$NR^{16}NR^{16}$; —$OR^{16}$; —$SR^{16}$; triflouromethyl; alkyl of 1–6 carbon atoms; —$SO_2R^{17}$; —$CO_2R^{17}$; —$OCOR^{17}$; —$NR^{16}COR^{17}$; —$COR^{17}$; —$NR^{16}SO_2R^{17}$; —$NR^{16}CO_2R^{16}$; Ar which may be optionally mono- or di-substituted by $R^{16}$, —$OR^{16}$, —$NR^{16}R^{16}$, or halogen; or Het which may be optionally mono- or di-substituted by $R^{16}$, —$OR^{16}$, —$NR^{16}R^{16}$, or halogen;
(c) Het optionally mono- or di-substituted by $R^{16}$, —$OR^{16}$, —$NR^{16}R^{16}$, or halogen; or
(d) Ar optionally mono- or di-substituted by $R^{16}$, —$OR^{16}$, —$NR^{16}R^{16}$, or halogen;

$R^{16}$ is hydrogen, alkyl of 1–6 carbon atoms, cycloalkylalkyl of 4–14 carbon atoms, benzyl, Ar or Het, wherein the Ar or Het moieties may be optionally mono-, di-, or tri- substituted with halogen, nitro, alkylamino of 1–6 carbon atoms, dialkylamino of 1–6 carbon atoms per alkyl moiety, trifluoromethyl, alkyl of 1–6 carbon atoms, alkoxy of 1–6 carbon atoms, alkylthio of 1–6 carbon atoms, —CO$_2$H, —CO$_2$alkyl of 1–6 carbon atoms, or —SO$_2$alkyl of 1–6 carbon atoms;

$R^{17}$ is $R^{16}$ or —NR$^{16}$R$^{16}$;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

Ar is an aromatic ring system containing 1–2 carbocyclic aromatic rings having 6–10 carbon atoms;

m=1–3;

n=1–3;

or a pharmaceutically acceptable salt thereof, which are selective agonists at human $\beta_3$ adrenergic receptors and are useful in treating or inhibiting metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, such as alkali metal salts (for example, sodium, lithium, or potassium), alkaline earth metal salts, ammonium salts, alkylammonium salts containing 1–6 carbon atoms or dialkylammonium salts containing 1–6 carbon atoms in each alkyl group, and trialkylammonium salts containing 1–6 carbon atoms in each alkyl group, when a compound of this invention contains an acidic moiety.

The compounds of the instant invention all contain at least one asymmetric center. Additional asymmetric centers may be present on the molecule depending upon the nature of the various substituents on the molecule. Each such asymmetric center will produce two optical isomers and all such optical isomers, as separated, pure or partially purified optical isomers or racemic mixtures thereof, are included within the scope of the instant invention. Any enantiomer of a compound of the general Formula I may be obtained by stereospecific synthesis using optically pure starting materials of know configuration.

The compounds of the present invention may also contain geometric isomers. Thus, the present invention includes all individual isomers and mixtures thereof.

Alkyl, alkenyl, and alkynyl include both straight chain as well as branched moieties. Halogen means bromine, chlorine, fluorine, and iodine. Where a substituent contains one or more moieties which have the same designation, each of the moieties can be the same or different. Ar and the term "aryl" includes monocyclic or bicyclic aromatic carbocyclic groups such as phenyl and naphthyl. Benzyl is the preferred arylalkyl moiety.

Preferred Het moieties include: (a) 6-membered saturated, partially unsaturated, or unsaturated heterocycles containing 1–2 nitrogens, optionally fused to a phenyl ring; (b) 5-membered saturated, partially saturated, or unsaturated heterocycles containing 1–3 nitrogen, oxygen, or sulfur atoms, optionally fused to a phenyl ring; (c) saturated, partially unsaturated, or unsaturated bicyclic heterocycles containing 1–4 nitrogen, oxygen, or sulfur atoms; (d) carbazole, dibenzofuran, and dibenzothiophene. In the Het of categories (a), (b), and (c), ring carbon atoms may be carbonyl moieties, where the ring does not contain a double bond in that position (for example, thiazolidine-2,4-dione).

More preferred Het rings include pyrrole, furan, thiophene, imidazole, pyrazole, furazan, triazole, tetrazole, oxazole, oxadiazole, isoxazole, thiazole, isothiazole, thiadiazole, pyridine, pyrimidine, pyridazine, pyrazine, 1,3,5-triazine, 1,2,4,5-tetrazine, benzofuran, isobenzofuran, indole, isoindole, benzothiophene, benzimidazol, 3H-benzoxazol-2-one, benzotriazole, quinoline, isoquinoline, quinazoline, indazole, 1 H-quinolin-2-one, 3,4-dihydro-1H-quinolin-2-one, 2,3-dihydro-1H-indole, 1,3-dihydro-benzoinimidazol-2-thione, carbazole, 3,5-dioxo-[1,2,4]oxadiazolidine, 2,4-dioxo-3-thiazolidine, 1H-benzoimidazole, 2-thioxo-thiazolidin-4-one, 2-imino-4-oxo-thiazolidine, 2-oxo-1,2,3,4-tetrahydro-quinoline, 2,4-dioxo-thiazolidine, 5-oxo-2,5-dihydro-1H-pyrazole, 2-oxo-2,3-dihydro-1H-benzimidazole, 9H-carbazole, benzothiophene, morpholine, piperidine, and 1,3-benzodioxole. It is understood that Het do not contain heteroatoms in arrangements which would make them inherently unstable. For example, the term Het does not include ring systems containing O—O bonds in the ring backbone.

Preferred amino acids include alanine, valine, leucine, isoleucine, proline, phenylalanine, tryptophan, methionine, glycine, serine, threonine, cysteine, tyrosine, asparagine, glutamine, aspartic acid, glutamic acid, lysine, arginine, histidine, β-alanine, cyclopropane amino acids (such as 1-aminocyclopropane-1-carboxylic acid, allo-coronamic acid and 2,3-methanohomoserine), 1-aminocyclohexane-1-carboxylic acid, isonipecotic acid, 2-azetidinecarboxylic acid, and esters thereof.

Preferred compounds of Formula I are those in which

A is Ar or Het;

X is —OCH$_2$— or a bond;

$T^1$ is (CH$_2$)$_m$;

$T^2$ is (CH$_2$)$_n$;

T is a bond, alkyl of 1–6 carbon atoms optionally substituted with $R^{11}$, alkenyl of 2–7 carbon atoms optionally substituted with $R^{11}$, or alkoxyalkyl of 1–6 carbon atoms per alkyl moiety;

$R^1$, $R^2$, and $R^3$ are each, independently, hydrogen, alkyl of 1–6 carbon atoms, hydroxy, halogen, trifluoromethyl, alkoxy of 1–6 carbon atoms, benzyloxy, acyloxy of 2–7 carbon atoms, cyano, nitro, amino, aminocarbonyl, alkylamino of 1–6 carbon atoms, dialkylamino of 1–6 carbon atoms per alkyl group, acylamino of 2–7 carbon atoms, alkylsulfonylamino of 1–6 carbon atoms, arylsulfonylamino, —CO$_2$-alkyl of 1–6 carbon atoms, or Ar optionally substituted with $R^{11}$;

$R^4$ is hydrogen or halogen;

$R^5$ is

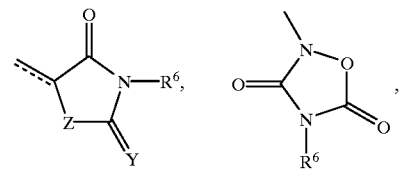

-continued

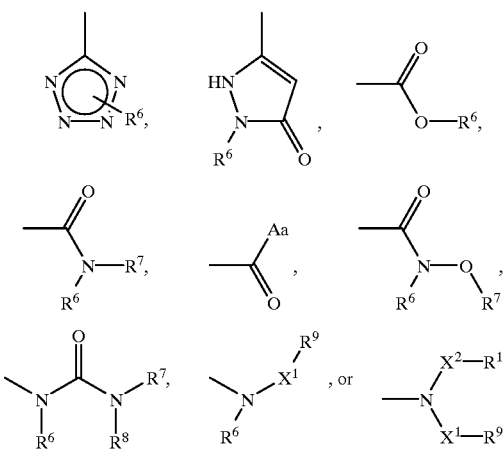

Aa is (i) an amino acid, wherein the nitrogen of amino acid attached to the adjacent carbonyl of $R^5$; or (ii) an alkyl ester of an amino acid, wherein the nitrogen of amino acid attached to the adjacent carbonyl of $R^5$, and the alkyl moiety of the alkyl ester contains 1–6 carbon atoms;

Y and Z are each, independently, $NR^7$, O, or S;

$X^1$ and $X^2$ are each, independently, CO or $SO_2$;

a dotted line represents and optional double bond;

$R^6$, $R^7$, and $R^8$ are each, independently, hydrogen; alkyl of 1–6 carbon atoms optionally substituted by $R^{11}$, $R^{12}$, and $R^{13}$; cycloalkyl of 3–8 carbon atoms optionally substituted by $R^{11}$, $R^{12}$, and $R^{13}$; bicycloalkyl of 7–11 carbon atoms optionally substituted by $R^{11}$, $R^{12}$, and $R^{13}$; —$CO_2$-alkyl of 1–6 carbon atoms; Het optionally substituted by $R^{11}$, $R^{12}$, or $R^{13}$; or Ar optionally substituted by $R^{11}$, $R^{12}$, and $R^{13}$; or when $R^6$ and $R^7$ are contained on a common nitrogen, they may be taken together to form a saturated 5–7 membered heterocycle that is optionally substituted with $R^{11}$;

$R^9$ and $R^{10}$ are each, independently, alkyl optionally substituted by by $R^{11}$, $R^{12}$, and $R^{13}$; Ar optionally mono-, di-, or tri-substituted by $R^{15}$; Het optionally mono-, di-, or tri-substituted by $R^{15}$;

$R^{11}$, $R^{12}$, or $R^{13}$ are each, independently, alkyl of 1–6 carbon atoms, halogen, alkenyl of 2–7 carbon atoms, alkynyl of 2–7 carbon atoms, cycloalkyl of 3–8 carbon atoms, Ar-alkyl having 1–6 carbon atoms in the alkyl moiety, Ar optionally substituted with $R^{14}$, Het optionally substituted with $R^{14}$, hydroxy, alkoxy of 1–6 carbon atoms, Ar-oxy, oxo, —CN, —CHO, —$CO_2H$, —$OCO_2$-alkyl of 1–6 carbon atoms, —$CO_2$-alkyl of 1–6 carbon atoms, —$CO_2$—Ar, —$CO_2$-alkyl-Ar wherein the alkyl moiety has 1–6 carbon atoms, —$OCO_2$—Ar, —$CONH_2$, —CONHOH, amino, alkylamino of 1–6 carbon atoms, dialkylamino of 1–6 carbon atoms per alkyl moiety, —NHCONH-alkyl of 1–6 carbon atoms, —$NHSO_2$-alkyl of 1–6 carbon atoms, —$NHSO_2$—Ar, or —$NHSO_2$-Het; or when $R^{11}$ and $R^{12}$ are contained on a common carbon atom of an alkyl moiety, they may be taken together to form a spiro cycloalkyl ring of 3–8 carbon atoms;

$R^{14}$ is halogen, alkoxy of 1–6 carbon atoms, alkyl of 1–6 carbon atoms, hydroxy, acyl of 2–7 carbon atoms, —$SO_2$-alkyl of 1–6 carbon atoms, —$CO_2$-alkyl of 1–6 carbon atoms, or alkoxycarbonylalkyl of 3–13 carbon atoms;

$R^{15}$ is
(a) halogen, —CN, —$OR^{16}$, triflouromethyl, alkyl of 1–6 carbon atoms, —$SO_2R^{17}$, —O-alkyl-$CO_2R^{17}$ wherein the alkyl moiety contains 1–6 carbon atoms, —$CO_2R^{17}$, —$NR^{16}COR^{17}$, —$COR^{17}$; or
(b) alkyl of 1–6 carbon atoms mono-, or di-substituted with halogen; —$NR^{16}COR^{17}$; Ar which may be optionally mono- or di-substituted by $R^{16}$, —$OR^{16}$, —$NR^{16}R^{16}$, or halogen; or Het which may be optionally mono- or di-substituted by $R^{16}$, —$OR^{16}$, —$NR^{16}R^{16}$, or halogen;
(c) Het optionally mono- or di-substituted by $R^{16}$, $OR^{16}$, —$NR^{16}R^{16}$, or halogen; or
(d) Ar optionally mono- or di-substituted by $R^{16}$, $OR^{16}$, —$NR^{16}R^{16}$, or halogen;

$R^{16}$ is hydrogen, alkyl of 1–6 carbon atoms, cycloalkylalkyl of 4–14 carbon atoms, benzyl, Ar or Het, wherein the Ar or Het moieties may be optionally mono-, di-, or tri- substituted with halogen, nitro, alkylamino of 1–6 carbon atoms, dialkylamino of 1–6 carbon atoms per alkyl moiety, trifluoromethyl, alkyl of 1–6 carbon atoms, alkoxy of 1–6 carbon atoms, alkylthio of 1–6 carbon atoms, —$CO_2H$, —$CO_2$alkyl of 1–6 carbon atoms, or —$SO_2$alkyl of 1–6 carbon atoms;

$R^{17}$ is $R^{16}$ or —$NR^{16}R^{16}$;

Het is a monocyclic or bicyclic heterocycle of 5–10 ring atoms, having 1–4 heteroatoms selected from oxygen, nitrogen, and sulfur; wherein the heterocycle may be saturated, unsaturated, or partially unsaturated; and may be optionally fused to a phenyl ring;

Ar is an aromatic ring system containing 1–2 carbocyclic aromatic rings having 6–10 carbon atoms;

m=1–2;

n=1–2;

or a pharmaceutically acceptable salt thereof.

Specifically preferred compounds of this invention are:
a) N-[5-((1R)-2-{1-[4-(3,5-dioxo-[1,2,4]oxadiazolidin-2-ylmethyl)-phenyl]-piperidine-4-ylamino}-1-hydroxy-ethyl)-2-hydroxy-phenyl]-methanesulfonamide;
b) 5-[[4-[4-[[(R)-2-hydroxy-2-[4-hydroxy-3-[(methylsulfonyl)amino]phenyl]ethyl]amino]-1-piperidineyl]phenyl]methyl]-2,4-dioxo-3-thiazolidineacetic acid tert-butyl-ester;
c) 5-[[4-[4-[[(R)-2-hydroxy-2-[4-hydroxy-3-[(methylsulfonyl)amino]phenyl]ethyl]amino]-1-piperidineyl]phenyl]methyl]-2,4-dioxo-3-thiazolidineacetic acid;
d) 5-[[4-[4-[[(R)-2-hydroxy-2-[4-hydroxy-3-[(methylsulfonyl)amino]phenyl]ethyl]amino]-1-piperidineyl]phenyl]methyl]-2,4-dioxo-3-thiazolidineacetic acid ethyl-ester;
e) 5-(3-fluoro-4-{4-[(2S)-2-hydroxy-3-(2-oxo-2,3-dihydro-1H-benzoimidazol-4-yloxy)-propylamino]-piperidine-1-yl}-benzyl)-thiazolidine-2,4-dione;
f) 5-(3-bromo-4-{4-[(2S)-2-hydroxy-3-(2-oxo-2,3-dihydro-1H-benzoimidazol-4-yloxy)-propylamino]-piperidine-1-yl}-benzylidene)-thiazolidine-2,4-dione;
g) 5-(3-fluoro-4-{4-[(2S)-2-hydroxy-3-(2-oxo-2,3-dihydro-1H-benzoimidazol-4-yloxy)-propylamino]-piperidine-1-yl}-benzylidene)-thiazolidine-2,4-dione;
h) N-[5-(2-{1-[2-bromo-4-(2,4-dioxo-thiazolidin-5-ylidenemethyl)-phenyl]-piperidine-4-ylamino}-1-hydroxy-ethyl)-2-hydroxy-phenyl]-methanesulfonamide;
i) N-[5-(2-{1-[4-(2,4-dioxo-thiazolidin-5-ylidenemethyl)-2-fluoro-phenyl]-piperidine-4- j) 5-{4-[4-((2S)-2-hydroxy-3-phenoxy-propylamino)-piperidine-1-yl]-benzylidene}-2-thioxo-thiazolidin-4-one;
k) 5-{4-[4-((2S)-2-hydroxy-3-phenoxy-propylamino)-piperidine-1-yl]-benzyl}-thiazolidin-2,4-dione;
l) 5-(4-{4-[(2S)-3-(4-benzyloxy-phenoxy)-2-hydroxy-propylamino]-piperidine-1-}-benzyl)-thiazolidine-2,4-dione;
m) 5-(4-{4-[(2S)-2-hydroxy-3-(2-oxo-2,3-dihydro-1H-benzoimidazol-4-yloxy)-propylamino]-piperidine-1-yl}-benzylidene)-thiazolidine-2,4-dione;
n) 5-(4-{4-[(2S)-2-hydroxy-3-(4-hydroxy-phenoxy)-propylamino]-piperidine-1-yl}-benzylidene)-thiazolidine-2,4-dione;
o) N-[5-(2-{1-[4-(2,4-dioxo-thiazolidin-5-ylidenemethyl)-phenyl]-piperidine-4-ylamino}-1-hydroxy-ethyl)-2-hydroxy-phenyl]-methanesulfonamide;
p) N-[5-(2-{1-[4-(2,4-dioxo-thiazolidin-5-ylmethyl)-phenyl]-piperidine-4-ylamino-1-hydroxy-ethyl)-2-hydroxy-phenyl]-methanesulfonamide;
q) 5-(4-{4-[2-(3-chloro-phenyl)-(2R)-2-hydroxy-ethylamino}-piperidine-1-yl}-benzyl)-thiazolidine-2,4-dione;
r) 5-(4-{4-[(2S)-2-hydroxy-3-(2-oxo-2,3-dihydro-1H-benzoimidazol-4-yloxy)-propylamino]-piperidine-1-yl}-benzyl)-thiazolidine-2,4-dione;
s) 5-(4-{4-[(2S)-2-hydroxy-3-(4-hydroxy-phenoxy)-propylamino]-piperidine-1-yl}-benzyl)-thiazolidine-2,4-dione;
t) 5-(4-{4-[(2S)-2-hydroxy-3-(4-hydroxy-phenoxy)-propylamino]-piperidine-1-yl}-benzylidene)-2-thioxo-thiazolidin-4-one;
u) 5-{4-[4-((2S)-2-hydroxy-3-phenoxy-propylamino)-piperidine-1-yl]-benzylidene}-thiazolidin-2,4-dione;
v) N-[5-((2R)-2-{1-[4-(2,4-dioxo-thiazolidin-5-ylmethyl)-phenyl]-piperidine-4-ylamino}-1-hydroxy-ethyl)-2-hydroxy-phenyl]-methanesulfonamide;
w) N-[5-(2-{1-[4-(2,5-dioxo-imidazolidin-4-ylidenemethyl)-phenyl]-piperidine-4-ylamino}-1-hydroxy-ethyl)-2-hydroxy-phenyl]-methanesulfonamide;
x) 5-(4-{4-[2-hydroxy-3-(2-oxo-2,3-dihydro-1H-benzoimidazol-4-yloxy)-propylamino]-piperidine-1-yl}-benzyl)-imidazolidine-2,4-dione-piperidine-1-yl}-benzyl)-imidazolidine-2,4-dione;
y) N-[5-(2-{1-[4-(2,5-dioxo-imidazolidin-4-ylmethyl)-phenyl]-piperidine-4-ylamino-1-hydroxy-ethyl)-2-hydroxy-phenyl]-methanesulfonamide;
z) N-[2-hydroxy-5-(1-hydroxy-2-{1-[4-(2-imino-4-oxo-thiazolidin-5-ylidenemethyl)-phenyl]-piperidine-4-ylamino}-ethyl)-phenyl]-methanesulfonamide;
aa) 4-((2S)-2-hydroxy-3-{1-[4-(2-imino-4-oxo-thiazolidin-5-ylmethyl)-phenyl]-piperidine-4-ylamino}-propoxy)-1,3-dihydro-benzoimidazol-2-one;
bb) N-[2-hydroxy-5-(1-hydroxy-2-(1-[4-(2-imino-4-oxo-thiazolidin-5-ylmethyl)-phenyl]-piperidine-4-ylamino}-ethyl)-phenyl]-methanesulfonamide;
cc) 5-(4-{4-[(2S)-2-hydroxy-3-(8-hydroxy-2-oxo-1,2,3,4-tetrahydro-quinolin-5-yloxy)-propylamino]-piperidine-1-yl}-benzyl)-thiazolidine-2,4-dione;
dd) N-[5-((2S)-3-{1-[4-(2,4-dioxo-thiazolidin-5-ylmethyl)-phenyl]-piperidine-4-ylamino}-2-hydroxy-propoxy)-2-hydroxy-phenyl]-methanesulfonamide;
ee) N-[5-((2S)-3-{1-[4-(2,4-dioxo-thiazolidin-5-ylmethyl)-phenyl]- piperidine-4-ylamino}-2-hydroxy-propoxy)-2-hydroxy-phenyl]-benzenesulfonamide;
ff) (R)-propane-2-sulfonic acid [5-(2-{1-[4-(2,4-dioxo-thiazolidin-5-ylmethyl)-phenyl]-piperidine-4-ylamino}-1-hydroxy-ethyl)-2-hydroxy-phenyl]-amide;
gg) N-[2-chloro-5-((1R)-2-{1-[4-(2,4-dioxo-thiazolidin-5-ylmethyl)-phenyl]-piperidine-4-ylamino}-1-hydroxy-ethyl)-phenyl]-methanesulfonamide;
hh) N-(5-{(1R)-2-[(1-{4-[(2,4-dioxo-1,3-thiazolidin-5-yl)methyl]phenyl}piperidine-4-yl)amino]-1-hydroxyethyl}-2-hydroxyphenyl)benzenesulfonamide;
ii) N-[2-hydroxy-5-(1-hydroxy-2-{1-[4-(1H-tetrazol-5-yl)-phenyl]-piperidine-4-ylamino}-ethyl)-phenyl]-methanesulfonamide;
jj) ethyl [5-(4-{4-[((2R)-2-hydroxy-2-{4-hydroxy-3-[(methylsulfonyl)amino]phenyl}ethyl)amino]-1-piperidineyl}phenyl)-1H-tetraazol-1-yl]acetate;
kk) [5-(4-{4-[((2R)-2-hydroxy-2-{4-hydroxy-3-[(methylsulfonyl)amino]phenyl}ethyl)amino]-1-piperidineyl}phenyl)-1H-tetraazol-1-yl]acetic acid;
ll) [5-(4-{4-[((2R)-2-hydroxy-2-{4-hydroxy-3-[(methylsulfonyl)amino]phenyl}ethyl)amino]-1-piperidineyl}phenyl)-2H-tetraazol-2-yl]acetic acid;
mm) 5-{4-[4-({(2S)-2-hydroxy-2-[2-(trifluoromethyl)-1,3-thiazol-4-yl]ethyl}amino)piperidine-1-yl]benzyl}-1,3-thiazolidine-2,4-dione;
nn) 5-{4-[4-({(2S)-2-[3-(3,4-dichlorophenyl)isoxazol-5-yl]-2-hydroxyethyl}amino)piperidine-1-yl}benzyl}-1,3-thiazole-2,4-dione;
oo) N-(4-{(1R)-2-[(1-{4-[(2,4-dioxo-1,3-thiazolidin-5-yl)methyl]phenyl}piperidine-4yl)amino]-1-hydroxyethyl)}phenyl)methanesulfonamide;
pp) 5-[4-(4-{[4-(2S)-2-(3-bromoisoxazol-5-yl)-2-hydroxyethyl]amino}piperidine-1-yl)benzyl]-1,3-thiazolidine-2,4-dione;
qq) 5-(4-{4-[(2S)-2-hydroxy-3-(pyridin-3-yloxy)-propylamino]-piperidine-1-yl}-benzyl)-thiazolidine-2,4-dione;
rr) 5-(4-{4-[(2S)-2-hydroxy-3-(6-methyl-pyridin-3-yloxy)-propylamino]-piperidine-1-yl}-benzyl)-thiazolidine-2,4-dione;
ss) 5-{4-[4-((2S)-2-hydroxy-2-pyridin-3-yl-ethylamino)-piperidine-1-yl]- benzyl}-thiazolidine-2,4-dione;
tt) 5-(4-{4-[(2S)-2-(6-amino-pyridin-3-yl)-2-hydroxy-ethylamino]-piperidine-1-yl}-benzyl)-thiazolidine-2,4-dione hydrochloride;
uu) 5-{4-[4-((2R)-2-hydroxy-2-pyridin-3-yl-ethylamino)-piperidine-1-yl]-benzyl}-thiazolidine-2,4-dione;
vv) N-[5-(2-{1-[4-(2,4-dioxo-thiazolidin-5-ylmethyl)-phenyl]-piperidine-4-ylamino}-1-hydroxy-ethyl)-pyridin-2-yl]-methanesulfonamide;
ww) 5-(3-{1-[4-(2,4-dioxo-thiazolidin-5-ylmethyl)-2-fluoro-phenyl]-piperidine-4-ylamino}-(2S)-2-hydroxy-propoxy)-2-methyl-1H-indole-3-carboxylic acid ethyl ester;
xx) N-[(2R)-2-hydroxy-5-(1-hydroxy-2-{1-[4-(5-oxo-2,5-dihydro-1H-pyrazol-3-yl)-phenyl]-piperidine-4-ylamino}-ethyl)-phenyl]-methanesulfonamide;
yy) 4-{4-[(2S)-2-hydroxy-3-(2-oxo-2,3-dihydro-1H-benzoimidazol-4-yloxy)-propylamino]-piperidine-1-yl}-benzoic acid ethyl ester;

zz) {4-[(2R)-2-hydroxy-2-(4-hydroxy-3-methane-sulfonylamino-phenyl)-ethylamino]-piperidine-1-yl}-benzoic acid ethyl ester;

aaa) {4-[(2R)-2-(3-chloro-phenyl)-2-hydroxy-ethylamino]-piperidine-1-yl}-benzoic acid ethyl ester hydrochloride;

bbb) (4-{4-[(2R)-2-hydroxy-2-(4-hydroxy-3-methanesulfonylamino-phenyl)-ethylamino]-piperidine-1-yl}-phenyl)-acetic acid;

ccc) 3-(4-{4-[(2R)-2-hydroxy-2-(4-hydroxy-3-methanesulfonylamino-phenyl)-ethylamino]-piperidine-1-yl}-phenyl)-acrylic acid ethyl ester;

ddd) 3-(4-{4-[(2R)-2-hydroxy-2-(4-hydroxy-3-methanesulfonylamino-phenyl)-ethylamino]-piperidine-1-yl}-phenyl)-propionic acid;

eee) (4-{4-[(2R)-2-hydroxy-2-(4-hydroxy-3-methanesulfonylamino-phenyl)-ethylamino]-piperidine-1-yl}-benzyloxy)-acetic acid;

fff) 4-{4-[(2R)-2-hydroxy-2-(4-hydroxy-3-methanesulfonylamino-phenyl)-ethylamino]-piperidine-1-yl}-benzoic acid;

ggg) 3-(4-(4-[(2R)-2-hydroxy-2-(4-hydroxy-3-methanesulfonylamino-phenyl)-ethylamino]-piperidine-1-yl}-phenyl)-propionic acid ethyl ester;

hhh) 2-(4-{4-[2-hydroxy-2-(4-hydroxy-3-methanesulfonylamino-phenyl)-ethylamino]-piperidine-1-yl}-benzylidene)-malonic acid diethyl ester;

iii) 2-(4-{4-[(2R)-2-hydroxy-2-(4-hydroxy-3-methanesulfonylamino-phenyl)-ethylamino]-piperidine-1-yl}-benzylidene)-malonic acid monoethyl ester;

jjj) 4-{4-[(2R)-2-hydroxy-2-(4-hydroxy-3-methanesulfonylamino-phenyl)-ethylamino]-piperidine-1-yl}-benzamide;

kkk) N-benzyloxy-4-{4-[(2R)-2-hydroxy-2-(4-hydroxy-3-methanesulfonylamino-phenyl)-ethylamino]-piperidine-1-yl}-benzamide;

lll) diethyl (2S)-2-[(4-{4-[((2R)-2-hydroxy-2-{4-hydroxy-3-[(methylsulfonyl)amino]phenyl}ethyl)amino]-1-piperidinyl}benzoyl)amino]pentanedioate;

mmm) ethyl 3-[(4-{4-[((2R)-2-hydroxy-2-{4-hydroxy-3-[(methylsulfonyl)amino]phenyl}ethyl)amino]-1-piperidinyl}benzoyl)amino]propanoate;

nnn) (2S)-2-[(4-{4-[((2R)-2-hydroxy-2-(4-hydroxy-3-[(methylsulfonyl)amino]phenyl}ethyl)amino]-1-piperidinyl}benzoyl)amino]pentanedioic acid;

ooo) N-(4-{4-[((2R)-2-hydroxy-2-{4-hydroxy-3-[(methylsulfonyl)amino]phenyl}ethyl)amino]-1-piperidinyl}benzoyl)-beta-alanine;

ppp) ethyl [(4-{4-[((2R)-2-hydroxy-2-{4-hydroxy-3-[(methylsulfonyl)amino]phenyl}ethyl)amino]-1-piperidinyl}benzoyl)amino]acetate;

qqq) [(4-{4-[((2R)-2-hydroxy-2-{4-hydroxy-3-[(methylsulfonyl)amino]phenyl}ethyl)amino]-1-piperidinyl}benzoyl)amino]acetic acid;

rrr) (2S)-2-(4-{4-[(2R)-2-hydroxy-2-(4-hydroxy-3-methanesulfonylamino-phenyl)-ethylamino]-piperidine-1-yl}-benzoylamino)-4-methyl-pentanoic acid ethyl ester;

sss) (2S)-2-(4-{4-[(2R)-2-hydroxy-2-(4-hydroxy-3-methanesulfonylamino-phenyl)-ethylamino]-piperidine-1-yl}-benzoylamino)-4-methyl-pentanoic acid;

ttt) 1-(4-{4-[(2R)-2-hydroxy-2-(4-hydroxy-3-methanesulfonylamino-phenyl)-ethylamino]-piperidine-1-yl}-benzoyl)-pyrrolidine-(2S)-2-carboxylic acid methyl ester;

uuu) 1-(4-{4-[(2R)-2-hydroxy-2-(4-hydroxy-3-methanesulfonylamino-phenyl)-ethylamino]-piperidine-1-yl}-benzoyl)-pyrrolidine-(2S)-2-carboxylic acid;

vvv) (2S)-2-(4-{4-[(2R)-2-hydroxy-2-(4-hydroxy-3-methanesulfonylamino-phenyl)-ethylamino]-piperidine-1-yl}-benzoylamino)-3-methyl-butyric acid ethyl ester;

www) (2S)-2-(4-{4-[(2R)-2-hydroxy-2-(4-hydroxy-3-methanesulfonylamino-phenyl)-ethylamino]-piperidine-1-yl}-benzoylamino)-3-methyl-butyric acid;

xxx) (2S)-2-(4-{4-[(2R)-2-hydroxy-2-(4-hydroxy-3-methanesulfonylamino-phenyl)-ethylamino]-piperidine-1-yl}-benzoylamino)-3-phenyl-propionic acid methyl ester;

yyy) (2S)-2-(4-{4-[(2R)-2-hydroxy-2-(4-hydroxy-3-methanesulfonylamino-phenyl)-ethylamino]-piperidine-1-yl}-benzoylamino)-3-phenyl-propionic acid;

zzz) methyl 1-[(4-{4-[((2R)-2-hydroxy-2-{4-hydroxy-3-piperidineyl}benzoyl)amino]cyclopropanecarboxylate;

aaaa) [butyl-(4-{4-[(2R)-2-hydroxy-2-(4-hydroxy-3-methanesulfonylamino-phenyl)-ethylamino]-piperidine-1-yl}-benzoyl)-amino]-acetic acid ethyl ester;

bbbb) methyl [(4-{4-[((2R)-2-hydroxy-2-{4-hydroxy-3-[(methylsulfonyl)amino]phenyl}ethyl)amino]-1-piperidineyl}benzoyl)amino]acetate;

cccc) (2S)-2-(4-{4-[2-hydroxy-2-(4-hydroxy-3-methanesulfonylamino-phenyl)-ethylamino]-piperidine-1-yl}-benzoylamino)-4-methyl-pentanoic acid methyl ester;

dddd) (2E)-3-(4-{4-[(2R)-2-hydroxy-2-(4-hydroxy-3-methanesulfonylamino-phenyl)-ethylamino]-piperidine-1-yl}-phenyl)-acrylic acid;

eeee) 4-{4-[((2R)-2-hydroxy-2-{4-hydroxy-3-[(methylsulfonyl)amino]phenyl}ethyl)amino]-1-piperidineyl}-N-[(1S)-1-(hydroxymethyl)-3-methylbutyl]benzamide;

ffff) 4-{4-[((2R)-2-hydroxy-2-{4-hydroxy-3-[(methylsulfonyl)amino]phenyl}ethyl)amino]-sulfonyl)amino]phenyl}ethyl)amino]-1-piperidineyl}-N-[(3S)-2-1]ethyl)amino]-1-piperidineyl}-N-[(3S)-2-oxoazepanyl]benzamide;

gggg) N-butyl-4-{4-[((2R)-2-hydroxy-2-{4-hydroxy-3-[(methylsulfonyl)amino]phenyl}ethyl)amino]-1-piperidineyl}-N-(1H-tetraazol-5-ylmethyl)benzamide.

hhhh) N-{4-[4-(2-hydroxy-2-phenyl-ethylamino)-piperidine-1-yl]-phenyl}-4-methoxy-benzenesulfonamide;

iiii) N-(4-{4-[2-hydroxy-2-(3-hydroxy-phenyl)-ethylamino]-piperidine-1-yl}-phenyl)-4-methoxy-benzenesulfonamide;

jjjj) N-[4-(4-{4-[2-hydroxy-2-(3-hydroxy-phenyl)-ethylamino]-piperidine-1-yl}-phenylsulfamoyl)-phenyl]-acetamide;

kkkk) N-(4-{4-[4-((2R)-2-hydroxy-2-phenyl-ethylamino)-piperidine-1-yl]-phenylsulfamoyl}-phenyl)-acetamide;

llll) N-(4-{[4-(4-{[2-hydroxy-2-(4-hydroxyphenyl)ethyl]amino}-1-piperidinyl)anilino]sulfonyl}phenyl)acetamide;

mmmm) N-[4-(4-{[(2R)-2-(3-chlorophenyl)-2-hydroxyethyl]amino}-1-piperidinyl)phenyl]-4-methoxybenzenesulfonamide;

nnnn) N-[4-(4-{[(2R)-2-hydroxy-2-phenylethyl]amino}-1-piperidinyl)phenyl]-4-methoxybenzenesulfonamide;

oooo) N-(4-{[4-(4-{[2-hydroxy-3-(4-methoxyphenoxy)propyl]amino}-1-piperidinyl)anilino]sulfonyl}-phenyl)acetamide;

pppp) N-(4-{[4-(4-{[(2R)-2-(3,4-dihydroxyphenyl)-2-hydroxyethyl]amino}-1-piperidinyl)anilino]sulfonyl}phenyl)acetamide;

qqqq) N-(4-{[2-(4-{[2-hydroxy-2-(3-hydroxyphenyl)ethyl]amino}-1-piperidinyl)anilino]sulfonyl}phenyl)acetamide;

rrrr) N-(4-{[2-(4-{[(2R)-2-(3,4-dihydroxyphenyl)-2-hydroxyethyl]amino}-1-piperidinyl)anilino]sulfonyl}phenyl)acetamide;

ssss) N-[4-(4-{[(2R)-2-(3,4-dihydroxyphenyl)-2-hydroxyethyl]amino-1-piperidinyl)phenyl]-4-methoxybenzenesulfonamide;

tttt) N-(4-{[4-(4-{[2-hydroxy-2-(4-hydroxy-3-methoxyphenyl)ethyl]amino}-1-piperidinyl)anilino]sulfonyl}phenyl)acetamide;

uuuu) N-(4-{[4-(4-{[2-(2,4-dihydroxyphenyl)-2-hydroxyethyl]amino-1-piperidinyl)anilino]sulfonyl}phenyl)acetamide;

vvvv) N-(4-{[4-(4-{[(2S)-2-hydroxy-3-(4-hydroxyphenoxy)propyl]amino}-1-piperidinyl)anilino]sulfonyl}phenyl)acetamide;

wwww) N-{4-[(4-{4-[(2-hydroxy-2-{4-hydroxy-3-[(methylsulfonyl)amino]phenyl}ethyl)amino]-1-piperidinyl}anilino)sulfonyl]phenyl}acetamide;

xxxx) 4-{[(hexylamino)carbonyl]amino}-N-[4-(4-{[2-hydroxy-2-(6-methyl-3-pyridinyl)ethyl]amino}-1-piperidinyl)phenyl]benzenesulfonamide;

yyyy) N-(4-{[4-(4-{[(2S)-2-hydroxy-3-phenoxypropyl]amino}-1-piperidinyl)anilino]sulfonyl}phenyl)acetamide;

zzzz) 5-[2-({1-[4-({[4-(acetylamino)phenyl]sulfonyl}amino)phenyl]-4-piperidinyl}amino)-1-hydroxyethyl]-1H-indole-7-carboxamide;

aaaaa) N-[4-({4-[4-({(2S)-2-hydroxy-3-[(2-oxo-2,3-dihydro-1H-benzimidazol-4-yl)oxy]propyl}amino)-1-piperidinyl]anilino}sulfonyl)phenyl]acetamide;

bbbbb) 4-{[(hexylamino)carbonyl]amino}-N-{4-[4-({(2S)-2-hydroxy-3-[(2-oxo-2,3-dihydro-1H-benzimidazol-4-yl)oxy]propyl}amino)-1-piperidinyl]phenyl}benzenesulfonamide;

ccccc) 4-{[(hexylamino)carbonyl]amino}-N-(4-{4-[((2R)-2-hydroxy-2-{4-hydroxy-3-[(methylsulfonyl)amino]phenyl}ethyl)amino]-1-piperidinyl}phenyl)benzenesulfonamide;

ddddd) 4-[4-(3-cyclopentylpropyl)-5-oxo-4,5-dihydro-1H-tetraazol-1-yl]-N-{4-[4-({(2S)-2-hydroxy-3-[(2-oxo-2,3-dihydro-1H-benzimidazol-4-yl)oxy]propyl}amino)-1-piperidinyl]phenyl}benzenesulfonamide;

eeeee) N-{4-[4-({(2S)-2-hydroxy-3-[(2-oxo-2,3-dihydro-1H-benzimidazol-4-yl)oxy]propyl}amino)-1-piperidinyl]phenyl}-5-(2-pyridinyl)-2-thiophenesulfonamide;

fffff) N-[4-(4-{[(2S)-2-hydroxy-3-(4-hydroxyphenoxy)propyl]amino}-1-piperidinyl)phenyl]-3,4-dimethoxybenzenesulfonamide;

ggggg) N-(4-{4-[(2-hydroxy-2-{4-hydroxy-3-[(methylsulfonyl)amino]phenyl}ethyl)amino]-1-piperidinyl}phenyl)-3,4-dimethoxybenzenesulfonamide;

hhhhh) 4-butoxy-N-(4-{4-[(2-hydroxy-2-{4-hydroxy-3-[(methylsulfonyl)amino]phenyl}ethyl)amino]-1-piperidinyl}phenyl)benzenesulfonamide;

iiiii) N-(4-{[4-(4-{[(2S)-3-(9H-carbazol-4-yloxy)-2-hydroxypropyl]amino}-1-piperidinyl)anilino]sulfonyl}phenyl)acetamide;

jjjjj) 5-chloro-N-{4-[4-({(2S)-2-hydroxy-3-[(2-oxo-2,3-dihydro-1H-benzimidazol-4-yl)oxy]propyl}amino)-1-piperidinyl]phenyl}-3-methyl-1-benzothiophene-2-sulfonamide;

kkkkk) 4-cyano-N-{4-[4-({(2S)-2-hydroxy-3-[(2-oxo-2,3-dihydro-1H-benzimidazol-4-yl)oxy]propyl}amino)-1-piperidinyl]phenyl}benzenesulfonamide;

lllll) 4-cyano-N-[(4-cyanophenyl)sulfonyl]-N-{4-[4-({(2S)-2-hydroxy-3-[(2-oxo-2,3-dihydro-1H-benzimidazol-4-yl)oxy]propyl}amino)-1-piperidinyl]phenyl}benzenesulfonamide;

mmmmm) 3-bromo-5-chloro-N-{4-[4-({(2S)-2-hydroxy-3-[(2-oxo-2,3-dihydro-1H-benzimidazol-4-yl)oxy]propyl}amino)-1-piperidinyl]phenyl}-2-thiophenesulfonamide;

nnnnn) N-{4-[4-({(2S)-2-hydroxy-3-[(2-oxo-2,3-dihydro-1H-benzimidazol-4-yl)oxy]propyl}amino)-1-piperidinyl]phenyl}-5-(3-isoxazolyl)-2-thiophenesulfonamide;

ooooo) 4-[4-(3-cyclopentylpropyl)-5-oxo-4,5-dihydro-1H-tetraazol-1-yl]-N-(4-{4-[(2-hydroxy-2-{4-hydroxy-3-[(methylsulfonyl)amino]phenyl}ethyl)amino]-1-piperidinyl}phenyl)benzenesulfonamide;

ppppp) 4-butoxy-N-[4-(4-{[(2S)-3-(9H-carbazol-4-yloxy)-2-hydroxypropyl]amino}-1-piperidinyl)phenyl]benzenesulfonamide;

qqqqq) N-[4-(4-{[3-(9H-carbazol-4-yloxy)-(2S)-2-hydroxypropyl]amino}-1-piperidinyl)phenyl]-4-{[(hexylamino)carbonyl]amino}benzenesulfonamide;

rrrrr) N-{4-[(4-{4-[((2R)-2-hydroxy-2-{4-hydroxy-3-[(methylsulfonyl)amino]phenyl}ethyl)amino]-1-piperidinyl}anilino)sulfonyl]phenyl}acetamide;

sssss) N-[4-(4-{[(2S)-3-(9H-carbazol-4-yloxy)-2-hydroxypropyl]amino}-1-piperidinyl)phenyl]-3,4-dimethoxybenzenesulfonamide;

ttttt) N-[4-(4-{[(2S)-2-hydroxy-3-(4-hydroxyphenoxy)propyl]amino}-1-piperidinyl)phenyl]-5-(2-pyridinyl)-2-thiophenesulfonamide;

uuuuu) N-(4-{4-[(2-hydroxy-2-{4-hydroxy-3-[(methylsulfonyl)amino]phenyl}ethyl)amino]-1-piperidinyl}phenyl)-5-(2-pyridinyl)-2-thiophenesulfonamide;

vvvvv) N-(4-{4-[(2-hydroxy-2-{4-hydroxy-3-[(methylsulfonyl)amino]phenyl}ethyl)amino]-1-piperidineyl}phenyl)-1-butanesulfonamide;

wwwww) N-{4-[4-({(2S)-2-hydroxy-3-[(2-oxo-2,3-dihydro-1H-benzimidazol-4-yl)oxy]propyl}amino)-1-piperidineyl]phenyl}-1-butanesulfonamide;

xxxxx) N-(4-{4-[(2-hydroxy-2-{4-hydroxy-3-[(methylsulfonyl)amino]phenyl}ethyl)amino]-1-piperidineyl}phenyl)-1-octanesulfonamide;

yyyyy) N-{4-[4-({(2S)-2-hydroxy-3-[(2-oxo-2,3-dihydro-1H-benzimidazol-4-yl)oxy]propyl}amino)-1-piperidineyl]phenyl}-1-octanesulfonamide;

zzzzz) N-{4-[4-({(2S)-2-hydroxy-3-[(2-oxo-2,3-dihydro-1H-benzimidazol-4-yl)oxy]propyl}amino)-1-piperidineyl]phenyl}-5-{[5-(trifluoromethyl)-2-pyridinyl]sulfonyl}-2-thiophenesulfonamide;

aaaaaa) N-[4-(4-{[(2S)-2-hydroxy-3-(4-hydroxyphenoxy)propyl]amino}-1-piperidineyl)phenyl]-5-{[5-(trifluoromethyl)-2-pyridinyl]sulfonyl}-2-thiophenesulfonamide;

bbbbbb) 4-[(2,4-dioxo-1,3-thiazolidin-5-yl)methyl]-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide;

cccccc) 4-[(2,4-dioxo-1,3-thiazolidin-5-yl)methyl]-N-(4-{4-[(2-hydroxy-2-{4-hydroxy-3-[(methylsulfonyl)amino]phenyl}ethyl)amino]-1-piperidineyl}phenyl)benzenesulfonamide;

dddddd) N-{4-[4-({(2S)-2-hydroxy-3-[(8-hydroxy-2-oxo-1,2,3,4-tetrahydro-5-quinolinyl)oxy]propyl}amino)-1-piperidineyl]phenyl}-3,4-dimethoxybenzenesulfonamide;

eeeeee) N-[4-(4-{[(2S)-2-hydroxy-3-(4-hydroxyphenoxy)propyl]amino}-1-piperidineyl)phenyl]-1-octanesulfonamide;

ffffff) 4-{[(hexylamino)carbonyl]amino}-N-{4-[4-({(2S)-2-hydroxy-3-[(8-hydroxy-2-oxo-1,2,3,4-tetrahydro-5-quinolinyl)oxy]propyl}amino)-1-piperidineyl]phenyl}benzenesulfonamide;

gggggg) N-{4-[4-({(2S)-2-hydroxy-3-[(8-hydroxy-2-oxo-1,2,3,4-tetrahydro-5-quinolinyl)oxy]propyl}amino)-1-piperidineyl]phenyl}-1-butanesulfonamide;

hhhhhh) N-[4-({4-[4-({(2S)-2-hydroxy-3-[(8-hydroxy-2-oxo-1,2,3,4-tetrahydro-5-quinolinyl)oxy]propyl}amino)-1-piperidineyl]anilino}sulfonyl)phenyl]acetamide;

iiiiii) N-(4-{4-[((2S)-2-hydroxy-3-{4-hydroxy-3-[(methylsulfonyl)amino]phenoxy}propyl)amino]-1-piperidineyl}phenyl)-,4-dimethoxybenzenesulfonamide;

jjjjjj) N-(4-{4-[((2S)-2-hydroxy-3-{4-hydroxy-3-[(methylsulfonyl)amino]phenoxy}propyl)amino]-1-piperidineyl}phenyl)-1-butanesulfonamide;

kkkkkk) 4-{[(hexylamino)carbonyl]amino}-N-(4-{4-[((2S)-2-hydroxy-3-{4-hydroxy-3-[(methylsulfonyl)amino]phenoxy}propyl)amino]-1-piperidineyl}phenyl)benzenesulfonamide;

llllll) N-[4-(4-{[(2R)-2-(3-chlorophenyl)-2-hydroxyethyl]amino}-1-piperidineyl)phenyl]-4-{[(hexylamino)carbonyl]amino}benzenesulfonamide;

mmmmmm) ethyl {4-[(4-{4-[((2S)-2-hydroxy-3-{4-hydroxy-3-[(methylsulfonyl)amino]phenoxy}propyl)amino]-1-piperidineyl}anilino)sulfonyl]phenyl}acetate;

nnnnnn) methyl {4-[(4-{4-[((2R)-2-hydroxy-3-{4-hydroxy-3-[(methylsulfonyl)amino]phenyl}ethyl)amino]-1-piperidineyl}anilino)sulfonyl]phenoxy}acetate;

oooooo) methyl [4-({4-[4-({(2S)-2-hydroxy-3-[(2-oxo-2,3-dihydro-1H-benzimidazol-4-yl)oxy]propyl}amino)-1-piperidineyl]anilino}sulfonyl)phenoxy]acetate;

pppppp) N-[5-({(2S)-3-[(1-{4-[(butylsulfonyl)amino]phenyl}-4-piperidineyl)amino]-2-hydroxypropyl}oxy)-2-hydroxyphenyl]benzenesulfonamide;

qqqqqq) N-(4-{4-[((2R)-2-hydroxy-2-{4-hydroxy-3-[(isopropylsulfonyl)amino]phenyl}ethyl)amino]-1-piperidineyl}phenyl)-1-butanesulfonamide;

rrrrrr) 4-[(4-{4-[((2R)-2-hydroxy-2-{4-hydroxy-3-[(methylsulfonyl)amino]phenyl}ethyl)amino]-1-piperidineyl}anilino)sulfonyl]benzoic acid;

ssssss) ethyl 4-[(4-{4-[((2R)-2-hydroxy-2-{4-hydroxy-3-[(methylsulfonyl)amino]phenyl}ethyl)amino]-1-piperidineyl}anilino)sulfonyl]benzoate;

tttttt) methyl {4-[(4-{4-[((2R)-2-{4-chloro-3-[(methylsulfonyl)amino]phenyl}-2-hydroxyethyl)amino]-1-piperidineyl}anilino)sulfonyl]phenoxy}acetate;

uuuuuu) methyl 3-[(4-{4-[((2R)-2-hydroxy-2-{4-hydroxy-3-[(methylsulfonyl)amino]phenyl}ethyl)amino]-1-piperidineyl}anilino)sulfonyl]-2-thiophenecarboxylate;

vvvvvv) 3-[(4-{4-[((2R)-2-hydroxy-2-{4-hydroxy-3-[(methylsulfonyl)amino]phenyl}ethyl)amino]-1-piperidineyl}anilino)sulfonyl]-2-thiophenecarboxylic acid;

wwwwww) benzyl [(4-{4-[((2R)-2-hydroxy-2-{4-hydroxy-3-[(methylsulfonyl)amino]phenyl}ethyl)amino]-1-piperidineyl}anilino)sulfonyl]acetate;

xxxxxx) [(4-{4-[((2R)-2-hydroxy-2-{4-hydroxy-3-[(methylsulfonyl)amino]phenyl}ethyl)amino]-1-piperidineyl}anilino)sulfonyl]acetic acid;

yyyyyy) benzyl [(butyl-4-{4-[((2R)-2-hydroxy-2-{4-hydroxy-3-[(methylsulfonyl)amino]phenyl}ethyl)amino]-1-piperidineyl}anilino)sulfonyl]acetate;

zzzzzz) [(butyl-4-{4-[((2R)-2-hydroxy-2-{4-hydroxy-3-[(methylsulfonyl)amino]phenyl}ethyl)amino]-1-piperidineyl}anilino)sulfonyl]acetic acid;

aaaaaaa) N-(4-{4-[((2R)-2-hydroxy-2-{4-hydroxy-3-[(methylsulfonyl)amino]phenyl}ethyl)amino]-1-piperidineyl}phenyl)-3-pyridinesulfonamide;

bbbbbbb) 3,4-dichloro-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide;

ccccccc) N-{4-[4-({(2S)-2-hydroxy-3-[(2-oxo-2,3-dihydro-1H-benzimidazol-4-yl)oxy]propyl}amino)-1-piperidineyl]phenyl}-4-(trifluoromethyl)benzenesulfonamide;

ddddddd) N-{4-[4-({(2S)-2-hydroxy-3-[(2-oxo-2,3-dihydro-1H-benzimidazol-4-yl)oxy]propyl}amino)-1-piperidineyl]phenyl}-4-(trifluoromethoxy)benzenesulfonamide;

eeeeeee) N-{4-[4-({(2S)-2-hydroxy-3-[(2-oxo-2,3-dihydro-1H-benzimidazol-4-yl)oxy]propyl}amino)-1-piperidineyl]phenyl}-4-methoxybenzenesulfonamide;

fffffff) 4-chloro-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide;

ggggggg) 4-butyl-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide;

hhhhhhh) 3,5-dichloro-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide;

iiiiiii) N-{4-[4-({(2S)-2-hydroxy-3-[(2-oxo-2,3-dihydro-1H-benzimidazol-4-yl)oxy]propyl}amino)-1-piperidineyl]phenyl}-2,5-dimethoxybenzenesulfonamide;

jjjjjjj) N-(4-{4-[((2R)-2-hydroxy-2-{4-hydroxy-3-[(methylsulfonyl)amino]phenyl}ethyl)amino]-1-piperidineyl}phenyl)-2,5-dimethoxybenzenesulfonamide;

kkkkkkk) ethyl {[(4-butylphenyl)sulfonyl]-4-[4-({(2S)-2-hydroxy-3-[(2-oxo-2,3-dihydro-1H-benzimidazol-4-yl)oxy]propyl}amino)-1-piperidineyl]anilino}acetate;

lllllll) 5-bromo-N-[(5-bromo-2-methoxyphenyl)sulfonyl]-N-{4-[4-({(2S)-2-hydroxy-3-[(2-oxo-2,3-dihydro-1H-benzimidazol-4-yl)oxy]propyl}amino)-1-piperidineyl]phenyl}-2-methoxybenzenesulfonamide;

mmmmmmm) 5-bromo-N-{4-[4-({(2S)-2-hydroxy-3-[(2-oxo-2,3-dihydro-1H-benzimidazol-4-yl)oxy]propyl}amino)-1-piperidineyl]phenyl}-2-methoxybenzenesulfonamide;

nnnnnnn) ethyl ([(3,4-dimethoxyphenyl)sulfonyl]-4-{4-[((2R)-2-hydroxy-2-{4-hydroxy-3-[(methylsulfonyl)amino]phenyl}ethyl)amino]-1-piperidineyl}anilino)acetate;

ooooooo) ethyl 5-[((2S)-3-{[1-(4-{[(3,4-dimethoxyphenyl)sulfonyl]amino}phenyl)-4-piperidineyl]amino}-2-hydroxypropyl)oxy]-2-methyl-1H-indole-3-carboxylate;

ppppppp) ethyl 4-[((2S)-3-{[1-(4-{[(3,4-dimethoxyphenyl)sulfonyl]amino}phenyl)-4-piperidineyl]amino}-2-hydroxypropyl)oxy]-2-methyl-5-phenyl-1H-pyrrole-3-carboxylate;

qqqqqqq) benzyl ((butylsulfonyl)-4-{4-[((2R)-2-hydroxy-2-{4-hydroxy-3-[(methylsulfonyl)amino]phenyl}ethyl)amino]-1-piperidineyl}anilino)acetate;

rrrrrrr) ((butylsulfonyl)-4-{4-[((2R)-2-hydroxy-2-{4-hydroxy-3-[(methylsulfonyl)amino]phenyl}ethyl)amino]-1-piperidineyl}anilino)acetic acid;

sssssss) ([(3,4-dimethoxyphenyl)sulfonyl]-4-{4-[((2R)-2-hydroxy-2-{4-hydroxy-3-[(methylsulfonyl)amino]phenyl}ethyl)amino]-1-piperidineyl}anilino)acetic acid;

ttttttt) ethyl ((butylsulfonyl)-4-{4-[((2R)-2-hydroxy-2-{4-hydroxy-3-[(methylsulfonyl)amino]phenyl}ethyl)amino]-1-piperidineyl}anilino)acetate;

uuuuuuu) 4-{[3-chloro-5-(trifluoromethyl)-2-pyridinyl]oxy}-N-[4-(4-{[(2S)-2-hydroxy-3-phenoxypropyl]amino}-1-piperidineyl)phenyl]benzenesulfonamide;

vvvvvvv) N-{[5-({4-[4-({(2S)-2-hydroxy-3-[(2-oxo-2,3-dihydro-1H-benzimidazol-4-yl)oxy]propyl}amino)-1-piperidineyl]anilino}sulfonyl)-2-thienyl]methyl}benzamide;

wwwwwww) N-[(5-{[4-(4-{[(2S)-2-hydroxy-3-phenoxypropyl]amino}-1-piperidineyl)anilino]sulfonyl}-2-thienyl)methyl]benzamide;

xxxxxxx) N-[(5-{[4-(4-{[2-hydroxy-2-(3-hydroxyphenyl)ethyl]amino}-1-piperidineyl)anilino]sulfonyl}-2-thienyl)methyl]benzamide;

yyyyyyy) 4-{[3-chloro-5-(trifluoromethyl)-2-pyridinyl]oxy}-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide;

zzzzzzz) 4-{[3-chloro-5-(trifluoromethyl)-2-pyridinyl]oxy}-N-[4-(4-{[2-hydroxy-2-(3-hydroxyphenyl)ethyl]amino}-1-piperidineyl)phenyl]benzenesulfonamide;

aaaaaaaa) 3,5-dichloro-4-(2-chloro-4-nitrophenoxy)-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide;

bbbbbbbb) 3,5-dichloro-4-(2-chloro-4-nitrophenoxy)-N-[4-(4-{[(2S)-2-hydroxy-3-phenoxypropyl]amino}-1-piperidineyl)phenyl]benzenesulfonamide;

cccccccc) 3,5-dichloro-4-(2-chloro-4-nitrophenoxy)-N-[4-(4-{[2-hydroxy-2-(3-hydroxyphenyl)ethyl]amino}-1-piperidineyl)phenyl]benzenesulfonamide;

dddddddd) N-[4-(4-{[(2S)-2-hydroxy-3-phenoxypropyl]amino}-1-piperidineyl)phenyl]-2-thiophenesulfonamide;

eeeeeeee) 4-butoxy-N-[4-(4-{[(2S)-2-hydroxy-3-phenoxypropyl]amino}-1-piperidineyl)phenyl]benzenesulfonamide;

ffffffff) N-[4-(4-{[(2S)-2-hydroxy-2-(3-hydroxyphenyl)ethyl]amino}-1-piperidineyl)phenyl]-2-thiophenesulfonamide;

gggggggg) 4-butoxy-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide;

hhhhhhhh) N-{4-[4-({(2S)-2-hydroxy-3-[(2-oxo-2,3-dihydro-1H-benzimidazol-4-yl)oxy]propyl}amino)-1-piperidineyl]phenyl}-3,4-dimethoxybenzenesulfonamide;

iiiiiiii) N-[4-(4-{[(2S)-2-hydroxy-3-phenoxypropyl]amino}-1-piperidineyl)phenyl]-3,4-dimethoxybenzenesulfonamide;

jjjjjjjj) N-[4-(4-{[2-hydroxy-2-(3-hydroxyphenyl)ethyl]amino}-1-piperidineyl)phenyl]-3,4-dimethoxybenzenesulfonamide;

kkkkkkkk) N-{4-[4-({(2S)-2-hydroxy-3-[(2-oxo-2,3-dihydro-1H-benzimidazol-4-yl)oxy]propyl}amino)-1-piperidineyl]phenyl}-2-thiophenesulfonamide;

llllllll) ethyl 3-(4-{4-[((2R)-2-hydroxy-2-{4-hydroxy-3-[(methylsulfonyl)amino]phenyl}ethyl)amino]-1-piperidineyl}anilino)-3-oxopropanoate;

mmmmmmmm) 3-(4-{4-[((2R)-2-hydroxy-2-{4-hydroxy-3-[(methylsulfonyl)amino]phenyl}ethyl)amino]-1-piperidineyl}anilino)-3-oxopropanoic acid;

nnnnnnnn) ethyl 3-(butyl-4-{4-[((2R)-2-hydroxy-2-{4-hydroxy-3-[(methylsulfonyl)amino]phenyl}ethyl)amino]-1-piperidineyl}anilino)-3-oxopropanoate;

oooooooo) 3-(butyl-4-{4-[((2R)-2-hydroxy-2-{4-hydroxy-3-[(methylsulfonyl)amino]phenyl}ethyl)amino]-1-piperidineyl}anilino)-3-oxopropanoic acid;

pppppppp) ethyl 3-(cyclohexyl-4-{4-[((2R)-2-hydroxy-2-{4-hydroxy-3-[(methylsulfonyl)amino]phenyl}ethyl)amino]-1-piperidineyl}anilino)-3-oxopropanoate;

qqqqqqqq) 3-(cyclohexyl-4-{4-[((2R)-2-hydroxy-2-{4-hydroxy-3-[(methylsulfonyl)amino]phenyl}ethyl)amino]-1-piperidineyl}anilino)-3-oxopropanoic acid;

rrrrrrrr) ethyl {[(4-{4-[((2R)-2-hydroxy-2-{4-hydroxy-3-[(methylsulfonyl)amino]phenyl}ethyl)amino]-1-piperidineyl}anilino)carbonyl]amino}acetate;

ssssssss) {[(4-{4-[((2R)-2-hydroxy-2-{4-hydroxy-3-[(methylsulfonyl)amino]phenyl}ethyl)amino]-1-piperidineyl}anilino)carbonyl]amino}acetic acid;

tttttttt) ethyl {[(butyl-4-{4-[((2R)-2-hydroxy-2-{4-hydroxy-3-[(methylsulfonyl)amino]phenyl}ethyl)amino]-1-piperidineyl}anilino)carbonyl]amino}acetate;

uuuuuuuu) {[(butyl-4-{4-[((2R)-2-hydroxy-2-{4-hydroxy-3-[(methylsulfonyl)amino]phenyl}ethyl)amino]-1-piperidineyl}anilino)carbonyl]amino}acetic acid;

vvvvvvvv) N-{4-[4-({(2S)-2-hydroxy-3-[(2-oxo-2,3-dihydro-1H-benzimidazol-4-yl)oxy]propyl}amino)-1-piperidineyl]phenyl}-3,4-dimethoxybenzamide;

wwwwwwww) 2-chloro-N-{4-[4-({(2S)-2-hydroxy-3-[(2-oxo-2,3-dihydro-1H-benzimidazol-4-yl)oxy]propyl}amino)-1-piperidineyl]phenyl}acetamide;

xxxxxxxx) N-{4-[4-({(2S)-2-hydroxy-3-[(2-oxo-2,3-dihydro-1H-benzimidazol-4-yl)oxy]propyl}amino)-1-piperidineyl]phenyl}-2-(4-morpholinyl)acetamide;

yyyyyyyy) 2-(dimethylamino)-N-{4-[4-({(2S)-2-hydroxy-3-[(2-oxo-2,3-dihydro-1H-benzimidazol-4-yl)oxy]propyl}amino)-1-piperidineyl]phenyl}acetamide;

zzzzzzzz) N-(4-{4-[(2-hydroxy-2-{4-hydroxy-3-[(methylsulfonyl)amino]phenyl}ethyl)amino]-1-piperidineyl}phenyl)-3,4-dimethoxybenzamide;

aaaaaaaaa) N-{4-[4-({(2S)-2-hydroxy-3-[(2-oxo-2,3-dihydro-1H-benzimidazol-4-yl)oxy]propyl}amino)-1-piperidineyl]phenyl}butanamide;

bbbbbbbbb) N-[4-(4-{[(2S)-3-(9H-carbazol-4-yloxy)-2-hydroxypropyl]amino}-1-piperidineyl)phenyl]butanamide;

cccccccc) N-[4-(4-{[(2S)-2-hydroxy-3-(4-hydroxyphenoxy)propyl]amino}-1-piperidineyl)phenyl]-3,4-dimethoxybenzamide;

dddddddd) N-[4-(4-{[(2S)-3-(9H-carbazol-4-yloxy)-2-hydroxypropyl]amino}-1-piperidineyl)phenyl]-3,4-dimethoxybenzamide;

eeeeeeee) N-{4-[4-({(2S)-2-hydroxy-3-[(2-oxo-2,3-dihydro-1H-benzimidazol-4-yl)oxy]propyl}amino)-1-piperidineyl]phenyl}-1,3-benzodioxole-5-carboxamide;

ffffffff) N-[4-(4-{[(2S)-3-(9H-carbazol-4-yloxy)-2-hydroxypropyl]amino}-1-piperidineyl)phenyl]-1,3-benzodioxole-5-carboxamide;

gggggggg) 3-cyclopentyl-N-{4-[4-({(2S)-2-hydroxy-3-[(2-oxo-2,3-dihydro-1H-benzimidazol-4-yl)oxy]propyl}amino)-1-piperidineyl]phenyl}propanamide;

hhhhhhhh) 3-cyclopentyl-N-(4-{4-[((2R)-2-hydroxy-2-{4-hydroxy-3-[(methylsulfonyl)amino]phenyl}ethyl)amino]-1-piperidineyl}phenyl)propanamide;

iiiiiiii) N-(4-{4-[((2R)-2-hydroxy-2-{4-hydroxy-3-[(methylsulfonyl)amino]phenyl}ethyl)amino]-1-piperidineyl}phenyl)-1,3-benzodioxole-5-carboxamide;

jjjjjjjj) N-acetyl-N-[4-(3-{[(2S)-2-hydroxy-3-(4-hydroxyphenoxy)propyl]amino}-1-azetidinyl)phenyl]acetamide;

kkkkkkkk) 4-butoxy-N-[4-(3-{[(2S)-2-hydroxy-3-(4-hydroxyphenoxy)propyl]amino}-1-azetidinyl)phenyl]benzenesulfonamide;

llllllll) N-[4-(3-{[(2S)-2-hydroxy-3-(4-hydroxyphenoxy)propyl]amino}-1-azetidinyl)phenyl]-3,4-dimethoxybenzenesulfonamide;

mmmmmmmm) N-(4-{[4-(3-{[(2S)-2-hydroxy-3-(4-hydroxyphenoxy)propyl]amino}-1-azetidinyl)anilino]sulfonyl}phenyl)acetamide;

nnnnnnnn) 4-butoxy-N-[4-(3-{[(2S)-3-(9H-carbazol-4-yloxy)-2-hydroxypropyl]amino}-1-azetidinyl)phenyl]benzenesulfonamide;

oooooooo) N-[4-(3-{[(2S)-3-(9H-carbazol-4-yloxy)-2-hydroxypropyl]amino}-1-azetidinyl)phenyl]acetamide;

pppppppp) N-[4-(3-{[(2S)-3-(9H-carbazol-4-yloxy)-2-hydroxypropyl]amino}-1-azetidinyl)phenyl]-3,4-dimethoxybenzenesulfonamide;

qqqqqqqq) N-(4-{[4-(3-{[(2S)-3-(9H-carbazol-4-yloxy)-2-hydroxypropyl]amino}-1-azetidinyl)anilino]sulfonyl}phenyl)acetamide or a pharmaceutically acceptable salt thereof.

The compounds of this invention can be prepared according to the following schemes from commercially available starting materials or starting materials which can be prepared using literature procedures. These schemes show the preparation of representative compounds of this invention.

According to one route (Scheme 1), 1,4-dioxa-8-azaspiro[4.5]decane is reacted with 4-fluorobenzaldehyde 1 in the presence of base such as pyridine or potassium carbonate to afford aldehyde 2. This reaction can be carried out in a polar solvent such as anhydrous acetonitrile, acetone, N,N-dimethylformamide, or pyridine. Compound 4 is obtained via a Knoevenagel condensation between an appropriate cyclic lactam 3 and the aldehyde 2. In this reaction sodium acetate, p-alanine, glycine, pyridine, piperidine, pyrrolidine, sodium methoxide, potassium acetate, sodium carbonate and the like can be used as a base, and an alcohol such as methanol, ethanol, isopropanol, methoxyethanol and the like, N,N-dimethylformamide, water, acetic acid and the like can be used as a solvent. Ketal hydrolysis is accomplished in the presence of strong acid such as concentrated hydrochloric acid or 10–30% sulfuric acid. The desired final product 7, wherein A, $R_1$, $R_2$, $R_3$, $R_4$, $R_6$, X, Y and Z are as defined above, is prepared by utilizing reductive amination of piperidione 5 with appropriate arylethanolamines or aryloxypropanolamines 6, many of which are comercially available or can be readily prepared as described in Scheme 19 and Scheme 20. The reductive amination can be carried out, for example, with hydrogen and catalytic palladium, or with sodium borohydride, sodium triacetoxyborohydride and the like in a polar solvent such as methanol, N,N-dimethylformamide and the like. The final products can be purified by recrystallization, trituration, preparative thin layer chromatography, flash column chromatography on silica gel, or high performance liquid chromatography. Purification of intermediates can be achieved in the same manner. A salt is optionally produced by the addition of an acid or base, such as hydrogen chloride gas or hydrochloric acid.

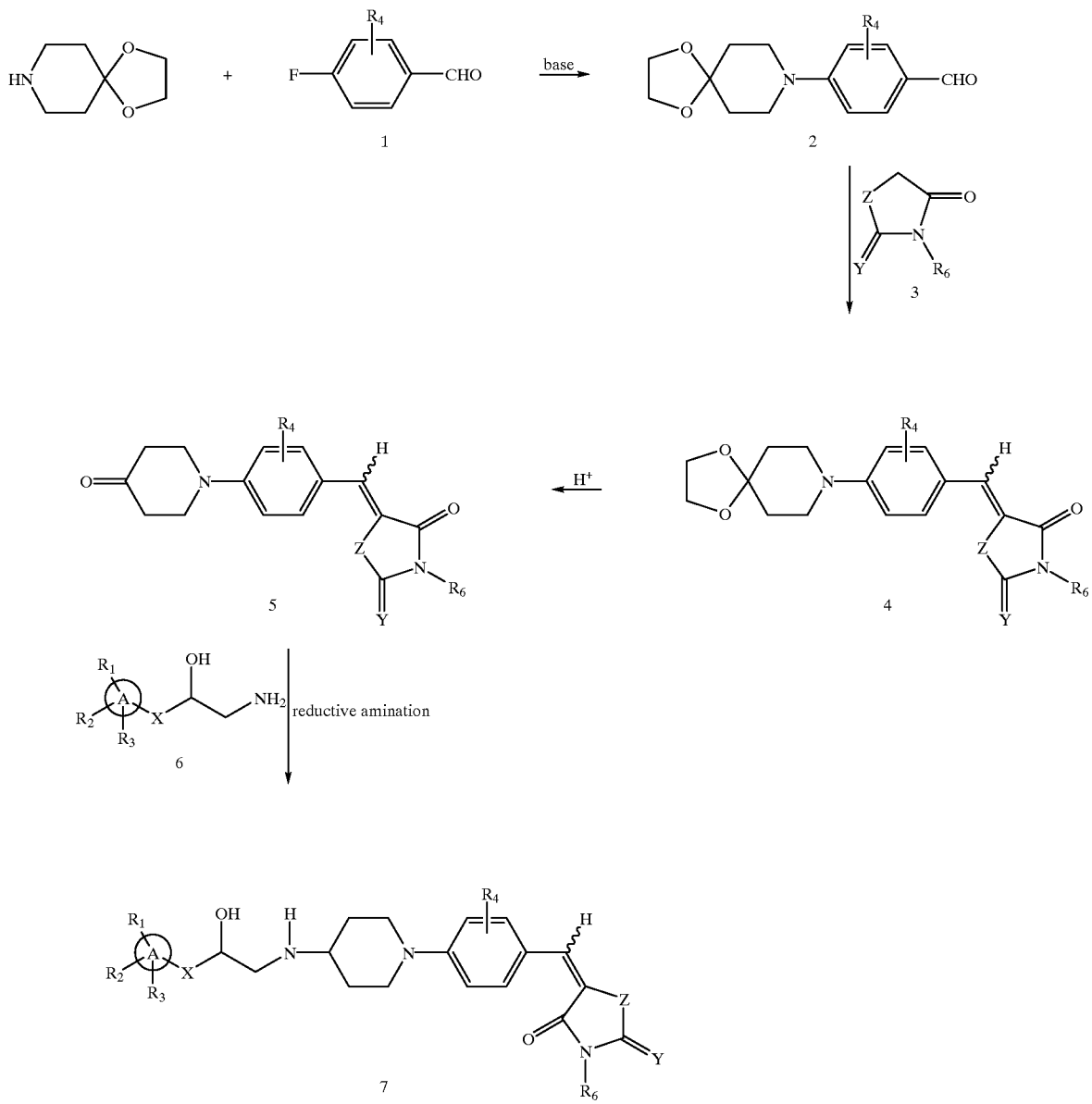

In some cases the C—C double bond of compound 4 can be reduced (Scheme 2) by catalytic hydrogenation in the presence of a metal catalyst such as palladium, platinum, rhodium and the like. An alcohol such as methanol, ethanol, isopropanol and the like, acetic acid, tetrahydrofuran (THF), dioxane and the like can be used as a solvent in the hydrogenation. In other cases, owing to the presence of sulfur in the molecule, the C—C double bond of compound 4 can not be reduced by ordinary catalytic hydrogenation. However, the reduction can be achieved by a hydrogen transfer reaction using 3–10% sodium mercury amalgam, zinc, dihydropyridine, tin and the like as a hydrogen donor. In this reaction THF/water, acetic acid, toluene, ethanolic hydrogen iodide and the like can be used as a solvent. Ketal hydrolysis under acidic conditions followed by reductive amination, as previously described in Scheme 1, furnishes the desired final product 10, wherein A, $R_1$, $R_2$, $R_3$, $R_4$, X, Y and Z are as defined above (Scheme 2). A salt is optionally produced by the addition of an acid or base, such as hydrogen chloride gas or hydrochloric acid.

Compound 9 could be optionally alkylated with an appropriate alkylating agents $R_6$-halo in the presence of base to give the alkylated compound 11 (Scheme 2). At this time, bases to be used include cesium carbonate, potassium carbonate, sodium carbonate, sodium acetate, potassium acetate and the like. Solvents used include N,N-dimethylformamide, acetone, acetonitrile and the like. A reductive amination between ketone 11 and amine 6, as previously described in Scheme 1, furnishes the final product 12, wherein A, $R_1$, $R_2R_3$, $R_4$, $R_6$, X, Y and Z are as defined above. A salt is optionally produced by the addition of an acid or base, such as hydrogen chloride gas or hydrochloric acid.

Scheme 2
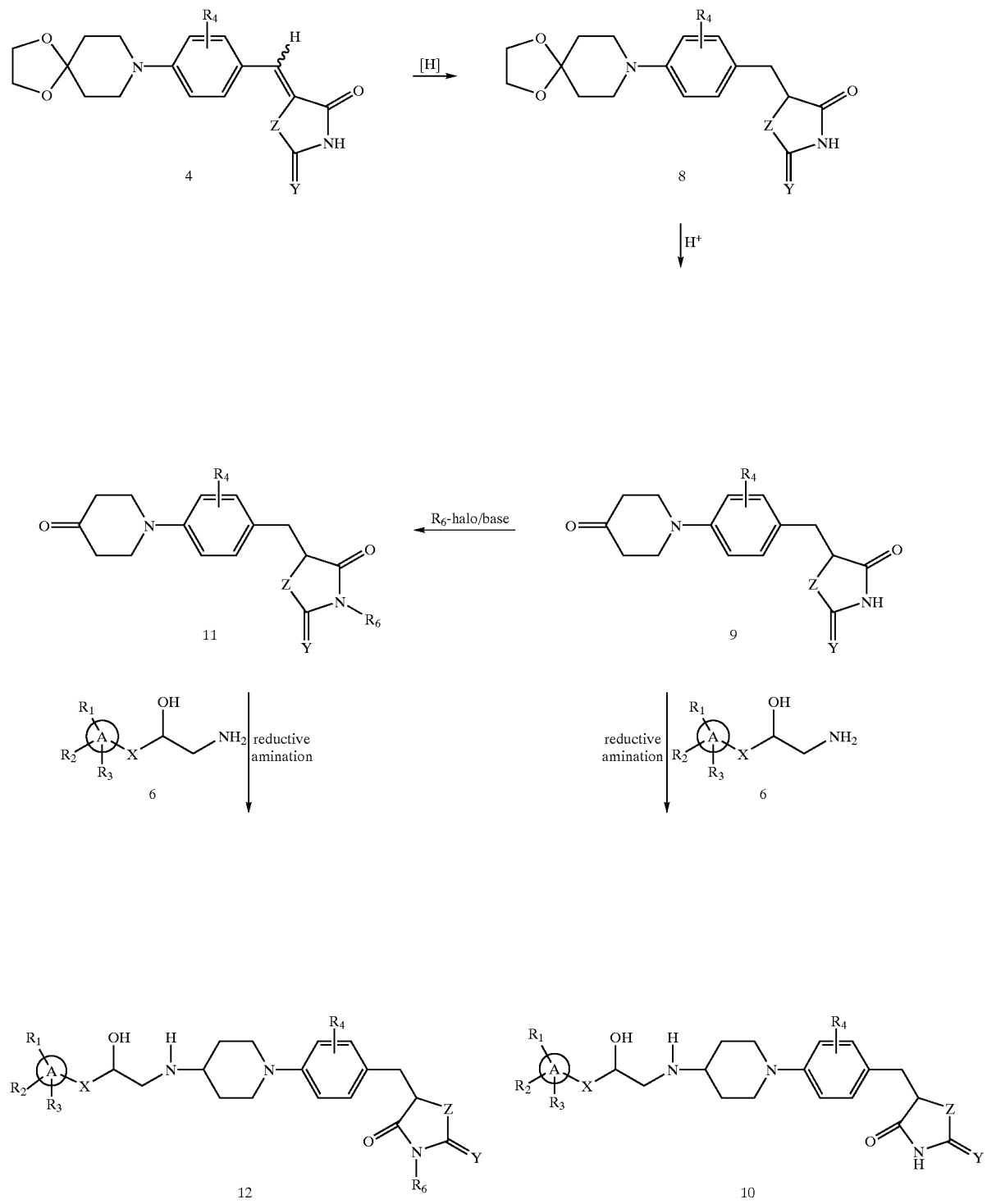

The compound represented by the above formula I wherein $R_5$ is tetrazole can be prepared by one of the following synthetic schemes (Scheme 3 & Scheme 4). Nitrile compound 14 can be obtained by condensing 1,4-dioxa-8-azaspiro[4.5]decane with 4-fluorobenzonitrile as previously described in Scheme 1. The reaction for the formation of the tetrazoles can be carried out by reacting nitriles 14 with sodium azide, tributyltin azide and the like in the presence of an amine salt such as ammonium chloride, triethylamine hydrochloride, diethylamine hydrochloride, tripropylamine hydrosulfate and the like. Solvents used in this reaction include aromatic hydrocarbons such as toluene, xylene, benzene, nitrobenzene and the like. Sometimes the cycloaddition can also be performed in a polar solvent such as N,N-dimethylformamide, dimethylsulfoxide and the like. Ketal hydrolysis under acidic conditions followed by reductive amination, as previously described in Scheme 1, furnishes the final product 17 (Scheme 3), wherein A, $R_1$, $R_2$, $R_3$, $R_4$ and X are as defined above. A salt is optionally produced by the addition of an acid or base, such as hydrogen chloride gas or hydrochloric acid.

Scheme 3

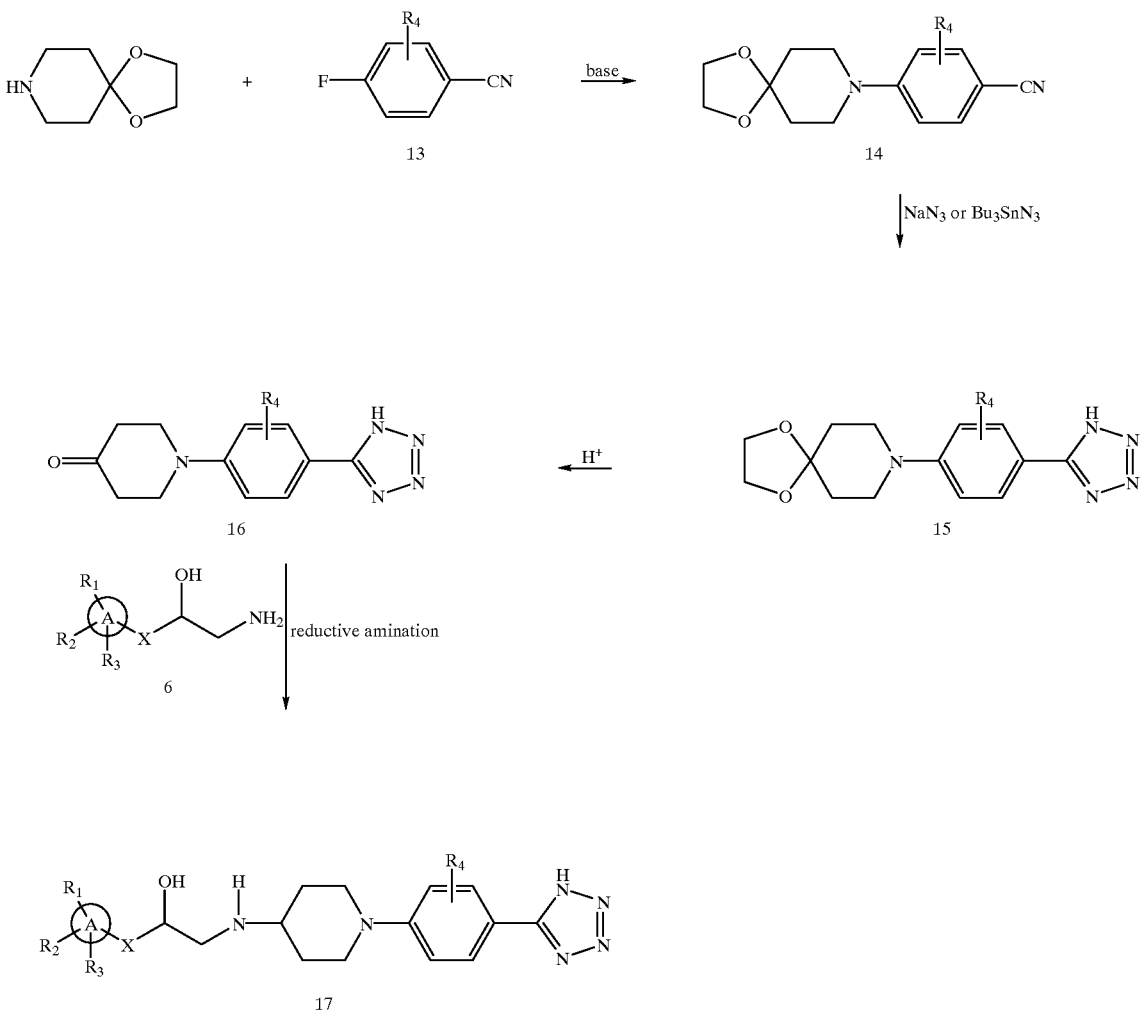

Tetrazole 15 could be optionally alkylated with an appropriate alkylating agents $R_6$-halo in the presence of base such as cesium carbonate to give a pair of isomers (18 & 19) which could be separated by flash column chromatography on silica gel. Ketal hydrolysis under acidic conditions followed by reductive amination, as previously described in Scheme 1, furnishes the final products 22 or 23, wherein A, $R_1$, $R_2$, $R_3$, $R_4$, $R_6$ and X are as defined above. A salt is optionally produced by the addition of an acid or base, such as hydrogen chloride gas or hydrochloric acid.

Scheme 4

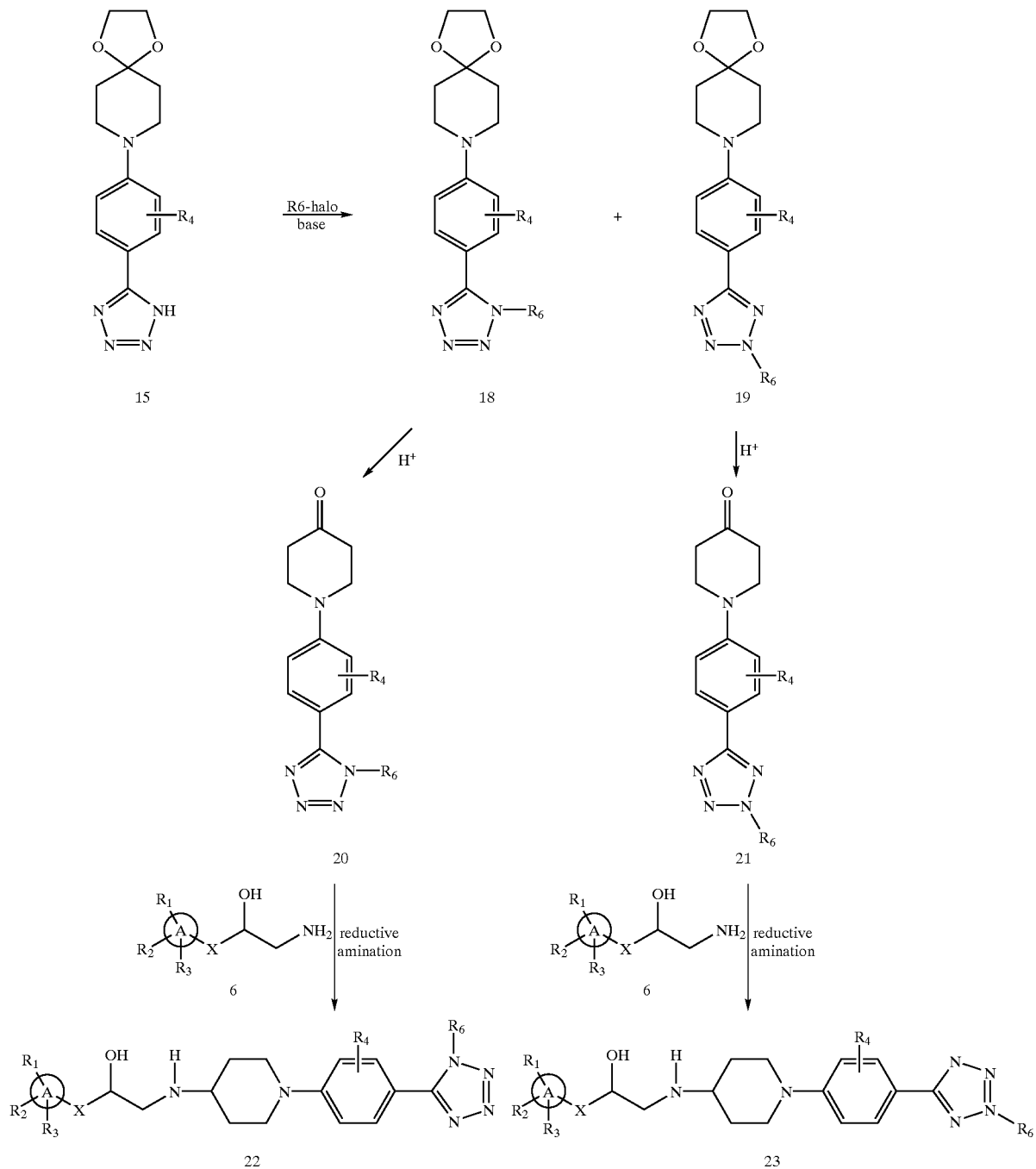

The compound represented by the above formula I wherein $R_5$ is oxadiazolidine can be prepared by the following synthetic scheme (Scheme 5). Compound 24 is obtained by a reductive amination reaction between aldehyde 2 and hydroxylamine. This reductive amination can be carried out essentially under the same conditions as that previously described in Scheme 1. N-Hydroxyurea 25 is obtained by reacting compound 24 with isocyanate such as chlorocarbonyl isocanate, trimethylsilyl isocyanate and the like, followed by ketal hydrolysis. In the isocyanate reaction a polar solvent such as 1,4-dioxane, tetrahydrofuran, N,N-dimethylformamide, dimethylsulfoxide and the like can be used as a solvent. Ketal hydrolysis is conveniently conducted under acidic conditions as that previously described in Scheme 1. The oxadiazolidine ring is formed by reacting the N-hydroxyurea 25 with chloroformate such as methyl chloroformate, ethyl chloroformate, isobutyl chloroformate and the like in the presence of strong base such as sodium hydride, potassium hydroxide and the like. The final product 27, wherein A, $R_1$, $R_2$, $R_3$, $R_4$ and X are as defined above, is obtained by reductive amination between ketone 26 and amine 6 using basically the same conditions as previously described in Scheme 1. A salt is optionally produced by the addition of an acid or base, such as hydrogen chloride gas or hydrochloric acid.

Scheme 5

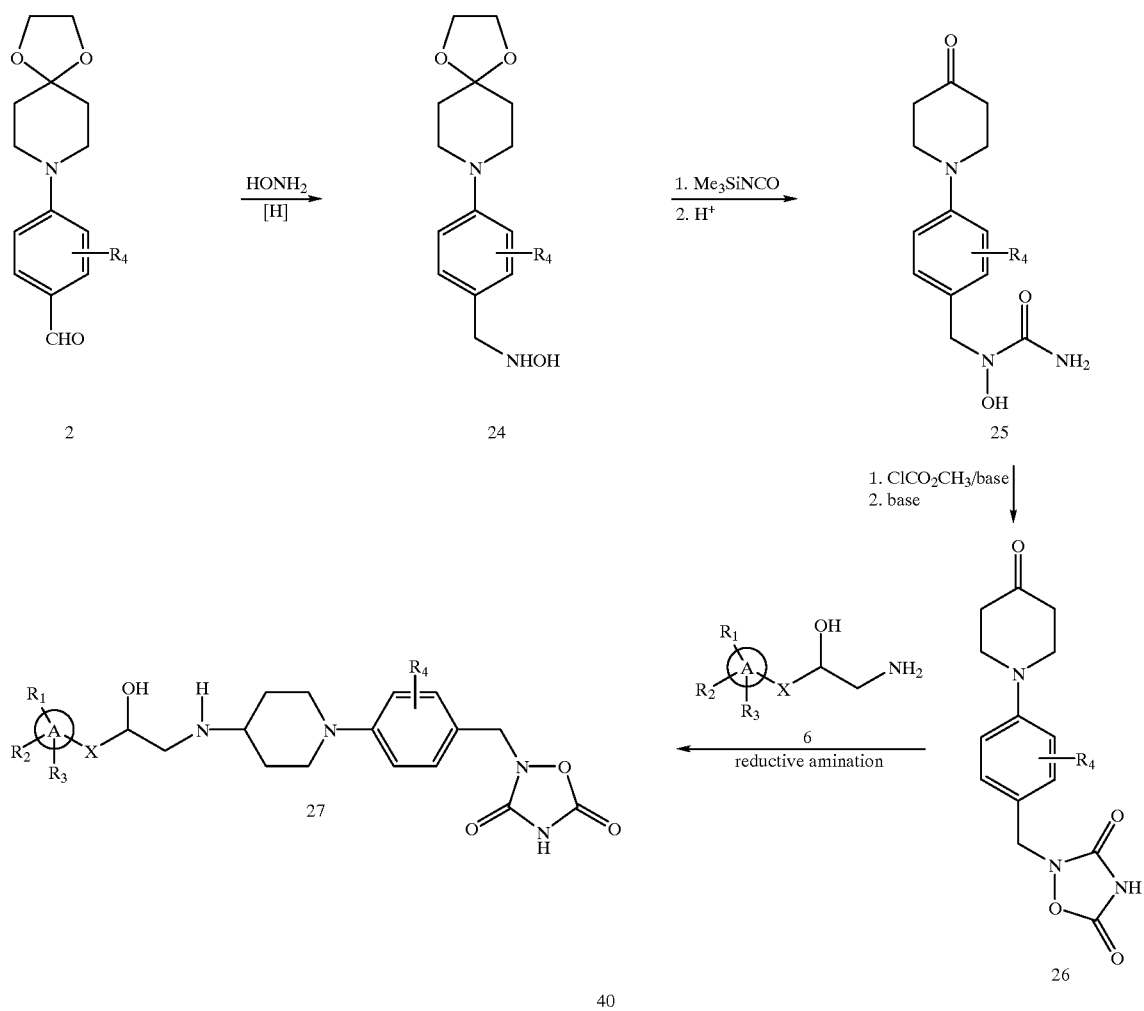

The compound represented by the above formula I wherein $R_5$ is pyrazole can be prepared by the following synthetic scheme (Scheme 6). Pyrazole compound 29 can be obtained by condensing 1,4-dioxa-8-azaspiro[4.5]decane with 4-fluorobenzonate 28 as previously described in Scheme 1, followed by pyrazole ring formation which can be carried out by reacting with hydrazine. Solvents used in this ring formation include methanol, ethanol, tetrahydrofuran and the like. Ketal hydrolysis under acidic conditions followed by reductive amination, as previously described in Scheme 1, furnishes the final product 31, wherein A, $R_1$, $R_2$, $R_3$, $R_4$ and X are as defined above. A salt is optionally produced by the addition of an acid or base, such as hydrogen chloride gas or hydrochloric acid.

Scheme 6

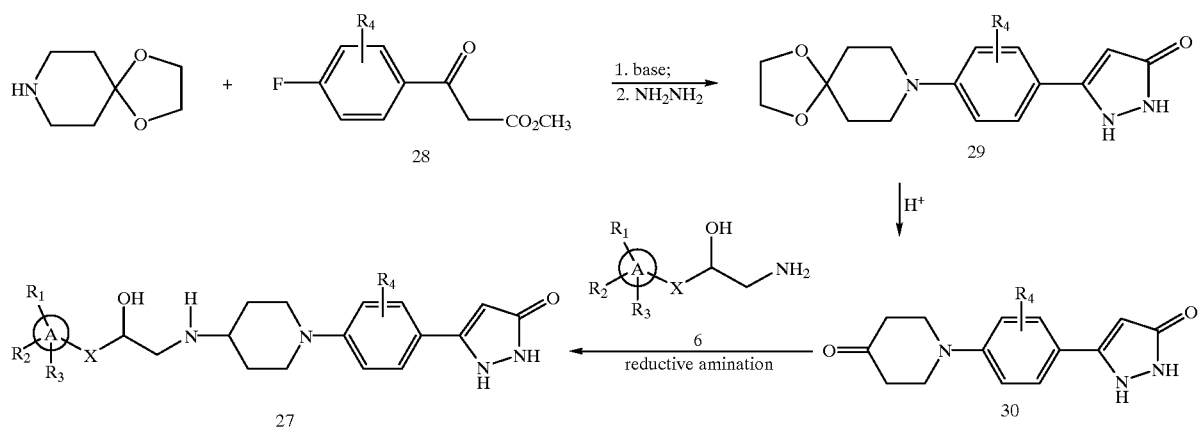

The compound represented by the above formula I wherein $R_5$ is acid or ester can be prepared by the following synthetic scheme (Scheme 7). According to one route, 1,4-dioxa-8-azaspiro[4.5]decane is reacted with 4-fluorobenzoate 32 in the presence of base such as pyridine or potassium carbonate to afford ester 33. This reaction can be carried out in a polar solvent such as anhydrous acetonitrile, acetone, dimethylformamide, or pyridine. Acid 35 is obtained via a basic hydrolysis of ester 33. In this reaction lithium hydroxide, sodium hydroxide, potassium hydroxide and the like can be used as a base, and water or a mixture of water with methanol, ethanol, dioxane and the like can be used as a solvent. Ketal 35 hydrolysis is accomplished in the presence of strong acid such as concentrated hydrochloric acid or 10–30% sulfuric acid. The desired final product (acid 37), wherein A, $R_2$, $R_2$, $R_3$, $R_4$ and X are as defined above, is prepared by utilizing reductive amination of piperidiones 36 with appropriate arylethanolamines or aryloxypropanolamines 6, as previously described in Scheme 1. The corresponding ester 38, wherein A, $R_1$, $R_2$, $R_3$, $R_4$, $R_6$ and X are as defined above (provided that in 38 $R_6$ can not be hydrogen), could be synthesized in the same manner starting with the ester 33 by ketal hydrolysis followed by reductive amination sequence. A salt is optionally produced by the addition of an acid or base, such as hydrogen chloride gas or hydrochloric acid.

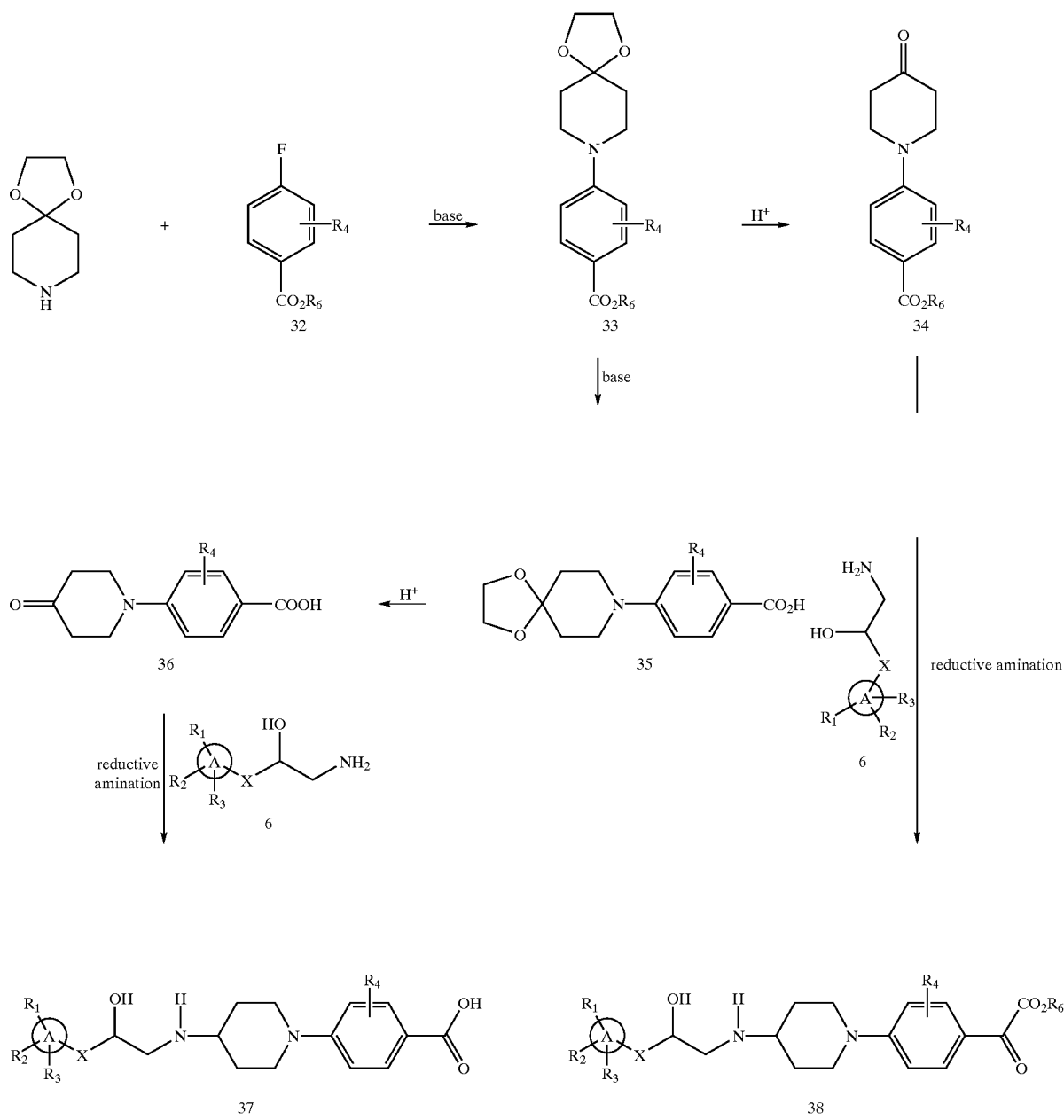

Scheme 7

Mono peptide derived from the acid 36 and amino acid and its ester thereof, can be prepared by, for example, the following synthetic scheme(Scheme 8). The carboxylic acid 36 is coupled to the amine nitrogen of amino acid (ester), wherein the amino acid (ester) means the carboxylic acid functionality of the amino acid was protected as an ester. In this amide bond formation process 1,3-dicyclohexylcarbodiimide, 1-[3-(dimethylamino)propyl]-3-ethylcarbodiimide, diisopropylcarbodiimide, 1,1'-carbonyldiimidazole, 6-chloro-2,4-dimethoxy-1,3,5-triazine and the like can be used as a coupling agent and triethylamine, diisopropylethyl amine, N-methyl morpholine and the like can be used as a base. At this time, as a solvent, methylene chloride, diethyl ether, tetrahydrofuran, dioxane and the like is used. Reductive amination followed by ester hydrolysis, as previously described in Scheme 7, furnishes the desired final product 41, wherein A, $R_1$, $R_2$, $R_3$, $R_4$, X and Aa are as defined above (Scheme 8). A salt is optionally produced by the addition of an acid or base, such as hydrogen chloride gas or hydrochloric acid. The corresponding hydroxamic acid or amide derivative 44, wherein A, $R_1$, $R_2$, $R_3$, $R_4$, $R_6$, $R_{18}$ ($R_{18}$ is either $R_7$ or $OR_7$) and X are as defined above, could be synthesized (Scheme 9) in an analogous manner starting with the acid 35 by amide bond formation between acid 35 and amine ($NHR_6R_7$) or hydroxylamine ($NHR_6OR_7$), followed by ketal hydrolysis and reductive amination, as previously described in Scheme 8. A salt is optionally produced by the addition of an acid or base, such as hydrogen chloride gas or hydrochloric acid.

Scheme 8

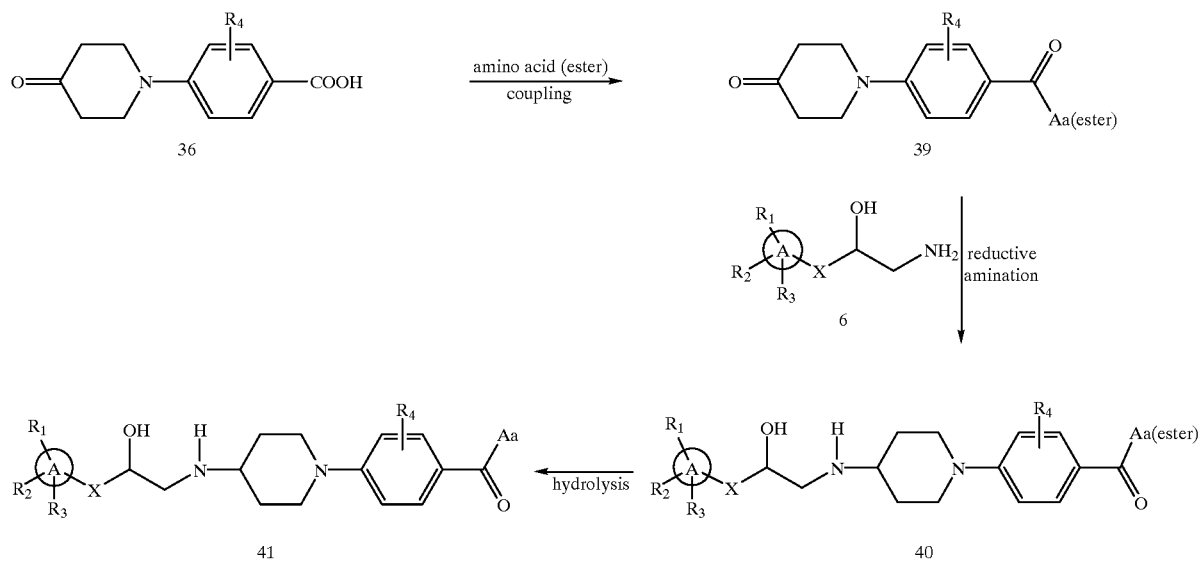

Scheme 9

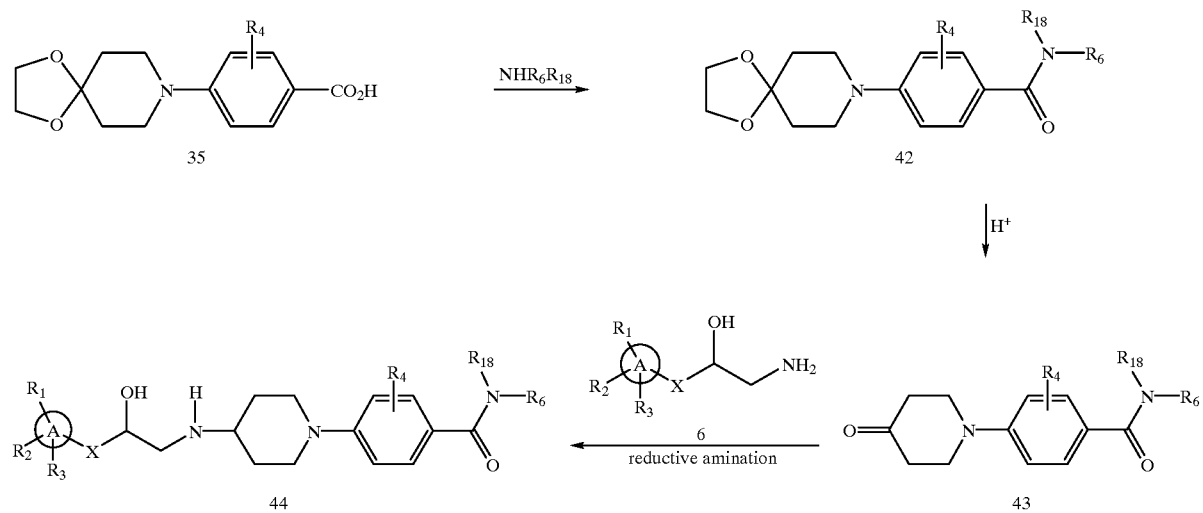

Homo analogues (here homo analogues means one carbon chain extended analogues) of compounds 37, 38, 41, 44 can be prepared by, for example, the following synthetic scheme (Scheme 10). 1,4-Dioxa-8-azaspiro[4.5]decane is reacted with 4'-fluoroacetonephenone 45, as previously described in Scheme 1, to give acetonephenone 46. The methyl ketone compound 46 is converted into arylalkanoate 47 using an oxidative rearrangement procedure. In this reaction thallium (ll) nitrate, iodine-silver nitrate and the like is used as an oxidation agent and an alcoholic solvent ($R_6OH$) such as methanol or ethanol is used as a solvent. Ketal and ester hydrolysis followed by reductive amination, as previously described in Scheme 1, generates the desired homo analog 49, wherein A, $R_1$, $R_2$, $R_3$, $R_4$, and X are as defined above. A salt is optionally produced by the addition of an acid or base, such as hydrogen chloride gas or hydrochloric acid. Homo analogues of mono peptide 41 or compound 44 derived from the acid 48 can be prepared in an analogous manner as previously described in Scheme 8 and Scheme 9.

acidic conditions followed by reductive amination, as previously described in Scheme 1, generates the desired olefinic analog 52, wherein A, $R_1$, $R_2$, $R_3$, $R_4$, $R_6$, and X are as defined above. A salt is optionally produced by the addition of an acid or base, such as hydrogen chloride gas or hydrochloric acid. The corresponding olefinic acid analog 55, wherein A, $R_1$, $R_2$, $R_3$, $R_4$, and X are as defined above, can be obtained by a basic hydrolysis process. In this case, lithium hydroxide, sodium hydroxide and the like can be used as a base and aqueous methanol, ethanol, tetrahydrofuran and the like can be used as a solvent. The carbon-carbon double bond of compound 52 can be reduced by catalytic hydrogenation in the presence of a metal catalyst such as palladium, platinum, rhodium and the like to give the reduced analog 53, wherein A, $R_1$, $R_2$, $R_3$, $R_4$, $R_6$ and X are as defined above. An alcohol such as methanol, ethanol, isopropanol and the like, acetic acid, tetrahydrofuran, dioxane can be used as solvent in the hydrogenation. The corresponding propanic acid analog 54, wherein A, $R_1$, $R_2$, $R_3$, $R_4$ and X are as defined above, was produced by basic

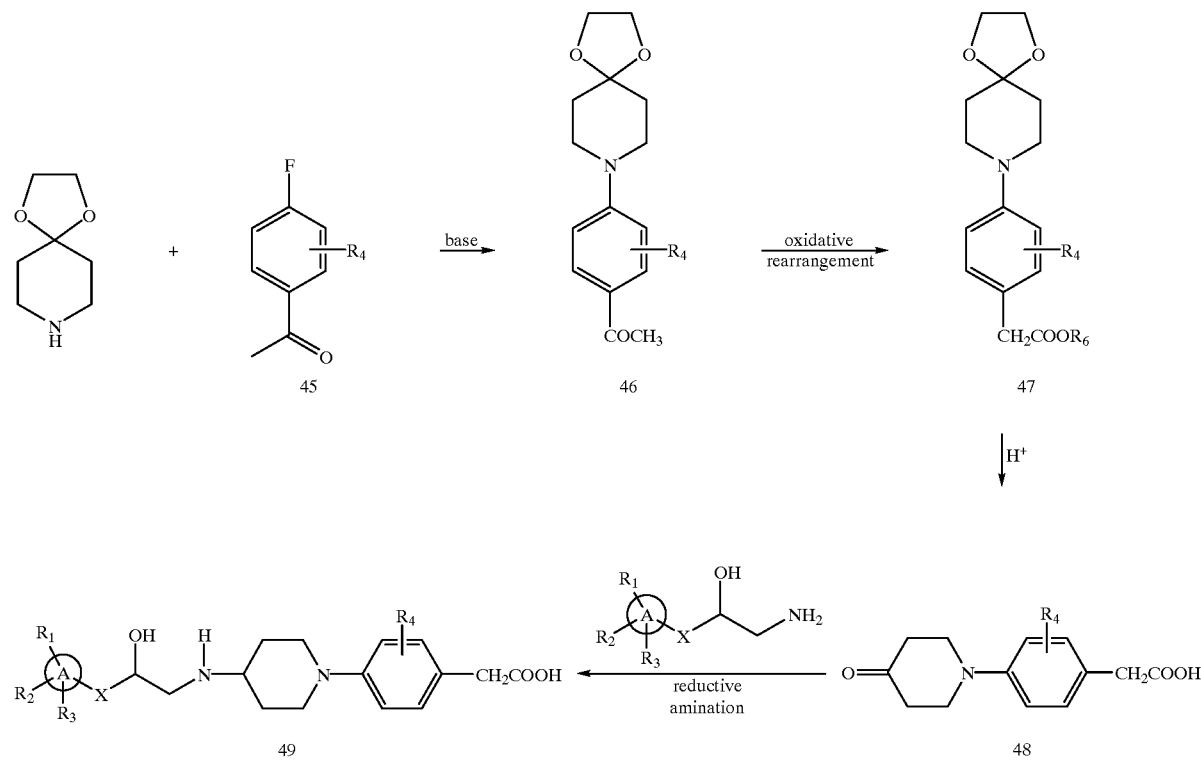

Two carbon chain extended analogues of compounds 37, 38, 41, 44 can be prepared by, for example, the following synthetic scheme (Scheme 11). Compound 50 can be obtained by a Wittig or related reaction between aldehyde 2 and a Wittig reagent in the presence of a base. In this reaction diethyl ethoxycarbonylmethanephosphonate, (ethoxycarbonylmethyl) triphenylphosphonium chloride, triphenyl(ethoxy-carbonylmethyl)phosphonium bromide and the like can be used as a Wittig reagent and lithium diisopropylamide, sodium hydride, potassium hydroxide and the like can be used as a base. Ketal hydrolysis under hydrolysis of 53, as previously described in Scheme 7. Alternatively, ester 50 is treated with a base to produce the acid 56, which in turn is treated with a strong acid to remove the protecting ketal group of 56, thus exposing the terminal ketone for a reductive amination process (with hydrogen and catalytic palladium) to generate the same compound 54. A salt is optionally produced by the addition of an acid or base, such as hydrogen chloride gas or hydrochloric acid. Mono peptide 41 or compound 44 analogues derived from compound 51 or 57 can be prepared in an analogous manner as previously described in Scheme 8 and Scheme 9.

Scheme 11

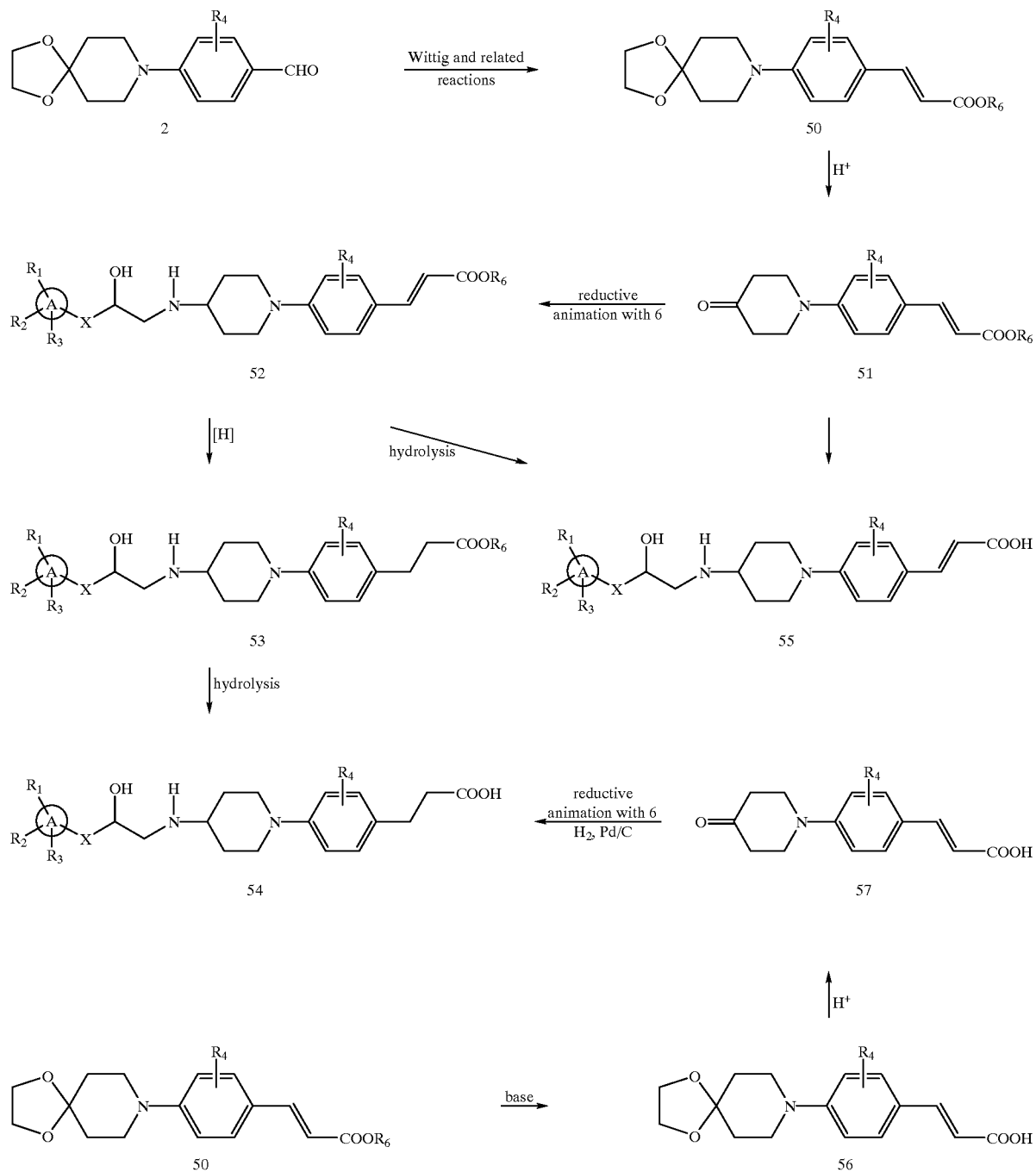

Malonic acid analogues of compounds 37, 38, 41, 44 can be prepared as described in Scheme 12 starting from compound 2. A Knoevenagel condensation between a malonic acid diester and the aldehyde 2 yields compound 58. In this reaction sodium acetate, piperidine, piperidineum acetate, pyrrolidine, potassium acetate, sodium carbonate and the like can be used as a base, and an alcohol such as methanol, ethanol, isopropanol, methoxyethanol and the like can be used as a solvent. Ketal hydrolysis followed by reductive amination of piperidione 59 with amine 6, as previously described in Scheme 1, gives the malonic acid analog 60, wherein A, $R_1$, $R_2$, $R_3$, $R_4$, $R_6$ (provided that in 60 $R_6$ can not be hydrogen) and X are as defined above. A salt is optionally produced by the addition of an acid or base, such as hydrogen chloride gas or hydrochloric acid. The diester group in compound 60 could be converted to mono acid or diacid by a basic hydrolysis process, which is well known in the art, to yield compound 61 wherein A, $R_1$, $R_2$, $R_3$, $R_4$, $R_6$ and X are as defined above. Mono peptide 41 or compound 44 analogues derived from compound 59 can be prepared in an analogous manner as previously described in Scheme 8 and Scheme 9.

Scheme 12

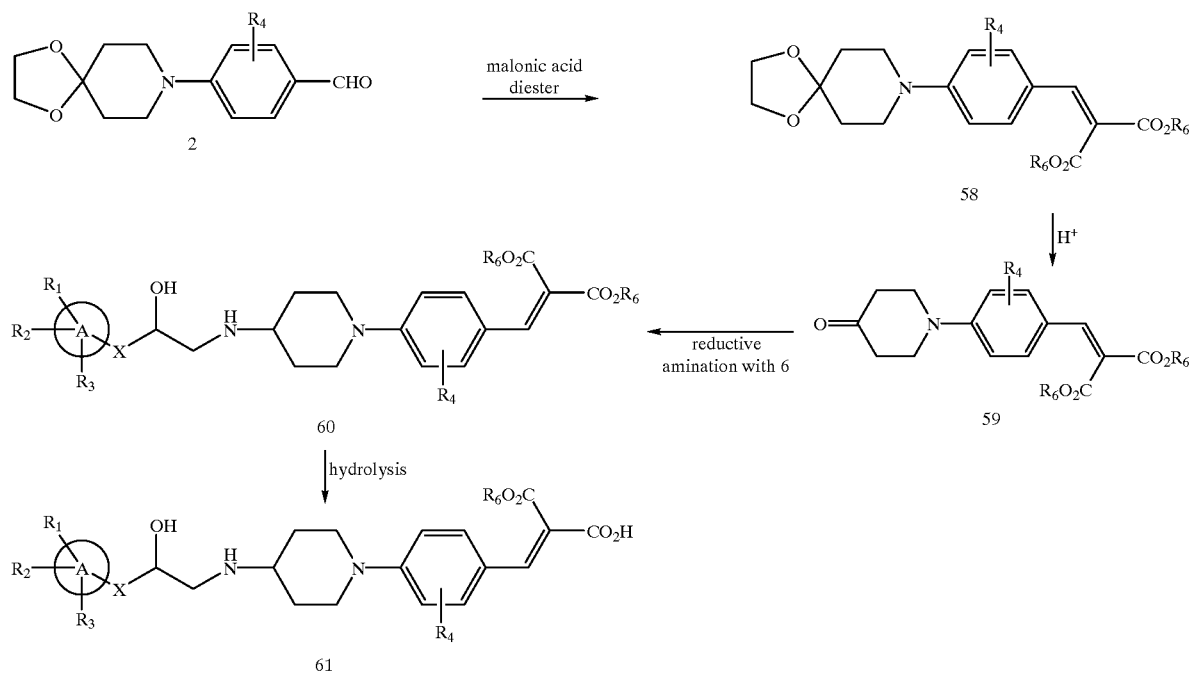

Ether analogues of compounds 37, 38, 41, 44 can be prepared by, for example, the following synthetic scheme (Scheme 13). The aldehyde group in compound 2 is reduced by a reducing agent such as sodium borohydride, in an alcoholic solvent, e.g., methanol to yield alcohol 62. Alcohol 62 is alkylated with, for example, iodoacetate sodium salt to generate acid 63, which is then converted to ether analog 65, wherein A, $R_1$, $R_2$, $R_3$, $R_4$ and X are as defined above, using ketal hydrolysis/reductive amination sequence as previously described in Scheme 1. A salt is optionally produced by the addition of an acid or base, such as hydrogen chloride gas or hydrochloric acid. Mono peptide 41 and compound 44 analogues derived from compound 64 can be prepared in an analogous manner as previously described in Scheme 8 and Scheme 9.

Scheme 13

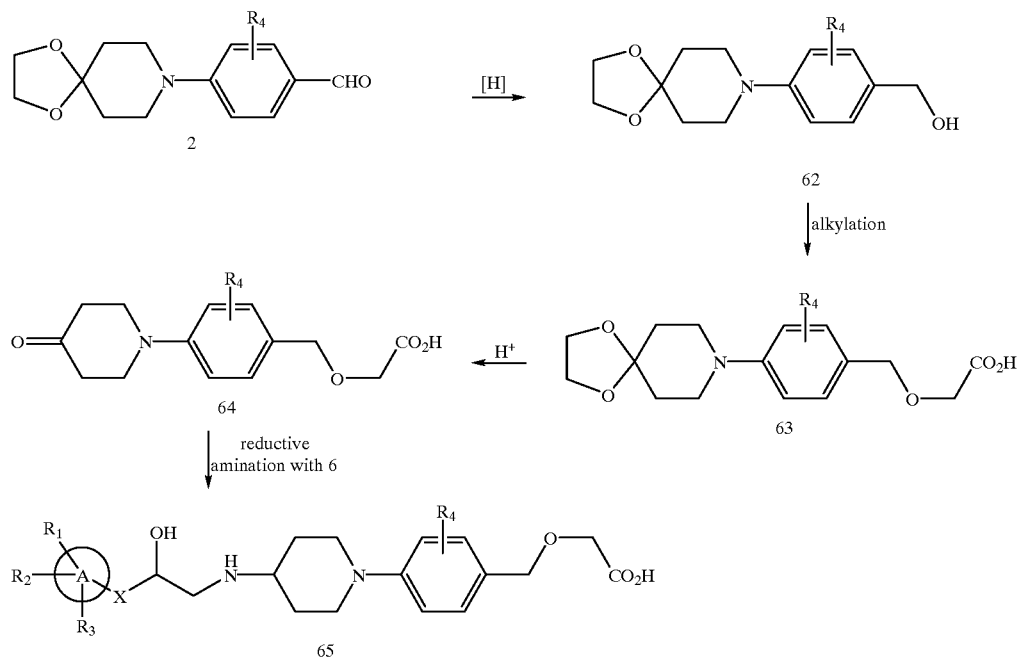

Sulfonamide or amide 72 can be conveniently prepared by a variety of methods known in the art. According to one route (Scheme 14), 1,4-dioxa-8-azaspiro[4.5]decane is reacted with 4-nitroarylfluoride 66 in the presence of base such as pyridine or potassium carbonate to afford ketal 67. This reaction can be carried out in a polar solvent such as anhydrous acetonitrile, acetone, dimethylformamide, or pyridine. The nitro group is then reduced by, for example, catalytic hydrogenation to provide aniline 68. The aniline 68 could be acylated with either sulfonyl chlorides or acyl chlorides in the presence of base such as triethylamine or pyridine to give the corresponding acylation product 69. Compound 69 could be optionally alkylated with appropriate alkylating agents ($R_6$-halo) in the presence of base such as potassium carbonate to give the alkylated product 70. Alternatively, a sequence of reductive amination between aniline 68 and appropriate aldehydes or ketones followed by acylation with $R_9X_1Cl$ furnishes the same alkylated product 70. Ketal hydrolysis followed by reductive amination of piperidiones 71 with amine 6 as previously described in Scheme 1, gives the sulfonamide or amide analog 72, wherein A, X, $X_1$, $R_1$, $R_2$, $R_3$, $R_4$, $R_6$ and $R_9$ are as defined above. A salt is optionally produced by the addition of an acid or base, such as hydrogen chloride gas or hydrochloric acid.

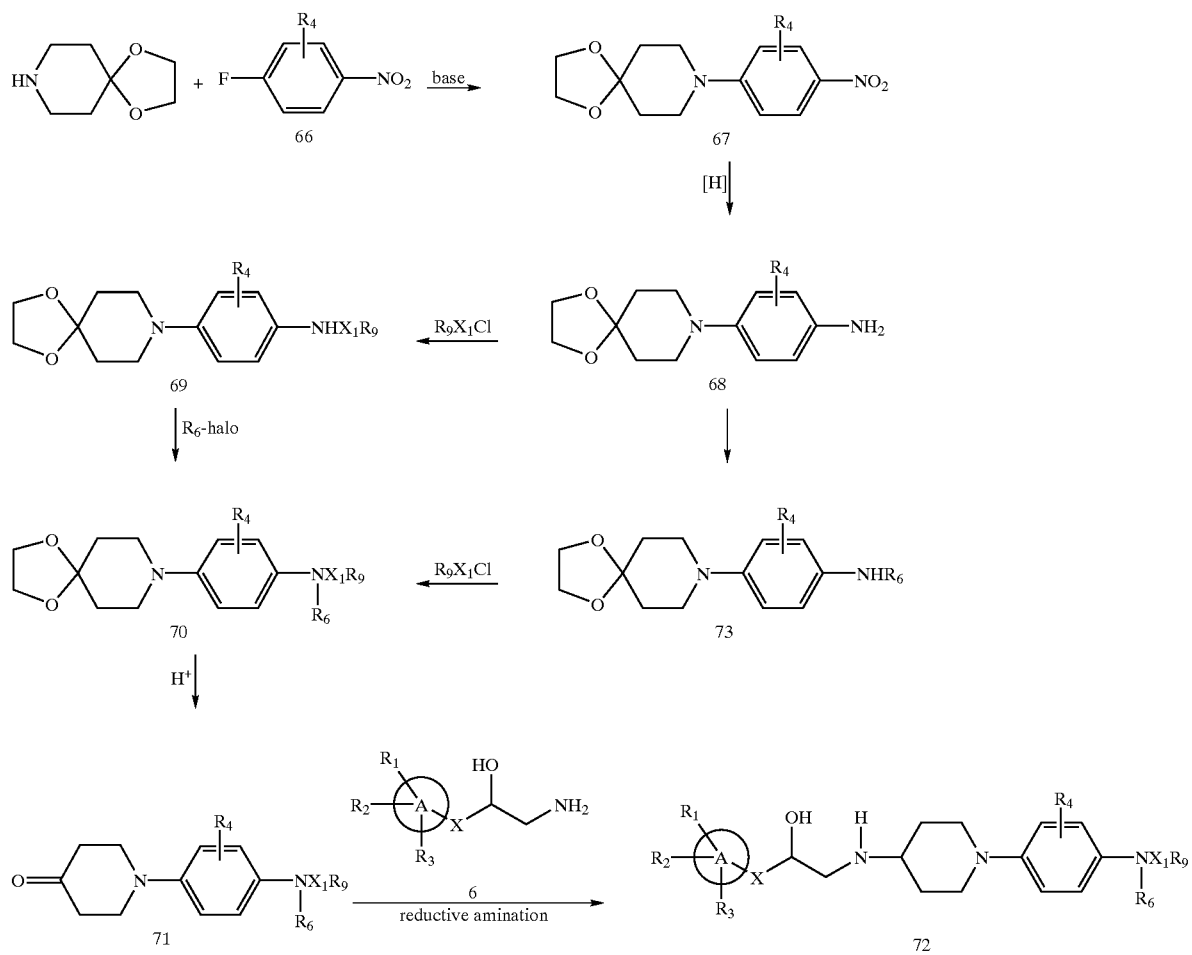

Scheme 14

Diacylated amine derivatives 78 are also readily prepared by methods known in the literature. For example, as shown in Scheme 15, the hydrochloric salt of 4-piperidone is condensed with 4-nitroarylfluorides, conveniently in pyridine, to give piperidone 74. The nitro group in 74 is then reduced to the corresponding aniline by catalytic hydrogenation as previously described. Diacylation of aniline 75 by $R_9X_1Cl$ followed by $R_{10}X_2Cl$ ($R_9X_1Cl$ and $R_{10}X_2Cl$ could be the same in some cases) gives the desired intermediate 77, which could be converted to the final product 78, wherein A, X, $X_1$, $X_2$, $R_1$, $R_2$, $R_3$, $R_4$, $R_6$, $R_9$ and $R_{10}$ are as defined above, by a reductive amination process as previously described in Scheme 1.

Scheme 15

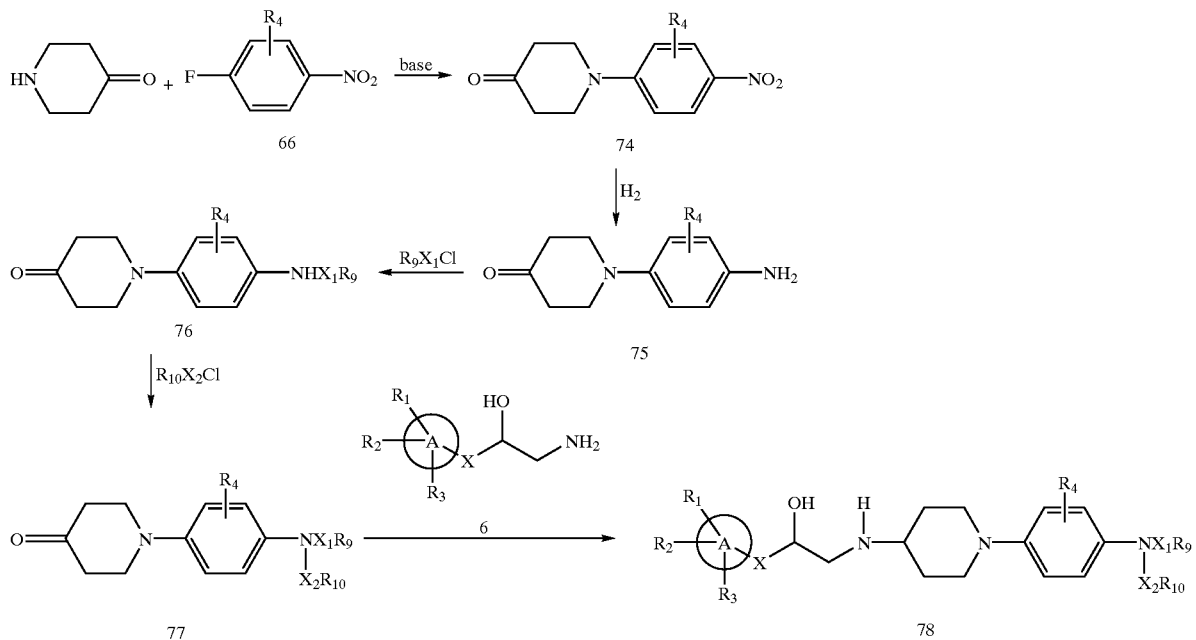

Some of the compounds of the present invention are prepared by a novel solution phase methodology (Scheme 16). In this method the product is formed in solution phase reactions and excess reagents are removed from solutions by solid scavenging agents. Treatment of aniline 75 with excess sulfonyl chloride and an resin base such as (piperidineomethyl)polystyrene in a solvent such as dichloromethane or 1,4-dioxane for 1 to 24 hours at room temperature gives the desired sulfonamide 76. The excess sulfonyl chloride is then removed by a nucleophilic scavenging agent, for example, aminomethylated polystyrene resin. The intermediate piperidone 76 could be isolated by filtration and evaporation. The imine formation between the piperidiones and excess arylethanolamines or aryloxypropanolamines is accomplished in a solvent such as methanol and in a water scavenging agent such as trimethyl orthoformate. The imine reduction is achieved by using a solid supported borohydride such as Amberlite IRA-400 borohydride resin. The excess amine is readily removed by quenched with a carboxaldehyde resin such as formylpolystyrene. The final product 79, wherein A, X, $X_1$, $R_1$, $R_2$, $R_3$, $R_4$, $R_6$ and $R_9$ are as defined above, could be purified by the same manner as described in Scheme 1.

Scheme 16

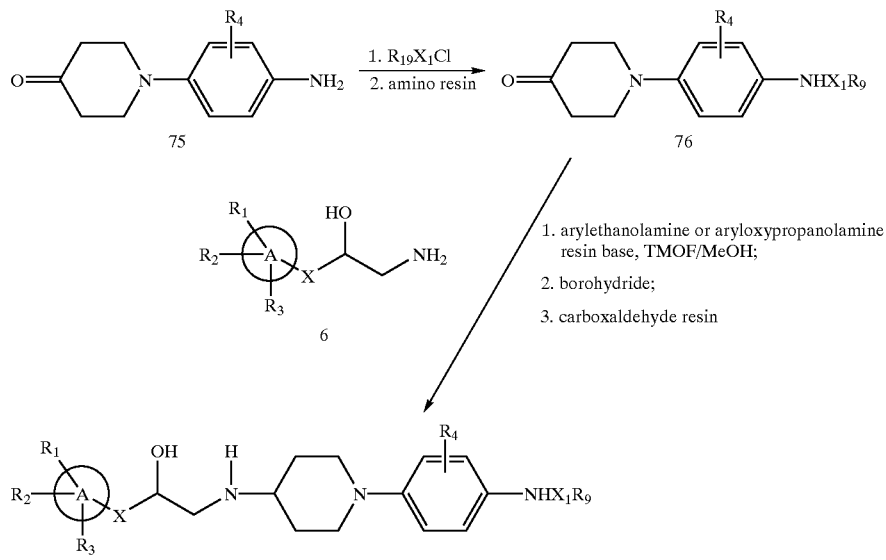

The compounds of the present invention where acidic group $R_5$ is urea can be prepared starting from aniline 73, as shown in Scheme 17. Aniline 80 is available from 73 by treatment of 73 with strong acid such as aqueous concentrated hydrochloric acid. Aniline 80 can be added to isocyanates to give the corresponding substituted urea 81. A reductive amination between amine 6 and 81, as previously described, gives the desired urea 82, wherein A, $R_1$, $R_2$, $R_3$, $R_4$, $R_6$, $R_7$ and X are as defined above. A salt is optionally produced by the addition of an acid or base, such as hydrogen chloride gas or hydrochloric acid.

Scheme 17

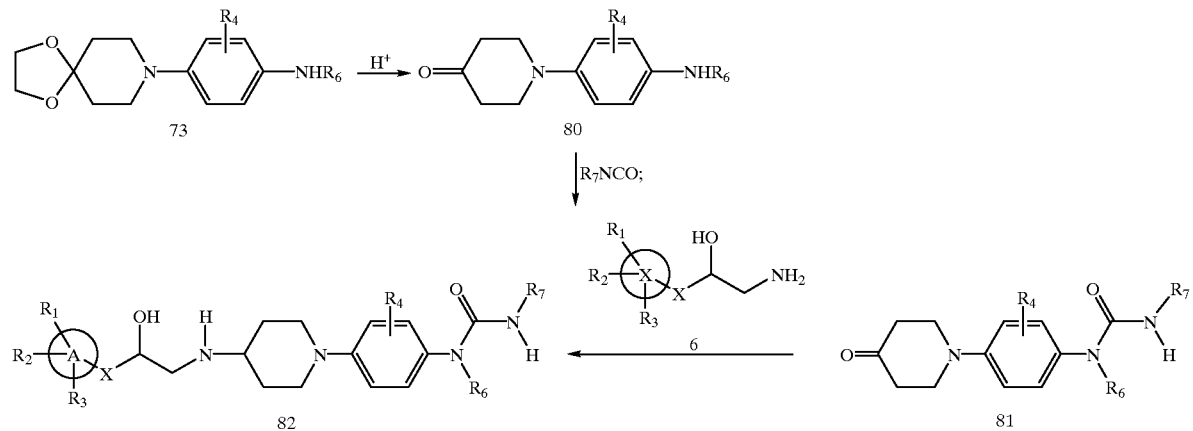

The compounds of the present invention where the cyclic amine is azetidine can be prepared as illustrated in Scheme 18. The alcohol of 83 is protected, for example, as its t-butyldimethylsilyl(TBS) ether to give TBS derivative 84. The protecting diphenylmethyl group in 84 is then removed by trearment of 84 with ammonium formate in the presence of palladium catalyst or raney nickle, typically in refluxing methanol. Condensation of azitidine 85 with arylfluoride 66 as before gives the key intermediate 86. The alcohol of 86 is then converted to the corresponding amine 88 by treatment with mesyl (Ms) chloride followed by benzylamine. The epoxides 89, many of which are commercially available or can be readily prepared as described in Scheme 19, are coupled with amine 88 by heating them neat or in a polar solvent. Preferably, the reaction is carried under refluxing methanol. The nitro group in 90 is then reduced, for example, by sodium hydrosulfite, to give an aniline. The aniline is then acylated with sulfonyl chloride, acyl chloride or isocyanates followed by deprotection of benzyl group with ammonium formate/palladium on carbon to give the desired azitidine 92, wherein A, $R_1$, $R_2$, $R_3$, $R_4$, $R_9$ and $X_1$ are as defined above. A salt is optionally produced by the addition of an acid or base, such as hydrogen chloride gas or hydrochloric acid.

Scheme 18

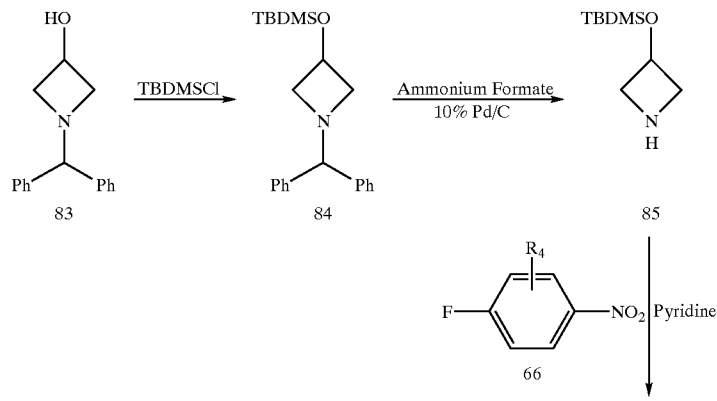

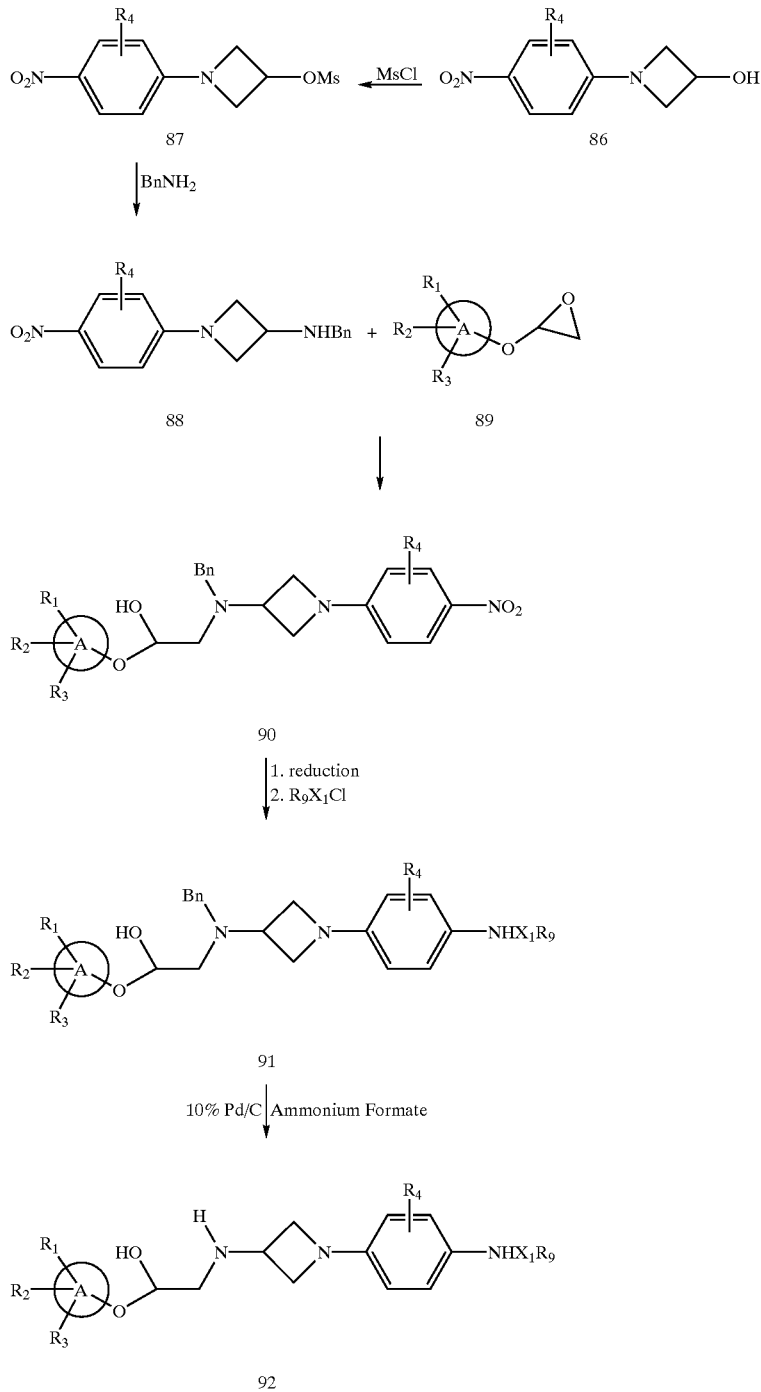

Many of arylethanolamines or aryloxypropanolamines 6 are commercially available or readily prepared by known methods [1. Guy, A., Ferroud, D. C., Garreay, R., Godefroy-Falguieres A. *Synthesis*, 1992, 821; 2. Leclerc, G., Bizec, J. C. *J. Med. Chem.*, 1980, 23, 738; 3. Tominaga, M., Ogawa, H., Yo, E., Yamashita, S., Yabuuchi, Y., Nakagawa, K. *Chem. Pharm. Bull.* 1987, 35, 3699]. In one route (Scheme 19) equimolecular amounts of alcohol 93 and enantiomerically pure (2S)-glycidyl 3-nitrobenzene sulfonate 94 are dissolved in an organic solvent such as acetone or N,N-dimethylformamide and treated with a base such as sodium hydride or potassium carbonate for 0.5 to 24 hours at a temperature of 20–100° C. to provide oxirane 89. The oxirane 89 is converted to the corresponding amine 97 or 98, wherein A, $R_1$, $R_2$, and $R_3$ are as defined above (provided that in 98 $R_1$, $R_2$, and $R_3$ can not be benzyloxy), by regioselective ring opening of oxirane 89 with either lithium azide in a solvent such as hexamethylphosphoramide (HMPA) followed by reduction with, for example, triphenylphosphine in aqueous tetrahydrofuran, or with one equivalent of dibenzylamine followed by ammonium formate/palladium on carbon reduction. The other enantiomer is available through an analogous preparative sequence with the corresponding (2R)-glycidyl 3-nitrobenzene sulfonate.

Scheme 19

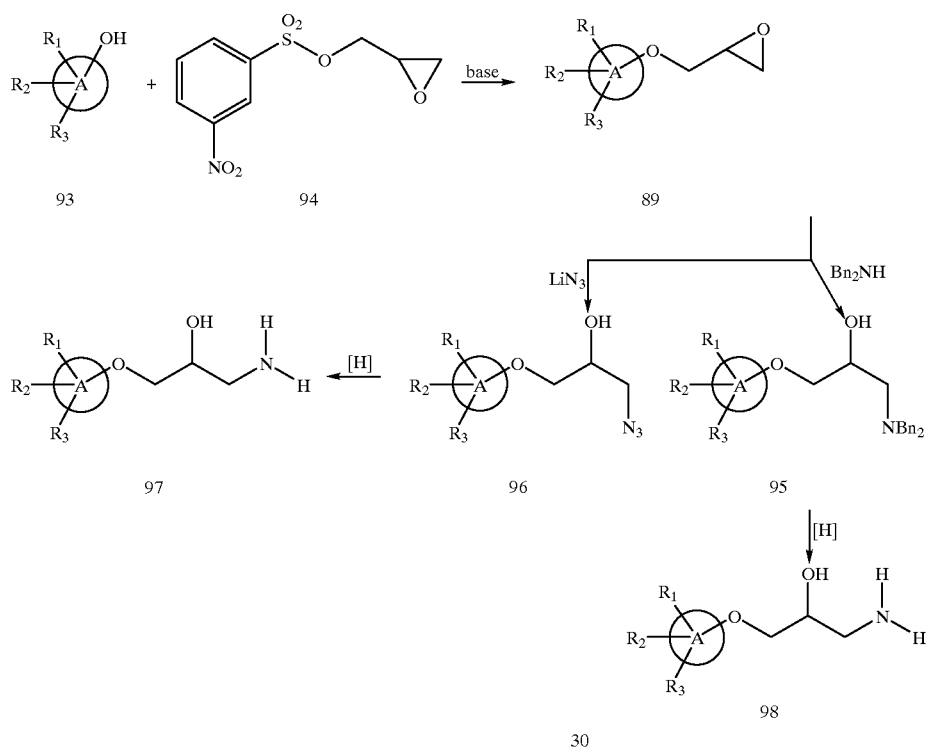

One route to the desired arylethanolamines 6 is illustrated in Scheme 20. Methylketones 99 are all available commercially or can be prepared by conventional methods disclosed in the art. Compound 99 can be easily converted to the corresponding α-haloketone 100, wherein halo is chlorine, bromine or iodine, using well known halogenation agents such as chlorine, bromine, N-chlorosuccinimide, N-bromosuccinimide and the like. The resultant α-haloketone 100 is then reduced, for example, by sodium borohydride, to give the corresponding racemic alcohol 101. An enantiomerically enriched alcohol 101 may be prepared by asymmetric reduction of α-haloketone 100 with chiral reducing agents such as (+) or (−)-B-chlorodiisopinocampheylborane (DIP-Cl), R or S-Alpine borane, cis-(1R, 2S) or cis (1S, 2R)-oxazaborolidine and the like. The alcohol of intermediate 101 may be protected, for example, as its triethylsilyl ether. In some cases, however, the alcohol protecting group is not required. The halo compound 101 can be easily converted to the corresponding benzylamine 102 by heating to 30–80° C. with large excess of benzylamine neat or as a solution in a polar solvent such as tetrahydrofuran, acetonitrile or methanol for 1 to 24 hours. The protecting group is then removed, in the case of silyl ether, by treatment of 102 with a fluoride agent such as tetrabutylammonium fluoride (TBAF). Compound 103 is then subjected to catalytic hydrogenation in the presence of ammonium formate/Pd to give the desired aminoethanol 104, wherein A, $R_1$, $R_2$ and $R_3$ are as defined above. The reduction is conveniently conducted in refluxing methanol in the presence of a large excess of ammonium formate.

Alternatively, the halo compound 101 could be converted to the corresponding amine 104 by either treatment with a sodium azide/sodium iodide mixture in a polar solvent such as dimethyl sulfoxide, hexamethylphosphoramide and the like followed by catalytic hydrogenation in the presence of a metal catalyst such as palladium, platinum and the like; or treatment with a base such as sodium hydroxide, potassium carbonate or the like followed by ammonia in a polar solvent such as methanol, tetrahydrofuran or the like.

Scheme 20

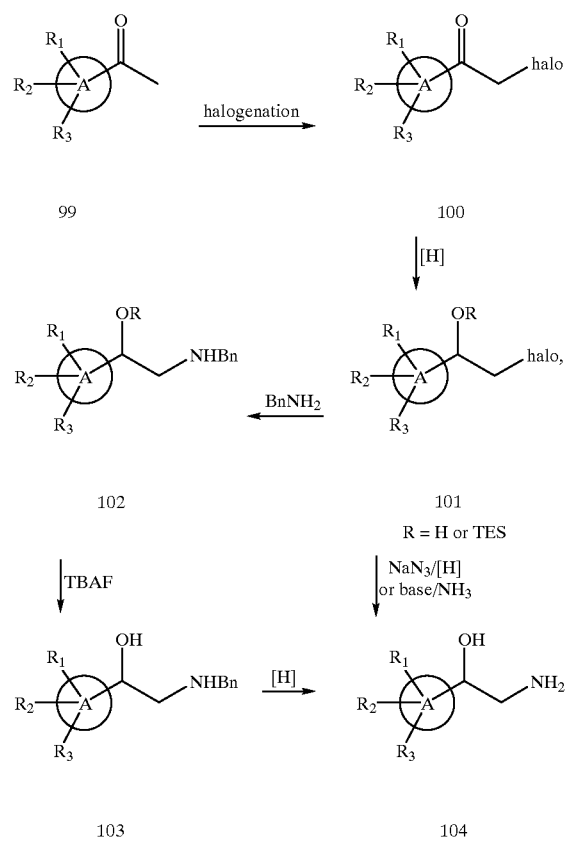

The compounds of this invention are useful in treating metabolic disorders related to insulin resistance or hyperglycemia, typically associated with obesity or glucose intolerance. The compounds of this invention are therefore, particularly useful in the treatment or inhibition of type II diabetes. The compounds of this invention are also useful in modulating glucose levels in disorders such as type I diabetes.

The ability of compounds of this invention to treat or inhibit disorders related to insulin resistance or hyperglycemia was confirmed with representative compounds of this invention in the following standard pharmacological test procedures, which measured the binding selectivity to the $\beta_1$, $\beta_2$, and $\beta_3$ adrenergic receptors. Binding to the receptors was measured in Chinese Hamster ovary (CHO) cells that were transfected with adrenergic receptors. The following briefly summarizes the procedure used and results obtained.

Transfection of CHO cells with $\beta_1$ and $\beta_2$ adrenergic receptors: CHO cells were transfected with human $\beta_1$- or $\beta_2$-adrenergic receptors as described in Tate, K. M., *Eur. J. Biochem.*, 196:357–361 (1991).

Cloning of Human $\beta_3$-AR Genomic DNA: cDNA was constructed by ligating four polymerase chain reaction (PCR) products using the following primers: an ATG-NarI fragment, sense primer 5'-CTTCCCTACC-GCCCCACGCGCGATC3' and anti-sense primer 5'CTG-GCGCCCAACGGCCAGTGGCCAGTC3'; a NarI-AccI fragment, 5'TTGGCGCTGATGGCCACTGGCCGTTTG3' as sense and 5'GCGCGTAGACGAAGAGCATCACGAG3' as anti-sense primer; an AccI-StyI fragment, sense primer 5'CTCGTGATGCTCTTCGTCTCACGCGC3' and anti-sense primer 5'GTGAAGGTGCCCATGATGAGAC-CCAAGG3' and a StyI-TAG fragment, with sense primer 5'CCCTGTGCACCTTGGGTCTCATCATGG3' and anti-sense primer 5'CCTCTGCCCCGGTTACCTACCC3'. The corresponding primer sequences are described in Mantzoros, C. S., etal., *Diabetes* 45: 909–914 (1996). The four fragments are ligated into a pUC 18 plasmid (Gibco-BRL) and sequenced. Full length $\beta_3$ AR clones (402 amino acids) containing the last 6 amino acids of h$\beta_3$-AR are prepared with the $\beta_3$-$\beta$ARpcDNA3 from ATTC.

Binding Procedure: Clones expressing receptor levels of 70 to 110 fmoles/mg protein were used in the test procedures. CHO cells were grown in 24-well tissue culture plates in Dulbecco's Modified Eagle Media with 10% fetal bovine serum, MEM non-essential amino acids, Penicillin-Streptompycin and Geneticin. On the day of test procedure, growth medium was replaced with preincubation media (Dulbecco's Modified Eagle Media) and incubated for 30 minutes at 37° C. Preincubation medium was replaced with 0.2 ml treatment medium containing DMEM media containing 250 $\mu$M IBMX (isobutyl-1-methylxantine) plus 1 mM ascorbic acid with test compound dissolved in DMSO. Test compounds were tested over a concentration range of $10^{-9}$ M to $10^{-5}$ M for $\beta_3$ cells and $10^{-8}$ to $10^{-4}$ M for $\beta_1$ and $\beta_2$ transfected cells. Isoproterenol ($10^{-5}$ M) was used as an internal standard for comparison of activity. Cells were incubated at 37° C. on a rocker for 30 min with the $\beta_3$ cells and 15 min for $\beta_1$ and $\beta_2$ cells. Incubation was stopped with the addition of 0.2N HCl and neutralized with 2.5N NaOH. The plates, containing the cells and neutralized media, were stored at −20 degrees celsius until ready to test for cAMP using the SPA test kit (Amersham).

Data Analysis and Results: Data collected from the SPA test procedure were analyzed as per cent of the maximal isoproterenol response at $10^{-5}$ M. Activity curves were plotted using the SAS statistical and graphics software. $EC_{50}$ values were generated for each compound and the maximal response (IA) developed for each compound is compared to the maximal response of isoproternol at $10^{-5}$ M from the following formula:

$$IA = \frac{\% \text{ activity compound}}{\% \text{ activity isoproterenol}}$$

Table I shows the $\beta_3$-adronergic receptor $EC_{50}$ and IA values for the representative compounds of this invention that were evaluated in this standard pharmacological test procedure. These results show that compounds of the present invention have activity at the $\beta_3$-adrenergic receptor. The compounds of this inventon had weaker or no activity at $\beta_1$ and/or $\beta_2$-adrenergic receptor.

TABLE I

| Compound No. | $EC_{50}(\beta_3, \mu M)$ | $IA(\beta_3)$ |
|---|---|---|
| Example 63 | 20 | 1 |
| Example 64 | 3 | 1 |
| Example 65 | 34 | 1.1 |
| Example 66 | 8 | 0.81 |
| Example 67 | 9 | 1.06 |
| Example 68 | 8 | 1 |
| Example 69 | 6 | 1 |
| Example 70 | 0.7 | 1.2 |
| Example 71 | 1 | 1.2 |
| Example 72 | 89 | 0.68 |
| Example 73 | 40 | 0.71 |
| Example 74 | 233 | 0.23 |
| Example 75 | 2 | 1.08 |
| Example 76 | 33 | 0.94 |
| Example 77 | 6 | 1.03 |
| Example 78 | 9 | 1.1 |
| Example 79 | 167 | 0.56 |
| Example 80 | 1 | 1.1 |
| Example 81 | 12 | 0.89 |
| Example 82 | 63 | 1.07 |
| Example 83 | 33 | 0.68 |
| Example 84 | 10 | 1.19 |
| Example 85 | 34 | 0.94 |
| Example 86 | 380 | 0.69 |
| Example 87 | 230 | 1 |
| Example 88 | 9 | 1 |
| Example 89 | 24 | 1.1 |
| Example 90 | 86 | 1.2 |
| Example 91 | 13 | 1.2 |
| Example 92 | 3 | 1.1 |
| Example 93 | 0.4 | 1 |
| Example 95 | 660 | 0.59 |
| Example 96 | 6 | 0.93 |
| Example 97 | 49 | 0.9 |
| Example 98 | 5 | 1 |
| Example 99 | 132 | 0.97 |
| Example 100 | 43 | 0.9 |
| Example 122 | 179 | 0.46 |
| Example 125 | 760 | 0.36 |
| Example 131 | 1,320 | 0.52 |
| Example 136 | 900 | 0.9 |
| Example 146 | 17 | 0.91 |
| Example 179 | 89 | 0.85 |
| Example 180 | 4 | 1 |
| Example 181 |  | 0.56 |
| Example 182 | 197 | 0.86 |
| Example 183 | 42 | 0.84 |
| Example 184 | 65 | 1.1 |
| Example 185 | 53 | 0.69 |
| Example 186 | 179 | 1.1 |
| Example 187 | 37 | 1.03 |
| Example 188 | 9 | 0.91 |
| Example 189 | 10 | 1.3 |
| Example 190 | 23 | 1.12 |
| Example 191 | 4 | 1 |
| Example 192 | 20 | 0.97 |

TABLE I-continued

| Compound No. | EC$_{50}$($\beta_3$, μM) | IA($\beta_3$) |
|---|---|---|
| Example 193 | 5 | 0.9 |
| Example 194 | 7,124 | 0.88 |
| Example 195 | 195 | 0.98 |
| Example 196 | 9 | 1.1 |
| Example 197 | 40 | 0.94 |
| Example 198 | 1 | 0.97 |
| Example 199 | 8 | 1 |
| Example 200 | 4 | 1.1 |
| Example 201 | 55 | 1.1 |
| Example 202 | 8 | 1.2 |
| Example 203 | 16 | 1.1 |
| Example 204 | 3 | 1.2 |
| Example 205 | 7 | 1.2 |
| Example 206 | 16 | 0.94 |
| Example 207 | 9 | 1 |
| Example 208 | 13 | 0.97 |
| Example 209 | 2 | 1 |
| Example 210 | 55 | 1.36 |
| Example 211 | 8 | 1 |
| Example 212 | 9 | 1.1 |
| Example 213 | 6 | 0.97 |
| Example 255 | 1,360 | 0.72 |
| Example 256 | 910 | 0.85 |
| Example 257 | 610 | 0.88 |
| Example 258 | 3,126 | 0.7 |
| Example 259 | 916 | 0.97 |
| Example 260 | 3,755 | 0.63 |
| Example 261 | 12,185 | 0.73 |
| Example 263 | 8 | 0.93 |
| Example 264 | 1,830 | 0.37 |
| Example 265 | 94 | 0.8 |
| Example 266 | 10 | 0.86 |
| Example 267 | 15,400 | 0.99 |
| Example 268 | 797 | 0.64 |
| Example 270 | 21 | 1.09 |
| Example 271 | 20 | 0.84 |
| Example 272 | 1,553 | 0.57 |
| Example 273 | 3,840 | 1.05 |
| Example 274 | 165 | 1.15 |
| Example 275 | 100 | 0.73 |
| Example 276 | 1 | 1.1 |
| Example 277 | 3 | 0.58 |
| Example 278 | 10 | 1.04 |
| Example 279 | 470 | 0.74 |
| Example 280 | 20 | 1.16 |
| Example 281 | 9 | 1.14 |
| Example 282 | 22 | 0.63 |
| Example 283 | 10 | 0.81 |
| Example 284 | 20 | 0.87 |
| Example 285 | 39 | 0.76 |
| Example 286 | 9 | 0.91 |
| Example 287 | 10 | 0.92 |
| Example 288 | 66 | 1.24 |
| Example 289 | 70 | 0.59 |
| Example 290 | 34 | 0.72 |
| Example 291 | 13 | 1.07 |
| Example 292 | 3 | 0.75 |
| Example 293 | 210 | 0.94 |
| Example 294 | 33 | 1.07 |
| Example 295 | 6 | 0.87 |
| Example 296 | 8 | 0.81 |
| Example 297 | 16 | 1 |
| Example 298 | 59 | 0.78 |
| Example 299 | 0.6 | 1.1 |
| Example 300 | 55 | 0.78 |
| Example 301 | 30 | 0.95 |
| Example 302 | 10 | 0.95 |
| Example 303 | 20 | 0.96 |
| Example 304 | 110 | 0.35 |
| Example 305 | 1 | 1 |
| Example 306 | 5 | 1.1 |
| Example 307 | 4 | 1 |
| Example 308 | 2 | 1.4 |
| Example 309 | 1 | 1 |
| Example 310 | 25 | 1 |
| Example 311 | 210 | 0.82 |
| Example 312 | 1 | 1.1 |
| Example 313 | 13 | 1 |
| Example 315 | 1 | 1.2 |
| Example 317 | 50 | 0.97 |
| Example 318 | 13 | 1 |
| Example 319 | 4,160 | 0.79 |
| Example 320 | 11 | 0.87 |
| Example 321 | 13 | 1.05 |
| Example 322 | 2 | 0.89 |
| Example 323 | 35 | 0.92 |
| Example 324 | 4 | 0.9 |
| Example 325 | 4 | 1 |
| Example 326 | 79 | 1.3 |
| Example 327 | 6 | 0.86 |
| Example 328 | 8 | 0.89 |
| Example 329 | 15 | 0.9 |
| Example 330 | 12 | 0.98 |
| Example 331 | 9 | 1 |
| Example 332 | 20 | 1.1 |
| Example 333 | 13 | 0.83 |
| Example 334 | 40 | 0.91 |
| Example 335 | 3 | 0.98 |
| Example 336 | 20 | 0.82 |
| Example 337 | 29 | 0.72 |
| Example 338 | 4 | 1 |
| Example 339 | 10 | 0.89 |
| Example 342 | 3 | 1 |
| Example 343 | 20 | 0.86 |
| Example 345 | 4 | 1 |
| Example 346 | 1,580 | 0.76 |
| Example 347 | 14 | 0.91 |
| Example 348 | 95 | 0.63 |
| Example 349 | 390 | 1.26 |
| Example 350 | 1,070 | 1.26 |
| Example 351 | 888 | 0.76 |
| Example 352 | 109 | 1.02 |
| Example 353 | 1,380 | 0.97 |
| Example 354 | 283 | 0.73 |
| Example 357 | 96 | 0.87 |
| Example 358 | 33 | 1.1 |
| Example 359 | 73 | 0.91 |
| Example 360 | 155 | 0.54 |
| Example 361 | 1,134 | 0.55 |
| Example 362 | 30 | 0.9 |
| Example 371 | 10 | 0.91 |
| Example 372 | 127 | 1 |
| Example 373 | 9 | 1.1 |
| Example 374 | 9 | 1.2 |
| Example 375 | 1 | 1 |
| Example 376 | 1 | 1 |
| Example 377 | 16 | 0.66 |
| Example 378 | 56 | 0.94 |
| Example 379 | 13 | 0.93 |
| Example 380 | 8 | 1.1 |
| Example 381 | 57 | 0.97 |
| Example 382 | 19 | 0.64 |
| Example 383 | 740 | 0.64 |
| Example 384 | 199 | 0.64 |
| Example 385 | 55 | 1.12 |
| Example 386 | 51 | 0.89 |
| Example 387 | 168 | 0.56 |
| Example 388 | 740 | 0.75 |
| Example 389 | 50 | 0.61 |
| Example 390 | 14 | 0.82 |
| Example 391 | 337 | 0.81 |
| Example 392 | 18 | 0.9 |
| Example 393 | 10 | 1 |
| Example 394 | 66 | 1.3 |
| Example 411 | 954 | 0.49 |
| Example 412 | 1,329 | 0.56 |
| Example 413 | 580 | 0.73 |
| Example 415 | 537 | 0.35 |
| Example 416 | 53 | 0.48 |
| Example 417 | 24 | 0.71 |

Evaluation in $\beta_3$ Knockout(KO) and $\beta_3$ Transgenic(Tg) Mice: The ability of compounds of this invention to treat or inhibit disorders related to insulin resistance or hyperglycemia was also confirmed with representative compounds of this invention in an in vivo standard pharmacoligical test procedure which compared thermogenesis in transgenic mice (Tg mice) and $\beta_3$-knockout mice (KO mice). The procedure used and results obtained and provided below.

$\beta_3$-Adrenergic receptor knockout mice and $\beta_3$ human transgenic mice are created on an inbred FVB background (Susulic, V. S., et.al., *J. Biol. Chem.,* 1995, 270 (49), 29483–29492). Female FVB $\beta_3$ transgenic and $\beta_3$ knockout mice were used to determine in vivo activity and selectivity of $\beta_3$ agonists. Compounds selected for in vivo testing had $\beta_3$ $EC_{50}$<30 nm and were full agonists in CHO cells expressing human $\beta_3$ receptors. These compounds were also selective in being 100-fold less responsive and partial agonists when tested in $\beta_1$ and $\beta_2$ transfected CHO cells. Compounds were tested for increased thermogenesis using the Oxymax indirect calorimeter (Columbus Instruments, Columbus, Ohio). Fed animals were placed in chambers for 3 hours to obtain baseline $O_2$ and $CO_2$ values. Eight fed mice were weighed in pairs and placed in 4 chambers, two per chamber. The relative gas content of each chamber was sampled and recorded at 10 to 12 minute intervals. For each sample, energy expenditure values were calculated by the Oxymax and expressed as kcal/hr. After 3 hours of baseline measurement, the mice were removed, treated and replaced in the chambers. The $\beta_3$ agonists were injected at doses between 0.1 and 20 mg/kg i.p. and between 1.0 and 30 mg/kg for oral administration. Compounds in 10 mM or 10 mg/ml DMSO solutions were suspended in 0.5% methylcellulose: 0.1% tween-80 and injected i.p. or administered by oral gavage. Some compounds were suspended in 5.0% tween-80 for oral administration. Post-treatment kcal/hr values were taken between 40 minutes and 2.5 hours later. The 6 to 10 sample sections of the pre-treatment and post-treatment periods, which appear to best represent stable resting thermogenesis, were selected. Each of these sample values was corrected for body weight and used such that each pair of mice serves as its own baseline for both T test and percent increase in thermogenesis calculations. An ANOVA and a one sided T test (H1: Post>Pre) are performed using the SAS software modified to down weight extreme values. In a separate set of calculations, values that appear to be too high to represent resting thermogenesis are discarded (activity monitor sampling associated spikes in thermogenesis with ambulatory activity). The mean baseline value for each chamber is subtracted from mean post-treatment value for that chamber. This baseline-subtracted value is divided by the mean baseline value and multiplied by 100 to obtain a percent increase in thermogenesis for each chamber. The combined mean percent increase, standard deviation, and standard error of the mean for each chamber is calculated. Compounds were considered active if they were able to produce a statistically significant 15% increase in thermogenesis in $\beta_3$ transgenic mice and no significant increase in $\beta_3$ knockout mice. The results are shown in the table below.

Thermogenesis in β3 Knockout(KO) and β3 Transgenic(Tg) Mice

| Compound No # | Thermogenesis (Tg mice) | Thermogenesis (KO mice) |
|---|---|---|
| Example 63 | 30 ± 8% | 16 ± 4% |
| Example 84 | 30 ± 4% | −2 ± 4% |
| Example 180 | 42 ± 4% | 9 ± 5% |
| Example 186 | 77 ± 12% | 16 ± 7% |
| Example 189 | 33 ± 7% | 6 ± 3% |

Based on the results obtained in these standard pharmacological test procedures, representative compounds of this invention have been shown to be selective $\beta_3$ adrenergic receptor agonists and are therefore useful in treating metabolic disorders related to insulin resistance or hyperglycemia (typically associated with obesity or glucose intolerance), atherosclerosis, gastrointestinal disorders, neurogenetic inflammation, glaucoma, ocular hypertension, and frequent urination; and are particularly useful in the treatment or inhibition of type II diabetes, and in modulating glucose levels in disorders such as type I diabetes. As used herein, the term modulating means maintaining glucose levels within clinically normal ranges.

As used in accordance with this invention, the term providing an effective amount means either directly administering such a compound of this invention, or administering a prodrug, derivative, or analog which will form an effective amount of the compound of this invention within the body.

It is understood that the effective dosage of the active compounds of this invention may vary depending upon the particular compound utilized, the mode of administration, the condition, and severity thereof, of the condition being treated, as well as the various physical factors related to the individual being treated. As used in accordance with invention, satisfactory results may be obtained when the compounds of this invention are administered to the individual in need at a daily dosage of from about 0.1 mg to about 1 mg per kilogram of body weight, preferably administered in divided doses two to six times per day, or in a sustained release form. For most large mammals, the total daily dosage is from about 3.5 mg to about 140 mg. It is preferred that the administration of one or more of the compounds herein begin at a low dose and be increased until the desired effects are achieved.

Such doses may be administered in any manner useful in directing the active compounds herein to the recipient's bloodstream, including orally, via implants, parenterally (including intravenous, intraperitoneal and subcutaneous injections), rectally, intranasally, vaginally, and transdermally. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectals and vaginal).

Oral formulations containing the active compounds of this invention may comprise any conventionally used oral forms, including tablets, capsules, buccol forms, troches, lozenges and oral liquids, suspensions or solutions. Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc. Useful tablet formulations may be made by conventional compression, wet granulation or dry granulation methods and utilize pharmaceutically acceptable diluents, binding agents, lubricants, disentegrants, suspending or stabilizing agents, including, but not limited to, magnesium stearate, stearic acid, talc, sodium lauryl sulfate, microcrystalline cellulose, carboxymethylcellulose calcium, polyvinylpyrrolidone, gelatin, alginic acid, acacia gum, xanthum gum, sodium citrate, complex silicates, calcium carbonate, glycine, dextrin, sucrose, sorbitol, dicalcium phosphate, calcium sulfate, lactose, kaolin, mannitol, sodium chloride, talc, dry starches and powdered sugar. Oral formulations herein may utilize standard delay or time release formulations to alter the absorption of the active compound(s).

In some cases it may be desirable to administer the compounds directly to the airways in the form of an aerosol.

The compounds of this invention may also be administered parenterally or intraperitoneally. Solutions or suspensions of these active compounds as a free base or pharmacologically acceptable salt can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparation contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Suppository formulations may be made from traditional materials, including cocoa butter, with or without the addition of waxes to alter the suppository's melting point, and glycerin, Water soluble suppository bases, such as polyethylene glycols of various molecular weights, may also be used.

The compounds of the present invention also possess utility for increasing lean meat deposition and/or improving lean meat to fat ratio in edible animals, i.e. ungulate animals and poultry.

Animal feed compositions effective for increasing lean meat deposition and for improving lean meat to fat ratio in poultry, swine, sheep, goats, and cattle are generally prepared by mixing the compounds of the present invention with a sufficient amount of animal feed to provide from about 1 to 1000 ppm of the compound in the feed. Animal feed supplements can be prepared by admixing about 75% to 95% by weight of a compound of the present invention with about 5% to about 25% by weight of a suitable carrier or diluent. Carriers suitable for use to make up the feed supplement compositions include the following: alfalfa meal, soybean meal, cottonseed oil meal, linseed oil meal, sodium chloride, cornmeal, cane molasses, urea, bone meal, corncob meal and the like. The carrier promotes a uniform distribution of the active ingredients in the finished feed into which the supplement is blended. It thus performs an important function by ensuring proper distribution of the active ingredient throughout the feed. The supplement is used as a top dressing for the feed, it likewise helps to ensure uniformity of distribution of the active material across the top of the dressed feed.

The preferred medicated swine, cattle, sheep and goat feed generally contain from 0.01 to 400 grams of active ingredient per ton of feed, the optimum amount for these animals usually being about 50 to 300 grams per ton of feed. The preferred poultry and domestic pet feed usually contain about 0.01 to 400 grams and preferably 10 to 400 grams of active ingredient per ton of feed.

For parenteral administration the compounds of the present invention may be prepared in the form of a paste or a pellet and administered as an implant, usually under the skin of the head or ear of the animal in which increase in lean meat deposition and improvement in lean mean to fat ratio is sought. In general, parenteral administration involves injection of a sufficient amount of the compounds of the present invention to provide the animal with 0.001 to 100 mg/kg/day of body weight of the active ingredient. The preferred dosage for swine, cattle, sheep and goats is in the range of from 0.001 to 50 mg/kg/day of body weight of active ingredient; whereas, the preferred dose level for poultry and domestic pets is usually in the range of from 0.001 to 35 mg/kg/day of body weight.

Paste formulations can be prepared by dispersing the active compounds in a pharmaceutically acceptable oil such as peanut oil, sesame oil, corn oil or the like. Pellets containing an effective amount of the compounds of the present invention can be prepared by admixing the compounds of the present invention with a diluent such as carbowax, carnuba wax, and the like, and a lubricant, such as magnesium or calcium stearate, can be added to improve the pelleting process. It is, of course, recognized that more than one pellet may be administered to an animal to achieve the desired dose level which will provide the increase in lean meat deposition and improvement in lean meat to fat ratio desired. Moreover, it has been found that implants may also be made periodically during the animal treatment period in order to maintain the proper drug level in the animal's body. For the poultry and swine raisers, using the method of the present invention yields leaner animals.

Additionally, the compounds of this invention are useful in increasing the lean mass to fat ratio in domestic pets, for the pet owner or veterinarian who wishes to increase leanness and trim unwanted fat from pet animals, the present invention provides the means by which this can be accomplished.

The following procedures describe the preparation of representative compounds of this invention.

EXAMPLE 1

(1R)-2-Amino-1-(3-chloro-phenyl)-ethanol hydrochloride

Lithium azide (7.5 g, 150 mmol) was added to a solution of (1R)-1-(3-chloro-phenyl)oxirane (15.5 g, 100 mmol) in hexamethylphosphoramide (HMPA) (70 mL). After being stirred at room temperature for 16 hours the suspension was poured into ice-water and the mixture was extracted with diethyl ether. The combined extracts were dried over magnesium sulfate ($MgSO_4$) and concentrated. The residue was dissolved in 550 mL of tetrahydrofuran (THF)/water ($H_2O$) (10:1) and triphenylphosphine (30 g, 114 mmol) was added. After overnight sitrring at room temperature, the solvents were removed and the residue was purified by column chromatography on silica gel using triethylamine-methanol-methylene chloride ($CH_2Cl_2$) (1:1:8) as the eluent to give the title compound as a free base.

The title compound was characterized as its hydrochloric salt: The free base from above was then dissolved in diethyl ether and slowly treated with hydrogen chloride gas. The precipitate was collected by filtration to yield 15 g (72%) of the title compound as a white powder; $^1$H NMR (300 MHz, DMSO-$_6$) δ 2.83 (dd, J=12.8, 9.5 Hz, 1H), 3.06 (dd, J=12.8, 3.2 Hz, 1H), 4.80–4.90 (m, 1H), 6.22 (d, J=4.0 Hz, 1H), 7.10–7.75 (m, 4H), 8.08 (brs, 2H); MS (ES) m/z: 171.7, 173.7 (MH$^+$); HRMS Calcd. for $C_8H_{10}ClNO$ (MH$^+$): 172.0529. Found: 172.0531.

EXAMPLE 2

(2S)-2-Phenoxymethyl-oxirane

A solution of phenol (9.4 g, 100 mmol) and (2S)-(+)-glycidyl 3-nitrobenzenesulfonate (25.9 g, 100 mmol) in 500 mL of acetone was treated with 3 equivalents of potassium carbonate (41.5 g, 300 mmol) and stirred at reflux for 1 day. The suspension was cooled to ambient temperature; the solid was filtered; and the filtrate was concentrated to dryness. The residue was partitioned between methylene chloride and water. The aqueous layer was extracted with $CH_2Cl_2$. The organic layers were combined and dried over $MgSO_4$ and concentrated to give the title compound (15.0 g, 99%) as an orange oil; $^1H$ NMR (300 MHz, $CDCl_3$) δ 2.76 (dd, J=4.9, 2.6 Hz, 1H), 2.90 (dd, J=4.9, 4.9 Hz, 1H), 3.30–3.40 (m, 1H), 3.95 (dd, J=11.0, 5.4 Hz, 1H), 4.18 (dd, J=11.0, 3.0 Hz, 1H), 6.85–7.00 (m, 3H), 7.25–7.35 (m, 2H); MS (ES) m/z: 151.0 ($MH^+$).

EXAMPLE 3

(2S)-1-Amino-3-phenoxypropan-2-ol

The title compound was prepared from (2S)-2-phenoxymethyl-oxirane (which was obtained in Example 2) according to the procedure of Example 1 with one change. The free base was obtained as a white solid; $^1H$ NMR (300 MHz, DMSO-$d_6$) δ 2.56 (dd, J=12.8, 6.3 Hz, 1H), 2.67 (dd, J=12.8, 4.9 Hz, 1H), 3.65–3.75 (m, 1H), 3.82 (dd, J=9.8, 6.0 Hz, 1H), 3.93 (dd, J=9.8, 5.0 Hz, 1H), 6.85–6.95 (m, 3H), 7.20–7.30 (m, 2H); MS (ES) m/z: 167.7 ($MH^+$); HRMS Calcd. for $C_9H_{13}NO_2(M^+)$: 167.0946. Found: 167.0945.

EXAMPLE 4

(2S)-1-Amino-3-(4-benzyloxy-phenoxy)-propan-2-ol

The title compound was prepared from (2S)-2-(4-benzyloxy-phenoxymethyl-oxirane (EP 0 714 883) according to the procedure of Example 1 with one change. The free base was obtained as as a white solid; $^1H$ NMR (300 MHz, $CDCl_3$) δ 2.50–2.70 (m, 2H), 3.33 (brs, 2H), 3.60–3.90 (m, 3H), 5.02 (s, 2H), 6.90 (d, J=6.7 Hz, 2H), 6.93 (d, J=6.7 Hz, 2H), 7.25–7.50 (m, 5H); MS (ES) m/z: 274.1 ($MH^+$); HRMS Calcd. for $C_{16}H_{19}NO_3(M^+)$: 273.1365. Found: 273.1347. Anal. Calcd. for $C_{16}H_{19}NO_3$: C, 70.31; H, 7.01; N, 5.12. Found: C, 70.39; H, 6.80; N, 5.23.

EXAMPLE 5

(2S)-1-Amino-3-(4-hydroxy-phenoxy)-propan-2-ol

A mixture of (2S)-1-amino-3-(4-benzyloxy-phenoxy)-propan-2-ol (0.9 g, 3.3 mmol) (which was obtained in Example 4), 0.2 mL of acetic acid and 10% palladium on carbon (Pd/C) (0.3 g) in 70 mL of ethanol was pressurized with 20 psi hydrogen and shaken over 2 hours. The catalyst was then removed by filtering through a short pad of silica gel and the solvent was removed to give the title compound as an off-white solid; $^1H$ NMR (300 MHz, DMSO-$d_6$) δ 1.86 (s, 1H), 2.66 (dd, J=12.8, 5.3 Hz, 1H), 2.85 (dd, J=12.8, 3.5 Hz, 1H), 3.79–3.95 (m, 3H), 6.67 (d, J=6.6 Hz, 2H), 6.75 (d, J=6.6 Hz, 2H); MS (ES) m/z: 183.1 ($MH^+$); HRMS Calcd. for $C_9H_{13}NO_3(MH^+)$: 183.0895. Found: 183.0892.

EXAMPLE 6

N-[2-Benzyloxy-5-(2-dibenzylamino-1-oxo-ethyl)-phenyl]-methanesulfonamide

N-[2-Benzyloxy-5-(2-chloro-1-oxo-ethyl)-phenyl]-methanesulfonamide (EP 0 659 737) (17.0 g, 42.8 mmol) was dissolved in 200 mL of N,N-dimethylformamide (DMF) and treated with dibenzylamine (22.0 g, 110 mmol). The mixture was stirred at room temperature overnight and then the solvent was removed. The residue was purified by silica gel chromatography using 20–50% ethyl acetate/hexanes as eluent to give the title compound as a white solid; $^1H$ NMR (300 MHz, $CDCl_3$) δ 2.94 (s, 3H), 3.77 (s, 2H), 3.82 (s, 2H), 5.16 (s, 2H), 6.75 (brs, 1H), 6.96 (d, J=8.7 Hz, 1H), 7.20–7.50 (m, 15H), 7.67 (dd, J=8.7, 2.1 Hz1H), 8.10 (d, J=2.1 Hz, 1H); MS (ES) m/z: 515.2 ($MH^+$); HRMS Calcd. for $C_{30}H_{30}N_2O_4S(M^+)$: 514.1926. Found: 514.1927.

EXAMPLE 7

N-[2-Benzyloxy-5-(2-dibenzylamino-1-hydroxy-ethyl)-phenyl]-methanesulfonamide

Sodium borohydride (0.37 g, 9.7 mmol) was added in portions to a stirred solution of N-[2-benzyloxy-5-(2-dibenzylamino-1-oxo-ethyl)-phenyl]-methanesulfonamide (1.0 g, 1.9 mmol) (which was obtained in Example 6) in 20 mL of methanol/THF (5:2) at room temperature and the resulting solution was stirred for 2 hours. Methylene chloride was added and the resulting solution was washed with aqueous sodium bicarbonate, dried over $MgSO_4$ and the solvents were removed. Recrystallization from methylene chloride/hexanes gave the title compound as a crystalline solid; $^1H$ NMR (300 MHz, $CDCl_3$) δ 2.58 (d, J=6.7 Hz, 2H), 2.86 (s, 2H), 2.92 (s, 2H), 3.55 (d, J=13.5 Hz, 2H), 3.70 (d, J=13.5 Hz, 2H), 4.11 (s, 1H), 4.64 (t, J=6.7 Hz, 1H), 5.10 (s, 2H), 6.92 (d, J=8.5 Hz, 1H), 7.00 (dd, J=8.5, 2.0 Hz, 1H), 7.20–7.50 (m, 16H), 7.89 (brs, 1H); MS (ES) m/z: 517.1 ($MH^+$); HRMS Calcd. for $C_{30}H_{32}N_2O_4S(M^+)$: 516.2083. Found: 516.2074.

EXAMPLE 8

N-[2-Benzyloxy-5-(2-amino-(1R)-1-hydroxy-ethyl)-phenyl]-methanesulfonamide

A mixture of N-{2-benzyloxy-5-(2-iodo-(1R)-1-[(triethylsilyl)oxy]-ethyl)-phenyl}-methanesulfonamide (EP 0 659 737) (4.48 g, 8 mmol) and sodium azide (0.65 g, 10 mmol) in 100 mL of HMPA was stirred at 60° C. overnight. After cooling to room temperature the mixture was diluted with diethyl ether, washed with water, dried over sodium sulfate ($Na_2SO_4$) and concentrated under reduced pressure. The residue was dissolved in 200 mL of THF/$H_2O$ (10:1) and triphenylphosphine (2.62 g, 10 mmol) was added. After overnight stirring at room temperature, the solvents were removed and the resiude was partitioned between ethyl acetate and water. The organic layers were combined and dried over $MgSO_4$ and concentrated. The residue was redissolved in 100 mL of THF and tetrabutylammonium fluoride (TBAF) (10 mL, 1 M solution in THF) was added. The reaction was stirred for 2 hours then the solvent was removed in vacuo. The residue was purified by column chromatography on silica gel using triethylamine-methanol-$CH_2Cl_2$ (1:1:3) to give the title compound as a white solid; MS (ES) m/z: 337.4 ($MH^+$).

EXAMPLE 9

N-[5-(2-Amino-1-hydroxy-ethyl)-2-hydroxy-phenyl]-methanesulfonamide

To a stirred suspension of N-[2-benzyloxy-5-(2-dibenzylamino-1-hydroxy-ethyl)-phenyl]-methanesulfonamide (1.03 g, 2 mmol) (which was obtained in Example 7) and 10% palladium on carbon (Pd/C)(0.4 g) in methanol (100 mL) at room temperature was added anhydrous ammonium formate ($HCO_2NH_4$)(1.26 g, 20 mmol) under a nitrogen atmosphere. The resulting mixture was refluxed for 2 hours. After cooling to room temperature the catalyst was removed by filtration through a celite pad and washed with methanol. The filtrate is evaporated under reduced pressure to give the title compound (Leclerc, G., Bizec, J. C. *J. Med. Chem.*, 1980, 23,738) as a pale yellowish solid; $^1$H NMR (300 MHz, DMSO-d$_6$) δ 2.62 (dd, J=12.6, 8.7 Hz, 1H), 2.75 (dd, J=12.6, 3.7 Hz, 1H), 2.90 (s, 3H), 4.47 (dd, J=8.7, 3.7 Hz, 1H), 6.84 (d, J=9.1 Hz, 1H), 6.96 (dd, J=9.1, 2.0 Hz, 1H), 7.16 (d, J=2.1 Hz, 1H), 8.44 (s, 1H); MS (ES) m/z: 246.7 (MH$^+$); HRMS Calcd. for C$_9$H$_{14}$N$_2$O$_4$S(M$^+$): 246.0674. Found: 246.0672.

EXAMPLE 10

N-[5-(2-Amino-(1R)-1-hydroxy-ethyl)-2-hydroxy-phenyl]-methanesulfonamide

Method A: A mixture of N-{2-benzyloxy-5-(2-iodo-(1R)-1-[(triethylsilyl)oxy]-ethyl)-phenyl}-methanesulfonamide (EP 0 659 737) (8.60 g, 15.3 mmol) and benzylamine (21.4 g, 200 mmol) was heated at 60° C. for 24 hours. The reaction mixture was cooled, diluted with hexanes (500 mL), and the residue was washed with diethyl ether. The combined solvents were removed and the residue was purified by silica gel column eluting with 30 to 100% diethyl ether/hexanes. The fractions with molecular weight of 540 were concentrated and re-dissolved in 200 mL of THF and TBAF (20 mL, 1.0 M solution in THF) was added. After stirring at room temperature for 4 hours the reaction mixture was then poured into water and extracted with CH$_2$Cl$_2$. The organic layers were passed through a short pad of silica gel eluting with 10% methanol/CH$_2$Cl$_2$. The solvents were removed and the residue was dissolved in methanol (200 mL). 10% Pd/C (0.6 g) and anhydrous HCO$_2$NH$_4$ (6.3 g, 100 mmol) were added. The resulting mixture was refluxed under a nitrogen atmosphere for 2 hours. After cooling to room temperature the catalyst was removed by filtration through a celite pad and washed with methanol. The filtrate was evaporated under reduced pressure to give the title compound as an off-white solid; $^1$H NMR (300 MHz, MeOH-d$_4$) δ 2.95 (s, 3H), 2.99 (dd, J=9.7, 9.2 Hz, 1H), 3.07 (dd, J=9.7, 3.6 Hz, 1H), 4.75 (dd, J=9.2, 3.6 Hz, 1H), 6.90 (d, J=8.3 Hz, 1H), 7.12 (dd, J=8.3, 2.1 Hz, 1H), 7.38 (d, J=2.1 Hz, 1H), 8.44 (s, 1H); MS (ES) m/z: 246.7 (MH$^+$); HRMS Calcd. for C$_9$H$_{14}$N$_2$O$_4$S: 246.0674. Found: 246.0672.

Method B: To a stirred solution of N-[2-benzyloxy-5-(2-bromo-1-hydroxy-ethyl)-phenyl]-methanesulfonamide (EP 0 659 737) (15.05 g, 0.376 mol) in dimethyl sulfoxide (300 MHz, DMSO-d$_6$) (150 mL) was added sodium iodide (3.76 g, 0.376 mol) and sodium azide (9.48 g, 0.150 mol). The mixture was stirred for 5 days under nitrogen atmosphere. The reaction mixture was poured onto water and extracted three times with ethyl acetate. The combined organic layers were dried over sodium sulfate and concentrated. The residue was triturated with water and hexanes. Recovered yellow solid as of N-[5-((1R)-2-azido-1-hydroxy-ethyl)-2-benzyloxy-phenyl]-methanesulfonamide (12.85 g, 94%); $^1$H NMR (300 MHz, CDCl$_3$) δ 2.93(s, 3H), 3.45 (d, J=9.0 Hz, 2H), 3.46 (m, 1H), 5.11 (s, 2H), 6.80 (s, 1H), 6.99 (d, J=8.4 Hz, 1H), 7.15 (dd, J=6 Hz, 2.1 Hz, 1H), 7.26 (s, 1H), 7.39 (s, 5H), 7.53 (d, J=2.1 Hz, 1H); MS (ES) m/z: 361.4 ((M−H)$^−$, 70%). A mixture of N-[5-((1R)-2-azido-1-hydroxy-ethyl)-2-benzyloxy-phenyl]-methanesulfonamide (12.85 g, 0.037 mol) and 10% Pd/C (2.75 g) in ethanol (100 mL) was hydrogenated under 45 psi for two days. The reaction mixture was filtered through celite and concentrated. The title compound was recovered as a tan solid. The product was found to be identical with that prepared by method A.

EXAMPLE 11

8-Benzyloxy-(5S)-5-oxiranylmethoxy-3,4-dihydro-1H-quinolin-2-one

The title compound was prepared from 8-benzyloxy-5-hydroxy-3,4-dihydro-1H-quinolin-2-one (Tominaga, M., Ogawa, H., Yo, E., Yamashita, S., Yabuuchi, Y., Nakagawa, K. *Chem. Pharm. Bull.* 1987, 35, 3699) according to the procedure of Example 2; $^1$H NMR (300 MHz, DMSO-d$_6$) δ 2.41 (t, J=7.1 Hz, 2H), 2.69 (dd, J=5.1, 2.7 Hz, 1H), 2.75–2.86 (m, 4H), 3.78 (dd, J=11.4, 6.3 Hz, 1H), 4.23 (dd, J=11.4, 2.6 Hz, 1H), 5.09 (s, 2H), 6.54 (d, J=9.0 Hz, 2H), 6.86 (d, J=9.0 Hz, 2H), 7.25–7.45 (m, 3H), 7.51 (d, J=8.2 Hz, 2H), 9.08 (s, 1H); MS (ES) m/z: 326.0 (MH$^+$); HRMS Calcd. for C$_{19}$H$_{20}$NO$_4$(MH$^+$): 326.1392. Found: 326.1343. Anal. Calcd. for C$_{19}$H$_{19}$NO$_4$: C, 70.14; H, 5.89; N, 4.30. Found: C, 70.14; H, 5.69; N, 4.20.

EXAMPLE 12

5-(3-Amino-(2S)-2-hydroxy-propoxy)-8-hydroxy-3,4-dihydro-1H-quinolin-2-one

Dibenzylamine (1.46 g, 7.4 mmol) was added to a stirred solution of 8-benzyloxy-(5S)-5-oxiranylmethoxy-3,4-dihydro-1H-quinolin-2-one (which was obtained in Example 11) (2.0 g, 6.2 mmol) in 100 mL of methanol. After refluxing overnight the mixture was cooled down to room temperature and 10% Pd/C (0.5 g) and HCO$_2$NH$_4$ (3.15 g, 50 mmol) were added. The suspension was refluxed for another hour. After cooling the suspension the reaction mixture was filtered through celite. The filtrate was concentrated to give the title compound as a pale grey solid; $^1$H NMR (300 MHz, DMSO-d$_6$) δ 2.42 (t, J=7.1 Hz, 2H), 2.74 (dd, J=12.8, 8.2 Hz, 1H), 2.81 (t, J=7.0 Hz, 2H), 2.95 (dd, J=12.8, 3.4 Hz, 1H), 3.65–3.95 (m, 3H), 6.45 (d, J=8.8 Hz, 2H), 6.62 (d, J=8.8 Hz, 2H), 8.38 (s, 1H), 8.77 (brs, 1H); MS (ES) m/z: 252.9 (MH$^+$)); HRMS Calcd. for C$_{12}$H$_{16}$N$_2$O$_4$ (M$^+$): 252.1188. Found: 252.1199.

EXAMPLE 13

N-Benzyl-N-(2-benzyloxy-5-oxiranylmethoxy-phenyl)-methanesulfonamide

The title compound was prepared from N-benzyl-N-(2-benzoxy-5-hydroxy-phenyl)-methanesulfonamide (Kaiser, C.; Jen, T.; Garvey, E.; and Bowen, W. D. *J. Med. Chem.* 1977, 20, 687) according to the procedure of Example 2 as a white solid; $^1$H NMR (300 MHz, DMSO-d$_6$) δ 2.63(dd, J=5.1, 2.6 Hz, 1H), 2.80 (t, J=4.9 Hz, 1H), 3.10–3.20 (m, 1H), 3.66 (dd, J=11.4, 6.6 Hz, 1H), 4.16 (dd, J=11.4, 2.6 Hz, 1H), 4.73 (brs, 2H), 5.12 (s, 2H), 6.69 (d, J=3.1 Hz, 1H), 6.88 (dd, J=9.1, 3.1 Hz, 1H), 7.08 (d, J=9.1 Hz, 1H), 7.15–7.60 (m, 10H); MS (ES) m/z: 439.9 (MH$^+$, 100%); HRMS Calcd. for C$_{24}$H$_{25}$NO$_5$S(M$^+$): 439.1454. Found: 439.1457.

EXAMPLE 14

N-[5-((2S)-3-Amino-2-hydroxy-propoxy)-2-hydroxy-phenyl]-methanesulfonamide

The title compound was prepared from N-benzyl-N-(2-benzyloxy-5-oxiranylmethoxy-phenyl)-methanesulfonamide (which was obtained in Example 13) according to the procedure of Example 12 as a pale grey solid; $^1$H NMR (300 MHz, DMSO-d$_6$) δ 2.61 (dd, J=12.7, 6.1 Hz, 1H), 2.75 (dd, J=12.7, 3.5 Hz, 1H), 2.86 (s, 3H), 3.69–3.90 (m, 3H), 6.55

(dd, J=8.7, 3.1 Hz, 1H), 6.70 (d, J=8.7 Hz, 1H), 6.75 (d, J=3.1 Hz, 1H); MS (ES) m/z: 276.8 (MH$^+$, 100%); HRMS Calcd. for $C_{10}H_{16}N_2O_5S(M^+)$: 276.0780. Found: 276.0792.

EXAMPLE 15

Benzoic acid 4-benzyloxy-3-nitro-phenyl ester

A mixture of benzoic acid 4-hydroxy-3-nitro-phenyl ester (Tapia, R.; Torres, G. and Valderrama, J. A. *Synth. Commun.* 1986, 16, 681) (20.7 g, 80 mmol), benzyl bromide (42.75 g, 250 mmol), potassium carbonate (48.3 g, 350 mmol) and DMF (300 mL) was stirred at room temperature for 2 days. After removing the solvent the residue was dissolved in water and extracted with $CH_2Cl_2$. The organic extracts were dried ($MgSO_4$) and concentrated. The product was purified by flash silica gel chromatography eluting with $CH_2Cl_2$ to give the title compound as a pale yellowish solid (25.1 g, 90%); $^1$H NMR (300 MHz, $CDCl_3$) δ 5.27(s, 2H), 7.17 (d, J=9.1 Hz, 1H), 7.30–7.55 (m, 8H), 7.60–7.70 (m, 1H), 7.80 (d, J=2.9 Hz, 1H), 8.15–8.25 (m, 2H); MS (ES) m/z: 345.0 (MH$^+$, 100%); HRMS Calcd. for $C_{20}H_{15}NO_5$ (M$^+$): 349.0951. Found: 349.0952.

EXAMPLE 16

Benzoic acid 3-amino-4-benzyloxy-phenyl ester

A Parr hydrogenator was charged with platinum(IV) oxide($PtO_2$) (0.3 g) and a solution of benzoic acid 4-benzyloxy-3-nitro-phenyl ester (5.23 g, 15 mmol) (which was obtained in Example 15) in methanol (80 mL) and $CH_2Cl_2$(40 mL). This mixture was then hydrogenated at 5 psi of hydrogen at 0~10° C. for 2 hours. The reaction mixture was filtered through a short pad of celite and concentrated. Recrystallization from $CH_2Cl_2$/hexanes gave the title compound as a white solid (3.80 g, 79%); $^1$H NMR (300 MHz, $CDCl_3$) δ 5.09 (s, 2H), 6.57 (dd, J=10.1, 2.7 Hz, 1H), 7.10 (d, J=2.7 Hz, 1H), 7.30–7.50 (m, 8H), 7.55–7.65 (m, 1H), 8.15–8.25 (m, 2H); MS (ES) m/z: 320.0 (MH$^+$, 100%); HRMS Calcd. for $C_{20}H_{18}NO_3$ (MH$^+$): 320.1281. Found: 320.1278.

EXAMPLE 17

Benzoic acid 3-benzenesulfonylamino-4-benzyloxy-phenyl ester

To a stirred solution of benzoic acid 3-amino-4-benzyloxy-phenyl ester (5.91 g, 18.5 mmol) (which was obtained in Example 16) in ethyl acetate (100 mL) and pyridine (20 mL) at 0° C. was added dropwise phenyl sulfonyl chloride (3.26 g, 18.5 mmol) in 50 mL of ethyl acetate. After one hour at 0° C. the mixture was warmed to room temperature and stirred at room temperature over night. The reaction mixture was washed with water and the organic layer was dried ($MgSO_4$) and concentrated. Recrystallization from $CH_2Cl_2$/hexanes gave the title compound as a white solid (4.65 g, 61%); $^1$H NMR (300 MHz, $CDCl_3$) δ 4.93 (s, 2H), 6.90–7.80 (m, 15H), 8.12 (d, J=8.5 Hz, 2H), 9.81 (s, 1H); MS (ES) m/z: 458.9 (MH$^+$, 100%); HRMS Calcd. for $C_{26}H_{22}NO_5S(MH^+)$: 459.1141. Found: 459.1151.

EXAMPLE 18

Benzoic acid 3-(benzenesulfonyl-benzyl-amino)-4-benzyloxy-phenyl ester

To a stirred solution of benzoic acid 3-benzenesulfonylamino-4-benzyloxy-phenyl ester (which was obtained in Example 17) (2.88 g, 7.27 mmol) in DMF (20 mL) was added 60% sodium hydride (0.32 g, 8 mmol). After hydrogen evolution had subsided the stirred mixture was heated at 70° C. for 15 minute, and then it was cooled down to room temperature and a solution of benzyl chloride (1.01 g, 8 mmol) in 5 mL of DMF was added dropwise. The mixture was then heated at 85–90° C. for 2 hours, then it was cooled down to room temperature, poured into ice-water. The aqueous layer was extracted with ethyl acetate and the organic layer was dried and concentrated. The product was purified by flash silica gel chromatography eluting with ethyl acetate and hexanes to give the title compound as a white solid (2.40 g, 70%); $^1$H NMR (300 MHz, $CDCl_3$) δ 4.74 (s, 2H), 4.83 (s, 2H), 8.83 (d, J=8.9 Hz, 1H), 8.10–8.50 (m, 2H); HRMS Calcd. for $C_{33}H_{28}NO_5S(MH^+)$: 550.1688. Found: 550.1680.

EXAMPLE 19

N-Benzyl-N-(2-benzyloxy-5-hydroxy-phenyl)-benzenesulfonamide

To a stirred solution of benzoic acid 3-(benzenesulfonyl-benzyl-amino)-4-benzyloxy-phenyl ester (which was obtained in Example 18) (1.80 g, 3.28 mmol) in THF (10 mL) and methanol (10 mL) was added 10% of sodium hydroxide (10 mL). The mixture was stirred at room temperature for 1.5 hours, acidified with concentrated hydrochloric acid and diluted with water (200 mL). The aqueous solution was extracted with $CH_2Cl_2$. The organic phase was dried over $MgSO_4$ and concentrated. The product was purified by flash silica gel chromatography eluting with ethyl acetate and hexanes to give the title compound as a white solid (1.20 g, 82%); $^1$H NMR (300 MHz, $CDCl_3$) δ 4.71 (brs, 4H), 6.49 (d, J=3.0 Hz, 1H), 6.62(dd, J=9.0, 3.0 Hz, 1H), 6.84 (d, J=9.0 Hz, 1H), 7.10–7.70 (m, 15H), 9.07 (brs, 1H); MS (ES) m/z: 444.0 ((M−H)$^-$, 100%); HRMS Calcd. for $C_{26}H_{22}NO_4S(M-H)^-$: 444.1275. Found: 444.1270.

EXAMPLE 20

N-Benzyl-N-(2-benzyloxy-5-oxiranylmethoxy-phenyl)-benzenesulfonamide

The title compound was prepared from N-benzyl-N-(2-benzyloxy-5-hydroxy-phenyl)-benzenesulfonamide (which was obtained in Example 19) according to the procedure of Example 2 as a white solid; $^1$H NMR (300 MHz, $CDCl_3$) δ 2.68 (dd, J=4.9, 2.7 Hz, 1H), 2.85 (t, J=4.7 Hz, 1H), 3.20–3.30 (m, 1H), 3.76 (dd, J=11.0, 5.7 Hz, 1H), 4.05 (dd, J=11.0, 3.1 Hz, 1H), 4.65 (s, 2H), 4.81 (brs, 2H), 6.65–6.80 (m, 3H), 7.05–7.15 (m, 2H), 7.15–7.50 (m, 11H), 7.65–7.75 (m, 2H); HRMS Calcd. for $C_{29}H_{28}NO_5S(MH^+)$: 502.1689. Found: 502.1675.

EXAMPLE 21

N-[5-(3-Amino-2-hydroxy-propoxy)-2-hydroxy-phenyl]-benzenesulfonamide

The title compound was prepared from N-benzyl-N-(2-benzyloxy-5-oxiranylmethoxy-phenyl)-benzenesulfonamide (which was obtained in Example 20) according to the procedure of Example 12 as a brown solid; $^1$H NMR (300 MHz, $CDCl_3$) δ 3.40–4.20 (m, 5H), 6.40–7.00 (m, 3H), 7.10–7.60 (m, 3H), 7.60–7.80 (m, 2H), 8.15 (brs, 1H); MS (ES) m/z: 338.8 (MH$^+$, 100%); HRMS Calcd. for $C_{15}H_{19}N_2O_5S(MH^+)$: 339.1009. Found: 339.1004.

EXAMPLE 22

5-Acetyl-2-chloro-phenylaniline

To a stirred solution of 4-chloro-3-nitroacetophenone (10 g, 50 mmol) in concentrated hydrochloric acid (150 mL) was added tin chloride dihydrate (33.8 g, 150 mmol). The mixture was stirred at room temperature for one day, basified with 28% of ammonium hydroxide and diluted with water (1 L). The aqueous solution was extracted with methylene chloride. The organic phase was dried over $MgSO_4$ and concentrated. Recrystallization from $CH_2Cl_2$/hexanes gave the title compound as a yellowish crystal (7.0 g, 83%); $^1H$ NMR (300 MHz, $CDCl_3$) δ 2.55 (s, 3H), 4.19 (brs, 2H), 7.22–7.38 (m, 3H); MS (ES) m/z: 169.8 (MH$^+$, 100%); HRMS Calcd. for $C_8H_9ClNO$ (MH$^+$): 170.3667. Found: 170.0368.

EXAMPLE 23

N-(5-Acetyl-2-chloro-phenyl)-methanesulfonamide

To a stirred solution of 5-acetyl-2-chloro-phenylaniline (which was obtained in Example 22) (7.40 g, 43.5 mmol) in $CH_2Cl_2$ (200 mL) and pyridine (40 mL) at 0~5° C. was added dropwise methanesulfonyl chloride (5.0 g, 43.6 mmol) in 50 mL of $CH_2Cl_2$. After 1 hour at 0° C. the mixture was warmed to room temperature and stirred at room temperature for another hour. The solvents were removed and the residue was dissolved in $CH_2Cl_2$(500 mL). The reaction mixture was washed with water and the organic layer was dried ($MgSO_4$) and concentrated. The product was purified by flash silica gel chromatography eluting with ethyl acetate and hexanes to give the title compound as a white solid (6.1 g, 57%); $^1H$ NMR (300 MHz, DMSO-$d_6$) δ 2.58 (s, 3H), 3.08 (s, 3H), 7.69 (d, J=8.3 Hz, 1H), 7.83 (dd, J=8.3, 2.1 Hz, 1H), 7.94 (d, J=2.1 Hz, 1H), 9.69 (s, 1H); MS (ES) m/z: 245.9 ((M–H)$^-$, 100%); HRMS Calcd. for $C_9H_{11}ClNO_3S$(MH$^+$): 248.0148. Found: 248.0135.

EXAMPLE 24

N-(5-Bromoacetyl-2-chloro-phenyl)-methanesulfonamide

A mixture of N-(5-acetyl-2-chloro-phenyl)-methanesulfonamide (2.47 g, 10 mmol) (which was obtained in Example 23) and copper(II) bromide (11.17 g, 50 mmol) in chloroform (150 mL) was refluxed for 5 hours. After cooling down to room temperature the solid was filtered off and the solution was concentrated. Recrystallization from chloroform/diethyl ether gave the title compound as a white solid (3.10 g, 96%); $^1H$ NMR (300 MHz, $CDCl_3$) δ 3.09 (s, 3H), 4.42 (s, 2H), 6.91 (brs, 1H), 7.58 (d, J=8.4 Hz, 1H), 7.77 (dd, J=8.4, 2.1 Hz, 1H), 8.24 (d, J=2.1 Hz, 1H); MS (ES) m/z: 323.7 ((M–H)$^-$, 100%); HRMS Calcd. for $C_9H_{10}BrClNO_3S$(MH$^+$): 325.9249. Found: 325.9245.

EXAMPLE 25

N-[5-((1R)-2-Azido-1-hydroxy-ethyl)-2-chloro-phenyl]-methanesulfonamide

R-2-Methyl-CBS-oxazaborolidine (1.0 M in THF, 2 mL, 2 mmol) in 50 mL of THF was added slowly to a stirred solution of borane-THF complex (1.0 M in THF, 12 mL, 12 mmol) at room temperature. The mixture was stirred for 30 minutes and then N-(5-bromoacetyl-2-chloro-phenyl)-methanesulfonamide (which was obtained in Example 24) (2.80 g, 8.6 mmol) in 50 mL of THF was added dropwise. Upon stirring over night hydrochloride (1.0 M solution in diethyl ether) was added until the pH was ~1. After stirring for one hour the reaction mixture was partitioned between ethyl acetate and water. The organic phase was dried over $MgSO_4$ and concentrated. The residue was then dissolved in 50 mL of DMSO. To the solution sodium azide (2.93 g, 45 mmol) and sodium iodide (3 g, 20 mmol) were added. After stirring at room temperature for 3 days the reaction was quenched with water, extracted with diethyl ether. The organic layer was dried over $MgSO_4$ and concentrated. The product was purified by flash silica gel chromatography eluting with ethyl acetate and hexanes to give the title compound as a white solid (1.6 g, 64%); $^1H$ NMR (300 MHz, $CDCl_3$) δ 2.60 (d, J=5.9 Hz, 1H), 3.06 (s, 3H), 3.45–3.50 (m, 2H), 4.85–4.95 (m, 1H), 6.84 (brs, 1H), 7.22 (dd, J=8.3, 2.0 Hz, 1H), 7.44 (d, J=8.3 Hz, 1H), 7.65 (d, J=2.0 Hz, 1H); MS (ES) m/z: 288.9 ((M–H)$^-$, 100%); HRMS Calcd. for $C_9H_{12}ClN_4O_3S$(M$^+$): 290.0241. Found: 290.0228.

EXAMPLE 26

Propane-2-sulfonic acid (5-acetyl-2-benzyloxy-phenyl)-amide

To a stirred solution of 1-(3-amino-4-benzyloxy-phenyl)-ethanone (EP 0 659 737) (30 g, 125.0 mmol) in $CH_2Cl_2$ (500 mL) and pyridine (250 mL) was added dropwise isopropyl-sufonyl chloride (28.6, 200 mmol) at room temperature. The reaction was stirred for 3 days under nitrogen atmosphere. The mixture was diluted with $CH_2Cl_2$ (700 mL) and washed with 1N hydrochloric acid, water, dried over $Na_2SO_4$, and concentrated. The product was purified by flash silica gel chromatography eluting with ethyl acetate/hexanes to give the title compound as a white solid(13 g, 30%); $^1H$ NMR (300 MHz, $CDCl_3$) δ 1.35 (d, J=6.9 Hz, 6H), 2.56 (s, 3H), 3.25–3.45 (m, 1H), 5.18 (s, 2H), 6.75 (brs, 1H), 7.02 (d, J=8.6 Hz, 1H), 7.30–7.50 (m, 5H), 7.70 (dd, J=8.6, 2.1 Hz, 1H), 8.18 (d, J=2.1 Hz, 1H); MS (ES) m/z: 364.9 ((M+$NH_4$)$^+$, 100%); HRMS Calcd. for $C_{18}H_{22}NO_4S$(MH$^+$): 348.1264. Found: 348.1259.

EXAMPLE 27

Propane-2-sulfonic acid [5-((1R)-2-amino-1-hydroxy-ethyl)-2-hydroxy-phenyl]-amide The title compound was prepared from propane-2-sulfonic acid (5-acetyl-2-benzyloxy-phenyl)-amide (which was obtained in Example 26) as described in the procedures of Example 25 and Example 10 as a white solid; $^1H$ NMR (300 MHz, DMSO-$d_6$) δ 1.26 (d, J=6.8 Hz, 6H), 2.74 (dd, J=12.6, 9.8 Hz, 1H), 2.92 (dd, J=12.6, 3.0 Hz, 1H), 3.10–3.20 (m, 1H), 4.63 (dd, J=9.8, 3.0 Hz, 1H), 6.85 (d, J=8.3 Hz, 1H), 7.01 (dd, J=8.3, 2.1 Hz, 1H), 7.27 (d, J=2.1 Hz, 1H); MS (ES) m/z: 274.8 (MH$^+$, 100%); HRMS Calcd. for $C_{11}H_{18}N_2O_4S$(MH$^+$): 274.0987. Found: 274.1004.

EXAMPLE 28

N-(5-Acetyl-2-benzyloxy-phenyl)-benzenesulfonamide

To a stirred solution of 1-(3-amino-4-benzyloxy-phenyl)-ethanone (EP 0 659 737) (16.98 g, 70.0 mmol) in pyridine (50 mL) was added dropwise benzenesulfonyl chloride (13.09 g, 73.5 mmol) in 100 mL of pyridine at room temperature. The reaction was stirred for 18 hours under nitrogen atmosphere. The mixture was diluted with $CH_2Cl_2$ (700 mL) and washed with 1N hydrochloric acid, water, dried over Na$_2$SO$_4$, and concentrated. The product was purified by flash silica gel chromatography eluting with CH$_2$Cl$_2$ to give the title compound as a tan solid (12.55 g, 47%); $^1$H NMR (300 MHz, DMSO-d$_6$) δ 3.33 (s, 3H), 5.03 (s, 2H), 7.02 (d, J=8.7 Hz, 1H), 7.35 (m, 3H), 7.44 (t, J=15 Hz, 2H), 7.58 (m, 1H), 7.50 (m, 3H), 7.81 (d, 1H), 9.83 (s, 1H); MS (ES) m/z: 381.9 (MH$^+$, 100%); HRMS Calcd. for C$_{21}$H$_{19}$NO$_4$S(MH$^+$): 382.1107. Found: 382.1100.

EXAMPLE 29

N-(2-Benzyloxy-5-bromoacetyl-phenyl)-benzenesulfonamide

A mixture of N-(5-acetyl-2-benzyloxy-phenyl)-benzenesulfonamide (which was obtained in Example 28) (1.0 g, 2.6 mmol) and copper (II) bromide (0.99 g, 4.4 mmol) in chloroform/ethyl acetate (45 mL) was refluxed under nitrogen atmosphere for 18 hours. Reaction mixture was filtered through celite and the filtrate was concentrated. Recrystallization from ethyl acetate gave the titled compound as a white solid (0.64 g, 53%); $^1$H NMR (300 MHz, DMSO-d$_6$) δ 4.79 (s, 2H), 5.06 (s, 2H), 7.05 (m, 1H), 7.33 (m, 5H), 7.43 (t, J=12 Hz, 2H), 7.58 (m, 1H), 7.69 (d, J=3 Hz, 2H), 7.86 (m, 2H) 9.89 (s, 1H); MS (ES) m/z: 459.8 (MH$^+$, 85%); HRMS Calcd. for C$_{21}$H$_{18}$BrNO$_4$S(MH$^+$): 460.0213. Found: 460.0212.

EXAMPLE 30

N-(2-Benzyloxy-5-(2-bromo-1-hydroxy-ethyl-phenyl)-benzenesulfonamide

R-2-Methyl-CBS-oxazaborolidine (1.0 M in THF, 0.54 mL, 0.54 mmol) was added slowly to to a stirred solution of borane-THF complex (1.0 M in THF, 3.23 mL, 3.23 mmol) at room temperature. The mixture was stirred for an additional 20–30 minutes. N-(2-benzyloxy-5-bromoacetyl-phenyl)-benzenesulfonamide (which was obtained in Example 29) (2.48 g, 5.4 mmol) in THF (40 mL) was added dropwise to the mixture. The reaction was stirred an additional 18 hours. The reaction was cooled to 0° C. and quenched with 1N hydrochloric acid. The mixture was stirred at 0° C. for one hour. The mixture was partitioned between water and ethyl acetate, dried over MgSO$_4$, and concentrated. The product was purified by flash silica gel chromatography eluting with 1% methanol in CH$_2$Cl$_2$ to give the titled compound (1.52 g, 61%); $^1$H NMR (300 MHz, CDCl$_3$) δ 2.56 (d, J=6 Hz, 1H), 3.53 (m, 2H), 4.86 (s, 2H), 6.77 (d, J=6 Hz, 1H), 7.13 (m, 4H), 7.35 (m, 4H), 7.53 (m, 1H), 7.59 (d, J=2.1 Hz, 1H), 7.69 (m, 2H); MS (ES) m/z: 459.9 ((M–H)$^-$, 100%); HRMS Calcd. for C$_{21}$H$_{20}$BrNO$_4$S (MH$^+$): 462.0369. Found: 462.0366.

EXAMPLE 31

N-[5-((1R)-2-Azido-1-hydroxy-ethyl)-2-benzyloxy-phenyl]-benzenesulfonamide

To a stirred solution of N-(2-benzyloxy-5-(2-bromo-1-hydroxy-ethyl-phenyl)-benzenesulfonamide (1.52 g, 3.3 mmol) (which was obtained in Example 30) in dimethyl-sulfoxide under nitrogen atmosphere was added sodium iodide (0.5 g, 3.3 mmol) and sodium azide (0.86 g, 13.2 mmol). The reaction was stirred for three days at room temperature. The reaction mixture was poured onto water, extracted with ethyl acetate three times, dried over magnesium sulfate, and concentrated to give the titled compound as an oil; $^1$H NMR (300 MHz, CDCl$_3$) δ 3.43 (m, 2H), 4.79 (m, 1H), 4.86 (s, 2H), 6.76 (d, J=9 Hz, 1H), 7.06 (m, 2H), 7.13 (m, 2H), 7.35 (m, 4H), 7.57 (m, 2H), 7.69 (d, J=9 Hz, 2H).

EXAMPLE 32

N-[5-((1R)-2-Amino-1-hydroxy-ethyl)-2-hydroxy-phenyl]-benzenesulfonamide

A mixture of N-[5-((1R)-2-azido-1-hydroxy-ethyl)-2-benzyloxy-phenyl]-benzenesulfonamide (1.4 g, 3.3 mmol) (which was obtained in Example 31), HCO$_2$NH$_4$ (2.08 g, 3.3 mmol), and 10% Pd/C in absolute ethanol (15 mL) under nitrogen atmosphere was heated under reflux for 2.5 hours. The mixture was cooled to room temperature, filtered through celite pad, and filtrate concentrated and placed under high vacuum to give the titled compound as yellow solid (0.7 g, 69%); $^1$H NMR (300 MHz, DMSO-d$_6$) δ 2.74 (d, J=15 Hz, 2H), 4.51 (d, J=6 Hz, 1H), 6.63 (d, J=9 Hz, 1H), 6.76 (d, J=9 Hz, 1H), 7.12 (s, 1H), 7.47 (m, 4H), 7.72 (d, J=6 Hz, 2H).

EXAMPLE 33

5-[4(1,4-Dioxa-8-aza-spiro[4.5]dec-8-yl)-benzylidene]-2-thioxothiazolidin-4-one

A mixture of 4-(1,4-dioxa-8-aza-spiro[4.5]dec-8-yl)-benzaldehyde(Taylor, E. C., Skotnicki, J. S. *Synthesis,* 1981, 606) (4.96 g, 20 mol), rhodanine (2.66 g, 20 mmol), and β-alanine (2.0 g, 22.5 mmol) in 50 mL of acetic acid (AcOH) was refluxed for 2 hours. The solid which was formed on cooling the solution was collected to give the title compound as a red solid (4.8 g, 66%); $^1$H NMR (300 MHz, CDCl$_3$) δ 1.81 (t, J=5.5 Hz, 4H), 3.55 (t, J=5.5 Hz, 4H), 4.00 (s, 4H), 6.92 (d, J=8.9 Hz, 2H), 7.58 (d, J=8.9 Hz, 2H), 7.38 (s, 1H); MS (ES) m/z: 362.8 (MH$^+$); HRMS Calcd. for C$_{17}$H$_{19}$N$_2$O$_3$S$_2$ (MH$^+$): 363.0837. Found: 363.0852. Anal. Calcd. for C$_{17}$H$_{18}$N$_2$O$_3$S$_2$: C, 56.33; H, 5.01; N, 7.73. Found: C, 56.28; H, 4.89; N, 7.73.

EXAMPLE 34

1-[4-(4-Oxo-2-thioxo-thiazolidin-5-ylidenemethyl)-phenyl]-piperidine-4-one

5-[4(1,4-Dioxa-8-aza-spiro[4.5]dec-8-yl)-benzylidene]-2-thioxothiazolidin-4-one (which was obtained in Example 33) (0.9 g, 2.5 mmol) was treated with concentrated hydrochloric acid (25 mL) at room temperature. After 15 hours ~28% ammonium hydroxide (NH$_4$OH) was added dropwise and the precipitate was collected by filtration, and dried over phosphorus pentoxide (P$_2$O$_5$) to give the title compound as a red solid (0.71 g, 89%); $^1$H NMR (300 MHz, DMSO-d$_6$) δ 2.46 (t, J=6.1 Hz, 4H), 3.79 (t, J=6.1 Hz, 4H), 7.11 (d, J=9.0 Hz, 2H), 7.48 (d, J=9.0 Hz, 2H), 7.56 (s, 1H); MS (ES) m/z: 316.9 (M–H)$^-$; HRMS Calcd. C$_{15}$H$_{14}$N$_2$O$_2$S$_2$ (M$^+$): 318.0497. Found: 318.0502.

EXAMPLE 35

5-[4-(1,4-Dioxa-8-aza-spiro[4.5]dec-8-yl)-benzylidene]-thiazolidine-2,4-dione

A mixture of 4-(1,4-dioxa-8-aza-spiro[4.5]dec-8-yl)-benzaldehyde benzaldehyde (Taylor, E. C., Skotnicki, J. S. *Synthesis,* 1981, 606) (15 g, 60 mol), 2,4-thiazolidinedione (7.0 g, 60 mmol), and piperidine (8.0 mL, 81.2 mmol) in 450 mL of ethanol was refluxed for 6 hours. The solid which was formed on cooling the solution was collected to give the title compound as an orange solid (20.5 g, 99%); $^1$H NMR (300 MHz, DMSO-d$_6$) δ 1.67 (t, J=5.6 Hz, 4H), 3.47 (t, J=5.6 Hz, 4H), 3.92 (s, 4H), 7.07 (d, J=9.0 Hz, 2H), 7.43 (d, J=9.0 Hz, 2H), 7.67 (s, 1H), 12.40 (brs, 1H); MS (ES) m/z: 346.8 (MH$^+$); HRMS Calcd. for C$_{17}$H$_{19}$N$_2$O$_4$S(MH$^+$): 346.0987. Found: 346.0994. Anal. Calcd. for C$_{17}$H$_{18}$N$_2$O$_4$S: C, 58.94; H, 5.24; N, 8.09. Found: C, 58.92; H, 5.11; N, 7.96.

EXAMPLE 36

5-[4-(Oxo-piperidine-1-yl)-benzylidene]-thiazolidine-2,4-dione

The title compound was prepared from 5-[4-(1,4-dioxa-8-aza-spiro[4.5]dec-8-yl)-benzylidene]-thiazolidine-2,4-dione (which was obtained in example 35) according to the procedure of Example 34 as an orange solid; $^1$H NMR (300 MHz, DMSO-d$_6$) δ 2.45 (t, J=6.0 Hz, 4H), 3.76 (d, J=6.0 Hz, 4H), 7.10 (d, J=9.0 Hz, 2H), 7.48 (d, J=9.0 Hz, 2H), 7.70 (s, 1H), 12.41 (brs, 1H); MS (ES) m/z: 301.0 (M–H)$^-$; HRMS Calcd. for C$_{15}$H$_{14}$N$_2$O$_3$S(M$^+$): 302.0726. Found: 302.0731.

EXAMPLE 37

5-[4-(1,4-Dioxa-8-aza-spiro[4.5]dec-8-vy)-benzyl]-thiazolidine-2,4-dione

Method A: A solution of 5-[4-(1,4-dioxa-8-aza-spiro[4.5]dec-8-yl)-benzylidene]-thiazolidine-2,4-dione (which was obtained in Example 35) (8.0 g, 23 mmol) in acetic acid (75 mL) and THF (225 mL) was hydrogenated (40 psi hydrogen) in a Parr shaker over 10% Pd/C (8 g) over 4 days. The catalyst was removed by filtration over celite and the solvent was evaporated. The product was purified by flash silica gel chromatography (hexanes/ethyl acetate) to give the title compound as an off-white solid; $^1$H NMR (300 MHz, DMSO-d$_6$) δ 1.68 (t, J=5.6 Hz, 4H), 2.76 (dd, J=14.1, 11.0 Hz, 1H), 3.22 (t, J=5.6 Hz, 4H), 3.30 (dd, J=14.1, 3.8 Hz, 1H), 3.91 (s, 4H), 4.50 (dd, J=11.0, 3.8 Hz, 1H), 6.86 (d, J=8.7 Hz, 2H), 7.04 (d, J=8.7 Hz, 2H); MS (ES) m/z: 349.3 (MH$^+$); HRMS Calcd. for C$_{17}$H$_{20}$N$_2$O$_4$S(M$^+$): 348.1144. Found: 348.1146. Anal. Calcd. for C$_{17}$H$_{20}$N$_2$O$_4$S: C, 58.60; H, 5.79; N, 8.04. Found: C, 58.42; H, 5.67; N, 7.86.

Method B: A mixture of 5-[4-(1,4-dioxa-8-aza-spiro[4.5]dec-8-yl)-benzylidene]-thiazolidine-2,4-dione (9.0 g, 25.9 mmol) (which was obtained in Example 35) and 5% sodium mercury amalgam (Na—Hg) (46 g, 100 mmol) in water (70 mL) and THF (200 mL) was stirred at room temperature overnight. The organic layer was decanted from mercury (Hg) and water. Evaporation of the solvent gave the title compound as an off-white solid. The product was found to be identical with that prepared by method A.

EXAMPLE 38

5-[4-(4-Oxo-piperidine-1-yl)-benzyl]-thiazolidine-2,4-dione

The title compound was prepared from 5-[4-(1,4-dioxa-8-aza-spiro[4.5]dec-8-yl)-benzyl]-thiazolidine-2,4-dione (which was obtained in Example 37) according to the procedure of Example 34 as an off-white solid; $^1$H NMR (300 MHz, DMSO-d$_6$) δ 2.40 (t, J=5.9 Hz, 4H), 3.01 (dd, J=14.1, 9.2 Hz, 1H), 3.29 (dd, J=14.1, 4.2 Hz, 1H), 3.57 (t, J=5.9 Hz, 4H), 4.86 (dd, J=9.2, 4.2 Hz, 1H), 6.96 (d, J=8.6 Hz, 2H), 7.10 (d, J=8.6 Hz, 2H); MS (ES) m/z: 304.8 (MH$^+$, 100%), 609.0 (2MH$^+$, 100%), 914.1 (3MH$^+$, 10%); HRMS Calcd. for C$_{15}$H$_{16}$N$_2$O$_3$S(M$^+$): 304.0881. Found: 304.0905. Anal. Calcd. for C$_{15}$H$_{16}$N$_2$O$_3$S: C, 59.19; H, 5.36; N, 9.20. Found: C, 58.96; H, 5.16; N, 8.91.

EXAMPLE 39

5-[4-(1,4-Dioxa-8-aza-spiro[4.5]dec-8-yl)-benzylidene]-imidazolizidine-2,4-dione The title compound was prepared from 4-(1,4-dioxa-8-aza-spiro[4.5]dec-8-yl)-benzaldehyde benzaldehyde(Taylor, E. C., Skotnicki, J. S. *Synthesis*, 1981, 606) and hydantoin according to the procedure of Example 35 as an orange solid; $^1$H NMR (300 MHz, DMSO-d$_6$) δ 1.68 (t, J=5.8 Hz, 4H), 3.38 (t, J=5.8 Hz, 4H), 3.91 (s, 4H), 6.34 (s, 1H), 6.95 (d, J=8.7 Hz, 2H), 7.49 (d, J=8.7 Hz, 2H), 10.33 (brs, 1H), 11.05 (brs, 1H); MS (ES) m/z: 330.0 (MH$^+$); HRMS Calcd. for C$_{17}$H$_{20}$N$_3$O$_4$ (MH$^+$): 330.1454. Found: 330.1477.

EXAMPLE 40

5-[4-(1,4-Dioxa-8-aza-spiro[4.5]dec-8-yl)-benzyl]-imidazolizidine-2,4-dione

The title compound was prepared from 5-[4-(1,4-dioxa-8-aza-spiro[4.5]dec-8-yl)-benzylidene]-imidazolizidine-2,4-dione (which was obtained in Example 39) according to the procedure of Example 37 as an orange solid; $^1$H NMR (300 MHz, DMSO-d$_6$) δ 1.68 (t, J=5.7 Hz, 4H), 2.56 (dd, J=13.9, 6.8 Hz, 1H), 2.81 (dd, J=13.9, 4.1 Hz, 1H), 3.16 (t, J=5.7 Hz, 4 H), 3.74–3.85 (m, 1H), 3.90 (s, 4H), 6.82 (d, J=8.7 Hz, 2H), 6.96 (d, J=8.7 Hz, 2H), 8.32 (s, 2H); MS (ES) m/z: 331.9 (MH$^+$); HRMS Calcd. for C$_{17}$H$_{22}$N$_3$O$_4$ (MH$^+$): 332.1610. Found: 332.1639.

EXAMPLE 41

5-[4-(1,4-Dioxa-8-aza-spiro[4.5]dec-8-yl)-benzylidene]-2-imino-thiazolidin-4-one The title compound was prepared from 4-(1,4-dioxa-8-aza-spiro[4.5]dec-8-yl)-benzaldehyde benzaldehyde (Taylor, E. C., Skotnicki, J. S. *Synthesis*, 1981, 606) and pseudothiohydantoin according to the procedure of Example 35 as an orange solid; $^1$H NMR (300 MHz, DMSO-d$_6$) δ 1.68 (t, J=5.6 Hz, 4H), 3.43 (t, J=5.6 Hz, 4H), 3.91 (s, 4H), 7.06 (d, J=8.9 Hz, 2H), 7.41 (d, J=8.9 Hz, 2H), 7.48 (s, 1H), 8.99 (brs, 1H), 9.33 (brs, 1H); MS (ES) m/z: 345.9 (MH$^+$); HRMS Calcd. for C$_{17}$H$_{20}$N$_3$O$_3$S(MH$^+$): 346.1226. Found: 346.1205. Anal. Calcd. for C$_{17}$H$_{19}$N$_3$O$_3$S: C, 59.11; H, 5.54; N, 12.16. Found: C, 58.80; H, 5.71; N, 12.38.

EXAMPLE 42

5-[4-(4-Oxo-piperidine-1-yl)-benzylidene]-imidazolidine-2,4-dione

The title compound was prepared from 5-[4-(1,4-dioxa-8-aza-spiro[4.5]dec-8-yl)-benzylidene]-imidazolizidine-2,4-dione (which was obtained in Example 39) according to the procedure of Example 34 as a yellowish solid; $^1$H NMR (300 MHz, DMSO-d$_6$) δ 2.43 (t, J=6.0 Hz, 4H), 3.70 (t, J=6.0 Hz, 4H), 6.36 (s, 1H), 7.01 (d, J=9.0 Hz, 2H), 7.53 (d, J=9.0 Hz, 2 H), 10.35 (brs, 1H), 11.10 (brs, 1H); MS (ES) m/z: 285.9 (MH$^+$); HRMS Calcd. for C$_{15}$H$_{16}$N$_3$O$_3$ (MH$^+$): 286.1192. Found: 286.1169.

EXAMPLE 43

1-[4-(2-Imino-4-oxo-thiazolidin-5-ylidenemethyl)-phenyl]-piperidine-4-one

The title compound was prepared from 5-[4-(1,4-dioxa-8-aza-spiro[4.5]dec-8-yl)-benzylidene]-2-iminothiazolidin-4-one (which was obtained in Example 41) according to the procedure of Example 34 as a yellowish solid; $^1$H NMR (300 MHz, DMSO-d$_6$) δ 2.44 (t, J=6.0 Hz, 4H), 3.74 (t, J=6.0 Hz, 4H), 7.14 (d, J=6.7 Hz, 2H), 7.46 (d, J=6.7 Hz, 2H), 7.50 (s, 1H), 9.00 (brs, 1H), 9.24 (brs, 1H); MS (ES) m/z: 301.9 (MH$^+$).

EXAMPLE 44

5-[4-(4-Oxo-piperidine-1-yl)-benzyl]-imidazolidine-2,4-dione

The title compound was prepared from 5-[4-(1,4-dioxa-8-aza-spiro[4.5]dec-8-yl)-benzyl]-imidazolizolidine-2,4-dione (which was obtained in example 40) according to the procedure of Example 34 as an off-white solid; $^1$H NMR (300 MHz, DMSO-d$_6$) δ 2.39 (t, J=6.0 Hz, 4H), 2.83 (d, J=4.8 Hz, 2H), 3.55 (t, J=6.0 Hz, 4H), 4.25 (t, J=4.8 Hz, 1H), 6.92 (d, J=8.7 Hz, 2H), 7.05 (d, J=8.7 Hz, 2H), 7.91 (s, 1H); MS (ES) m/z: 287.9 (MH$^+$); HRMS Calcd. for C$_{15}$H$_{18}$N$_3$O$_3$ (MH$^+$): 288.1348. Found: 288.1396.

EXAMPLE 45

1-[4-(2-Imino-4-oxo-thiazolidin-5-ylmethyl)-phenyl]-piperidine-4-one

The title compound was prepared from 5-[4-(1,4-dioxa-8-aza-spiro[4.5]dec-8-yl)-benzylidene]-2-imino-thiazolidin-4-one (which was obtained in Example 41) according to the procedures of Example 37 and Example 34 as a yellowish solid; $^1$H NMR (300 MHz, DMSO-d$_6$) δ 2.40 (t, J=5.9 Hz, 4H), 2.79 (dd, J=14.2, 9.7 Hz, 1H), 3.28 (dd, J=14.2, 4.0 Hz, 1H), 3.56 (t, J=5.9 Hz, 4H), 4.54 (dd, J=9.7, 4.0 Hz, 1H), 6.92 (d, J=8.6 Hz, 2H), 7.10 (d, J=8.6 Hz, 2H), 8.68 (brs, 1H), 8.90 (brs, 1H); MS (ES) m/z: 303.9 (MH$^+$); HRMS Calcd. for C$_{15}$H$_{18}$N$_3$O$_2$S (MH$^+$): 304.1119. Found: 304.1113.

EXAMPLE 46

8-[4-(1H-Tetrazol-5-yl)-phenyl]-1,4-dioxa-8-aza-spiro[4.5]decane

A mixture of 4-(1,4-dioxa-8-azaspiro(4.5)dec-8-yl) benzonitrile benzaldehyde (Taylor, E. C., Skotnicki, J. S. Synthesis, 1981, 606) (10 mmol, 2.44 g), sodium azide (30 mmol, 1.95 g) and triethylamine hydrochloride (30 mmol, 4.13 g) in toluene was heated to ~95° C. over night (Koguro, K., Oga, T., Missui, S. and Orita, R. Synthesis, 1998, 910). After cooling the mixture was poured into water and the solid which was formed was collected. To the aqueous layer 36% hydrochloric acid was added dropwise to salt out more solid. The combined solids were dried to yield the title compound as an off-white solid (2.30 g, 80%); $^1$H NMR (300 MHz, DMSO-d$_6$) δ 1.70 (t, J=5.7 Hz, 4H), 3.44 (t, J=5.7 Hz, 4H), 3.92 (s, 4H), 7.12 (d, J=9.0 Hz, 2H), 7.85 (d, J=9.0 Hz, 2H); MS (ES) m/z: 288.4 (MH$^+$); HRMS Calcd. for C$_{14}$H$_{17}$N$_5$O (M$^+$): 287.1382. Found: 287.1375.

EXAMPLE 47

1-[4-(1H-Tetrazol-5-yl)-phenyl]-piperidine-4-one

The title compound was prepared from 8-[4-(1H-tetrazol-5-yl)-phenyl]-1,4-dioxa-8-aza-spiro[4.5]decane (which was obtained in Example 46) according to the procedures of Example 34 as a white solid; $^1$H NMR (300 MHz, DMSO-d$_6$) δ 2.45 (t, J=6.0 Hz, 4H), 3.75 (t, J=6.0 Hz, 4H), 7.18 (d, J=9.0 Hz, 2H), 7.91 (d, J=9.0 Hz, 2H); MS (ES) m/z: 244.0 (MH$^+$); HRMS Calcd. for C$_{12}$H$_{13}$N$_5$O (M$^+$): 243.1120. Found: 243.1120.

EXAMPLE 48

Ethyl {5-[4-(1,4-dioxa-8-azaspiro[4.5]dec-8-yl)phenyl]-2H-tetraazol-2-yl}acetate and ethyl{5-[4-(1,4-dioxa-8-azaspiro[4.5]dec-8-yl)phenyl]-1H-tetraazol-1-yl}acetate To a solution of 8-[4-(1H-tetrazol-5-yl)-phenyl]-1,4-dioxa-8-aza-spiro[4.5]decane (0.57 g, 2 mmol) (which was obtained in Example 46) in DMF (10 mL) was added cesium carbonate (0.81 g, 2.5 mmol) and ethyl iodoacetate (0.43 g, 2 mmol). The mixture was stirred at room temperature over night, then the reaction was quenched with water, extracted with ethyl acetate. The products from the organic phase was seperated by silica gel chromatography (ethyl acetate/hexanes) to yield ethyl{5-[4-(1,4-dioxa-8-azaspiro[4.5]dec-8-yl)phenyl]-2H-tetraazol-2-yl}acetate as a colorless crystal (0.55 g, 73%) and ethyl{5-[4-(1,4-dioxa-8-azaspiro[4.5]dec-8-yl)phenyl]-1H-tetraazol-1-yl}acetate as a gum (0.12 g, 16%).

Ethyl{5-[4-(1,4-dioxa-8-azaspiro[4.5]dec-8-yl)phenyl]-2H-tetraazol-2-yl}acetate: $^1$H NMR (300 MHz, CDCl$_3$) δ 1.23 (t, J=7.1 Hz, 3H), 1.84 (t, J=5.8 Hz, 4H), 3.45 (t, J=5.8 Hz, 4H), 4.00 (s, 4H), 4.28 (q, J=7.1 Hz, 2H), 5.42 (s, 2H), 7.01 (d, J=9.0 Hz, 2H), 8.02 (d, J=9.0 Hz, 2H); MS (ES) m/z: 374.3 (MH$^+$); HRMS Calcd. for C$_{18}$H$_{23}$N$_5$O$_4$ (M$^+$): 373.1750. Found: 373.1750.

Ethyl{5-[4-(1,4-dioxa-8-azaspiro[4.5]dec-8-yl)phenyl]-1H-tetraazol-1-yl}acetate: $^1$H NMR (300 MHz, CDCl$_3$) δ 1.26 (t, J=7.1 Hz, 3H), 1.79 (t, J=5.7 Hz, 4H), 3.49 (t, J=5.7 Hz, 4H), 4.00 (s, 4H), 4.26 (q, J=7.1 Hz, 2H), 5.19 (s, 2H), 7.00 (d, J=8.7 Hz, 2H), 7.54 (d, J=8.7 Hz, 2H); MS (ES) m/z: 374.3 (MH$^+$); HRMS Calcd. for C$_{18}$H$_{23}$N$_5$O$_4$ (M$^+$): 373.1750. Found: 373.1761.

EXAMPLE 49 tert-Butyl 2-{2,4-dioxo-5-[4-(4-oxo-1-piperidineyl) benzyl]-1,3-thiazolidin-3-yl}acetate Sodium hydride (60% in mineral oil, 66 mg, 1.65 mmol) was added into a mixture of 5-[4-(4-oxo-1-piperidineyl) benzyl]-1,3-thiazolidine-2,4-dione (500 mg, 1.65 mmol) (which was obtained in Example 38), and DMF. The mixture was stirred for 1 hour at room temperature, and then tert-butyl bromoacetate (0.36 mL, 2.47 mmol) was added. The new mixture was stirred for 30 minutes, poured into water, and extracted with ethyl acetate. The organic extracts were dried over MgSO$_4$. Evaporation and purification by flash chromatography (hexanes/ethyl acetate 3/1) gave a viscous oil (525 mg, 76% yield); $^1$H NMR (300 MHz, DMSO-d$_6$) δ 1.40 (s, 9H), 2.40 (m, 4H), 2.9 (m, 1H), 3.45 (m, 1H), 3.56 (m, 4H), 4.20 (s, 2H), 5.05 (m, 1H), 6.97 (m, 2H), 7.18 (m, 2H); MS (ES) m/z: 419 (MH$^+$); Anal. Calcd. for C$_{15}$H$_{16}$N$_2$O$_3$S : C, 60.27; H, 6.26; N, 6.69. Found: C, 60.21; H, 6.44; N, 6.52.

EXAMPLE 50

Ethyl 2-{2,4-dioxo-5-[4-(4-oxo-1-piperidineyl) benzyl]-1,3-thiazolidin-3-yl}acetate Sodium hydride (60% in mineral oil, 66 mg, 1.65 mmol) was added into a mixture of 5-[4-(4-oxo-1-piperidineyl) benzyl]-1,3-thiazolidine-2,4-dione (500 mg, 1.65 mmol) (which was obtained in Example 38) and DMF. The mixture was stirred for one hour at room temperature, and then ethyl bromoacetate (0.27 mL, 2.47 mmol) was added. The new mixture was stirred for 30 minutes, poured into water, and extracted with ethyl acetate. The organic extracts were dried over $MgSO_4$. Evaporation and purification by flash chromatography (hexanes/ethyl acetate 2/1) gave a viscous oil (295 mg, 46% yield); $^1$H NMR (300 MHz, DMSO-$d_6$) δ 1.20 (t, J=7.16 Hz, 3H), 2.40 (m, 4H), 2.95–3.00 (m, 1H), 3.4 (m, 1H), 3.60 (m, 2H), 4.10 (q, J=7.16 Hz, 2H), 4.30 (s, 2H), 6.97 (m, 2H), 7.16 (m, 2H); MS (ES) m/z: 391 (MH$^+$);

EXAMPLE 51

4-(1,4-Dioxa-8-azaspiro[4.5]dec-8-yl)benzaldehyde oxime

A solution of sodium acetate (6.64 g, 60.72 mmol) in water (10 mL) was added into a mixture of 4-(1,4-dioxa-8-azaspiro[4.5]dec-8-yl)benzaldehyde (5.0 g, 20.24 mmol) benzaldehyde(Taylor, E. C., Skotnicki, J. S. *Synthesis*, 1981, 606), hydroxylamine hydrochloride (4.22 g, 60.72 mmol), ethyl alcohol (300 mL), and water (50 mL). The mixture was stirred at 70° C. for 10 hours, then poured into water and extracted with ethyl acetate. The organic extracts were dried over $MgSO_4$. Evaporation and purification by flash chromatography (hexanes/ethyl acetate 2/1) gave a white solid (6.3 g, 90% yield); mp 151–152° C.; $^1$H NMR (400 MHz, DMSO-$d_6$) δ 1.63 (m, 4H), 3.35 (m, 4H), 3.90 (s, 4H), 6.96 (m, 2H), 7.40 (m, 2H), 7.96 (s, 1H), 10.75 (s, 1H); MS (ES) m/z: 263 (MH$^+$); Anal. Calcd. for $C_{14}H_{18}N_2O_3$: C, 64.11; H, 6.92; N, 10.68. Found: C, 64.24; H, 6.81; N, 10.64.

EXAMPLE 52

8-{4-[(Hydroxyamino)methyl]phenyl]-1,4-dioxa-8-azaspiro[4.5]decane

Hydrochloric acid (4N, in dioxane) was added dropwise into a mixture of 4-(1,4-dioxa-8-azaspiro[4.5]dec-8-yl) benzaldehyde oxime (5.3 g, 20.24 mmol) (which was obtained in Example 51), sodium cyanoborohydride (6.3 g, 101.2 mmol), methyl alcohol(200 mL), and methyl orange (10 mg), until an acidic solution (pH about 4) was achieved. The mixture was then stirred for 1 hour, poured into water, neutralized with NaOH (2N) and extracted with ethyl acetate. The organic extracts were dried over $MgSO_4$. Evaporation and purification by flash chromatography (hexanes/ethyl acetate/methyl alcohol 10/5/1) gave a white solid (4.2 g, 78% yield); mp 107–109° C.; $^1$H NMR (400 MHz, DMSO-$d_6$) δ 1.64 (m, 4H), 3.20 (m, 4H), 3.74 (s, 2H), 3.90 (s, 4H), 5.84 (brs, 1H), 6.86 (m, 2H), 7.14 (m, 2H), 7.19 (brs, 1H); MS (ES) m/z: 265 (MH$^+$).

EXAMPLE 53

N-[4-(1,4-Dioxa-8-azaspiro[4.5]dec-8-yl)benzyl]-N-hydroxyurea

Trimethylsilyl isocyanate (2.1 mL, 14.85 mmol) was added dropwise into a mixture of 8-{4-[(hydroxyamino) methyl]phenyl}-1,4-dioxa-8-azaspiro[4.5]decane (2.61 g, 9.9 mmol) (which was obtained in Example 52), THF (20 mL) and dioxane (20 mL). The mixture was stirred at room temperature for 24 hours, poured into water and extracted with ethyl acetate. The organic extracts were dried over $MgSO_4$. Evaporation and purification by flash chromatography (hexanes/ethyl acetate/methyl alcohol 10/5/1) gave a white solid (2.2 g, 73% yield); mp 153–154° C.; $^1$H NMR (400 MHz, DMSO-$d_6$) δ 1.70 (m, 4H), 3.21 (m, 4H), 3.89 (s, 4H), 4.37 (s, 2H), 6.23 (brs, 2H), 6.86 (m, 2H), 7.10 (m, 2H), 9.19 (s, 1H); MS (ES) m/z: 308 (MH$^+$); Anal. Calcd. for $C_{15}H_{21}N_3O_4$: C, 58.62; H, 6.89; N, 13.67. Found: C, 58.37; H, 6.78; N, 13.47

EXAMPLE 54

N-Hydroxy-N-[4-(4-oxo-1-piperidineyl)benzyl]urea

A mixture of N-[4-(1,4-dioxa-8-azaspiro[4.5]dec-8-yl) benzyl]-N-hydroxyurea (2.2 g, 7.16 mmol) (which was obtained in Example 53) and hydrochloric acid (concentrated, 10 mL) was stirred at room temperature for three days. The mixture was then neutralized with ammonium hydroxide, and extracted with ethyl acetate. The organic extracts were dried over $MgSO_4$. Evaporation and purification by flash chromatography (ethyl acetate) gave a white solid (1.86 g, 98% yield); mp 138–140° C.; $^1$H NMR (300 MHz, DMSO-$d_6$) δ 2.41 (m, 4H), 3.60 (m, 4H), 4.43 (s, 2H), 6.37 (brs, 2H), 7.03 (m, 2H), 7.21 (m, 2H), 9.31 (s, 1H); MS (ES) m/z: 264 (MH$^+$);

EXAMPLE 55

2-[4-(4-Oxo-1-piperidineyl)benzyl]-1,2,4-oxadiazolidine-3,5-dione

Sodium hydride (60% in mineral oil, 456 mg, 11.4 mmol) was added into a mixture of N-hydroxy-N-[4-(4-oxo-1-piperidineyl)benzyl]urea (1.5 g, 5.7 mmol) (which was obtained in Example 54), and THF (10 mL). The mixture was stirred at room temperature for 2 hours, and then methyl chloroformate (2.0 mL, 22.8 mmol) was added. The new mixture was stirred for 2 hours, poured into water, acidified with hydrochloric acid (2N) to pH about 6, and extracted with ethyl acetate. The organic extracts were dried over $MgSO_4$. Evaporation gave a yellow solid (1.58 g). Part of those material (460 mg, 1.43 mmol) was taken in DMF (4 mL) and treated with sodium hydride (60% in mineral oil, 57.3 mg, 1.43 mmol). The mixture was stirred for 1 hour, poured into water, acidified with hydrochloric acid (2N) and extracted with ethyl acetate. The organic extracts were dried over $MgSO_4$. Evaporation and purification by flash chromatography (hexanes/ethyl acetate 1/1) gave the title compound as a yellow solid (3.55 g, 85% yield); $^1$H NMR (300 MHz, DMSO-$d_6$) δ 2.42 (m, 4H), 3.62 (m, 4H), 4.76 (s, 2H), 7.1 (m, 2H), 7.23 (m, 2H), 12.43 (brs, 1H); MS (ES) m/z: 290 (MH$^+$).

EXAMPLE 56

3-Bromo-4-(1,4-dioxa-8-aza-spiro[4.5]dec-8-yl)-benzaldehyde

A mixture of 1,4-dioxa-8-azaspiro[4.5]decane (6.87 g, 48 mmol), 3-bromo-4-fluorobenzaldehyde (8.12 g, 40 mmol), and potassium carbonate (6.63 g, 48 mmol) in 1,3-dimethyl-3,4,5,6-tetrahydro-2(1H)-pyrimidinone (12 mL) and acetonitrile (8 mL) was heated at 80° C. under $N_2$ atmosphere for one day. Reaction mixture was cooled down to room temperature and poured onto water (150 mL). The mixture was extracted with methylene chloride. The organic layer was dried ($MgSO_4$) and concentrated to give the title compound as an off-white solid (12.4 g, 96%); mp 63–64° C.; $^1$H NMR (300 MHz, CDCl$_3$) δ 1.93 (t, J=5.7 Hz, 4H), 3.25 (t, J=5.4 Hz, 4H), 4.02 (s, 4H), 7.12 (d, J=4.2 Hz, 1H), 7.75 (dd, J=8.4, 2.1 Hz, 2H), 8.06 (d, J=1.8 Hz, 1H), 9.84 (s, 1H); MS (ES) m/z: 325.7 (MH$^+$); HRMS Calcd. for $C_{14}H_{16}BrNO_3$ (MH$^+$): 325.0314. Found: 325.0288.

EXAMPLE 57

5-[3-Bromo-4-(1,4-dioxa-8-aza-spiro[4.5]dec-8-yl)-benzvidenel-thiazolidine-2,4-dione The title compound was prepared from 3-bromo-4-(1,4-dioxa-8-aza-spiro[4.5]dec-8-yl)-benzaldehyde (which was obtained in Example 56), 2,4-thiazolidinedione and β-alanine according to the procedure of Example 33 as a yellow solid; mp 109–111° C.; $^1$H NMR (300 MHz, DMSO-d$_6$) δ 1.79 (t, J=5.1 Hz, 4H), 3.12 (m, 4H), 3.93 (s, 4H), 6.87 (d, J=8.7 Hz, 1H), 7.52–7.55 (m, 1H), 7.61 (s, 1H), 7.83–7.87 (m, 1H), 12.5 (s, 1H); MS (ES) m/z: 425.1 (MH$^+$).

EXAMPLE 58

5-[3-Bromo-4-(4-oxo-piperidine-1-yl)-benzylidene]-thiazolidine-2,4-dione

The title compound was prepared from 5-[3-bromo-4-(1,4-dioxa-8-aza-spiro[4.5]dec-8-yl)-benzylidene]-thiazolidine-2,4-dione (which was obtained in Example 57) according to the procedure of Example 34 as a yellow solid; mp >210° C.; $^1$H NMR (300 MHz, DMSO-d$_6$) δ 2.54 (t, J=4.5 Hz, 4H), 3.37 (t, J=4.5 Hz, 4H), 7.32 (d, J=6.3 Hz, 1H), 7.56 (dd, J=6.3, 1.5 Hz, 1H), 7.74 (s, 1H), 7.88 (d, J=1.5 Hz, 1H), 12.6 (s, 1H); MS (ES) m/z: 380.8 (MH$^+$); HRMS Calcd. for C$_{15}$H$_{14}$BrN$_2$O$_3$S(MH$^+$): 380.9909. Found: 380.9874.

EXAMPLE 59

4-(1,4-Dioxa-8-aza-spiro[4.5]dec-8-yl)-3-fluoro-benzaldehyde

The title compound was prepared from 1,4 dioxa-8-azaspiro[4.5]decane and 3,4-difluorobenzaldehyde according to the procedure of Example 56 as an orange oil; $^1$H NMR (300 MHz, CDCl$_3$) δ 1.88 (t, J=5.7 Hz, 4H), 3.35 (t, J=5.8 Hz, 4H), 4.01 (s, 4H), 6.96 (t, J=7.8 Hz, 1H), 7.47–7.49 (m, 1H), 7.53–7.58 (m, 1H), 9.81 (s, 1H); MS (ES) m/z: 265.8 (MH$^+$).

EXAMPLE 60

5-[4-(1,4-Dioxa-8-aza-spiro[4.5]dec-8-yl)-3-fluoro-benzylidene]-thiazolidine-2,4-dione The title compound was prepared from 4-(1,4-dioxa-8-aza-spiro[4.5]dec-8-yl)-3-fluoro-benzaldehyde (which was obtained in Example 59), 2,4 thiazolidinedione and β-alanine according to the procedure of Example 33 as an orange solid; mp 159–160° C.; $^1$H NMR (300 MHz, CDCl$_3$) δ 7.01 (m, 1H), 7.13–7.22 (m, 2H), 7.71–7.77 (m, 1H); MS (ES) m/z: 363.3 (M–H)$^-$.

EXAMPLE 61

5-[3-Fluoro-4-(4-oxo-piperidine-1-yl)-benzyl]-thiazolidine-2,4-dione

The title compound was prepared from 5-[4-(1,4-dioxa-8-aza-spiro[4.5]dec-8-yl)-3-fluoro-benzylidene]-thiazolidine-2,4-dione (which was obtained in Example 60) according to the procedures of Example 37 and Example 34 as a yellow solid; mp 129–130° C.; $^1$H NMR (300 MHz, CDCl$_3$) δ 2.62 (t, J=6.0 Hz, 4H), 3.09–3.19 (m, 2H), 3.40 (t, J=6.0 Hz, 4H), 4.47–4.54 (m, 1H), 6.88–7.00 (m, 3H), 8.22 (brs, 1H); MS (ES) m/z: 322.9 (MH$^+$); HRMS Calcd. for C$_{15}$H$_{16}$FN$_2$O$_3$S(MH$^+$): 323.0865. Found: 323.0837.

EXAMPLE 62

5-[3-Fluoro-4-(4-oxo-piperidine-1-yl)-benzylidene]-thiazolidine-2,4-dione

The title compound was prepared from 5-[4-(1,4-dioxa-8-aza-spiro[4.5]dec-8-yl)-3-fluoro-benzylidene]-thiazolidine-2,4-dione (which was obtained in Example 60) according to the procedure of Example 34 as a yellow solid; mp >200° C.; $^1$H NMR (300 MHz, DMSO-d$_6$) δ 2.51 (m, 4H), 3.54 (t, J=5.97 Hz, 4H), 7.24–7.30 (m, 1H), 7.31–7.49 (m, 2H), 7.73 (s, 1H), 12.5 (s, 1H); MS (ES) m/z: 319.0 (M–H)$^-$; HRMS Calcd. for C$_{15}$H$_{14}$FN$_2$O$_3$S(MH$^+$): 321.0709. Found: 321.0712

EXAMPLE 63

N-[5-((1R)-2-{1-[4-(3,5-Dioxo-[[1,2,4] oxadiazolidin-2-ylmethyl)-phenyl]-piperidine-4-ylamino}-1-hydroxy-ethyl)-2-hydroxy-phenyl]-methanesulfonamide Acetic acid (0.09 mL, 1.6 mmol) was added to a mixture of N-{5-[(1R)-2-amino-1-hydroxyethyl]-2-hydroxy-phenyl}methanesulfonamide (197 mg, 0.8 mmol) (which was obtained in Example 10), 2-[4-(4-oxo-1-piperidineyl)benzyl]-1,2,4-oxadiazolidine-3,5-dione (231 mg, 0.8 mmol) (which was obtained in Example 55), and DMF (5 mL). The mixture was stirred for 20 minutes and then, sodium triacetoxyborohydride (203 mg, 0.96 mmol) was added, and the new mixture was stirred at room temperature for 24 hours. The volatiles were removed in vacuo and the residue was purified by flash chromatography (dichloromethane/methyl alcohol 4/1) to produce an off-white solid (296 mg, 71% yield); mp 193–195° C.; $^1$H NMR (400 MHz, DMSO-d$_6$) δ 1.58–1.62 (m, 2H), 1.96–2.07 (m, 2H), 2.60–2.70 (m, 2H), 2.86–3.17 (m, 6H), 3.72–3.8 (m, 2H), 4.28 (s, 2H), 2.70–2.74 (m, 1H), 6.83–6.87 (m, 3H), 7.03–7.13 (m, 3H), 7.23 (m, 1H), 8.60 (brs, 2H); MS (ES) m/z: 518 (M–H)$^-$.

EXAMPLE 64

5-[[4-[4-[[(R)-2-Hydroxy-2-[4-hydroxy-3-[(methylsulfonyl)amino]phenyl]ethyl]amino]-1-piperidineyl]phenyl]methyl]-2,4-dioxo-3-thiazolidineacetic acid tert-butyl-ester Acetic acid (0.12 mL, 2.16 mmol) was added to a mixture of N-{5-[(1R)-2-amino-1-hydroxyethyl]-2-hydroxy-phenyl}methanesulfonamide (266 mg, 1.08 mmol) (which was obtained in Example 10), tert-butyl 2-{2,4-dioxo-5-[4-(4-oxo-1-piperidineyl)benzyl]-1,3-thiazolidin-3-yl}acetate (450 mg, 1.08 mmol) (which was obtained in Example 49), and DMF (5 mL). The mixture was stirred for 20 minutes and then, sodium triacetoxyborohydride (276 mg, 1.3 mmol) was added, and the new mixture was stirred at room temperature for 24 hours. The volatiles were removed in vacuo and the residue was purified by flash chromatography (dichloromethane/methyl alcohol 5/1) to produce a yellow solid (480 mg, 68% yield); mp 130–132° C.; $^1$H NMR (400 MHz, DMSO-d$_6$) δ 1.20–1.50 (m, 11H), 1.81–1.85 (m, 2H), 2.60–2.80 (m, 4H), 2.85–2.9 (m, 4H), 3.40 (m, 1H), 3.60 (m, 1H), 4.20 (s, 2H), 4.50 (m, 1H), 5.04 (m, 1H), 6.80–6.87 (m, 3H), 7.02 (m, 1H), 7.08 (m, 2H), 7.20 (m, 1H); Anal. Calcd. for C$_{30}$H$_{40}$N$_4$O$_8$S$_2$: C, 55.54; H, 6.21; N, 8.64. Found: C, 53.86; H, 6.11; N, 7.65.

EXAMPLE 65

5-[[4-[4-[[(R)-2-Hydroxy-2-[4-hydroxy-3-[(methylsulfonyl)amino]phenyl]ethyl]amino]-1-piperidineyl]phenyl]methyl]-2,4-dioxo-3-thiazolidineacetic acid A mixture of 5-[[4-[4-[[(R)-2-hydroxy-2-[4-hydroxy-3-[(methylsulfonyl)amino]-phenyl]ethyl]amino]-1- piperidineyl]phenyl]methyl]-2,4-dioxo-3-thiazolidineacetic acid tert-butyl-ester (300 mg, 0.46 mmol) (which was obtained in Example 64), dichloromethane (5 mL), and trifluoroacetic acid (0.5 mL) was stirred at room temperature for 10 hours. The mixture was then poured into ethyl ether (50 mL), and the precipitated solid was filtered and dried to give an off-white solid (189 mg, 58% yield); mp 158–160° C.; $^1$H NMR (400 MHz, DMSO-d$_6$) δ 1.58–1.66 (m, 2H), 2.02–2.10 (m, 2H), 2.60–2.64 (m, 2H), 2.85–3.04 (m, 4H), 3.16–3.40 (m, 4H), 3.80 (m, 2H), 4.20 (s, 2H), 4.80 (m, 1H), 5.06 (m, 1H), 6.17 (brs, 1H), 6.87–6.91 (m, 3H), 7.05–7.1 (m, 3H), 7.23 (m, 1H), 8.60 (brs, 1H), 8.80 (s, 1H), 9.94 (s, 1H), 13.3 (brs, 1H); MS (ES) m/z: 649 (MH$^+$).

EXAMPLE 66

5-[[4-[4-[[(R)-2-Hydroxy-2-[4-hydroxy-3-[(methylsulfonyl)amino]phenyl]ethyl]amino]-1-piperidineyl]phenyl]methyl]-2,4-dioxo-3-thiazolidineacetic acid ethyl-ester Acetic acid (0.05 mL, 0.92 mmol) was added to a mixture of N-{5-[(1R)-2-amino-1-hydroxyethyl]-2-hydroxyphenyl}methanesulfonamide (which was obtained in Example 10) (113 mg, 0.46 mmol), ethyl 2-[2,4-dioxo-5-[4-(4-oxo-1-piperidineyl)benzyl]-1,3-thiazolidin-3-yl}acetate (which was obtained in Example 50) (180 mg, 0.46 mmol), and DMF (3 mL). The mixture was stirred for 20 minutes and then, sodium triacetoxyborohydride (117 mg, 0.55 mmol) was added, and the new mixture was stirred at room temperature for 24 hours. The volatiles were removed in vacuo and the residue was purified by flash chromatography (dichloromethane/methyl alcohol 5/1) to produce an off-white solid (210 mg, 74% yield); mp 153–155° C.; $^1$H NMR (400 MHz, DMSO-d$_6$) δ 1.18 (t, J=7.1 Hz, 3H), 1.30–1.60 (m, 2H), 1.80–1.83 (m, 2H), 2.50–2.65 (m, 4H), 2.80–2.85 (m, 4H), 3.40 (m, 2H), 3.60 (m, 1H), 4.13 (q, J=7.1 Hz, 2H), 4.47 (m, 1H), 5.04 (m, 1H), 6.80–6.90 (m, 3H), 6.97 (m, 1H), 7.1 (m, 2H), 7.19 (m, 1H); MS (ES) m/z: 621 (MH$^+$); Anal. Calcd. for: $C_{28}H_{36}N_4O_8S_2 \times 1CH_3CO_2H$: C, 52.93; H, 5.92; N, 8.23. Found: C, 52.69; H, 5.63; N, 8.23.

EXAMPLE 67

5-(3-Fluoro-4-{4-[(2S)-2-hydroxy-3-(2-oxo-2,3-dihydro-1H-benzoimidazol-4-yloxy)-propylamino]-piperidine-1-yl}-benzyl)-thiazolidine-2,4-dione The title compound was prepared from 4-((2S)-3-amino-2-hydroxy-propoxy)-1,3-dihydro-benzoimidazol-2-one (U.S. Pat. No. 5,786,356/1998) and 5-[3-fluoro-4-(4-oxo-piperidine-1-yl)-benzyl]-thiazolidine-2,4-dione (which was obtained in Example 61) according to the procedure of Example 63 as a pale yellow solid; $^1$H NMR (300 MHz, DMSO-d$_6$) δ 1.56–1.62 (m, 2H), 2.04 (m, 2H), 2.63–2.75 (m, 5H), 2.86–2.95 (m, 4H), 3.01–3.10 (m, 4H), 4.50–4.55 (m, 1H), 5.33 (brs, 1H), 6.57–6.65 (m, 2H), 6.84–7.09 (m, 3H), 8.22 (s, 1H), 7.22–7.29 (m, 1H), 10.55 (s, 1H), 10.65 (s, 1H); MS (ES) m/z: 530.0 (MH$^+$); HRMS Calcd. for $C_{25}H_{29}FN_5O_5S$(MH$^+$): 530.1873. Found: 530.1876.

EXAMPLE 68

5-(3-Bromo-4-{4-[(2S)-2-hydroxy-3-(2-oxo-2,3-dihydro-1H-benzoimidazol-4-yloxy)-propylamino]-piperidine-1-yl}-benzylidene)-thiazolidine-2,4-dione The title compound was prepared from 4-((2S)-3-amino-2-hydroxy-propoxy)-1,3-dihydro-benzoimidazol-2-one (U.S. Pat. No. 5,786,356/1998) and 5-[3-bromo-4-(4-oxo-piperidine-1-yl)-benzylidene]-thiazolidine-2,4-dione (which was obtained in Example 58) according to the procedure of Example 63 as an olive green solid; $^1$H NMR (300 MHz, DMSO-d$_6$) δ 1.66–1.77 (m, 4H), 2.10–2.19 (m, 4H), 2.68–2.76 (m, 2H), 3.07–3.14 (m, 3H), 3.99–4.09 (m, 2H), 5.62 (brs, 1H), 6.58–6.66 (m, 2H), 6.88 (t, J=8.1 Hz, 1H), 7.20–7.25 (m, 3H), 7.50 (dd, J=8.5, 2.0 Hz, 25 1H), 7.75 (d, J=2.0 Hz, 1H), 10.55 (s, 1H), 10.65 (s, 1H); MS (ES) m/z: 589.9 (MH$^+$).

EXAMPLE 69

5-(3-Fluoro-4-{4-[(2S)-2-hydroxy-3-(2-oxo-2,3-dihydro-1H-benzoimidazol-4-yloxy)-propylamino]-piperidine-1-yl}-benzylidene)-thiazolidine-2,4-dione The title compound was prepared from 4-((2S)-3-amino-2-hydroxy-propoxy)-1,3-dihydro-benzoimidazol-2-one (U.S. Pat. No. 5,786,356/1998) and 5-[3-fluoro-4-(4-oxo-piperidine-1-yl)-benzylidene]-thiazolidine-2,4-dione (which was obtained in Example 62) according to the procedure of Example 63 as an olive green solid; mp 162–164° C.; $^1$H NMR (300 MHz, DMSO-d$_6$) δ 1.66–1.74 (m, 2H), 2.07–2.17 (m, 2H), 2.74–2.83 (m, 2H), 3.12–3.15 (m, 2H), 3.43–3.48 (m, 1H), 3.52–3.56 (m, 2H), 3.98–4.11 (m, 1H), 5.63 (brs, 1H), 6.62 (m, 2H), 6.87 (t, J=8.1 Hz, 1H), 7.18 (t, J=9.1 Hz, 3H), 7.27–7.35 (m, 1H), 10.60 (s, 1H), 10.7 (s, 1H); MS (ES) m/z: 527.9 (MH$^+$); HRMS Calcd. for $C_{25}H_{28}FN_5O_5S$(MH$^+$): 528.1716. Found: 528.1702.

EXAMPLE 70

N-[5-(2-{1-[2-Bromo-4-(2 4-dioxo-thiazolidin-5-ylidenemethyl)-phenyl]-piperidine-4-ylamino]-1-hydroxy-ethyl)-2-hydroxy-phenyl]-methanesulfonamide The title compound was prepared from N-[5-(2-amino-1-hydroxy-ethyl)-2-hydroxy-phenyl]-methanesulfonamide (which was obtained in Example 9) and 5-[3-bromo-4-(4-oxo-piperidine-1-yl)-benzylidene]-thiazolidine-2,4-dione (which was obtained in Example 58) according to the procedure of Example 63 as a dull yellow solid; mp >200° C.; $^1$H NMR (300 MHz, DMSO-d$_6$) δ 1.70–1.82 (m, 2H), 2.07–2.17 (m, 2H), 2.65–2.73 (m, 3H), 2.95 (s, 3H), 3.07–3.17 (m, 4H), 4.74–4.77 (m, 3H), 6.00 (brs, 1H), 6.89 (d, J=8.3 Hz, 1H), 7.09 (dd, J=8.4, 2.0 Hz, 1H), 7.20 (d, J=8.4 Hz, 1H), 7.26–7.27 (m, 2H), 7.50 (dd, J=8.4, 2.0 Hz, 1H), 7.75 (d, J=2.0 Hz, 1H), 8.7 (brs, 1H), 9.9 (brs, 1H); MS (ES) m/z: 612.8 (MH$^+$).

EXAMPLE 71

N-[5-(2-{1-[4-(2,4-Dioxo-thiazolidin-5-ylidenemethyl)-2-fluoro-phenyl]-piperidine-4-ylamino}-1-hydroxy-ethyl)-2-hydroxy-phenyl]-methanesulfonamide The title compound was prepared from N-[5-(2-amino-1-hydroxy-ethyl)-2-hydroxy-phenyl]-methanesulfonamide (which was obtained in Example 9) and 5-[3-fluoro-4-(4-oxo-piperidine-1-yl)-benzylidene]-thiazolidine-2,4-dione (which was obtained in Example 62) according to the procedure of Example 63 as a yellow solid; mp >225° C.; $^1$H NMR (300 MHz, DMSO-d$_6$) δ 1.62–1.71 (m, 2H), 2.03–2.12 (m, 2H), 2.70–2.83 (m, 3H), 2.95 (s, 3H), 3.12–3.33 (m, 2H), 3.49–3.52 (m, 2H), 4.72–4.75 (m, 1H), 5.96 (brs, 1H), 6.89 (d, J=8.1 Hz, 1H), 7.05–7.13 (m, 3H), 7.25–7.38 (m, 3H), 8.70 (brs, 1H), 9.8 (brs, 1H); MS (ES) m/z: 551.0 (MH$^+$); HRMS for $C_{24}H_{27}FN_4O_6S_2$ (MH$^+$): 551.1434. Found: 551.1438.

EXAMPLE 72

5-{4-[4-((2S)-2-Hydroxy-3-phenoxy-propylamino)-piperidine-1-yl]-benzylidene}-2-thioxo-thiazolidin-4-one 1-[4-(4-Oxo-2-thioxo-thiazolidin-5-ylidenemethyl)-phenyl]-piperidine-4-one (which was obtained in Example 34) (0.16 g, 0.5 mmol) and (2S)-1-amino-3-phenoxy-propan-2-ol (which was obtained in Example 3) (0.12 g, 0.75 mmol) were mixed in 1,2-dichloroethane (10 mL) and then treated with sodium triacetoxyborohydride (0.16 g, 0.75 mmol) and acetic acid (0.045 g, 0.75 mmol). After stirring at room temperature under a nitrogen atmosphere for one day the mixture was quenched with 1N sodium hydroxide (NaOH) and then poured into a saturated aqueous sodium bicarbonate (NaHCO$_3$). The aqueous layer was extracted with dichloromethane and the combined organic layers were dried and concentrated. The residue was purified by preparative thin layer chromatography (16% MeOH/CH$_2$CH$_2$) to give the title compound as a pale yellowish solid; mp >220° C. (decomposed); $^1$H NMR (300 MHz, DMSO-d$_6$) δ 1.50–1.70 (m, 2H), 1.90–2.10 (m, 2H), 2.60–3.40 (m, 7H), 3.90–4.20 (m, 3H), 6.70–7.15 (m, 6H), 7.30 (d, J=8.8 Hz, 2H), 7.38 (d, J=8.8 Hz, 2H); MS (ES) m/z: 470.0 (MH$^+$); HRMS Calcd. for $C_{24}H_{27}N_3O_3S_2$ (M$^+$): 469.1494. Found: 469.1488.

EXAMPLE 73

5-{4-[4-((2S)-2-Hydroxy-3-phenoxy-propylamino)-piperidine-1-yl]-benzyl}-thiazolidin-2,4-dione 5-[4-(4-Oxo-piperidine-1-yl)-benzyl]-thiazolidine-2,4-dione (which was obtained in Example 38) (0.15 g, 0.5 mmol) and (2S)-1-amino-3-phenoxy-propan-2-ol (which was obtained in Example 3) (0.12 g, 0.75 mmol) were mixed in N,N-dimethylformamide (15 mL) and then treated with sodium triacetoxyborohydride (0.16 g, 0.75 mmol) and acetic acid (0.045 g, 0.75 mmol). After stirring at room temperature under a nitrogen atmosphere for one day the mixture was quenched with 1N NaOH and then poured into a saturated aqueous NaHCO$_3$. The aqueous solution was extracted with 1-butanol and the combined organic layers were concentrated. The residue was purified by preparative thin layer chromatography (10% MeOH/CH$_2$CH$_2$) to give the title compound as a pale yellowish solid; mp 218–220° C.; $^1$H NMR (300 MHz, DMSO-d$_6$) δ 1.30–1.60 (m, 2H), 1.80–2.00 (m, 2H), 2.50–3.00 (m, 5H), 3.00–3.50 (m, 3H), 3.50–3.70 (m, 2H), 3.85–4.00 (m, 3H), 4.48 (dd, J=9.8, 3.8 Hz, 1H), 6.85 (d, J=8.6 Hz, 2H), 6.90–6.97 (m, 3H), 7.04 (d, J=8.6 Hz, 2H), 7.25–7.38 (m, 3H); MS (ES) m/z: 456.0 (MH$^+$); HRMS Calcd. for $C_{24}H_{29}N_3O_4S$(M$^+$): 455.1878. Found: 455.1880.

EXAMPLE 74

5-(4-{4-[(2S)-3-(4-Benzyloxy-phenoxy)-2-hydroxy-propylamino]-piperidine-1-}-benzyl)-thiazolidine-2,4-dione The title compound was prepared from 5-[4-(4-oxo-piperidine-1-yl)-benzyl]-thiazolidine-2,4-dione (which was obtained in Example 38) and (2S)-1-amino-3-(4-benzyloxy-phenoxy)-propan-2-ol (which was obtained in Example 4) according to the procedure of Example 73 as a pale yellowish solid; mp >70° C. (decomposed); $^1$H NMR (300 MHz, DMSO-d$_6$) δ 1.45–1.60 (m, 2H), 1.90–2.15 (m, 2H), 2.67 (brt, J=11.7 Hz, 2H), 2.75–3.05 (m, 4H), 3.26 (dd, J=14.1, 3.9 Hz, 1H), 3.60–3.75 (m, 2H), 3.80–3.95 (m, 2H), 3.95–4.05 (m, 1H), 4.62 (dd, J=9.5, 4.0 Hz, 1H), 5.04 (s, 2H), 6.60–7.05 (m, 6H), 7.05 (d, J=8.6 Hz, 2H), 7.25–7.45 (m, 5H); MS (ES) m/z: 562.0 (MH$^+$, 100%); 1123.5 (2MH$^+$, 5%). HRMS Calcd. for $C_{31}H_{36}N_3O_5S$(M$^+$): 562.2375. Found: 562.2392.

EXAMPLE 75

5-(4-{4-[(2S)-2-Hydroxy-3-(2-oxo-2,3-dihydro-1H-benzoimidazol-4-yloxy)-propylamino]-piperidine-1-yl}-benzylidene)-thiazolidine-2,4-dione The title compound was prepared from 5-[4-(4-oxo-piperidine-1-yl)-benzylidene]-thiazolidine-2,4-dione (which was obtained in Example 36) and (S)-4-[2-hydroxy-3-aminopropoxy]-1,3-dihydro-2H-benzimidazol-2-one (U.S. Pat. No. 5,786,356/1998) according to the procedure of Example 73 as a pale yellowish solid; mp >240° C. (decomposed); $^1$H NMR (300 MHz, DMSO-d$_6$) δ 1.45–1.60 (m, 2H), 2.00–2.15 (m, 2H), 2.86 (brt, J=9.0 Hz, 2H), 2.90–3.60 (m, 3H), 3.91 (brd, J=9.4 Hz, 1H), 3.93–4.10 (m, 3H), 5.40 (brs, 1H), 6.59 (d, J=6.0 Hz, 1H), 6.63 (d, J=6.0 Hz, 1H), 6.86 (t, J=6.0 Hz, 1H), 7.02 (d, J=6.6 Hz, 2H), 7.36 (s, 1H), 7.40 (d, J=6.6 Hz, 2H), 11.60 (s, 1H), 11.70 (brs, 1H); MS (ES) m/z: 509.9 (MH$^+$); HRMS Calcd. for $C_{25}H_{28}N_5O_5S$(MH$^+$): 510.1811. Found: 510.1861.

EXAMPLE 76

5-(4-{4-[(2S)-2-Hydroxy-3-(4-hydroxy-phenoxy)-propylamino]-piperidine-1-yl}-benzylidene)-thiazolidine-2,4-dione The title compound was prepared from 5-[4-(4-oxo-piperidine-1-yl)-benzylidene]-thiazolidine-2,4-dione (which was obtained in Example 36) and 4-[(2S)-3-amino-2-hydroxy-propoxy]-phenol (which was obtained in Example 5) according to the procedure of Example 73 as a pale yellowish solid; mp >208° C. (decomposed); $^1$H NMR (300 MHz, DMSO-d$_6$) δ 1.40–1.60 (m, 2H), 1.90–2.05 (m, 2H), 2.70–3.50 (m, 5H), 3.80–4.10 (m, 5H), 6.90 (d, J=6.7 Hz, 2 H), 6.77 (d, J=6.7 Hz, 2H), 7.02 (d, J=8.9 Hz, 2H), 7.35 (s, 1H), 7.39 (d, J=8.9 Hz, 2H), 8.95 (brs, 1H); MS (ES) m/z: 469.9 (MH$^+$); HRMS Calcd. for $C_{24}H_{28}N_3O_5S$(M$^+$): 469.1671. Found: 469.1648.

EXAMPLE 77

N-[5-(2-{1-[4-(2,4-Dioxo-thiazolidin-5-ylidenemethyl)-phenyl]-piperidine-4-ylamino}-1-hydroxy-ethyl)-2-hydroxy-phenyl]-methanesulfonamide The title compound was prepared from 5-[4-(4-oxo-piperidine-1-yl)-benzylidene]-thiazolidine-2,4-dione (which was obtained in Example 36) and N-[5-(2-amino-1-hydroxy-ethyl)-2-hydroxy-phenyl]-methanesulfonamide (which was obtained in Example 9) according to the procedure of Example 73 as a pale yellowish solid; mp >200° C. (decomposed); $^1$H NMR (300 MHz, DMSO-d$_6$) δ 1.45–1.60 (m, 2H), 1.90–2.05 (m, 2H), 2.70–3.50 (m, 5H), 2.94 (s, 3H), 3.88 (brd, J=9.9 Hz, 2H), 4.67 (dd, J=7.2, 2.1 Hz, 1H), 6.87 (d, J=6.3 Hz, 1H), 7.00 (d, J=6.8 Hz, 2H), 7.06 (dd, J=6.3, 1.5 Hz, 1H), 7.23 (d, J=1.5 Hz, 1H), 7.33 (s, 1H), 7.38

(d, J=6.8 Hz, 2H); MS (ES) m/z: 533.0 (MH$^+$); HRMS Calcd. for C$_{24}$H$_{29}$N$_4$O$_6$S$_2$ (MH$^+$): 533.1529. Found: 533.1544.

EXAMPLE 78

N-[5-(2-{1-[4-(2,4-Dioxo-thiazolidin-5-ylmethyl)-phenyl]-piperidine-4-ylamino}-1-hydroxy-ethyl)-2-hydroxy-phenyl]-methanesulfonamide The title compound was prepared from 5-[4-(4-oxo-piperidine-1-yl)-benzyl]-thiazolidine-2,4-dione (which was obtained in Example 38) and N-[5-(2-amino-1-hydroxy-ethyl)-2-hydroxy-phenyl]-methanesulfonamide (which was obtained in Example 9) according to the procedure of Example 73 as a pale yellowish solid; mp >150° C. (decomposed); $^1$H NMR (300 MHz, DMSO-d$_6$) δ 1.40–1.60 (m, 2H), 1.90–2.10 (m, 2H), 2.55–3.60 (m, 7H), 2.93 (s, 3H), 3.67 (brd, J=12.8 Hz, 2H), 4.56 (dd, J=9.6, 4.0 Hz, 1H), 4.64 (brd, J=6.5 Hz, 1H), 6.70–6.95 (m, 3H), 6.95–7.15 (m, 3H), 7.22 (d, J=2.1 Hz, 1H); MS (ES) m/z: 535.0 (MH$^+$); HRMS Calcd. for C$_{24}$H$_{31}$N$_4$O$_6$S$_2$ (MH$^+$): 535.1685. Found: 535.1720.

EXAMPLE 79

5-(4-{4-[2-(3-Chloro-phenyl)-(2R)-2-hydroxyethylamino}-piperidine-1-yl}-benzyl)-thiazolidine-2,4-dione The title compound was prepared from 5-[4-(4-oxo-piperidine-1-yl)-benzyl]-thiazolidine-2,4-dione (which was obtained in Example 38) and (1R)-2-amino-1-(3-chloro-phenyl)-ethanol (which was obtained in Example 1) according to the procedure of Example 73 as a pale yellowish solid; mp >195–198° C.; $^1$H NMR (300 MHz, DMSO-d$_6$) δ 1.40–1.60 (m, 2H), 1.85–2.10 (m, 2H), 2.60–3.50 (m, 7H), 3.65 (brd, J=12.5 Hz, 2H), 4.63 (dd, J=9.5, 4.1 Hz, 1H), 4.74 (dd, J=8.8, 3.1 Hz, 1H), 6.86 (d, J=8.7 Hz, 2H), 7.05 (d, J=8.7 Hz, 2H), 7.20–7.50 (m, 4H); MS (ES) m/z: 460.0 (MH$^+$); HRMS Calcd. for C$_{23}$H$_{26}$ClN$_3$O$_3$S(M$^+$): 459.1383. Found: 459.1376.

EXAMPLE 80

5-(4-{4-[(2S)-2-Hydroxy-3-(2-oxo-2,3-dihydro-1H-benzoimidazol-4-yloxy)-propylamino]-piperidine-1-yl}-benzyl)-thiazolidine-2,4-dione The title compound was prepared from 5-[4-(4-oxo-piperidine-1-yl)-benzyl]-thiazolidine-2,4-dione (which was obtained in Example 38) and (S)-4-[2-hydroxy-3-aminopropoxy]-1,3-dihydro-2H-benzimidazol-2-one (U.S. Pat. No. 5,786,356/1998) according to the procedure of Example 73 as a pale yellowish solid; mp 173–175° C. (decomposed); $^1$H NMR (300 MHz, DMSO-d$_6$) δ 1.45–1.60 (m, 2H), 1.90–2.15 (m, 2H), 2.10–2.95 (m, 5H), 3.03 (brd, J=10.5 Hz, 1H), 3.26 (dd, J=14.1, 3.8 Hz, 1H), 3.68 (brd, J=12.4 Hz, 2H), 3.95–4.05 (m, 3H), 4.51 (dd, J=10.0, 4.0 Hz, 1H), 6.58 (d, J=7.8 Hz, 1H), 6.63 (d, J=8.1 Hz, 1H), 6.75–6.95 (m, 3H), 7.05 (d, J=8.7 Hz, 2H), 11.60 (s, 1H), 11.85 (brs, 1H); MS (ES) m/z: 512.0 (MH$^+$); HRMS Calcd. for C$_{25}$H$_{30}$N$_5$O$_5$S (MH$^+$): 512.1968. Found: 512.1982.

The free base from above was dissolved in 20 mL of concentrated hydrochloric acid and stirred for 1 hour. The solvent was removed and the residue was dissolved in methanol. Upon addition of diethyl ether the solid which was formed was collected to give 5-(4-{4-[(2S)-2-hydroxy-3-(2-oxo-2,3-dihydro-1H-benzoimidazol-4-yloxy)-propylamino]-piperidine-1-yl}-benzyl)-thiazolidine-2,4-dione dihydrochloride salt as a pale yellowish solid; $^1$H NMR (300 MHz, DMSO-d$_6$) δ 1.80–2.10 (m, 2H), 2.10–2.30 (m, 2H), 2.90–4.30 (m, 12H), 4.90 (dd, J=9.0, 3.0 Hz, 1H), 6.60 (d, J=6.0 Hz, 1H), 6.64 (d, J=6.0 Hz, 1H), 6.88 (t, J=6.0 Hz, 1H), 7.10–7.40 (m, 4H), 8.90 (brs, 1H), 9.21 (brs, 1H), 10.62 (s, 1H), 10.75 (s, 1H), 12.04 (s, 1H); MS (ES) m/z: 512.0 (M–2HCl+H)$^+$; HRMS Calcd. for C$_{25}$H$_{30}$N$_5$O$_5$S(M–2HCl+H)$^+$: 512.1968. Found: 512.1964.

EXAMPLE 81

5-(4-{4-[(2S)-2-Hydroxy-3-(4-hydroxy-phenoxy)-propylamino]-piperidine-1-yl}-benzyl)-thiazolidine-2,4-dione The title compound was prepared from 5-[4-(4-oxo-piperidine-1-yl)-benzyl]-thiazolidine-2,4-dione (which was obtained in Example 38) and 4-[(2S)-3-amino-2-hydroxy-propoxy]-phenol (which was obtained in Example 5) according to the procedure of Example 73 as a pale yellowish solid; mp >160° C. (decomposed); $^1$H NMR (300 MHz, DMSO-d$_6$) δ 1.35–1.60 (m, 2H), 1.85–2.05 (m, 2H), 2.60–3.50 (m, 7H), 3.67 (brd, J=12.1 Hz, 2H), 3.75–3.95 (m, 3H), 4.57 (dd, J=9.6, 3.8 Hz, 1H), 6.66 (d, J=8.9 Hz, 2H), 6.77 (d, J=8.9 Hz, 2H), 6.85 (d, J=8.6 Hz, 2H), 7.03 (d, J=8.6 Hz, 2H), 8.92 (brs, 1H); MS (ES) m/z: 472.0 (MH$^+$); HRMS Calcd. for C$_{24}$H$_{30}$N$_3$O$_5$S(MH$^+$): 472.1906. Found: 472.1898.

EXAMPLE 82

5-(4-{4-[(2S)-2-Hydroxy-3-(4-hydroxy-phenoxy)-propylamino]-piperidine-1-yl}-benzylidene)-2-thioxo-thiazolidin-4-one The title compound was prepared from 1-[4-(4-oxo-2-thioxo-thiazolidin-5-ylidenemethyl)-phenyl]-piperidine-4-one (which was obtained in Example 34) and 4-[(2S)-3-amino-2-hydroxy-propoxy]-phenol (which was obtained in Example 5) according to the procedure of Example 73 as a pale yellowish solid; MS (ES) m/z: 485.9 (MH$^+$).

EXAMPLE 83

5-{4-[4-((2S)-2-Hydroxy-3-phenoxy-propylamino)-piperidine-1-yl]-benzylidene}-thiazolidine-2,4-dione The title compound was prepared from 5-[4-(4-oxo-piperidine-1-yl)-benzylidene]-thiazolidine-2,4-dione (which was obtained in Example 36) and (2S)-1-amino-3-phenoxy-propan-2-ol (which was obtained in Example 3) according to the procedure of Example 73 as a pale yellowish solid; mp 208–210° C.; MS (ES) m/z: 454.0 (MH$^+$); HRMS Calcd. for C$_{24}$H$_{27}$N$_3$O$_4$S (M$^+$): 453.1723. Found: 453.1710.

EXAMPLE 84

N-[5-((2R)-2-{1-[4-(2,4-Dioxo-thiazolidin-5-ylmethyl)-phenyl]-piperidine-4-ylamino}-1-hydroxy-ethyl)-2-hydroxy-phenyl]-methanesulfonamide The title compound was prepared from 5-[4-(4-oxo-piperidine-1-yl)-benzyl]-thiazolidine-2,4-dione (which was obtained in Example 38) and N-[5-(2-amino-(1R)-1-hydroxy-ethyl)-2-hydroxy-phenyl]-methanesulfonamide (which was obtained in Example 10) according to the procedure of Example 73 as a pale yellowish solid; mp >180° C. (decomposed); $^1$H NMR (300 MHz, DMSO-d$_6$) δ

1.40–1.65 (m, 2H), 1.90–2.10 (m, 2H), 2.55–3.60 (m, 7H), 2.94 (s, 3H), 3.61 (brd, J=9.6 Hz, 2H), 4.61 (dd, J=9.7, 4.0 Hz, 1H), 4.69 (dd, J=9.1, 2.7 Hz, 1H), 6.70–6.90 (m, 3H), 7.00–7.15 (m, 3H), 7.23 (d, J=2.1 Hz, 1H); MS (ES) m/z: 535.0 (MH$^+$); HRMS Calcd. for $C_{24}H_{31}N_4O_6S_2$ (MH$^+$): 535.1685. Found: 535.1692.

The free base (0.15 g) prepared above was dissolved in 30 mL of MeOH/CH$_2$Cl$_2$ (1/4) and treated with hydrogen chloride gas for 10 minutes. Diethyl ether was then added and the solid which was formed was collected to give N-[5-((2R)-2-{1-[4-(2,4-dioxo-thiazolidin-5-ylmethyl)-phenyl]-piperidine-4-ylamino}-1-hydroxy-ethyl)-2-hydroxy-phenyl]-methanesulfonamide dihydrochloride salt as a white solid; $^1$H NMR (300 MHz, DMSO-d$_6$) δ 1.80–2.10 (m, 2H), 2.15–2.30 (m, 2H), 2.95–4.00 (m, 10H), 2.95 (s, 3H), 4.89 (dd, J=6.9, 3.0 Hz, 1H), 6.94 (d, J=6.0 Hz, 1H), 7.10 (dd, J=6.0, 3.0 Hz, 1H), 7.10–7.30 (m, 5H), 8.79 (s, 1H), 8.85 (brs, 1H), 9.32 (brs, 1H), 10.02 (brs, 1H), 12.05 (s, 1H); MS (ES) m/z: 535.0 (M−2HCl+H)$^+$; HRMS Calcd. for $C_{24}H_{31}N_4O_6S_2$ (M−2HCl+H)$^+$: 535.1685. Found: 535.1715.

EXAMPLE 85

N-[5-(2-1-[4-(2,5-Dioxo-imidazolidin-4-ylidenemethyl)-phenyl]-piperidine-4-ylamino}-1-hydroxy-ethyl)-2-hydroxy-phenyl]-methanesulfonamide The title compound was prepared from 5-[4-(4-oxo-piperidine-1-yl)-benzylidene]-imidazolidine-2,4-dione (which was obtained in Example 42) and N-[5-(2-amino-1-hydroxy-ethyl)-2-hydroxy-phenyl]-methanesulfonamide (which was obtained in Example 9) according to the procedure of Example 73 as a pale yellowish solid; mp >201° C. (decomposed); $^1$H NMR (300 MHz, DMSO-d$_6$) δ 1.20–1.40 (m, 2H), 1.75–1.95 (m, 2H), 2.50–2.90 (m, 5H), 2.92 (s, 3H), 3.70–3.85 (m, 2H), 4.48 (dd, J=8.0, 4.2 Hz, 1H), 6.33 (s, 1H), 6.81 (d, J=8.1 Hz, 1H), 6.95 (d, J=8.7 Hz, 2H), 7.02 (dd, J=8.1, 1.8 Hz, 1H), 7.18 (d, J=61.8 Hz, 1H), 7.47 (d, J=8.7 Hz, 2H); MS (ES) m/z: 516.1 (MH$^+$); HRMS Calcd. for $C_{24}H_{30}N_5O_6S$(MH$^+$): 516.1917. Found: 516.1922.

EXAMPLE 86

5-(4-{4-[2-Hydroxy-3-(2-oxo-2,3-dihydro-1H-benzoimidazol-4-yloxy)-propylamino]-piperidine-1-yl}-benzyl)-imidazolidine-2,4-dione-piPeridin-1-yl}-benzyl) imidazolidine-2,4-dione The title compound was prepared from 5-[4-(4-oxo-piperidine-1-yl)-benzyl]-imidazolidine-2,4-dione (which was obtained in Example 44) and (S)-4-[2-hydroxy-3-aminopropoxy]-1,3-dihydro-2H-benzimidazol-2-one (U.S. Pat. No. 5,786,356/1998) according to the procedure of Example 73 as a pale yellowish solid; mp >132° C. (decomposed); $^1$H NMR (300 MHz, DMSO-d$_6$) δ 1.20–1.40 (m, 2H), 1.80–1.95 (m, 2H), 2.50–2.85 (m, 8H), 3.50–3.65 (m, 2H), 3.75–4.05 (m, 3H), 4.22 (t, J=4.6 Hz, 1H), 6.57 (d, J=7.5 Hz, 1H), 6.62 (d, J=8.1 Hz, 1H), 6.80–6.90 (m, 3H), 6.99 (d, J=8.4 Hz, 2H), 7.87 (s, 1H), 10.50 (s, 1H), 10.70 (brs, 1H); MS (ES) m/z: 495.1 (MH$^+$); HRMS Calcd. for $C_{25}H_{31}N_6O_5$ (M$^+$): 495.2356. Found: 495.2368.

EXAMPLE 87

N-[5-(2-{1-[4-(2,5-Dioxo-imidazolidin-4-ylmethyl)-phenyl]-piperidine-4-ylamino}-1-hydroxy-ethyl)-2-hydroxy-phenyl]-methanesulfonamide The title compound was prepared from 5-[4-(4-oxo-piperidine-1-yl)-benzyl]-imidazolidine-2,4-dione (which was obtained in Example 44) and N-[5-(2-amino-1-hydroxy-ethyl)-2-hydroxy-phenyl]-methanesulfonamide (which was obtained in Example 9) according to the procedure of Example 73 as a pale yellowish solid; mp >105° C. (decomposed); $^1$H NMR (300 MHz, DMSO-d$_6$) δ 1.20–1.40 (m, 2H), 1.80–2.00 (m, 2H), 2.50–2.75 (m, 5H), 2.86 (d, J=4.8 Hz, 2H), 2.93 (s, 3H), 3.50–3.65 (m, 2H), 4.24 (t, J=4.8 Hz, 1H), 4.51 (dd, J=8.2, 4.0 Hz, 1H), 6.81 (d, J=6.3 Hz, 1H), 6.84 (d, J=5.7 Hz, 2H), 7.18 (d, J=1.8 Hz, 1H), 7.85 (brs, 1H); MS (ES) m/z: 518.0 (MH$^+$); HRMS Calcd. for $C_{24}H_{32}N_5O_6S$(MH$^+$): 518.2073. Found: 518.2056.

EXAMPLE 88

N-[2-Hydroxy-5-(1-hydroxy-2-{1-[4-(2-imino-4-oxo-thiazolidin-5-ylidenemethyl)-phenyl]-piperidine-4-ylamino}-ethyl)-phenyl]-methanesulfonamide The title compound was prepared from 1-[4-(2-imino-4-oxo-thiazolidin-5-ylidenemethyl)-phenyl]-piperidine-4-one (which was obtained in Example 43) and N-[5-(2-amino-1-hydroxy-ethyl)-2-hydroxy-phenyl]-methanesulfonamide (which was obtained in Example 9) according to the procedure of Example 73 as a pale yellowish solid; mp >210° C. (decomposed); $^1$H NMR (300 MHz, DMSO-d$_6$) δ 1.20–1.40 (m, 2H), 1.80–2.00 (m, 2H), 2.50–3.00 (m, 5H), 2.92 (s, 3 H), 3.70–3.90 (m, 2H), 4.47 (dd, J=7.9, 4.4 Hz, 1H), 6.81 (d, J=8.3 Hz, 1H), 6.90–7.10 (m, 3 H), 7.18 (d, J=2.0 Hz, 2H), 7.39 (d, J=8.9 Hz, 2H), 7.47 (s, 1H); MS (ES) m/z: 532.0 (MH$^+$); HRMS Calcd. for $C_{24}H_{30}N_5O_5S_2$ (MH$^+$): 532.1688. Found: 532.1672.

EXAMPLE 89

4-((2S)-2-Hydroxy-3-{1–4-(2-imino-4-oxo-thiazolidin-5-ylmethyl)-phenyl]-piperidine-4-ylamino}-propoxy)-1,3-dihydro-benzoimidazol-2-one The title compound was prepared from 1-[4-(2-imino-4-oxo-thiazolidin-5-ylmethyl)-phenyl]-piperidine-4-one (which was obtained in Example 45) and (S)-4-[2-hydroxy-3-aminopropoxy]-1,3-dihydro-2H-benzimidazol-2-one (U.S. Pat. No. 5,786,356/1998) according to the procedure of Example 73 as a pale yellowish solid; mp >155° C. (decomposed); $^1$H NMR (300 MHz, DMSO-d$_6$) δ 1.20–1.40 (m, 2H), 1.80–1.95 (m, 2H), 2.50–2.90 (m, 6H), 3.24 (dd, J=14.1, 4.0 Hz, 1H), 3.50–3.75 (m, 2H), 3.80–4.05 (m, 3H), 4.50 (dd, J=9.8, 4.0 Hz, 1H), 4.88 (brs, 1H), 6.57 (d, J=7.8 Hz, 1H), 6.62 (d, J=8.1 Hz, 1H), 6.80–6.90 (m, 3H), 7.04 (d, J=8.7 Hz, 2H), 8.73 (brs, 1H); MS (ES) m/z: 256.3 ((M+2H)$^{2+}$, 100%), 511.2 (MH$^+$, 10%); HRMS Calcd. for $C_{25}H_{31}N_6O_4S$(MH$^+$): 511.2128. Found: 511.2122.

EXAMPLE 90

N-[2-Hydroxy-5-(1-hydroxy-2-{1-[4-(2-imino-4-oxo-thiazolidin-5-ylmethyl)-phenyl]-piperidine-4-ylamino}-ethyl)-phenyl]-methanesulfonamide The title compound was prepared from 1-[4-(2-imino-4-oxo-thiazolidin-5-ylmethyl)-phenyl]-piperidine-4-one (which was obtained in Example 45) and N-[5-(2-amino-1-hydroxy-ethyl)-2-hydroxy-phenyl]-methanesulfonamide (which was obtained in Example 9) according to the procedure of Example 73 as a pale yellowish solid; mp >90° C. (decomposed); $^1$H NMR (300 MHz, DMSO-d$_6$) δ 1.20–1.40 (m, 2H), 1.80–2.00 (m, 2H), 2.50–2.80 (m, 6H), 2.93 (s, 3H), 3.25 (dd, J=14.2, 3.9 Hz, 1H), 3.45–3.60 (m, 2H), 4.40–4.55 (m, 2H), 6.81 (d, J=8.3 Hz, 1H), 6.88 (d, J=8.6 Hz, 2H), 6.96 (dd, J=8.3, 2.0 Hz, 1H), 7.04 (d, J=8.6 Hz, 2H), 7.16 (d, J=2.0 Hz, 1H); MS (ES) m/z: 267.7 ((M+2H)$^{2+}$, 100%), 534.3 (MH$^+$, 45%), 1067.0 (2MH$^+$, 2%); HRMS Calcd. for $C_{24}H_{32}N_5O_5S_2$ (MH$^+$): 534.1845. Found: 534.1850.

EXAMPLE 91

5-(4-{4-[(2S)-2-Hydroxy-3-(8-hydroxy-2-oxo-1,2,3,4-tetrahydro-quinolin-5-yloxy)-propylamino]-piperidine-1-yl}-benzyl)-thiazolidine-2,4-dione The title compound was prepared from 5-[4-(4-oxo-piperidine-1-yl)-benzyl]-thiazolidine-2,4-dione (which was obtained in Example 38) and (S)-5-(3-amino-2-hydroxy-propoxy)-8-hydroxy-3,4-dihydro-1H-quinolin-2-one) (which was obtained in Example 12) according to the procedure of Example 73 as a pale yellowish solid; mp >140° C. (decomposed); $^1$H NMR (300 MHz, DMSO-d$_6$) δ 1.40–1.55 (m, 2H), 1.85–2.00 (m, 2H), 2.40 (t, J=8.0 Hz, 2H), 2.60–3.00 (m, 8H), 3.25 (dd, J=15.9, 3.9 Hz, 1H), 3.50–3.70 (m, 2H), 3.80–4.00 (m, 3H), 4.50 (dd, J=9.7, 3.9 Hz, 1H), 6.34 (d, J=8.9 Hz, 1H), 6.61 (d, J=8.9 Hz, 1H), 6.85 (d, J=8.6 Hz, 2H), 7.05 (d, J=8.6 Hz, 2H), 8.76 (s, 1H), 9.24 (brs, 1H); MS (ES) m/z: 541.1 (MH$^+$); HRMS Calcd. for $C_{27}H_{33}N_4O_6S$(MH$^+$): 541.2121. Found: 541.2148.

EXAMPLE 92

N-[5-((2S)-3-{1–4-(2,4-Dioxo-thiazolidin-5-ylmethyl)-phenyl]-piperidine-4-ylamino}-2-hydroxy-propoxy)-2-hydroxy-phenyl]-methanesulfonamide The title compound was prepared from 5-[4-(4-oxo-piperidine-1-yl)-benzyl]-thiazolidine-2,4-dione (which was obtained in Example 38) and N-[5-((2S)-3-amino-2-hydroxy-propoxy)-2-hydroxy-phenyl]-methanesulfonamide (which was obtained in Example 14) according to the procedure of Example 73 as a grey solid; mp >70° C. (decomposed); $^1$H NMR (300 MHz, DMSO-d$_6$) δ 1.45–1.55 (m, 2H), 1.85–2.00 (m, 2H), 2.60–2.90 (m, 6H), 2.94 (s, 3H), 3.23 (dd, J=14.0, 3.8 Hz, 1H), 3.60–4.00 (m, 5H), 4.49 (dd, J=8.8, 3.9 Hz, 1H), 6.64 (dd, J=8.8, 3.0 Hz, 1H), 6.75–6.90 (m, 4H), 7.04 (d, J=8.6 Hz, 2H); MS (ES) m/z: 564.8 (MH$^+$, 100%); HRMS Calcd. for $C_{25}H_{33}N_4O_7S_2$ (MH$^+$): 565.1791. Found: 565.1783.

EXAMPLE 93

N-[5-((2S)-3-{1-[4-(2,4-Dioxo-thiazolidin-5-ylmethyl)-phenyl]-piperidine-4-ylamino}-2-hydroxy-propoxy)-2-hydroxy-phenyl]-benzenesulfonamide The title compound was prepared from 5-[4-(4-oxo-piperidine-1-yl)-benzyl]-thiazolidine-2,4-dione (which was obtained in Example 38) and N-[5-(3-amino-2-hydroxy-propoxy)-2-hydroxy-phenyl]-benzenesulfonamide (which was obtained in Example 21) according to the procedure of Example 73 as an off-white solid; mp >120° C. (decomposed); $^1$H NMR (300 MHz, DMSO-d$_6$) δ 1.30–1.55 (m, 2H), 1.80–2.00 (m, 2H), 2.50–4.00 (m, 12H), 4.55 (dd, J=9.6, 4.0 Hz, 1H), 6.49 (dd, J=8.7, 2.9 Hz, 1H), 6.61 (d, J=8.7 Hz, 1H), 6.77 (d, J=2.9 Hz, 1H), 6.86 (d, J=8.7 Hz, 2H), 7.05 (d, J=8.7 Hz, 2H), 7.40–7.60 (m, 3H), 7.70–7.80 (m, 2H); MS (ES) m/z: 627.0 (MH$^+$, 100%); HRMS Calcd. for $C_{30}H_{35}N_4O_7S_2$ (MH$^+$): 627.1941. Found: 627.1954.

EXAMPLE 94

(R)-Propane-2-sulfonic acid [5-(2-{1-[4-(2,4-dioxo-thiazolidin-5-ylmethyl)-phenyl]-piperidine-4-ylamino}-1-hydroxy-ethyl)-2-hydroxy-phenyl]-amide The title compound was prepared from 5-[4-(4-oxo-piperidine-1-yl)-benzyl]-thiazolidine-2,4-dione (which was obtained in Example 38) and propane-2-sulfonic acid [5-((1R)-2-amino-1-hydroxy-ethyl)-2-hydroxy-phenyl]-amide (which was obtained in Example 27) according to the procedure of Example 73 as a white solid; mp >175° C. (decomposed); $^1$H NMR (300 MHz, DMSO-d$_6$) δ 1.25 (d, J=6.8 Hz, 6H), 1.30–1.55 (m, 2H), 1.80–2.00 (m, 2H), 2.60–3.70 (m, 9H), 4.47 (dd, J=9.7, 3.9 Hz, 1H), 4.58 (dd, J=8.7, 3.4 Hz, 1H), 6.75–6.90 (m, 3H), 6.90–7.10 (m, 3H), 7.26 (d, J=2.0 Hz, 1H); MS (ES) m/z: 563.0 (MH+, 100%); HRMS Calcd. for $C_{26}H_{35}N_4O_6S_2$ (MH$^+$): 563.1992. Found: 563.1985.

EXAMPLE 95

N-[2-Chloro-5-((1R)-2-{1-[4-(2,4-dioxo-thiazolidin-5-ylmethyl)-phenyl]-piperidine-4-ylamino}-1-hydroxy-ethyl)-phenyl]-methanesulfonamide To a stirred mixture of copper(ll) sulfate pentahydrate (0.042 g, 0.17 mmol) in N,N-dimethylformamide (15 mL) was added sodium borohydride (0.037 g, 1 mmol). To the resulting suspension was added N-[5-((1R)-2-azido-1-hydroxy-ethyl)-2-chloro-phenyl]-methanesulfonamide (which was obtained in Example 25) (0.11 g, 0.38 mmol). After stirring for 20 minutes more copper(II) sulfate pentahydrate (0.042 g, 0.17 mmol) and sodium triacetoxyborohydride (0.064 g, 0.3 mmol) was added. The reaction mixture was stirred for 2.5 hours and then 5-[4-(4-oxo-piperidine-1-yl)-benzyl]-thiazolidine-2,4-dione (which was obtained in Example 38) (0.116 mg, 0.38 mmol), sodium triacetoxyborohydride (0.212 g, 1.0 mmol), and acetic acid (0.2 mL) were added. After stirring for 1.5 hours aqueous sodium bicarbonate solution was added and the resulting solid was collected. The product was purified by flash silica gel chromatography eluting with methylene chloride and methanol to give the title compound as a pale grey solid; mp >105° C. (decomposed); $^1$H NMR (300 MHz, DMSO-d$_6$) δ 1.30–1.50 (m, 2H), 1.80–2.00 (m, 2H), 2.60–3.60 (m, 9H), 3.00 (s, 3H), 4.40–4.55 (m, 1H), 4.65–4.75 (m, 1H), 6.84 (d, J=8.4 Hz, 2H), 7.04 (d, J=8.4 Hz, 1H), 7.20 (d, J=8.1 Hz, 1H), 7.40–7.50 (m, 2H); MS (ES) m/z: 553.2 (MH$^+$, 100%); HRMS Calcd. for $C_{24}H_{30}ClN_4O_5S_2$ (MH$^+$): 553.1440. Found: 553.1336.

EXAMPLE 96

N-(5-{(1R)-2-[(1-[4-[(2,4-Dioxo-1,3-thiazolidin-5-yl)methyl]phenyl}piperidine-4-yl)amino]-1-hydroxyethyl}-2-hydroxyphenyl)benzenesulfonamide The title compound was prepared from 5-[4-(4-oxo-piperidine-1-yl)-benzyl]-thiazolidine-2,4-dione (which was obtained in Example 38) and N-[5-((R)-2-amino-1-hydroxy-ethyl)-2-hydroxy-phenyl]-phenylsulfonamide (which was obtained in Example 32) according to the procedure of Example 73 as a white solid; mp >150° C. (decomposed); $^1$H NMR (300 MHz, DMSO- d$_6$) δ 1.39 (m, 4H), 1.85 (m, 4H), 2.64 (m, 2H), 2.89 (s, 3H), 4.48 (m, 1H), 6.67 (d, J=6 Hz, 1H), 6.86 (m, 2H), 7.02 (m, 2H), 7.48 (m, 2H), 7.72 (d, J=6

Hz, 1H); MS (ES) m/z: 597.0 (MH+, 100%); HRMS Calcd. for $C_{29}H_{32}N_4O_6S_2$ (MH+): 597.1836. Found: 597.1827.

EXAMPLE 97

N-[2-Hydroxy-5-(1-hydroxy-2-{1-[4-(1H-tetrazol-5-yl)-phenyl]-piperidine-4-ylamino}-ethyl)-phenyl]-methanesulfonamide The title compound was prepared from 1-[4-(1H-tetrazol-5-yl)-phenyl]-piperidine-4-one (which was obtained in Example 47) and N-[5-((1R)-2-amino-1-hydroxy-ethyl)-2-hydroxy-phenyl]-methanesulfonamide (which was obtained in Example 10) according to the procedure of Example 73 as a white solid; mp >175° C. (decomposed); $^1$H NMR (300 MHz, DMSO-d$_6$) δ 1.40–1.65 (m, 2H), 1.90–2.10 (m, 2H), 2.70–3.10 (m, 5H), 2.95 (s, 3H), 3.70–3.85 (m, 2H), 4.69 (dd, J=9.3, 3.0 Hz, 1H), 6.89 (d, J=8.3 Hz, 1H), 6.97 (d, J=8.9 Hz, 2H), 7.06 (dd, J=8.3, 2.0 Hz, 1H), 7.24 (d, J=2.0 Hz, 1H), 7.80 (d, J=8.9 Hz, 2H); MS (ES) m/z: 474.1 (MH+); HRMS Calcd. for $C_{21}H_{28}N_7O_4S$(MH+): 474.1918. Found: 474.1912.

EXAMPLE 98

Ethyl [5-(4-{4-[((2R)-2-hydroxy-2-{4-hydroxy-3-[(methylsulfonyl)amino]phenyl}ethyl)amino]-1-piperidineyl}phenyl)-1H-tetraazol-1-yl]acetate The title compound was prepared from ethyl{5-[4-(1,4-dioxa-8-azaspiro[4.5]dec-8-yl)phenyl]-1H-tetraazol-1-yl}acetate (which was obtained in Example 48) and N-[5-((1R)-2-amino-1-hydroxy-ethyl)-2-hydroxy-phenyl]-methanesulfonamide (which was obtained in Example 10) according to the procedures of Example 34 and Example 73 as a white solid; mp >140° C. (decomposed); $^1$H NMR (300 MHz, DMSO-d$_6$) δ 1.17 (t, J=7.1 Hz, 3H), 1.20–1.40 (m, 2H), 1.80–1.95 (m, 2H), 2.50–3.50 (m, 5H), 2.89 (s, 3H), 3.70–3.90 (m, 2H), 4.11 (q, J=7.1 Hz, 2H), 4.47 (dd, J=7.8, 4.4 Hz, 1H), 5.60 (brs, 2H), 6.79 (d, J=8.2 Hz, 1H), 6.96 (dd, J=8.2, 2.0 Hz, 1H), 7.07 (d, J=8.9 Hz, 2H), 7.16 (d, J=2.0 Hz, 1H), 7.56 (d, J=8.9 Hz, 2 H); MS (ES) m/z: 560.2 (MH+); HRMS Calcd. for $C_{21}H_{28}N_7O_4S$(MH+): 560.2286. Found: 560.2282.

EXAMPLE 99

[5-(4-{4-[((2R)-2-Hydroxy-2-{4-hydroxy-3-[(methylsulfonyl)amino]phenyl}ethyl)amino]-1-piperidineyl}phenyl)-1H-tetraazol-1-yl]acetic acid The title compound was prepared from ethyl [5-(4-{4-[((2R)-2-hydroxy-2-{4-hydroxy-3-[(methylsulfonyl)amino]phenyl}ethyl)amino]-1-piperidineyl}phenyl)-1H-tetraazol-1-yl]acetate (which was obtained in Example 98) by NaOH hydrolysis as an off -white solid; mp >210° C. (decomposed); $^1$H NMR (300 MHz, DMSO-d$_6$) δ 1.30–1.50 (m, 2H), 1.80–2.00 (m, 2H), 2.60–3.50 (m, 5H), 2.92 (s, 3H), 3.70–3.85 (m, 2H), 4.50–4.60 (m, 1H), 4.70–4.80 (m, 2H), 6.84 (d, J=8.2 Hz, 1H), 6.95–7.05 (m, 3H), 7.20 (d, J=1.6 Hz, 1H), 7.66 (d, J=8.7 Hz, 2H); MS (ES) m/z: 530.2 (M–H)−; HRMS Calcd. for $C_{21}H_{28}N_7O_4S$(M–H)−: 530.1827. Found: 530.1827.

EXAMPLE 100

[5-(4-{4-[((2R)-2-Hydroxy-2-[4-hydroxy-3-[(methylsulfonyl)amino]phenyl}ethyl)amino]-1-piperidineyl}phenyl)-2H-tetraazol-2-yl]acetic acid The title compound was prepared from ethyl{5-[4-(1,4-dioxa-8-azaspiro[4.5]dec-8-yl)phenyl]-2H-tetraazol-2-yl}acetate (which was obtained in Example 48) and N-[5-((1R)-2-amino-1-hydroxy-ethyl)-2-hydroxy-phenyl]-methanesulfonamide (which was obtained in Example 10) according to the procedures of Example 98 and Example 99 as a white solid; mp >240° C. (decomposed); $^1$H NMR (300 MHz, DMSO-d$_6$) δ 1.45–1.65 (m, 2H), 1.90–2.10 (m, 2H), 2.50–3.10 (m, 5H), 2.95 (s, 3H), 3.65–3.85 (m, 2H), 4.89 (brd, J=8.3 Hz, 1H), 5.08 (d, J=15.9 Hz, 1H), 5.15 (d, J=15.9 Hz, 1H), 6.88 (d, J=8.3 Hz, 1H), 6.95 (d, J=8.7 Hz, 2H), 7.09 (dd, J=8.3, 2.0 Hz, 1H), 7.26 (d, J=2.0 Hz, 1H), 7.87 (d, J=8.7 Hz, 2H); MS (ES) m/z: 532.1 (MH+); HRMS Calcd. for $C_{21}H_{30}N_7O_4S$(MH+): 532.1973. Found: 532.1965.

EXAMPLE 101

Trifluoromethylthioacetamide

A mixture of trifluoroacetamide (45.2 g, 0.4 mol), Lawesson's Reagent(2,4-bis(4-methoxyphenyl)-1,3-thia-2,4-diphosphetane-2,4-disulfide) (81.7 g, 0.202 mol) and benzene (600 mL) was refluxed for 20 hours. The volatiles were removed in vacuo and the residue was purified by silica gel filtration (hexanes/dichloromethane 1/1) to give light yellow solid (24 g, 47% yield); MS (ES) m/z: 130 (MH+); $^1$H NMR (300 MHz, DMSO-d$_6$) δ 6.90 (d, 1H), 7.60 (d, 1H).

EXAMPLE 102

2-Bromo-1-[2-(trifluoromethyl)-1,3-thiazole-4-yl]ethanone

A solution of trifluoromethylthioacetamide (which was obtained in Example 101) (14 g, 0.11 mol) in acetonitrile (200 mL) was added dropwise into a boiling solution of 1,4-dibromo-2,3-butanedione (26.4 g, 0.11 mol) in acetonitrile (200 mL) over a period of 2.5 hours. The volatiles were removed in vacuo and the residue was purified by flash chromatography (hexanes/toluene 6/4) to give a light pink colored solid (7.0 g, 24 % yield); mp 36–37° C.; MS (ES) m/z: 273 (M–H)−; $^1$H NMR (400 MHz, CDCl$_3$) δ 4.64 (s, 2H), 8.50 (s, 1H).

EXAMPLE 103

(1S)-2-Bromo-1-[2-(trifluoromethyl)-1,3-thiazole-4-yl]ethanol

Borane (in THF, 1M, 10.35 mL, 10.5 mmol) was added dropwise into a mixture of (R)-2-methyl-CBS-oxazaborolidine monohydrate (0.38 g, 1.31) mmol and tetrahydrofuran (15 mL) under a nitrogen atmosphere at ambient temperature. The mixture was stirred for 10 minutes and then 2-bromo-1-[2-(trifluoromethyl)-1,3-thiazole-4-yl]ethanone (which was obtained in Example 102) (3.6 g, 13.13 mmol) in tetrahydrofuran (20 mL) was added dropwise over 10 minutes. The new mixture was stirred at room temperature for 4 hours. The reaction mixture was cooled to 0° C. and quenched with a hydrogen chloride/ethyl ether solution (1M, 1.0 mL). After stirring at 0° C. for 30 minutes, H$_2$O (20 mL) was added dropwise and the mixture was extracted with ethyl ether. The organic layer was washed with aqueous ammonium chloride and dried over MgSO$_4$. Evaporation and purification by flash chromatography (hexanes/dichloromethane/ethanol 1/1/0.01) gave a clear oil (2,4 g, 66% yield); MS (ES) m/z: 334/336 (M+acetic acid–H)−; $^1$H NMR (400 MHz, CDCl$_3$) δ 2.94 (m, 1H), 3.74 (m, 1H), 3.94 (m, 1H), 5.16 (m, 1H), 7.62 (s, 1H).

EXAMPLE 104

4-[(2S)-Oxiran-2-yl]-2-trifluoromethyl-1,3-thiazole

Aqueous sodium hydroxide (5N, 11 mL) was added to a solution of (1S)-2-bromo-1-[2-(trifluoromethyl)-1,3- thiazole-4-yl]ethanol (which was obtained in Example 103) (1.52 g, 5.5 mmol) in tetrahydrofuran (6 mL). The mixture was stirred at room temperature for 18 hours. The reaction mixture was diluted with $H_2O$ (30 mL) and extracted with dichloromethane. The organic extracts were washed with $H_2O$ and brine, and dried over $MgSO_4$. Evaporation and purification by flash chromatography (hexanes/dichloromethane 6/4) gave a clear oil (1.33 g, 74% yield); MS (ES) m/z: 196 (MH$^+$); $^1$H NMR (400 MHz, CDCl$_3$) δ 3.09 (m, 1H), 3.19 (m, 1H), 4.11 (m, 1H), 7.48 (s, 1H).

EXAMPLE 105

(1S)-(2-Amino-1-[2-trifluoromethyl]-1,3-thiazole-4-yl]ethanol

Ammonia (20 g) was bubbled over 1 hour into a cold (−40° C.) pressure vessel containing 4-[(2S)-oxiran-2-yl]-2-trifluoromethyl-1,3-thiazole(which was obtained in Example 104) (0.13 g, 6.8 mmol) and methyl alcohol (40 mL). The reaction vessel was sealed, warmed up to room temperature and stirred for 48 hours. The methyl alcohol was removed in vacuo and the product was purified by flash chromatography (chloroform/methyl alcohol/triethylamine 8/2/0.01) to give a white solid (0.65 g, 45% yield); MS (ES) m/z: 213 (MH$^+$); $^1$H NMR (400 MHz, CDCl$_3$) δ 3.05 (m, 1H), 3.21 (m, 1H), 4.85 (m, 1H), 7.55 (s, 1H).

EXAMPLE 106

5-{4-[4-({(2S)-2-Hydroxy-2-[2-(trifluoromethyl)-1,3-thiazol-4-yl]etyl}amino)piperidine-1-yl]benzyl]-1,3-thiazolidine-2,4-dione A mixture of (1S)-(2-amino-1-[2-trifluoromethyl]-1,3-thiazole-4-yl]ethanol (which was obtained in Example 105) (0.34 g, 1.59 mmol) and 5-[4-(4-oxopiperidine-1-yl)benzyl]-1,3-thiazolidine-2,4-dione (which was obtained in Example 38) (0.48 g, 1.59 mmol), sodium triacetoxyborohydride (0.67 g, 3.18 mmol), and acetic acid (0.33 mL) in N,N-dimethylformamide (15 mL) was stirred at room temperature for 18 hours, poured into aqueous ammonium chloride and extracted with ethyl acetate. The organic extracts were washed with brine and dried over $MgSO_4$. Evaporation and purification by flash chromatography (chloroform/methyl alcohol 9.5/5) gave a yellow solid (0.1 g, 13% yield); mp 108–113° C.; MS (ES) m/z: 501 (MH$^+$); $^1$H NMR (400 MHz, DMSO-d$_6$) δ 1.44 (m, 2H), 1.93 (s, 2H), 3.23–2.66 (m, 7H), 3.62 (d, 2H), 4.68 (m, 1H), 4.94 (m, 1H), 6.86 (d, 2H), 7.5 (d, 2H), 8.3 (s, 1H); Anal. Calcd. for C$_{21}$H$_{23}$F$_3$N$_4$O$_3$S$_2$: C, 50.39; H, 4.63; N, 11.19. Found: C, 50.16; H, 5.16; N, 9.93.

EXAMPLE 107

(1S)-2-Bromo-1-[3-(3,4-dichlorophenyl)isoxazol-5-ylmethanol

The title compound was prepared from 5-(bromoacetyl)-3-(3,4-dichlorophenylisooxazole), 1M BH$_{6.3}$ 3/THF, and (R)-2-methyl-CBS-oxazaborolidine monohydrate in substantially the same manner as described in Example 103 and was obtained as a white solid (4.5 g, 89% yield), mp 103–104° C.; MS m/z: 335 (M$^+$); $^1$H NMR (400 MHz, DMSO-d$_6$) δ 3.76 (m, 2H), 5.05 (m, 1H), 6.50 (d, 1H), 7.17 (s, 1H), 7.90 (d, 1H), 7.92 (d, 1H), 8.34 (s, 1H).

EXAMPLE 108

3-(3,4-Dichlorophenyl)-5-[(2S)-oxiran-2-yl]isoxazole

The title compound was prepared from (1S)-2-bromo-1-[3-(3,4-dichlorophenyl)isoxazol-5-ylmethanol (which was obtained in Example 107), in aqueous sodium hydroxide (5N) in substantially the same manner as described in Example 104 and was obtained as a white solid (1.6 g, 84% yield); mp 74° C.; MS (ES) m/z: 256 (MH$^+$): $^1$H NMR (400 MHz, CDCl$_3$) δ 3.25 (m, 2H), 4.04 (d, 1H), 6.54 (s, 1H), 7.54 (d, 1H), 7.62 (d, 1H),7.89 (s, 1H).

EXAMPLE 109

(1S)-2-Amino-1-[3-(3,4-dichlorophenyl)isoxazol-5-yl]ethanol

The title compound was prepared from 3-(3,4-dichlorophenyl)-5-[(2S)-oxiran-2-yl]isoxazole (which was obtained in Example 108), in methyl alcohol and ammonia in substantially the same manner as described in Example 105, and was obtained as a white solid (0.43 g, 80% yield), mp 105° C.; MS (ES) m/z: 273 (MH$^+$); $^1$H NMR (400 MHz, CDCl$_3$) δ 3.18 (m, 2H), 4.83 (m, 1H), 6.56 (s, 1H),7.54 (d, 1H), 7.62 (d, 1H), 7.90 (s, 1H).

EXAMPLE 110

5-{4-[4-({(2S)-2-[3-(3,4-Dichlorophenyl)isoxazol-5-yl]-2-hydroxyethyl}-amino)piperidine-1-yl}benzyl}-1,3-thiazole-2,4-dione The title compound was prepared from (1S)-2-amino-1-[3-(3,4-dichloro-phenyl)isoxazol-5-yl]ethanol (which was obtained in Example 109) and 5-[4-(4-oxopiperidine-1-yl)benzyl]-1,3-thiazolidine-2,4-dione (which was obtained in Example 38) in substantially the same manner, as described in Example 106 and was obtained as a white solid (0.22 g, 48% yield), mp 110° C.; MS (ES) m/z: 561 (MH$^+$); $^1$H NMR (400 MHz, DMSO-d$_6$) δ 1.38 (m, 2H), 1.89 (m, 2H), 3.32–2.67 (m, 7H), 3.60 (m, 2H), 4.74 (m. 1H), 4.85 (m, 1H), 6.85 (d, 1H), 7.02 (d, 1H), 7.11 (s, 1H), 7.79 (d, 1H), 7.86 (d, 1H), 8.13 (s, 1H).

EXAMPLE 111

N-[4-(2-Bromoacetyl)phenyl]methanesulfonamide

A solution of bromine (0.73 mL, 14.06 mmol) in methylene chloride (5 mL) was added at room temperature over 10 minutes to a mixture of N-[4-(2-bromoacetyl)phenyl]-methanesulfonamide (Uloth, R. H. et al. *J Med. Chem.*, 1966, 88–97) (2.41 g, 8.25 mmol), (R)-2-methyl-CBS-oxazaborolidine monohydrate (3 g, 14.06 mmol), benzoylperoxide (0.05 g), and methylene chloride (40 mL). The new mixture was stirred for 60 hours. The precipitate was collected, washed with ethyl ether and crystallized from ethanol to give an off-white solid (2.5 g, 60% yield); MS (ES) m/z: 291 (M)$^+$; $^1$H NMR (400 MHz, DMSO-d$_6$) δ 3.14 (s, 3H), 4.82 (s, 2H), 7.25 (d, 2H), 7.95 (d, 2H), 10.21 (s, 1H); Anal. Calcd. for: C$_9$H$_{10}$BrNO$_3$S: C, 37.00, H, 3.45, N, 4.79. Found: C, 36.26, H, 3.19, N, 4.67.

EXAMPLE 112

N-{4-[(1R)-2-Bromo-1-hydroxyethyl]phenyl}methanesulfonamide

The title compound was prepared from N-[4-(2-bromoacetyl)phenyl]methanesulfonamide (0.23 g, 0.82 mmol)(which was obtained in Example 111), and 1M BH$_3$/THF solution (10.35 mL, 10.5 mmol) in substantially the same manner, as described in Example 103 and was obtained as a white solid (1.75 g, 72% yield); MS (ES) m/z: 293 (M)$^+$; $^1$H NMR (400 MHz, DMSO-d$_6$) δ 7.14 (d, 2H), 2.95 (s, 3H), 3.53 (m, 1H), 3.55 (m, 1H), 4.73, (m, 1H), 5.75 (d, 1H), 7.14 (d, 2H), 9.74 (s, 1H).

EXAMPLE 113

N-{4-[(1R)-Azido-1-hydroxyethyl]phenyl}methanesulfonamide

A mixture of N-{4-[(1S)-2-bromo-1-hydroxyethyl]phenyl}methanesulfonamide (which was obtained in Example 112) (1.73 g, 5.9 mmol), sodium iodide (0.88g, 5.9 mmol), sodium azide (1.53 g, 23.6 mmol), and methyl sulfoxide (15 mL) was stirred at ambient temperature for 7 days, poured into water and extracted with ethyl acetate. The organic extracts were washed with water, and dried over $MgSO_4$. Evaporation and purification by flash chromatography (hexanes/chloroform/isopropylalcohol 5/4.5/0.5) gave an off-white solid (0.56 g, 70% yield); MS (ES) m/z: 256 $(M)^+$; $^1H$ NMR (400 MHz, DMSO-$d_6$) δ 2.94 (s, 3H), 3.30 (m, 2H), 4.74 (m, 1H), 5.75 (d, 1H), 7.17 (d, 2H), 7.32 (d, 2H), 9.67 (s, 1H).

EXAMPLE 114

N-{4-[(1R)-2-Amino-1-hydroxyethyl]phenyl}methanesulfonamide

A mixture of N-{4-[(1S)-azido-1-hydroxyethyl]phenyl}methanesulfonamide (which was obtained in Example 113) (0.55 g, 2.146 mmol), 10% Pd/C (0.03 g) and methanol (30 mL) was hydrogenated on a Parr shaker at 50 psi for 3 hours. The catalyst was removed by filtration through celite. The filtrate was concentrated under vacuo to give an off-white solid (0.48 g, 97% yield); MS (ES) m/z: 231 $(MH^+)$; $^1H$ NMR (400 MHz, DMSO-$d_6$) δ 2.57 (m, 2H), 2.94 (s, 3H), 3.4–4.2 (br, 2H), 4.38 (m, 1H), 4.6–5.8 (br, 2H), 7.23 (d, 2H), 7.26 (d, 2H).

EXAMPLE 115

N-(4-{(1R)-2-[(1-{4-[(2,4-Dioxo-1,3-thiazolidin-5-yl)methyl]phenyl}piperidine-4yl)amino]-1-hydroxyethyl)}phenyl)methanesulfonamide The title compound was prepared from N-[4-[(1R)-2-amino-1-hydroxyethyl]phenyl}methanesulfonamide (which was obtained in Example 114) and 5-[4-(4-oxopiperidine-1-yl)benzyl]-1,3-thiazolidine-2,4-dione (which was obtained in Example 38) in substantially the same manner, as described in Example 106 and was obtained as a white solid(0.33 g, 50% yield); mp 138–145° C.; MS (ES) m/z: 519 $(MH^+)$; $^1H$ NMR (400 MHz, DMSO-$d_6$) δ 1.49 (m, 2H), 1.97 (m, 2H), 2.65 (t, 2H), 2.88–2.95 (br, 5H), 3.20–3.45 (br, 3H), 3.63 (d. 2H), 4.68 (m, 1H), 4.70 (m, 1H), 6.85 (d, 2H), 7.02 (d, 2H), 7.18 (d, 2H), 7.32 (d, 2H), 8.01–9.21 (br, 3H).

EXAMPLE 116

Dibromoformaldoxime

A mixture of glyoxylic acid monohydrate (96.63 g, 1.05 mol), hydroxylamine hydrochloride (73.7 g, 1.06 mol) and water was stirred at ambient temperature for 18 hours. Sodium bicarbonate (176.4 g, 2.1 mol) was carefully added over 30 minutes followed by methylene chloride (600 mL). The new mixture was cooled to 5° C. and a solution of bromine (75 mL, 2.9 mol) in methylene chloride (350 mL) was added at such a rate that the temperature did not rise above 5° C. Upon completion of the addition of bromine the mixture was further stirred at 5° C. and the organic layer was separated. The aqueous layer was extracted with methylene chloride. The combined organic extracts were dried over $MgSO_4$. Evaporation and purification by recrystallization from hexanes gave a white solid (32.5 g, 15% yield); $^1H$ NMR (400 MHz, DMSO-$d_6$) δ 11.73 (s, 1H).

EXAMPLE 117

3-Bromo-5-acetylisoxazole

A mixture of dibromoformaldoxime(which was obtained in Example 116) (32.5 g, 160.2 mmol), 3-butyn-one (13.41 g, 197 mmol), potassium carbonate (11 g, 80.1 mmol), and methylene chloride (300 mL) was stirred at ambient temperature for 20 hours. The slurry was then treated with aqueous hydrochloric acid (2N, 200 mL) and extracted with methylene chloride. The combined organic extracts were dried over $MgSO_4$. Evaporation and purification by flash chromatography (ethyl acetate/hexanes 5/95) gave a white solid (16.76 g, 56% yield); $^1H$ NMR (300 MHz, $CDCl_3$) δ 2.62 (s, 3H), 6.97 (s, 1H).

EXAMPLE 118

3-Bromo-5-(bromoacetyl)isoxazole

A mixture of 3-bromo-5-acetylisoxazole (which was obtained in Example 117) (16.7 g, 87.9 mmol), phenyltrimethylammonium tribromide (33.4 g, 88.8 mmol) and tetrahydrofuran (150 mL) was stirred at ambient temperature for 18 hours, poured into water and extracted with ether. The organic extracts were washed with brine and dried over $MgSO_4$. Evaporation and purification by distillation gave a light yellow oil (8.9 g, 40% yield); $^1H$ NMR (300 MHz, $CDCl_3$) δ 4.40. (s, 3H), 7.10 (s, 1H).

EXAMPLE 119

(1R)-2-Bromo-1-(3-bromoisoxazole-5-yl)ethanol

The title compound was prepared from 3-bromo-5-(bromoacetyl)isoxazole (which was obtained in Example 118), (R)-2-methyl-CBS-oxaborolidine monohydrate, and 1M $BH_3$/THF solution in substantially the same manner, as described in Example 103 with one change; the crude product was purified by flash chromatography and reverse phase chromatography to give a colorless oil (1.45 g, 16% yield): $^1H$ NMR (300 MHz, $CDCl_3$) δ 3.67 - 3.81 (m, 2H), 5.16. (m, 1H), 6.49 (s, 1H).

EXAMPLE 120

3-Bromo-5-[(2S)-oxiran-2-yl]isoxazole

A mixture of (1R)-2-bromo-1-(3-bromoisoxazole-5-yl) ethanol (which was obtained in Example 119) (1.44 g, 5.31 mmol), potassium carbonate (1.46 g, 10.62 mmol) and acetone (30 mL) was stirred at ambient temperature for 48 hours. The reaction mixture was filtered, and the solvent was removed in vacuo. The residue was purified by flash chromatography (hexanes/chloroform/isopropyl alcohol 8/1.8/0.2) to give a colorless oil (0.774 g, 53% yield); $^1H$ NMR (300 MHz, $CDCl_3$) δ 3.17 (m, 1H), 3.21 (m, 1H), 3.99 (m, 1H), 6.38 (s, 1H).

EXAMPLE 121

(1S)-2-Amino-1-(3-bromoisoxazole-5-yl)ethanol

The title compound was prepared from 3-bromo-5-[(2S)-oxiran-2-yl]isoxazole (which was obtained in Example 120)

in substantially the same manner as described in Example 105 and was obtained as an off-white solid (0.54 g, 90% yield): MS (ES) m/z: 207 (MH)$^+$; $^1$H NMR (400 MHz, CDCl$_3$) δ 1.7 (br, 3H), 3.13 (br, 2H), 4.77 (t, 1H), 6.35 (s, 1H).

EXAMPLE 122

5-[4-(4-{[4-(2S)-2-(3-Bromoisoxazol-5-yl)-2-hydroxyethyl]amino}piperidine-1-yl)benzyl]-1,3-thiazolidine-2,4-dione The title compound was prepared from (1S)-2-amino-1-(3-bromoisoxazole-5-yl)ethanol (which was obtained in Example 121) and 5-[4-(4-oxopiperidine-1-yl)benzyl]-1,3-thiazolidine-2,4-dione (which was obtained in Example 38) in substantially the same manner, as described in Example 106 and was obtained as a white solid (0.13 g, 88% yield); mp 145–150° C.; MS (ES) m/z: 519 (MH$^+$); $^1$H NMR (400 MHz, DMSO-d$_6$) δ 1.49 (m, 2H), 1.97 (m, 2H), 2.65 (t, 2H), 288–2.95 (br, 5H), 3.20–3.45 (br, 3H), 3.63 (d, 2H), 4.68 (m, 1H), 4.70 (m, 1H), 6.85 (d, 2H), 7.02 (d, 2H), 7.18 (d, 2H), 7.32 (d, 2H), 8.00–9.20 (br, 3H).

EXAMPLE 123

3-(2-Oxiranylmethoxy)pyridine

Sodium hydride (60%, 2.16 g, 54.0 mmol) was added portionwise into N,N-dimethylformamide (50 mL) with stirring at room temperature under a nitrogen atmosphere. A solution of 3-pyridinol (4.5 g, 46.28 mmol) in N,N-dimethylformamide (50 mL) was then added dropwise to this suspension over a period of 0.5 hour. After stirring for 1 hour a solution of (2S)-oxiranylmethyl 3-nitrobenzenesulfonate (10 g, 38.57 mmol) in N,N-dimethylformamide (50 mL) was added dropwise into this mixture over a period of 15 minutes. The mixture was then stirred at room temperature overnight. The reaction was quenched with aqueous ammonium chloride to pH 5 and extracted with ethyl acetate. The extracts were washed with water and dried with brine. Evaporation and purification by flash column chromatography (dichloromethane/methyl alcohol 95/5) gave a brown oil (1.44 g, 25% yield); $^1$H NMR (400 MHz, DMSO-d$_6$) δ 2.71–2.73 (m, 1H), 2.81–2.84 (m, 1H), 3.34–3.38 (m, 1H), 3.87–3.92 (m, 1H), 4.40–4.43 (m, 1H), 7.30–7.33 (m, 1H), 7.39–7.41 (m, 1H), 8.17–8.19 (m, 1H), 8.31 (s, 1H); MS (ES) m/z: 152 (MH$^+$).

EXAMPLE 124

(2S)-1-Amino-3-(3-pyridinyloxy)-2-propanol

A solution of 3-(2-oxiranylmethoxy)pyridine (which was obtained in Example 123) (1.41 g) in 120 mL of saturated ammonium methanol was stirred at 0° C. for two days. The reaction mixture was concentrated to give a yellow semi-solid (1.56 g, 99.5% yield); $^1$H NMR (400 MHz, DMSO-d$_6$) δ 1.60 (brs, 2H), 2.55–2.59 (m, 1H), 2.61–2.68 (m, 1H), 3.67–3.72 (m, 1H), 3.89–3.93 (m, 1H), 4.00–4.04 (m, 1H), 4.90 (brs, 1H), 7.29–7.32 (m, 1H), 7.36–7.38 (m, 1H), 8.13–8.14 (d, 1H), 8.27 (s, 1H); MS (ES) m/z: 138 (M$^+$); Anal. Calcd. for C$_7$H$_{10}$N$_2$O: C, 57.13; H, 7.19; N, 16.66. Found: C, 57.83; H, 7.17; N, 18.98.

EXAMPLE 125

5-(4-{4-[(2S)-2-Hydroxy-3-(pyridin-3-yloxy)-propylamino]-piperidine-1-yl}-benzyl)-thiazolidine-2,4-dione (2S)-1-Amino-3-(3-pyridinyloxy)-2-propanol (0.21 g, 1.25 mmol) (which was obtained in Example 124) and 5-[4-(4-oxo-1-piperidineyl)benzyl]-1,3-thiazolidine-2,4-dione (which was obtained in Example 38) (0.413, 1.25 mmol) were mixed in N,N-dimethylformamide (12 mL) and then treated with sodium triacetoxyborohydride (0.56 g, 2.5 mmol) and acetic acid (0.26 mL). After stirring at room temperature under a nitrogen atmosphere for one day, the mixture was purified by column chromatography (dichloromethane/methyl alcohol 85/5) to give the title compound as a yellow solid (0.25 g, 56% yield); mp: 130–132° C.; $^1$H NMR (400 MHz, DMSO-d$_6$) δ 1.20–1.54 (m, 2H), 1.90–2.02 (m, 2H), 2.67 (t, 2H), 2.78–2.97 (m, 4H), 3.22–3.26 (m, 1 H), 3.35 (brs, 2H), 3.64–3.70 (d, 2H), 3.97–4.08 (m, 3H), 4.60–4.63 (m, 1H), 6.84–6.86 (m, 2 H), 7.03–7.05 (m, 2H), 730–7.36 (m, 1H), 7.38–7.40 (m, 1H), 8.16–8.17 (m, 1H), 8.8.29–8.30 (m, 1H); MS (ES) m/z: 457 (MH$^+$).

EXAMPLE 126

2-Methyl-5-(2-oxiranylmethoxy)pyridine

The title compound was prepared from 6-methyl-3-pyridinol and (2S)-oxiranylmethyl 3-nitrobenzenesulfonate in substantially the same manner as described in Example 123. The product was obtained as a brown oil; $^1$H NMR (400 MHz, DMSO-d$_6$) δ 2.38 (s, 2.38, 1H), 2.68–2.70 (m, 1H), 2.81–2.84 (m, 1H), 3.30–3.34 (m, 1H), 3.83–3.87 (m, 1H), 4.34–4.38 (m, 1H), 7.15–7.17 (m, 1H), 7.28–7.31 (m, 1H), 8.15–8.16m (m, 1H); MS (ES) m/z: 165 (M)$^+$.

EXAMPLE 127

(2S)-1-Amino-3-[(6-methyl-3-pyridinyl)oxy]-2-propanol

The title compound was prepared from 2-methyl-5-(2-oxiranyl-methoxy)pyridine (which was obtained in Example 126) in substantially the same manner as described in Example 124. The product was obtained as an oil; $^1$H NMR (400 MHz, DMSO-d$_6$) δ 1.65 (brs, 2H), 2.37 (s, 1H), 2.53–2.58 (m, 1H), 2.63–2.69 (m, 1H), 4.60 (brs, 1H), 3.84–3.88 (m, 1H), 3.95–3.99 (m, 1H), 7.13–7.15 (m, 1H), 7.25–7.28 (m, 1H), 8.12–8.13 (m, 1H), 8.13–8.14 (d, 1H); MS (ES) m/z: 183 (MH$^+$).

EXAMPLE 128

5-(4-{4-[(2S)-2-Hydroxy-3-(6-methyl-pyridin-3-yloxy)-propylamino]-piperidine-1-yl}-benzyl)-thiazolidine-2,4-dione The title compound was prepared from (2S)-1-amino-3-[(6-methyl-3-pyridinyl)oxy]-2-propanol (which was obtained in Example 127) and 5-[4-(4-oxo-1-piperidineyl)benzyl]-1,3-thiazolidine-2,4-dione (which was obtained in Example 38) in substantially the same manner, as described in Example 125. The product was obtained as a yellow solid; mp 87° C. (decomposed); $^1$H NMR (400 MHz, DMSO-d$_6$) δ 1.44–1.49 (m, 2H), 1.93–1.97 (m, 2H), 2.38 (s, 3H), 2.64–2.70 (m, 2H), 2.77–2.95 (m, 4H), 3.23–3.27 (m, 1H), 3.35 (brs, 2H), 3.64–3.67 (m, 2H), 3.93–4.02 (m, 3H), 4.58–4.62 (m, 1H), 6.84–6.86 (m, 2H), 7.03–7.05 (m, 2H), 7.15–7.17 (m, 1H), 7.27–7.30 (m, 1H), 8.14–8.15 (m, 1H); MS (ES) m/z: 469 (M–H)$^-$.

EXAMPLE 129

3-[(2S)-Oxiranyl]pyridine

A solution of borane-THF (1.0 M solution, 22.8 mL) was added dropwise into a cold (0° C.) solution of (S)-2-methyl- CBS-oxazaborolidine monohydrate (1.12 g, 3.8 mmol) in tetrahydrofuran (20 mL), over a period of 10 minutes. After stirring at 0° C. for 10 minutes, the mixture was added dropwise to a cold (0° C.) suspension of 3-(2-bromoacetyl) pyridine hydrobromide (10.6 g, 38.0 mmol) in tetrahydrofuran (70 mL) over a period of 10 minutes. After the addition the mixture was stirred at room temperature, under a nitrogen atmosphere, overnight. The reaction was cooled to 0° C. and quenched with hydrogen chloride (0.5 M in methanol, 9 mL). The mixture was further diluted with water and extracted with ethyl acetate. The extracts were washed with water and dried with $MgSO_4$. Evaporation and purification by flash column chromatography (dichloromethane/methyl alcohol 95/5) gave (1R)-2-bromo-1-(3-pyridinyl)-1-ethanol as a brown oil (2.01 g, 27% yield). This oil was dissolved in tetrahydrofuran (18 mL) and then sodium hydroxide (5N, 35 mL) was added. The solution was stirred at room temperature for 10 minutes. The mixture was diluted with water and extracted with dichloromethane. The extracts were washed with water, dried with magnesium sulfate. The extracts were concentrated to give the title compound as a white solid (1.01 g, 84% yield); $^1H$ NMR (300 MHz, DMSO-$d_6$) δ 2.93–2.97 (m, 2H), 3.14–3.17 (m, 2H), 3.99–4.01 (m, 2H), 7.36–7.40 (m, 1H), 7.63–7.66 (m, 1H), 8.51–8.55 (m, 3H); MS (ES) m/z: 122 ($MH^+$).

EXAMPLE 130

(1S)-2-Amino-1-(3-pyridinyl)-1-ethanol

The title compound was prepared from 3-[(2S)-oxiranyl] pyridine (which was obtained in Example 129) and saturated ammonium methanol in substantially the same manner, as described in Example 124. The product was obtained as a brown oil; $^1H$ NMR (400 MHz, DMSO-$d_6$) δ 1.60 (brs, 2H), 2.59–2.71 (m, 2H), 4.47–4.50 (m, 1H), 5.20 (brs, 1H), 7.31–7.34 (m, 1H), 7.68–7.71 (m, 1H), 8.42–8.43 (m, 1H), 8.50–8.51 (m, 1H); MS (ES) m/z: 139 ($MH^+$).

EXAMPLE 131

5-{4-[4-((2S)-2-Hydroxy-2-pyridin-3-yl-ethylamino)-piperidine-1-yl]-benzyl}-thiazolidine-2,4-dione The title compound was prepared from (1S)-2-amino-1-(3-pyridinyl)-1-ethanol (which was obtained in Example 130) and 5-[4-(4-oxo-1-piperidineyl)benzyl]-1,3-thiazolidine-2,4-dione (which was obtained in Example 38) in substantially the same manner, as described in Example 125. The product was obtained as a yellow solid; mp: >88° C. decomposed; $^1H$ NMR (400 MHz, DMSO-$d_6$) δ 1.38–1.50 (m, 2H), 1.90–1.98 (m, 2H), 2.63–2.71 (t, 2H), 2.78–2.96 (m, 4H), 3.23–3.27 (m, 1H), 3.62–3.65 (m, 2H), 4.62–4.67 (m, 1H), 4.76–4.79 (m, 1H), 6.83–6.86 (d, 2H), 7.03–7.05 (d, 2H), 7.36–7.38 (m, 1H), 7.76–7.79 (m, 1H), 8.46–8.48 (m, 1H), 8.57–8.58 (m, 1H); MS (ES) m/z: 427 ($MH^+$); Anal. Calcd. for $C_{22}H_{36}N_4O_2 \times 0.3\ H_2O \times 0.3\ CH_2Cl_2$: C, 55.87; H, 5.51; N, 11.69. Found: C, 55.92; H, 5.80; N, 11.45.

EXAMPLE 132

(1R)-2-Amino-1-[1,2,3,4]tetraazolo[1,5-a]pyridin-6-yl-1-ethanol

The title compound was prepared from 6-[(2R)oxiranyl][1,2,3,4]tetraazolo[1,5-a]pyridine and saturated ammonium methanol in substantially the same manner, as described in Example 124. The product was obtained as an off-white solid; mp 153–154° C.; $^1H$ NMR (400 MHz, DMSO-$d_6$) δ 1.60 (brs, 2H), 2.73–2.84 (m, 2H), 4.65–4.68 (m, 1H), 5.70 (brs, 1H), 7.83–7.87 (m, 1H), 8.14–8.16 (m, 1H), 9.08–9.09 (m, 1H); MS (ES) m/z: 180 (M+H).

EXAMPLE 133

5-(4-{4-[(2S)-2-(6-Amino-pyridin-3-yl)-2-hydroxy-ethylamino]-piperidine-1-yl}-benzyl)-thiazolidine-2,4-dione hydrochloride 5-[4-(4-{[(2R)-2-Hydroxy-2-[1,2,3,4]tetraazolo[1,5-a]pyridin-6-ylethyl]amino}-1-piperidineyl)benzyl]-1,3-thiazolidine-2,4-dione was prepared from (1R)-2-amino-1-[1,2,3,4]tetraazolo[1,5-a]pyridin-6-yl-1-ethanol (which was obtained in Example 132) and 5-[4-(4-oxo-1-piperidineyl)benzyl]-1,3-thiazolidine-2,4-dione (which was obtained in Example 38) in substantially the same manner, as described in Example 125. The product was obtained as a yellow solid; mp: 130–132° C. This solid was dissolved in concentrated aqueous hydrochloric acid (0.3 mL) and methyl alcohol (2 mL). Tin chloride (0.196 g, 0.87 mmol) was added to the solution at room temperature. The mixture was then stirred at reflux for 2 hours. Evaporation and purification by flash column chromatography (dichloromethane/methyl alcohol 7/3)] gave a yellow solid. This solid was further purified by reverse phase HPLC to give a yellow solid (0.117 g, 61% yield); mp 182° C. (decomposed); $^1H$ NMR (400 MHz, DMSO-$d_6$) δ 1.90 (brs, 2H), 2.21 (brs, 2H), 3.03–3.36 (m, 8H), 3.75–3.79 (m, 1H), 4.86–4.90 (m, 1H), 4.98–5.01 (m, 1H), 7.03–7.05 (m, 1H), 1.20 (brs, 4H), 7.95–7.99 (m, 2H), 8.21 (brs, 1H), 9.13 (brs, 1H), 9.45 (brs, 1H), 12.04 (brs, 1H), 14.13 (brs, 1H); MS (ES) m/z: 442 ($MH^+$).

EXAMPLE 134

3-[(2R)-Oxiranyl]pyridine

The title compound was prepared from (R)-2-methyl-CBS-oxazaborolidine monohydrate and 3-(2-bromoacetyl) pyridine hydrobromide in substantially the same manner, as described in Example 123. The product was obtained as an oil; $^1H$ NMR (300 MHz, DMSO-$d_6$) δ 2.94–2.97 (m, 1H), 3.14–3.17 (m, 1H), 3.99–4.01 (m, 1H), 7.36–7.40 (m, 1H), 7.63–7.66 (m, 1H), 8.51–8.55 (m, 2H); MS (ES) m/z: 121 ($M^+$).

EXAMPLE 135

(1R)-2-Amino-1-(3-pyridinyl)-1-ethanol

The title compound was prepared from 3-[(2R)-oxiranyl] pyridine (which was obtained in Example 134) and saturated ammonium methanol in substantially the same manner, as described in Example 124. The product was obtained as a brown oil; $^1H$ NMR (300 MHz, DMSO-$d_6$) δ 1.70 (brs, 2H), 2.62–2.74 (m, 2H), 4.46–4.50 (m, 1H), 5.20 (brs, 1H), 7.30–7.34 (m, 1H), 7.68–7.71 (m, 1H), 8.42–8.50 (m, 2H); MS (ES) m/z: 139 ($MH^+$).

EXAMPLE 136

5-{4-[4-((2R)-2-Hydroxy-2-pyridin-3-yl-ethylamino)-piperidine-1-yl]-benzyl}-thiazolidine-2,4-dione The title compound was prepared from (1R)-2-amino-1-(3-pyridinyl)-1-ethanol (which was obtained in Example 135) and 5-[4-(4-oxo-1-piperidineyl)benzyl]-1,3- thiazolidine-2,4-dione (which was obtained in Example 38) in substantially the same manner, as described in Example 125. The product was obtained as a yellow solid; mp 87° C. (decomposed); $^1$H NMR (400 MHz, DMSO-d$_6$) δ 1.38–1.43 (m, 2H), 1.89–1.91 (m, 2H), 2.62–2.71 (t, 2H), 2.71–2.91 (m, 4H), 3.23–3.27 (m, 1H), 3.60–3.63 (m, 2H), 4.58–4.61 (m, 1H), 4.72–4.75 (m, 1H), 6.83–6.85 (d, 2H), 7.02–7.05 (d, 2H), 7.34–7.37 (m, 1H), 7.75–7.78 (m, 1H), 8.45–8.46 (m, 1H), 8.56–8.57 (m, 1H); MS (ES) m/z: 427 (MH$^+$).

EXAMPLE 137

N-[5-(2-Bromoacetyl)-2-pyridinyl]methanesulfonamide

A solution of methane sulfonyl chloride (7.5 mL, 96.80 mmol) in dichloromethane (50 mL) was added dropwise into a cold (−78° C.) solution of 1-(6-amino-3-pyridinyl)-1-ethanone (3.29 g, 24.20 mmol) and N,N-diisopropylethylamine (4.20 mL, 96.80 mmol) in dichloromethane/acetonitrile (1/1, 250 mL) over a period of 30 minutes. After the addition the dry-ice bath was removed and reaction mixture was warmed gradually to room temperature. After stirring at room temperature for 2 days, the mixture was evaporated and purified by flash column chromatography (hexanes/ethyl acetate 3/7) to give a grey solid (1.0 g, 19% yield). This solid (0.9 g, 4.2 mmol) was added portionwise to a room temperature stirred solution of 5,5-dibromobarbituric acid (2.17 g, 7.35 mmol) in tetrahydrofuran (18 mL). After stirred at 60° C. for 6 hours the mixture was evaporated and purified by flash column chromatography (hexanes/ethyl acetate 1/1) to give an off-white solid (1.03 g, 84% yield); $^1$H NMR (400 MHz, DMSO-d$_6$) δ 3.33 (s, 3H), 4.87 (s, 2H), 7.04–7.07 (m, 1H), 8.20–8.23 (m, 1H), 8.87 (s, 1H); MS (ES) m/z: 292 (M$^+$); Anal. Calcd. for C$_8$H$_9$BrN$_2$O$_3$S: C, 32.78; H, 3.09; N, 9.56. Found: C, 33.27; H, 2.92; N, 9.60.

EXAMPLE 138

N-[5-(2-{1-[4-(2,4-Dioxo-thiazolidin-5-ylmethyl)-phenyl]-piperidine-4-ylamino}-1-hydroxy-ethyl)-pyridin-2-yl]-methanesulfonamide Sodium borohydride (0.09 g, 2.34 mmol) was added portionwise into a cold (0° C.) solution of N-[5-(2-bromoacetyl)-2-pyridinyl]methanesulfonamide (which was obtained in Example 137) (0.91 g, 3.12 mmol) in THF (15 mL). After the mixture was stirred at 0° C. for 1.5 hours, the mixture was evaporated and purified by flash column chromatography (dichloromethane 95/5) to give an off-white solid (0.66 g, 72%). A mixture of this solid (0.44 g, 1.54 mmol), sodium iodide (0.23 g, 1.54 mmol) and sodium azide (0.41 g, 6.16 mmol) in dimethyl sulfoxide (4 mL) was stirred at room temperature for 3 days. The mixture was purified by flash column chromatography (hexanes/ethyl acetate 1/3) to give an oil. This oil was dissolved in methyl alcohol (25 mL) and 10% Pd-C. The mixture was hydrogenated to give N-[5-(2-amino-1-hydroxyethyl)-2-pyridinyl]methanesulfonamide as an oil. This oil was treated with 5-[4-(4-oxo-1-piperidineyl)benzyl]-1,3-thiazolidine-2,4-dione (which was obtained in Example 38) in substantially the same manner, as described in Example 125, to give the title compound as a white solid; mp 57–59° C.; $^1$H NMR (400 MHz, DMSO-d$_6$) δ 1.20–1.31 (m, 2H), 1.55–1.64 (m, 2H), 2.01–2.08 (m, 2H), 3.60–3.71 (t, 2H), 3.93–3.42 (m, 6H), 3.71–3.75 (m, 2H), 4.77–4.87 (m, 2H), 6.86–6.88 (d, 2H), 6.98–7.00 (m, 1H), 7.05–7.07 (d, 2H), 7.75–7.77 (m, 1H), 8.22–8.23 (m, 1H); MS (ES) m/z: 520 (MH$^+$); Anal. Calcd. for C$_{23}$H$_{29}$N$_5$O$_5$S$_2$×3 CF$_3$COOH: C, 40.42; H, 3.74; N, 8.13. Found: C, 40.15; H, 4.06; N, 8.10.

EXAMPLE 139

2-Methyl-5-oxiranylmethoxy-1H-indole-3-carboxylic acid ethyl ester

A solution of 2.19 g (10 mmol) of ethyl 5-hydroxy-2-methyl-indole-3-carboxylate, 2.6 g (10 mmol) of 2S(+) glycidyl-3-nitrobenzenesulfonate and 1.5 g (11 mmol) of potassium carbonate in 25 mL reagent grade acetone was refluxed overnight. The mixture was then allowed to cool to room temperature and the solids were removed by vacuum filtration. The filtrate was concentrated in vacuo and the residue was dissolved in ethyl acetate. The organics were washed once with water, twice with brine, dried over sodium sulfate and concentrated in vacuo. Then the solid was dried under vacuum to give 2.65 g of the title compound as a dull tan solid; mp 93–94° C.; $^1$H NMR (300 MHz, CDCl$_3$) δ 1.44 (t, J=5.3 Hz, 3H), 2.71 (s, 3H), 2.74–2.80 (m, 1H), 2.92 (t, J=4.7 Hz, 1H), 3.37–3.43 (m, 1H), 4.00–4.06 (m, 1H), 4.27–4.31 (m, 1H), 4.37 (q, J=5.3Hz, 2H), 6.86 (dd, J=5.5, 3.0Hz, 1H), 7.18 (d, J=8.7 Hz, 1H), 7.67 (d, J=3.0 Hz, 1H), 8.32 (s, 1H); MS (ES) m/z: 275.9 (MH$^+$); HRMS Calcd. for C$_{15}$H$_{18}$NO$_4$ (MH$^+$): 276.1236. Found: 276.1228.

EXAMPLE 140

5-((2S)-3-Azido-2-hydroxy-propoxy)-2-methyl-1H-indole-3-carboxylic acid ethyl ester A solution of 1.4 g (5.1 mmol) of 2-methyl-5-oxiranylmethoxy-1 H-indole-3-carboxylic acid ethyl ester (which was obtained in Example 139), 0.5 g (7.6 mmol) of sodium azide and 0.43 g (10.2 mmol) of lithium chloride in 15 mL anhydrous DMF was heated at 60° C. overnight. The mixture was cooled to room temperature and quenched with water. The aqueous mixture was extracted with ethyl acetate. The organic layer was washed twice with water, dried over sodium sulfate and concentrated in vacuo. The residue was then purified by flash chromatography (10% EtOAc in hexanes to 50% EtOAc in hexanes) to give 0.63 g of the title compound as a yellow solid; mp 75–77° C.; $^1$H NMR (300 MHz, DMSO-d$_6$) δ 1.34 (t, J=7.1 Hz, 3H), 2.66 (s, 3H), 3.42 (d, 4.6 Hz, 1H), 3.89–3.95 (m, 2H), 4.00–4.06 (m, 1H), 4.26 (q, J=7.1 Hz, 2H), 5.55 (d, J=5.1 Hz, 2H), 6.76 (dd, J=8.7, 2.7 Hz, 1H), 7.24 (d, J=8.7 Hz, 1H), 7.43 (d, J=2.4 Hz, 1H), 11.65 (s, 1H); MS (ES) m/z: 319.0 (MH$^+$); HRMS Calcd. for C$_{15}$H$_{18}$N$_4$O$_4$ (M$^+$): 318.1328. Found: 318.1334.

EXAMPLE 141

5-((2S)-3-Amino-2-hydroxy-propoxy)-2-methyl-1H-indole-3-carboxylic acid ethyl ester A solution of 0.56 g (1.76 mmol) of 5-((2S)-3-azido-2-hydroxy-propoxy)-2-methyl-1H-indole-3-carboxylic acid ethyl ester (which was obtained in Example 140) and 1.2 g of triphenylphosphine polymer resin (3 mmol/g) was stirred in 15 mL toluene for 1.5 hours under nitrogen. The resin was collected by filtration and washed twice with 25 mL of toluene. The resin was then stirred in 60 mL of 9:1 THF/methanol for four hours. The resin was removed by vacuum filtration and washed with 9:1 THF/methanol. The filtrate was concentrated in vacuo. Then the solid was dried under vacuum to give 0.52 g of the title compound as a beige solid; mp 66–68° C.; $^1$H NMR (300 MHz, DMSO-d$_6$) δ 1.32–1.37 (m, 3H), 1.80 (brs, 1H), 2.61 (s, 3H), 2.69–2.75 (m, 2H), 3.69–3.76 (m, 1H), 3.82–3.95 (m, 2H), 4.23 (q, J=6.93 Hz, 2H), 4.90 (brs, 1H), 6.76 (dd, J=2.52 Hz, 8.73 Hz, 1H), 7.23 (d, J=8.7 Hz, 1H), 7.43 (d, J=2.4 Hz, 1H), 8.85 (brs, 1H), 11.65 (s, 1H); MS (ES) m/z: 293.0 (MH$^+$); HRMS Calcd. for $C_{15}H_{21}N_2O_4$ (MH$^+$): 293.1501. Found: 293.1498.

EXAMPLE 142

5-(3-{1-[4-(2,4-Dioxo-thiazolidin-5-ylmethyl)-2-fluoro-phenyl]-piperidine-4-ylamino}-(2S)-2-hydroxy-propoxy)-2-methyl-1H-indole-3-carboxylic acid ethyl ester The title compound was prepared from 5-((2S)-3-amino-2-hydroxy-propoxy)-2-methyl-1H-indole-3-carboxylic acid ethyl ester (which was obtained in Example 141) and 5-[3-fluoro-4-(4-oxo-piperidine-1-yl)-benzyl]-thiazolidine-2,4-dione (which was obtained in Example 61) according to the procedure of Example 73 as a yellow solid; $^1$H NMR (300 MHz, DMSO-d$_6$) δ 1.34 (t, J=7.1 Hz, 3H), 1.56–1.63 (m, 2H), 2.03 (m, 2H), 2.61 (s, 3H), 2.67–2.75 (m, 4H), 2.88–2.96 (m, 4H), 3.04–3.07 (m, 2H), 3.95–3.97 (m, 2H), 4.05 (m, 2H), 4.25 (q, J=7.1 Hz, 2H), 4.61–4.66 (m, 1H), 5.52 (brs, 1H), 6.79 (dd, J=8.7, 2.5 Hz, 1H), 6.94–7.03 (m, 2H), 7.24–7.29 (m, 2H), 7.46 (d, J=2.3 Hz, 1H) 11.65 (s, 1H); MS (ES) m/z: 599.1 (MH$^+$); HRMS for $C_{30}H_{36}FN_4O_6S$ (MH$^+$): 599.2339. Found: 599.2333.

EXAMPLE 143

1-(1,4-Dioxa-8-aza-spiro[4.5]dec-8-yl)-3-[4-(1,4-dioxa-8-aza-spiro[4,5]dec-8-yl)-phenyl]-propane-1,3-dione A mixture of methyl 4-fluorobenzoyl acetate (2.06 g, 10 mmol), 1,4-dioxa-8-aza-spiro[4.5]decane (2.19 g, 15 mmol), and potassium carbonate (1.66 g, 12 mmol) in 3 mL of 1,3-dimethyl-3,4,5,6-tetrahydro-2(1H)-pyrimidinone was stirred at 60° C. for 3 days. It was then diluted with water and the gummy precipitate was washed with water, ether, and ethyl acetate-ether (1:5), and then dried in vacuo to give 0.98 g of yellow solid; $^1$H NMR (300 MHz, CDCl$_3$) δ 1.66–1.72 (dd, 4H), 1.77–1.81 (d, 4H), 3.51–3.55 (m, 4H), 3.57–3.61 (m, 2H), 3.70–3.741 (m, 2H), 3.96 (s, 4H), 4.00 (s, 4H), 4.03 (s, 2H), 6.68 (d, 2H), 7.94 (d, 2H); MS (ES) m/z: 431 (MH$^+$).

EXAMPLE 144

5-[4-(1,4-Dioxa-8-aza-spiro[4.5]dec-8-yl)-phenyl]-1,2-dihydro-pyrazol-3-one 1-(1,4-Dioxa-8-aza-spiro[4.5]dec-8-yl)-3-[4-(1,4-dioxa-8-aza-spiro[4.5]dec-8-yl)-phenyl]-propane-1,3-dione (which was obtained in Example 143) (0.43 g, 1 mmol) was dissolved in a mixture of ethanol (10 mL) and tetrahydrofuran (4 mL). The solution was treated with 0.08 mL (2.4 mmol) of hydrazine and heated at reflux for 4 days. After cooling to room temperature, the resulting suspension was filtered, and the precipitate was washed with ethanol and dried in vacuo to give 0.24 g of light yellow solid; $^1$H NMR (DMSO-d$_6$) δ 1.67–1.71 (t, 4H), 3.29–3.32 (t, 4H), 3.91 (s, 4H), 5.72 (s, 1H), 6.97 (d, 2H), 7.48 (d, 2H), 9.50 (brs, 1H), 11.80 (brs, 1H); MS (ES) m/z: 302 (MH$^+$).

EXAMPLE 145

1-[4-(5-Oxo-2,5-dihydro-1H-pyrazol-3-yl)-phenyl]-piperidine-4-one

To a suspension of 5-[4-(1,4-dioxa-8-aza-spiro[4.5]dec-8-yl)-phenyl]-1,2-dihydro-pyrazol-3-one (which was obtained in Example 144) (0.15 g, 0.5 mmol) in acetone (5 mL) was added 5 mL of 10% sulfuric acid. The resulting solution was stirred at room temperature for 4 days. Water (5mL) was then added, and the acetone was evaporated. The aqueous residue was treated with sodium carbonate until pH 8, and the resulting suspension was filtered. The precipitate was washed with water and ether, and dried in vacuo to give 0.15 g of tan solid; $^1$H NMR (DMSO-d$_6$) δ 2.41 (t, 4H), 3.64 (t, 4H), 5.74 (s, 1H), 7.04 (d, 2H), 7.53 (d, 2H), 9.55 (brs, 1H), 11.80 (brs, 1H); MS (ES) m/z: 258 (MH$^+$).

EXAMPLE 146

N-[(2R)-2-Hydroxy-5-(1-hydroxy-2-{1-[4-(5-oxo-2,5-dihydro-1H-pyrazol-3-yl)-phenyl]-piperidine-4-ylamino}-ethyl)-phenyl]-methanesulfonamide The title compound was prepared from 1-[4-(5-oxo-2,5-dihydro-1H-pyrazol-3-yl)-phenyl]-piperidine-4-one (which was obtained in Example 145) (0.13 g, 0.5 mmol) and N-[5-((1R)-2-amino-1-hydroxy-ethyl)-2-hydroxy-phenyl]-methanesulfonamide (0.15 g, 0.6 mmol) (which was obtained in Example 10) according to the prodedure shown for Example 73 to give 0.14 g of orange solid; mp 225–227° C.; $^1$H NMR (DMSO-d$_6$) δ 1.15–1.20 (m, 2H), 1.87–1.99 (m, 2H), 2.64–2.75 (m, 5H), 2.92 (s, 3H), 3.66 (m, 2H), 4.49 (m, 2H), 5.71 (s, 1H), 6.82 (d, 2H), 6.93 (d, 2H), 7.02 (dd, 2H), 7.19 (d, 2H), 7.47 (d, 2H); MS (ES) m/z: 488 (MH$^+$).

EXAMPLE 147

4-(4-Oxo-1-piperidine-1-yl)benzamide

A suspension of 4-(1,4-dioxa-8-aza-spiro[4.5]dec-8-yl) benzonitrile (Taylor, E. C., Skotnicki, J. S. *Synthesis*, 1981, 606) (15 g, 61.5 mmol) in 150 mL of concentrated hydrochloric acid was stirred at room temperature overnight. The solution was neutralized with 5N sodium hydrochloride and the solid that formed was collected to give the title compound as a white solid; $^1$H NMR (300 MHz, CDCl$_3$) δ 2.58 (t, J=6.1 Hz, 4H), 3.74 (t, J=6.1 Hz, 4H), 5.76 (brs, 2H), 6.94 (d, J=9.0 Hz, 2H), 7.74 (d, J=9.0 Hz, 2H); MS (ES) m/z: 218.8 (MH$^+$); HRMS Calcd. for $C_{12}H_{14}N_2O_2$: 218.1055. Found: 218.1051

EXAMPLE 148

[4-(1,4-Dioxa-8-aza-spiro[4.5]dec-8-yl)-phenyl]-methanol

Sodium borohydride (3.78 g, 100 mmol) was added in four portions to a stirred solution of 4-(1,4-dioxa-8-aza-spiro[4.5]dec-8-yl)-benzaldehyde (4.94 g, 20 mmol) (Taylor, E. C., Skotnicki, J. S. *Synthesis*, 1981, 606) in methanol/tetrahydrofuran (1:1, 100 mL) at 0° C. and the resulting solution was stirred at 0° C. for 30 minutes and then at room temperature for 1 hour. Methylene chloride was added and the solution was washed with water and dried over sodium sulfate. The solvents were removed and the residue was solidified upon standing (5.0 g, 100%); $^1$H NMR (300 MHz, CDCl$_3$) δ 1.84 (t, J=5.7 Hz, 4H), 3.33 (t, J=5.7 Hz, 4H), 3.99 (s, 4H), 4.59 (d, J=5.8 Hz, 2H), 6.93 (d, J=8.7 Hz, 2H), 7.24 (d, J=8.7 Hz, 2H); MS (ES) m/z: 249.9 (MH$^+$); HRMS Calcd. for $C_{14}H_{20}NO_3$ (MH$^+$): 250.1443. Found: 250.1434.

EXAMPLE 149

[4-(4-Oxo-piperidine-1-yl)-phenyl]-acetic acid

1-[4-(1,4-Dioxa-8-aza-spiro[4.5]dec-8-yl)-phenyl]-ethanone (2.61 g, 10 mmol) (Taylor, E. C., Skotnicki, J. S.

*Synthesis*, 1981, 606) was added to a solution of thallium trinitrate trihydrate (4.44 g, 10 mmol) (McKillop, A., Swann, B. P., Taylor, E. C. *J. Am. Chem. Soc.*, 1971, 93, 4919) in methanol (40 mL) and methylene chloride (20 mL) containing perchloric acid (70%, 10 mL). After 5 hours at room temperature the precipitated thallium (I) nitrate was removed by filtration, and the filtrate was diluted with water (100 mL). The organic phase was separated, the aqueous layer was extracted with methylene chloride, and the combined organic phases were washed with water, dried over sodium sulfate and concentrated. The residue was dissolved in concentrated hydrochloric acid (250 mL) at room temperature. After 3 hours the solution pH was adjusted to 5 by ~28% ammonium hydroxide. The aqueous layer was extracted with methylene chloride, and the combined organic phases were washed with water, dried over sodium sulfate and concentrated. The product was purified by chromatography on silica gel with ethyl acetate/hexanes eluant to give the title compound as a pale yellowish solid (0.4 g, 17%); $^1$H NMR (300 MHz, DMSO-$d_6$) δ 2.42 (t, J=6.0 Hz, 4H), 3.41 (s, 2H), 3.56 (t, J=6.0 Hz, 4H), 6.98 (d, J=8.7 Hz, 2H), 7.12 (d, J=8.7 Hz, 2H), 12.20 (s, 1H); MS (ES) m/z: 234.3 (MH$^+$); HRMS Calcd. for $C_{13}H_{15}NO_3$ (M$^+$): 233.1052. Found: 233.1045.

EXAMPLE 150

4-(1,4-Dioxa-8-aza-spiro[4.5]dec-8-yl)-benzoic acid

A mixture of 4-(1,4-dioxa-8-aza-spiro[4.5]dec-8-yl)-benzoic acid ethyl ester (14 g, 48.1 mmol) (Taylor, E. C., Skotnicki, J. S. *Synthesis*, 1981, 606) in methanol/tetrahydrofuran (1:1, 100 mL) and sodium hydroxide (2N, 150 mL) was refluxed for 2 hours. After cooling to room temperature the solution was acidified by acetic acid and the solid which was formed was collected and dried to give the title compound as a white solid (12.5 g, 99%); $^1$H NMR (300 MHz, CDCl$_3$) δ 1.67 (t, J=5.6 Hz, 4H), 3.43 (t, J=5.6 Hz, 4H), 3.92 (s, 4H), 6.96 (d, J=9.0 Hz, 2H), 7.75 (d, J=9.0 Hz, 2H); MS (ES) m/z: 264.4 (MH$^+$); HRMS Calcd. for $C_{14}H_{17}NO_4$ (M$^+$): 263.1158. Found: 263.1160.

EXAMPLE 151

4-(4-Oxo-piperidine-1-y)-benzoic acid 4-(1,4-Dioxa-8-aza-spiro[4.5]dec-8-yl)-benzoic acid (which was obtained in Example 150) (12.5 g, 47.5 mmol) was treated with concentrated hydrochloric acid (500 mL) at room temperature. After 15 hours ~28% ammonium hydroxide was added dropwise and the precipitate was collected by filtration, and dried over phosphorus pentoxide to give the title compound as a white solid (9.2 g, 88%); $^1$H NMR (300 MHz, CDCl$_3$) δ 2.46 (t, J=6.1 Hz, 4H), 3.74 (t, J=6.1 Hz, 4H), 7.02 (d, J=9.0 Hz, 2H), 7.80 (d, J=9.0 Hz, 2H); MS (ES) m/z: 219.8 (MH$^+$); HRMS Calcd. for $C_{12}H_{14}NO_3$ (MH$^+$): 220.0974. Found: 220.0947.

EXAMPLE 152

2-[4-(1,4-Dioxa-8-aza-spiro[4.5]dec-8-yl)-benzylidene]-malonic acid diethyl ester A solution of 4-(1,4-dioxa-8-aza-spiro[4.5]dec-8-yl)-benzaldehyde (2.47, 10 mmol) (Taylor, E. C., Skotnicki, J. S. *Synthesis*, 1981, 606) and diethyl malonate (2.0 g, 12.5 mmol) in toluene (100 mL) containing a catalytic quantity of piperidineum acetate was refluxed for 18 hours. After cooling to room temperature the solution was washed with water, dried over sodium sulfate and concentrated. Purification by column chromatography on silica gel using ethyl acetate/hexanes as the eluent gave the title compound as a yellowish gum; $^1$H NMR (300 MHz, CDCl$_3$) δ 1.28 (t, J=7.1 Hz, 3H), 1.29 (t, J=7.1 Hz, 3H), 1.79 (t, J=5.8 Hz, 4H), 3.46 (t, J=5.8 Hz, 4H), 4.27 (q, J=7.1 Hz, 2H), 4.31 (q, J=7.1 Hz, 2H), 6.85 (d, J=8.9 Hz, 2H), 7.33 (d, J=8.9 Hz, 2H), 7.61 (s, 1H); MS (ES) m/z: 390.0 (MH$^+$); HRMS Calcd. for $C_{21}H_{27}NO_6$ (MH$^+$): 390.1911. Found: 390.1910.

EXAMPLE 153

2-[4-(4-Oxo-piperidine-1-yl)-benzylidene]-malonic acid diethyl ester

The title compound was prepared from 2-[4-(1,4-dioxa-8-aza-spiro[4.5]dec-8-yl)-benzylidene]-malonic acid diethyl ester (which was obtained in Example 152) according to the procedure of Example 147 as a yellowish gum; $^1$H NMR (300 MHz, CDCl$_3$) δ 1.20–1.40 (m, 6H), 2.56 (t, J=6.1 Hz, 4H), 3.73 (t, J=6.1 Hz, 4H), 4.28 (q, J=7.1 Hz, 2H), 4.46 (q, J=7.1 Hz, 2H), 6.90 (d, J=8.9 Hz, 2H), 7.41 (d, J=8.9 Hz, 2H), 7.41 (s, 1H); MS (ES) m/z: 345.9 (MH$^+$); HRMS Calcd. for $C_{21}H_{27}NO_6$ (MH$^+$): 346.1649. Found: 346.1647.

EXAMPLE 154

N-(Benzyloxy)-4-(1,4-dioxa-8-azaspiro[4.5]dec-8-yl)benzamide

A mixture of 4-(1,4-dioxa-8-aza-spiro[4.5]dec-8-yl)-benzoic acid (which was obtained in Example 150) (1.58 g, 6 mmol), 1-[3-(dimethylamino)propyl-3-ethylcarbodiimide hydrochloride (1.34 g, 7 mmol) and O-benzylhydroxyamine hydrochloride (1.05 g, 6.6 mmol) was stirred in methylene chloride (150 mL). N-methylmorpholine (1.82 g, 18 mol) was added dropwise and the mixture was stirred overnight. The mixture was then washed with 0.05 N hydrochloric acid and water. The resulting solution was dried with magnesium sulfate and concentrated. The residue was crystallized from methylene chloride/hexanes to give the title compound as a white solid; $^1$H NMR (300 MHz, CDCl$_3$) δ 1.67 (t, J=5.6 Hz, 4H), 3.42 (t, J=5.6 Hz, 4H), 3.91 (s, 4H), 4.89 (s, 2H), 6.97 (d, J=9.0 Hz, 2H), 7.30–7.50 (m, 5H), 7.62 (d, J=9.0 Hz, 2H); MS (ES) m/z: 369.3 (MH$^+$); HRMS Calcd. for $C_{21}H_{24}N_2O_4$ (M$^+$): 368.1736. Found: 368.1744.

EXAMPLE 155

N-(Benzyloxy)-4-(4-oxo-piperidine-yl)benzamide

The title compound was prepared from N-(benzyloxy)-4-(1,4-dioxa-8-azaspiro[4.5]dec-8-yl)benzamide (which was obtained in Example 154) according to the procedure of Example 147 as a grey solid; $^1$H NMR (300 MHz, CDCl$_3$) δ 2.41 (t, J=6.0 Hz, 4H), 3.71 (t, J=6.0 Hz, 4H), 4.89 (s, 2H), 7.19 (d, J=9.0 Hz, 2H), 7.30–7.50 (m, 5H), 7.67 (d, J=9.0 Hz, 2H), 11.50 (s, 1H); MS (ES) m/z: 325.4 (MH$^+$); HRMS Calcd. for $C_{19}H_{21}N_2O_3$ (MH$^+$): 325.1552. Found: 325.1540.

EXAMPLE 156

(2S)-2-[4-(4-Oxo-piperidine-1-yl)-benzoylamino]-pentanedioic acid dibenzyl ester The title compound was prepared from 4-(4-oxo-piperidine-1-yl)-benzoic acid (which was obtained in Example 151) and L-glutamic acid dibenzyl ester p-tosylate according to the procedure of Example 154 as a white solid; $^1$H NMR (300 MHz, DMSO-$d_6$) δ 1.90–2.20 (m, 4H), 2.42

(t, J=6.0 Hz, 4H), 3.72 (t, J=6.0 Hz, 4H), 4.45–4.55 (m, 1H), 5.07 (s, 2H), 5.13 (s, 2H), 7.03 (d, J=9.0 Hz, 2H), 7.25–7.40 (m, 5H), 7.85 (d, J=9.0 Hz, 2H), 8.49 (d, J=9.0 Hz, 2H); MS (ES) m/z: 529.1 (MH$^+$); HRMS Calcd. for $C_{31}H_{33}N_2O_6$ (MH$^+$): 529.2339. Found: 529.2331.

EXAMPLE 157

(2S)-2-[4-(4-Oxo-piperidine-1-yl)-benzoylamino]-pentanedioic acid diethyl ester

The title compound was prepared from 4-(4-oxo-piperidine-1-yl)-benzoic acid (which was obtained in Example 151) and L-glutamic acid diethyl ester hydrochloride according to the procedure of Example 154 as a yellowish gum; $^1$H NMR (300 MHz, CDCl$_3$) δ 1.22 (t, J=7.1 Hz, 3H), 1.31 (t, J=7.1 Hz, 3H), 2.10–2.50 (m, 4H), 2.57 (t, J=6.1 Hz, 4H), 3.73 (t, J=6.1 Hz, 4H), 4.10–4.30 (m, 4H), 4.70–4.85 (m, 1H), 6.90 (d, J=7.5 Hz, 1H), 7.08 (d, J=8.9 Hz, 2H), 7.78 (d, J=8.9 Hz, 2H); MS (ES) m/z: 405.3 (MH$^+$).

EXAMPLE 158

3-[4-(4-Oxo-piperidine-1-yl)-benzoylamino]-propionic acid ethyl ester

The title compound was prepared from 4-(4-oxo-piperidine-1-yl)-benzoic acid (which was obtained in Example 151) and beta-alanine ethyl ester hydrochloride according to the procedure of Example 154 as a yellowish solid; $^1$H NMR (300 MHz, CDCl$_3$) δ 1.28 (t, J=7.1 Hz, 3H), 2.56 (t, J=6.1 Hz, 4H), 2.64 (t, J=5.7 Hz, 2H), 3.55–3.65 (m, 6H), 4.15 (q, J=7.1 Hz, 2H), 6.82 (t, J=5.7 Hz, 1H), 6.95 (d, J=8.9 Hz, 2H), 7.70 (d, J=8.9 Hz, 2H); MS (ES) m/z: 319.1 (MH$^+$).

EXAMPLE 159

3-[4-(4-Oxo-piperidine-1-yl)-benzoylamino]-propionic acid benzyl ester

The title compound was prepared from 4-(4-oxo-piperidine-1-yl)-benzoic acid (which was obtained in Example 151) and beta-alanine benzyl ester p-tosylate according to the procedure of Example 154 as a white solid; $^1$H NMR (300 MHz, DMSO-d$_6$) δ 2.42 (t, J=6.0 Hz, 4H), 2.63 (t, J=6.9 Hz, 2H), 3.40–3.50 (m, 2H), 3.71 (t, J=6.0 Hz, 4H), 5.10 (s, 2H), 6.74 (d, J=8.9 Hz, 2H), 7.30–7.40 (m, 5H), 7.73 (d, J=8.9 Hz, 2H), 8.29 (t, J=5.5 Hz, 1H); MS (ES) m/z: 381.3 (MH$^+$); HRMS Calcd. for $C_{22}H_{24}N_2O_4$ (M$^+$): 380.1737. Found: 380.1755.

EXAMPLE 160

1-[4-(4-Oxo-piperidine-1-yl)-benzoyl]-pyrrolidine-(2S)-2-carboxylic acid methyl ester The title compound was prepared from 4-(4-oxo-piperidine-1-yl)-benzoic acid (which was obtained in Example 151) and L-proline methyl ester hydrochloride according to the procedure of Example 154 as a pale yellowish solid; $^1$H NMR (300 MHz, DMSO-d$_6$) δ 1.70–1.95 (m, 4H), 2.20–2.40 (m, 1H), 2.41 (t, J=6.0 Hz, 4H), 3.32 (s, 3H), 3.69 (t, J=6.0 Hz, 4H), 4.35–4.50 (m, 2H), 7.01 (d, J=8.7 Hz, 2H), 7.49 (d, J=8.7 Hz, 2H); MS (ES) m/z: 331.2 (MH$^+$); HRMS Calcd. for $C_{18}H_{22}N_2O_4$ (M$^+$): 330.1580. Found: 330.1572.

EXAMPLE 161

Ethyl {[4-(4-oxo-1-piperidineyl)benzoyl]amino}acetate

The title compound was prepared from 4-(4-oxo-piperidine-1-yl)-benzoic acid (which was obtained in Example 151) and glycine ethyl ester hydrochloride according to the procedure of Example 154 as a pale yellowish solid; $^1$H NMR (300 MHz, DMSO-d$_6$) δ 1.20 (t, J=7.1 Hz, 3H), 2.43 (t, J=6.1 Hz, 4H), 3.72 (t, J=6.1 Hz, 4H), 3.95 (d, J=5.8 Hz, 2H), 4.10 (q, J=7.1 Hz, 2H), 7.04 (d, J=8.9 Hz, 2H), 7.77 (d, J=8.9 Hz, 2H), 8.63 (t, J=5.8 Hz, 1H); MS (ES) m/z: 305.2 (MH$^+$); HRMS Calcd. for $C_{18}H_{22}N_2O_4$ (M$^+$): 304.1423. Found: 304.1422.

EXAMPLE 162

Methyl {[4-(4-oxo-1-piperidineyl)benzoyl]amino}acetate

The title compound was prepared from 4-(4-oxo-piperidine-1-yl)-benzoic acid (which was obtained in Example 151) and glycine methyl ester hydrochloride according to the procedure of Example 154 as a gum; MS (ES) m/z: 291.3 (MH$^+$).

EXAMPLE 163

3-Methyl-(2S)-2-[4-(4-oxo-piperidine-1-yl)-benzoylamino]-butyric acid ethyl ester The title compound was prepared from 4-(4-oxo-piperidine-1-yl)-benzoic acid (which was obtained in Example 151) and L-valine ethyl ester hydrochloride according to the procedure of Example 154 as a pale yellowish solid; $^1$H NMR (300 MHz, DMSO-d$_6$) δ 0.93 (d, J=6.8 Hz, 3H), 0.97 (d, J=6.8 Hz, 3H), 1.20 (t, J=7.1 Hz, 3H), 2.10–2.30 (m, 1H), 2.43 (t, J=6.0 Hz, 4H), 3.72 (t, J=6.0 Hz, 4H), 4.00–4.30 (m, 4H), 4.46 (t, J=5.1 Hz, 1H), 7.05 (d, J=8.9 Hz, 2H), 7.82 (d, J=8.9 Hz, 2H), 8.21 (d, J=7.9 Hz, 1H); MS (ES) m/z: 347.3 (MH$^+$); HRMS Calcd. for $C_{19}H_{26}N_2O_4$ (M$^+$): 346.1892. Found: 346.1896.

EXAMPLE 164

(2S)-2-[4-(4-Oxo-piperidine-1-yl)-benzoylamino]-3-phenyl-propionic acid methyl ester The title compound was prepared from 4-(4-oxo-piperidine-1-yl)-benzoic acid (which was obtained in Example 151) and L-phenylalanine methyl ester hydrochloride according to the procedure of Example 154 as a pale yellowish solid; $^1$H NMR (300 MHz, DMSO-d$_6$) δ 2.41 (t, J=6.0 Hz, 4H), 3.05–3.20 (m, 2H), 3.71 (t, J=6.0 Hz, 4H), 4.55–4.65 (m, 1H), 6.97 (d, J=8.9 Hz, 2H), 7.10–7.45 (m, 5H), 7.73 (d, J=8.9 Hz, 2H), 8.52 (d, J=7.8 Hz, 1H); MS (ES) m/z: 381.3 (MH$^+$); HRMS Calcd. for $C_{22}H_{25}N_2O_4$ (MH$^+$): 381.1809. Found: 380.1807.

EXAMPLE 165

4-Methyl-(2S)-2-[4-(4-oxo-piperidine-1-yl)-benzoylamino]-pentanoic acid ethyl ester The title compound was prepared from 4-(4-oxo-piperidine-1-yl)-benzoic acid (which was obtained in Example 151) and L-leucine ethyl ester hydrochloride according to the procedure of Example 154 as a white flake; $^1$H NMR (300 MHz, CDCl$_3$) δ 0.99 (t, J=6.2 Hz, 6H), 1.30 (t, J=7.1 Hz, 3H), 1.60–1.80 (m, 3H), 2.56 (t, J=6.0 Hz, 4H), 3.72 (t, J=6.0 Hz, 4H), 4.22 (q, J=7.1 Hz, 2H), 4.80–4.90 (m, 1H), 6.42 (d, J=8.2 Hz, 1H), 6.94 (d, J=7.0 Hz, 2H), 7.77 (d, J=7.0 Hz, 1H); MS (ES) m/z: 361.3 (MH$^+$); HRMS Calcd. for $C_{20}H_{28}N_2O_4$ (M$^+$): 360.2049. Found: 360.2081.

EXAMPLE 166

4-Methyl-(2S)-2-[4-(4-oxo-piperidine-1-yl)-benzoylamino]-pentanoic acid methyl ester The title compound was prepared from 4-(4-oxo-piperidine-1-yl)-benzoic acid (which was obtained in Example 151) and L-leucine methyl ester hydrochloride according to the procedure of Example 154 as a gum; $^1$H NMR (300 MHz, CDCl$_3$) δ 0.96 (t, J=6.2 Hz, 6H), 1.60–1.80 (m, 3H), 2.57 (t, J=6.1 Hz, 4H), 3.71 (t, J=6.1 Hz, 4H), 3.77 (s, 3H), 4.80–4.90 (m, 1H), 6.40 (d, J=8.2 Hz, 1H), 6.94 (d, J=7.0 Hz, 2H), 7.75 (d, J=7.0 Hz, 1H); MS (ES) m/z: 347.4 (MH$^+$); HRMS Calcd. for C$_{19}$H$_{26}$N$_2$O$_4$ (M$^+$): 346.1892. Found: 346.1881.

EXAMPLE 167

Methyl 1-[4-(4-oxo-piperidine-1-yl)-benzoylamino]-cyclopropanecarboxylate

The title compound was prepared from 4-(4-oxo-piperidine-1-yl)-benzoic acid (which was obtained in Example 151) and 1-aminocyclopropane-1-carboxylic acid methyl ester hydrochloride according to the procedure of Example 154 as a gum; MS (ES) m/z: 317.2 (MH$^+$).

EXAMPLE 168

(E)-3-[4-(1,4-Dioxa-8-aza-spiro[4.5]dec-8-yl)-phenyl]-acrylic acid ethyl ester

To a solution of lithium bromide (0.53 g, 6 mmol) in tetrahydrofuran (5 mL) was added triethyl phosphonoacetate (1.14 g, 5 mmol), followed by triethylamine (0.51 g, 5 mmol). After stirring for 10 min, a solution of 4-(1,4-dioxa-8-aza-spiro[4.5]dec-8-yl)-benzaldehyde (Taylor, E. C., Skotnicki, J. S. *Synthesis*, 1981, 606) (1.24 g, 5 mmol) in tetrahydrofuran (2 mL) was added, and the mixture was stirred at room temperature for 20 hours. Additional triethyl phosphonoacetate (0.57 g, 2.5 mmol) and triethylamine (0.25 g, 2.5 mmol) were then added, and stirring was continued for 3 days. The mixture was evaporated, and the residue stirred with 20 mL of water and 5 mL of 1 N hydrochloric acid. The aqueous suspension was filtered, and the precipitate was washed with water, and dried in vacuo to give 1.28 g of a light yellow solid; m.p. 115–116° C.; $^1$H NMR (CDCl$_3$) δ 1.33 (t, 3H), 1.81 (dd, 4H), 3.47 (dd, 4H), 4.00 (s, 4H), 4.25 (q, 2H), 6.26 (d, 1H), 6.89 (d, 2H), 7.42 (d, 2H), 7.62 (d, 1H); MS (ES) m/z: 318 (MH$^+$).

EXAMPLE 169

(E)-3-[4-(4-Oxo-piperidine-1-yl)-phenyl]-acrylic acid ethyl ester

Prepared according to Example 151 from 0.63 g (2 mmol) of 3-[4-(1,4-dioxa-8-aza-spiro[4.5]dec-8-yl)-phenyl]-acrylic acid ethyl ester (which was obtained in Example 168), yielding 0.37 g of light yellow solid; m.p. 96–98° C.; $^1$H NMR (CDCl$_3$) δ 1.33 (t, 3H), 2.57 (t, 4H), 3.71 (t, 4H), 4.25 (q, 2H), 6.28 (d, 1H), 6.93 (d, 2H), 7.47 (d, 2H), 7.63 (d, 1H); MS (ES) m/z: 274.3 (MH$^+$).

EXAMPLE 170

(E)-3-[4-(1,4-Dioxa-8-aza-spiro[4.5]dec-8-yl)-phenyl]-acrylic acid

A solution of 0.52 g (1.6 mmol) of 3-[4-(1,4-dioxa-8-aza-spiro[4.5]dec-8-yl)-phenyl]-acrylic acid ethyl ester (which was obtained in Example 168) in tetrahydrofuran (3 mL) and ethanol (2 mL) was treated with 5 mL of 1 N NaOH. After 18 h at room temperature, the mixture was acidified with acetic acid. The resulting suspension was filtered and the precipitate was washed with water, and dried in vacuo to give 0.47 g of light yellow solid; m.p. 221–222° C.; $^1$H NMR (DMSO-d$_6$) δ 1.67 (dd, 4H), 3.40 (dd, 4H), 3.91 (s, 4H), 6.26 (d, 1H), 6.96 (d, 2H), 7.47 (d, 1H), 7.50 (d, 2H), 12.10 (bs, 1H); MS (ES) m/z: 290 (MH$^+$).

EXAMPLE 171

(E)-3-[4-(4-Oxo-piperidine-1-yl)-phenyl]-acrylic acid

Prepared according to the procedure of Example 151 from 0.15 g (0.5 mmol) of 3-[4-(1,4-dioxa-8-aza-spiro[4.5]dec-8-yl)-phenyl]-acrylic acid (which was obtained in Example 170), yielding 0.11 g of yellow solid; m.p. 215° C.; $^1$H NMR (DMSO-d$_6$) δ 2.42 (t, 4H), 3.71 (t, 4H), 6.28 (d, 1H), 7.01 (d, 2H), 7.50 (d, 1H), 7.55 (d, 2H); MS (ES) m/z: 246.3 (MH$^+$).

EXAMPLE 172

4-(1,4-Dioxa-8-azaspiro[4.5]dec-8-yl)-N-[(1S)-1-(hydroxymethyl)-3-methylbutyl]-benzamide The title compound was prepared from 4-(1,4-dioxa-8-azaspiro[4.5]dec-8-yl)-benzoic acid (which was obtained in Example 150) (0.53 g, 2 mmol) and (S)-leucinol (0.30 g, 2.5 mmol) according to the procedure shown for Example 154 to give 0.53 g of a white solid; m.p. 90–91° C.; MS (ES) m/z: 363.3 (MH$^+$); HRMS (ES) Calcd. for C$_{20}$H$_{31}$N$_2$O$_4$ (MH$^+$): 363.2278, Found: 363.2275.

EXAMPLE 173

N-[(1S)-1-(Hydroxymethyl)-3-methylbutyl]-4-(4-oxo-1-piperidineyl)benzamide

Prepared according to the procedure of Example 151 from 0.22 g (0.6 mmol) of 4-(1,4-dioxa-8-azaspiro[4.5]dec-8-yl)-N-[(1S)-1-(hydroxymethyl)-3-methylbutyl]benzamide (which was obtained in Example 172), yielding 0.15 g of light yellow foam; MS (ES) m/z: 319.3 (MH$^+$); HRMS (ES) Calcd. for C$_{18}$H$_{27}$N$_2$O$_3$ (MH$^+$): 319.2016, Found: 319.2016.

EXAMPLE 174

4-(1,4-Dioxa-8-azaspiro[4.5]dec-8-yl)-N-[(3S)-2-oxoazepanyl]benzamide

The title compound was prepared from 4-(1,4-dioxa-8-azaspiro[4.5]dec-8-yl)-benzoic acid (which was obtained in Example 150) (0.26 g, 1 mmol) and L-α-amino-ε-caprolactam (0.20 g, 1.5 mmol) according to the procedure shown for Example 154 to give 0.31 g of a white solid; m.p. 185–186° C.; MS (ES) m/z: 374.3 (MH$^+$); HRMS (El) Calcd. for C$_{20}$H$_{27}$N$_3$O$_4$ (M$^+$): 373.2001, Found: 373.1995.

EXAMPLE 175

N-[(3S)-2-Oxoazepanyl]-4-(4-oxo-1-piperidineyl)benzamide

Prepared according to the procedure of Example 151 from 0.26 g (0.7 mmol) of 4-(1,4-dioxa-8-azaspiro[4.5]dec-8-yl)-N-[(3S)-2-oxoazepanyl]benzamide (which was obtained in Example 174), yielding 0.19 g of a white solid; m.p. 177–179° C.; MS (ES) m/z: 330.3 (MH$^+$); HRMS (El) Calcd. for C$_{18}$H$_{23}$N$_3$O$_3$ (M$^+$): 329.1740, Found: 329.1721.

EXAMPLE 176

N-Butyl-N-(cyanomethyl)-4-(1 4-dioxa-8-azaspiro[4.5]dec-8-yl)benzamide

The title compound was prepared from 4-(1,4-dioxa-8-azaspiro[4.5]dec-8-yl)-benzoic acid (which was obtained in Example 150) (0.37 g, 1.4 mmol) and (n-butylamino) acetonitrile (0.48 g, 4.2 mmol) according to the procedure shown for Example 154 to give 0.52 g of an amber gum; MS (ES) m/z: 358.3 (MH$^+$); HRMS (ES) Calcd. for $C_{20}H_{28}N_3O_3$ (MH$^+$): 358.2125, Found: 358.2120.

EXAMPLE 177

N-Butyl-4-(1,4-dioxa-8-azaspiro[4.5]dec-8-yl)-N-(1H-tetraazol-5-oxa-8-azaspiro[4.5]dec-8-yl)-N-(1H-tetraazol-5-ylmethyl)benzamide To a solution of N-butyl-N-(cyanomethyl)-4-(1,4-dioxa-8-azaspiro[4.5]dec-8-yl)benzamide (which was obtained in Example 176) (0.36 g, 1 mmol) in N,N'-dimethylpropyleneurea (3 mL) was added sodium azide (0.20 g, 3 mmol) and tiethylamine hydrochloride (0.21 g, 1.5 mmol). The mixture was stirred at 120° C. for 18 hours. It was then cooled to room temperature, diluted with water (30 mL), and saturated with sodium chloride. The resulting mixture was extracted with dichloromethane, and passed through a pad of silica gel. The filter pad was first eluted with ethyl acetate and 5% methanol in ethyl acetate, followed by 25% methanol in dichloromethane. Evaporation of solvents from the latter eluent and trituration with dichloromethane-ether gave 0.33 g of an off-white solid; m.p. 145–146° C.; MS (ES) m/z: 401.3 (MH$^+$); HRMS (ES) Calcd. for $C_{20}H_{29}N_6O_3$ (MH$^+$): 401.2296, Found: 401.2291.

EXAMPLE 178

N-Butyl-4-(4-oxo-1-piperidineyl)-N-(1H-tetraazol-5-ylmethyl)benzamide

Prepared according to the procedure of Example 151 from 0.27 g (0.7 mmol) of N-butyl-4-(1,4-dioxa-8-azaspiro[4.5] dec-8-yl)-N-(1H-tetraazol-5-oxa-8-azaspiro[4.5]dec-8-yl)-N-(1H-tetraazol-5-ylmethyl)benzamide (which was obtained in Example 177), yielding 0.18 g of a colorless foam; MS (ES) m/z: 357.4 (MH$^+$); HRMS (ES) Calcd. for $C_8H_{25}N_6O_2$ (MH$^+$): 357.2034, Found: 357.2034.

EXAMPLE 179

N-{4-[4-[(2S)-2-Hydroxy-3-(2-oxo-2,3-dihydro-1H-benzoimidazole-4-yloxy)-propylamino]-piperidine--1-yl}-benzoic acid ethyl ester A mixture of 1-(4-ethoxycarbonylphenyl)-4-piperidone (0.25 g, 1 mmol) (Taylor, E. C., Skotnicki, J. S. *Synthesis*, 1981, 606) and (S)-4-[2-hydroxy-3-aminopropoxy]-1,3-dihydro-2H-benzimidazol-2-one (0.22g, 1 mmol) (U.S. Pat. No. 5,786,356/1998) in 100 mL of ethanol and 0.5 mL of acetic acid was hydrogenated in the presence of 400 mg of 10% palladium on carbon under hydrogen (5~20 psi) for overnight. The catalyst was then removed by filtering through a short pad of silica gel. The filtrate was concentrated and purified by thin layer chromatography (12% methanol/methylene chloride) to give the title compound as a white solid (0.22 g, 48%); mp >170° C. (decomposed); $^1$H NMR (300 MHz, DMSO-d$_6$) δ 1.28 (t, J=7.0 Hz, 3H), 1.30–1.55 (m, 2H), 1.80–2.10 (m, 2H), 2.80–3.10 (m, 5H), 3.80–4.10 (m, 5H), 4.23 (q, J=7.0 Hz, 2H), 6.58 (d, J=7.8 Hz, 1H), 6.62 (d, J=8.4 Hz, 1H), 6.86 (dd, J=8.4, 7.8 Hz, 1H), 6.98 (d, J=8.6 Hz, 2H), 7.77 (d, J=8.6 Hz, 2H), 10.60 (s, 1H), 10.75 (s, 1H); MS (ES) m/z: 455.1 (MH$^+$); HRMS Calcd. for $C_{24}H_{30}N_4O_5$ (MH$^+$): 454.2216. Found: 454.2211.

EXAMPLE 180

{4-[(2R)-2-Hydroxy-2-(4-hydroxy-3-methanesulfonylamino-phenyl)-ethylamino]-piperidine-1-yl}-benzoic acid ethyl ester 1-(4-Ethoxycarbonylphenyl)-4-piperidone (Taylor, E. C., Skotnicki, J. S. *Synthesis*, 1981, 606) (0.29 g, 1.2 mmol) and N-[5-(2-amino-(1R)-1-hydroxy-ethyl)-2-hydroxy-phenyl]-methanesulfonamide (which was obtained in Example 10) (0.29 g, 1.2 mmol) were mixed in dimethylformamide (10 mL) and then treated with sodium triacetoxyborohydride (1.01 g, 4.7 mmol) and acetic acid (0.5 mL). After stirring at room temperature under a nitrogen atmosphere for 15 hours the mixture was poured into a saturated aqueous sodium bicarbonate. The precipitate which was formed was collected and purified by silica gel chromatography (methanol/methylene chloride) to give the titled compound as a white solid (0.28 g, 50%); mp >95° C. (decomposed); $^1$H NMR (300 MHz, DMSO-d$_6$) δ 1.28 (t, J=7.1 Hz, 3H), 1.30–1.55 (m, 2H), 1.80–1.95 (m, 2H), 2.55–3.50 (m, 5H), 2.92 (s, 3H), 3.75–3.90 (m, 2H), 4.22 (q, J=7.1 Hz, 2H), 6.82 (d, J=8.2Hz, 1H), 6.95 (d, J=8.9Hz, 2H), 7.00 (dd, J=8.2, 1.9Hz, 1H), 7.18 (d, J=1.9 Hz, 1H), 7.75 (d, J=8.9 Hz, 2H); MS (ES) m/z: 478.0 (MH$^+$); HRMS Calcd. for $C_{23}H_{32}N_3O_6S$(MH$^+$): 478.2006. Found: 478.2000.

EXAMPLE 181

{4-[(2R)-2-(3-Chloro-phenyl)-2-hydroxy-ethylamino]-piperidine-1-yl}-benzoic acid ethyl ester hydrochloride The free base was prepared from 1-(4-ethoxycarbonylphenyl)-4-piperidone (Taylor, E. C., Skotnicki, J. S. *Synthesis*, 1981, 606) and (1R)-2-amino-1-(3-chloro-phenyl)-ethanol hydrochloride(which was obtained in Example 1) according to the procedure of Example 180. The hydrochloride salt was produced by the addition of hydrochloride gas as a white solid; mp >205° C. (decomposed); $^1$H NMR (300 MHz, DMSO-d$_6$) δ 1.28 (t, J=7.1 Hz, 3H), 1.55–1.75 (m, 2H), 2.05–2.25 (m, 2H), 2.70–3.40 (m, 5H), 3.95–4.10 (m, 2H), 4.26 (q, J=7.1 Hz, 2H), 5.00–5.10 (m, 1H), 7.06 (d, J=9.0 Hz, 2H), 7.30–7.60 (m, 3H), 7.80 (d, J=9.0 Hz, 2H), 8.83 (br s, 1H), 9.50 (br s, 1H); MS (ES) m/z: 402.9 (MH$^+$); HRMS Calcd. for $C_{22}H_{28}ClN_2O_3$ (MH$^+$): 403.1783. Found: 403.1780.

EXAMPLE 182

(4-{4-[(2R)-2-Hydroxy-2-(4-hydroxy-3-methanesulfonylamino-phenyl)-ethylamino]-piperidine-1-yl}-phenyl)-acetic acid The title compound was prepared from [4-(4-oxo-piperidine-1-yl)-phenyl]-acetic acid (which was obtained in Example 149) and N-[5-(2-amino-(1 R)-1-hydroxy-ethyl)-2-hydroxy-phenyl]-methanesulfonamide (which was obtained in Example 10) according to the procedure of Example 179 as a pale yellowish solid; mp >140° C. (decomposed); $^1$H NMR (300 MHz, DMSO-d$_6$) δ 1.25–1.40 (m, 2H), 1.75–1.95 (m, 2H), 2.50–3.60 (m, 7H), 2.88 (s, 3H), 3.16 (s, 2H), 4.47 (dd, J=8.0, 4.1 Hz, 1H), 6.78 (d, J=8.2 Hz, 1H), 6.84 (d, J=8.3 Hz, 2H), 6.95 (dd, J=8.2, 1.7 Hz, 1H), 7.05 (d, J=8.3 Hz, 2H), 7.16 (d, J=1.7 Hz, 1H); MS (ES) m/z: 464.1 (MH$^+$); HRMS Calcd. for $C_{22}H_{28}N_3O_6S$(M−H)$^-$: 462.1704. Found: 462.1696.

EXAMPLE 183

(E)-3-(4-{4-[(2R)-2-Hydroxy-2-(4-hydroxy-3-methanesulfonylamino-phenyl)-ethylamino]-piperidine-1-yl}-phenyl)-acrylic acid ethyl ester The title compound was prepared from (E)-3-[4-(4-oxo-piperidine-1-yl)-phenyl]-acrylic acid ethyl ester (which was obtained in Example 169) (0.27 g, 1.0 mmol) and N-[5-

((1R)-2-Amino-1-hydroxy-ethyl)-2-hydroxy-phenyl]-methanesulfonamide (which was obtained in Example 10) (0.27 g, 1.1 mmol) according to the prodedure shown for Example 180 to give 0.40 g of yellow solid; m.p. 103–106° C.; $^1$H NMR (DMSO-$d_6$) δ 1.24 (t, 3H), 1.20–1.45 (m, 2H), 1.75–1.95 (m, 2H), 2.55–2.95 (m, 5H), 2.92 (t, 3H), 3.67–3.85 (m, 2H), 4.14 (q, 2H), 4.46–4.50 (m, 1H), 6.34 (d, 1H), 6.96 (d, 1H), 6.79–7.05 (m, 3H), 7.05 (d, 1H), 7.17 (d, 1H), 7.56 (d, 2H); MS (ES) m/z: 504.0 (MH$^+$).

EXAMPLE 184

3-(4-{4-[(R)-2-Hydroxy-2-(4-hydroxy-3-methanesulfonylamino-phenyl)-ethylamino]-piperidine-1-yl}-phenyl)-propionic acid A solution of (E)-3-[4-(4-oxo-piperidine-1-yl)-phenyl]-acrylic acid (which was obtained in Example 170) (0.10 g, 0.40 mmol) and N-[5-((1R)-2-Amino-1-hydroxy-ethyl)-2-hydroxy-phenyl]-methane-sulfonamide (which was obtained in Example 10) (0.12 g, 0.48 mmol) in methanol (15 mL) was treated with acetic acid (0.03 g, 0.5 mmol), and 0.05 g of 10% Pd/C. The mixture was hydrogenated at 25 psi for 24 h, and then filtered through Celite and evaporated. The residue was triturated with ether to give 0.18 g of an off-white solid; m.p. 130–133° C.; $^1$H NMR (DMSO-$d_6$) δ 1.30–1.46 (m, 2H), 1.84–1.95 (m, 2H), 2.37–2.50 (m, 4H), 2.60–2.78 (m, 4H), 2.92 (s, 3 H), 3.53–3.62 (m, 3H), 4.46–4.55 (m, 1H), 6.85 (d, 2H), 6.92–7.10 (m, 4H), 7.18 (dd, 1H); MS (ES) m/z: 478.3 (MH$^+$).

EXAMPLE 185

(4-{4-[(2R)-2-Hydroxy-2-(4-hydroxy-3-methanesulfonylamino-phenyl)-ethylamino]-piperidine-1-yl}-benzyloxy)-acetic acid A solution of [4-(1,4-dioxa-8-aza-spiro[4.5]dec-8-yl)-phenyl]-methanol(which was obtained in Example 148) (3.49 g, 14 mmol) in tetrahydrofuran (100 mL) was treated with 60% sodium hydride in mineral oil (0.50, 21 mmol) and heated to a gentle reflux for 2 hours. After cooling to room temperature, iodoacetic acid sodium salt (2.91 g, 14 mmol) was added in one portion. The resulting mixture was heated to a gentle reflux for another 2 hours. After cooling to room temperature the reaction was quenched by careful addition of water and then partitioned between water and methylene chloride. The aqueous layer was acidified by acetic acid and extracted with methylene chloride. The organic phase was dried over sodium sulfate, and concentrated. The residue was treated with concentrated hydrochloric acid (150 mL) at room temperature. After 3 hours the solution pH was adjusted to 4 by ~28% ammonium hydroxide. The aqueous layer was extracted with methylene chloride, and the combined organic phases were washed with water, dried over sodium sulfate and concentrated to give a gum (0.95 g) [$^1$H NMR (300 MHz, CDCl$_3$) δ 2.55 (t, J=6.1 Hz, 4H), 3.61 (t, J=6.1 Hz, 4H), 4.10 (s, 2H), 4.56 (s, 2H), 6.95 (d, J=8.6 Hz, 2H), 7.29 (d, J=8.6 Hz, 2H); MS (ES) m/z: 264.3 (MH$^+$)]. The gum (0.39 g) was dissolved in methanol (100 mL)/ acetic acid (0.5 mL) and mixed with N-[5-(2-amino-(1R)-1-hydroxy-ethyl)-2-hydroxy-phenyl]-methanesulfonamide (which was obtained in Example 10) (0.25 g, 1 mmol). The resulting solution was hydrogenated in the presence of 500 mg of 10% palladium on carbon under hydrogen (5~20 psi) for 4 hours. The catalyst was then removed by filtering through a short pad of silica gel. The filtrate was concentrated and purified by silica gel chromatography (methanol/ methylene chloride) to give the title compound as an off-white solid; mp >145° C. (decomposed); $^1$H NMR (300 MHz, DMSO-$d_6$) δ 1.30–1.50 (m, 2H), 1.80–2.00 (m, 2H), 2.60–2.80 (m, 5H), 2.90 (s, 3H), 3.50–3.70 (m, 2H), 3.65 (s, 2H), 4.52 (s, 2H), 4.54 (dd, J=8.3, 3.8 Hz, 1H), 6.75–6.90 (m, 3H), 7.00 (dd, J=8.3, 2.0 Hz, 1H), 7.02–7.20 (m, 3H); MS (ES) m/z: 494.2 (MH$^+$); HRMS Calcd. for $C_{23}H_{30}N_3O_7S$(M–H)$^-$: 492.1810. Found: 492.1804.

EXAMPLE 186

4-{4-[(2R)-2-Hydroxy-2-(4-hydroxy-3-methanesulfonylamino-phenyl)-ethylamino]-piperidine-1-yl}-benzoic acid The title compound was prepared from 4-(4-oxo-piperidine-1-yl)-benzoic acid (which was obtained in Example 151) and N-[5-((1R)-2-amino-1-hydroxy-ethyl)-2-hydroxy-phenyl]-methanesulfonamide (which was obtained in Example 10) according to the procedure of Example 179 as a white solid; mp >85° C. (decomposed); $^1$H NMR (300 MHz, DMSO-$d_6$) δ 1.20–1.40 (m, 2H), 1.80–1.95 (m, 2H), 2.60–3.00 (m, 5H), 2.92 (s, 3H), 3.75–3.85 (m, 2H), 4.53 (dd, J=8.3, 4.0 Hz, 1H), 6.82 (d, J=8.3 Hz, 1H), 6.92 (d, J=8.9 Hz, 2H), 7.01 (dd, J=8.3, 2.0 Hz, 1H), 7.19 (d, J=2.0 Hz, 1H), 7.73 (d, J=8.9 Hz, 2H); MS (ES) m/z: 449.9 (MH$^+$); HRMS Calcd. for $C_{21}H_{26}N_3O_6S$ (M–H)$^-$: 448.1549. Found: 448.1541.

EXAMPLE 187

3-(4-{4-[(2R)-2-Hydroxy-2-(4-hydroxy-3-methanesulfonylamino-phenyl)-ethylamino]-piperidine-1-yl}-phenyl)-propionic acid ethyl ester To a solution of (E)-3-(4-{4-[(2R)-2-hydroxy-2-(4-hydroxy-3-methanesulfonyl-amino-phenyl)-ethylamino]-piperidine-1-yl}-phenyl)-acrylic acid ethyl ester(which was obtained in Example 183) (0.12 g, 0.25 mmol) in ethanol (2 mL) and tetrahydrofuran (1 mL) was added ammonium formate (0.16 g, 2.5 mmol), and 0.03 g of 10% Pd/C. The mixture was stirred at reflux for 18 hours. After cooling to room temperature, it was filtered through celite. The solvent was evaporated and the residue triturated with ether to give 0.11 g of a tan solid; m.p. 76–78° C.; $^1$H NMR (DMSO-$d_6$) δ 1.15 (t, 3H), 1.20–1.40 (m, 2H), 1.81–1.89 (m, 2H), 2.50–2.75 (m, 9H), 2.91 (t, 3H), 3.45–3.60 (m, 2H), 4.03 (q, 2H), 4.46–4.50 (m, 1H), 6.80–6.84 (m, 3H), 6.98–7.04 (m, 3H), 7.17 (d, 1H)); MS (ES) m/z: 506.0 (MH$^+$).

EXAMPLE 188

2-(4-{4-[2-Hydroxy-2-(4-hydroxy-3-methanesulfonylamino-phenyl)-ethylamino]-piperidine-1-yl}-benzylidene)-malonic acid diethyl ester The title compound was prepared from 2-[4-(4-oxo-piperidine-1-yl)-benzylidene]-malonic acid diethyl ester (which was obtained in Example 153) and N-[5-(-2-amino-1-hydroxy- ethyl)-2-hydroxy-phenyl]-methanesulfonamide (which was obtained in Example 9) according to the procedure of Example 180 as a yellowish solid; mp >80° C. (decomposed); $^1$H NMR (300 MHz, DMSO-$d_6$) δ 1.21 (t, J=7.0 Hz, 3H), 1.23 (t, J=7.0 Hz, 3H), 1.75–1.95 (m, 2H), 2.50–3.50 (m, 7H), 2.92 (s, 3H), 3.75–3.90 (m, 2H), 4.21 (q, J=7.0 Hz, 2H), 4.31 (q, J=7.0 Hz, 2H), 4.47 (dd, J=8.0, 4.2 Hz, 1H), 6.81 (d, J=8.2 Hz, 1H), 6.94 (d, J=9.0 Hz, 2H), 7.00 (dd, J=8.2, 2.0 Hz, 1H), 7.17 (d, J=2.0 Hz, 1H), 7.33 (d, J=9.0 Hz, 2H), 7.52 (s, 1H); MS (ES) m/z: 576.1 (MH$^+$); HRMS Calcd. for $C_{28}H_{38}N_3O_8S$(MH$^+$): 576.2374. Found: 576.2375.

EXAMPLE 189

2-(4-{4-(2R)-2-Hydroxy-2-(4-hydroxy-3-methanesulfonylamino-phenyl)-ethylamino]-piperidine-1-yl}-benzylidene)-malonic acid monoethyl ester 2-(4-{4-[(2R)-2-Hydroxy-2-(4-hydroxy-3-methanesulfonylamino-phenyl)-ethylamino]-piperidine-1-yl}-benzylidene)-malonic acid diethyl ester was prepared from 2-[4-(4-oxo-piperidine-1-yl)-benzylidene]-malonic acid diethyl ester(which was obtained in Example 153) and N-[5-(-2-amino-(1R)-1-hydroxy-ethyl)-2-hydroxy-phenyl]-methanesulfonamide (which was obtained in Example 10) according to the procedure of Example 180 as a yellowish solid; $^1$H NMR (300 MHz, DMSO-$d_6$) δ 1.21 (t, J=7.0 Hz, 3H), 1.23 (t, J=7.0 Hz, 3H), 1.75–1.95 (m, 2H), 2.50–3.50 (m, 7H), 2.90 (s, 3H), 3.75–3.90 (m, 2H), 4.16 (q, J=7.0 Hz, 2H), 4.29 (q, J=7.0 Hz, 2 H), 4.47 (dd, J=8.0, 4.2 Hz, 1H), 6.84 (d, J=8.2 Hz, 1H), 6.94 (d, J=9.0 Hz, 2H), 7.00 (dd, J=8.2, 2.0 Hz, 1H), 7.17 (d, J=2.0 Hz, 1H), 7.33 (d, J=9.0 Hz, 2H), 7.52 (s, 1H); MS (ES) m/z: 576.0 (MH$^+$); HRMS Calcd. for $C_{28}H_{38}N_3O_8S$(MH$^+$): 576.2374. Found: 576.2373.

The title compound was prepared by sodium hydroxide hydrolysis of the above diethyl ester as a pale grey solid; mp >170° C. (decomposed); $^1$H NMR (300 MHz, DMSO-$d_6$) δ 1.21 (t, J=7.0 Hz, 3H), 1.40–1.60 (m, 2H), 1.90–2.05 (m, 2H), 2.93 (s, 3H), 2.70–4.00 (m, 7H), 4.65–4.75 (m, 1H), 6.86 (d, J=8.1 Hz, 1H), 6.93 (d, J=8.9 Hz, 2H), 7.07 (dd, J=8.1, 2.0 Hz, 1H), 7.15–7.30 (m, 4H); MS (ES) m/z: 547.9 (MH$^+$); HRMS Calcd. for $C_{26}H_{34}N_3O_8S$(MH$^+$): 548.2061. Found: 548.2057.

EXAMPLE 190

4-{4-[(2R)-2-Hydroxy-2-(4-hydroxy-3-methanesulfonylamino-phenyl)-ethylamino]-piperidine-1-yl}-benzamide The title compound was prepared from 4-(4-oxo-piperidine-1-yl)-benzamide (which was obtained in Example 147) and N-[5-((1R)-2-amino-1-hydroxy-ethyl)-2-hydroxy-phenyl]-methanesulfonamide (which was obtained in Example 10) according to the procedure of Example 180 as a white solid; mp >75° C. (decomposed); $^1$H NMR (300 MHz, DMSO-$d_6$) δ 1.2–1.40 (m, 2H), 1.70–1.90 (m, 2H), 2.55–2.95 (m, 5H), 2.97 (s, 3H), 3.70–3.85 (m, 2H), 4.48 (dd, J=8.0, 4.3 Hz, 1H), 6.81 (d, J=8.2 Hz, 1H), 6.91 (d, J=9.0 Hz, 2H), 6.99 (dd, J=8.2, 2.0 Hz, 1H), 7.17 (d, J=2.0 Hz, 1H), 7.67 (br s, 2H), 7.72 (d, J=9.0 Hz, 2H); MS (ES) m/z: 448.9 (MH$^+$); HRMS Calcd. for $C_{21}H_{29}N_4O_5S$(MH$^+$): 449.1853. Found: 449.1853.

EXAMPLE 191

N-Benzyloxy-4-{4-[(2R)-2-hydroxy-2-(4-hydroxy-3-methanesulfonylamino-phenyl)-ethylamino]-piperidine-1-yl}-benzamide The title compound was prepared from N-benzyloxy-4-(4-oxo-piperidine-1-yl)-benzamide (which was obtained in Example 155) and N-[5-((1R)-2-amino-1-hydroxy-ethyl)-2-hydroxy-phenyl]-methanesulfonamide (which was obtained in Example 10) according to the procedure of Example 180 as a white solid; mp >70° C. (decomposed); $^1$H NMR (300 MHz, DMSO-$d_6$) δ 1.2–1.40 (m, 2H), 1.70–1.90 (m, 2H), 2.50–2.95 (m, 5H), 2.92 (s, 3H), 3.70–3.85 (m, 2H), 4.47 (dd, J=8.0, 4.2 Hz, 1H), 4.89 (s, 2H), 6.81 (d, J=8.2 Hz, 1H), 6.92 (d, J=9.0 Hz, 2H), 7.00 (dd, J=8.2, 2.0 Hz, 1H), 7.18 (d, J=2.0 Hz, 1H), 7.30–7.50 (m, 5H), 7.60 (d, J=9.0 Hz, 2H); MS (ES) m/z: 555.3 (MH$^+$); HRMS Calcd. for $C_{28}H_{35}N_4O_6S$(MH$^+$): 555.2272. Found: 555.2260.

EXAMPLE 192

Diethyl(2S)-2-[(4-{4-[((2R)-2-hydroxy-2-{4-hydroxy-3-[(methylsulfonyl)amino]phenyl}ethyl)amino]-1-piperidineyl}benzoyl)amino]pentanedioate The title compound was prepared from (2S)-2-[4-(4-oxo-piperidine-1-yl)-benzoylamino]-pentanedioic acid diethyl ester (which was obtained in Example 157) and N-[5-((1R)-2-amino-1-hydroxy-ethyl)-2-hydroxy-phenyl]-methanesulfonamide (which was obtained in Example 10) according to the procedure of Example 180 as a white solid; mp >75° C. (decomposed); $^1$H NMR (300 MHz, DMSO-$d_6$) δ 1.18 (t, J=7.1 Hz, 3H), 1.19 (t, J=7.1 Hz, 3H), 1.20–1.45 (m, 2H), 1.80–2.10 (m, 4H), 2.41 (t, J=7.4 Hz, 2H), 2.50–2.95 (m, 5H), 2.93 (s, 3H), 3.75–3.85 (m, 2H), 4.05 (q, J=7.1 Hz, 2H), 4.10 (q, J=7.1 Hz, 2H), 4.35–4.45 (m, 1H), 4.45–4.55 (m, 1H), 6.82 (d, J=8.3 Hz, 1H), 6.94 (d, J=8.9 Hz, 2H), 7.01 (dd, J=8.3, 2.0 Hz, 1H), 7.18 (d, J=2.0 Hz, 1H), 7.74 (d, J=8.9 Hz, 2H), 8.38 (d, J=7.5 Hz, 1H); MS (ES) m/z: 635.1 (MH$^+$); HRMS Calcd. for $C_{30}H_{43}N_4O_9S$(MH$^+$): 635.2745. Found: 635.2735.

EXAMPLE 193

Ethyl3-[(4-{4-[((2R)-2-hydroxy-2-{4-hydroxy-3-[(methylsulfonyl)amino]phenyl}-ethyl)amino]-1-piperidineyl}benzoyl)amino]propanoate The title compound was prepared from 3-[4-(4-oxo-piperidine-1-yl)-benzoylamino]-propionic acid ethyl ester (which was obtained in Example 158) and N-[5-((1R)-2-amino-1-hydroxy-ethyl)-2-hydroxy-phenyl]-methanesulfonamide (which was obtained in Example 10) according to the procedure of Example 179 as a white solid; mp >95° C. (decomposed); $^1$H NMR (300 MHz, DMSO-$d_6$) δ 1.17 (t, J=7.1 Hz, 3H), 1.40–1.60 (m, 2H), 1.90–2.10 (m, 2H), 2.54 (t, J=7.0 Hz, 2H), 2.70–2.95 (m, 5H), 2.94 (s, 3H), 3.35–3.50 (m, 2H), 3.80–3.95 (m, 2H), 4.05 (q, J=7.1 Hz, 2H), 4.65–4.75 (m, 1H), 6.88 (d, J=8.2 Hz, 1H), 6.95 (d, J=8.9 Hz, 2H), 7.05 (dd, J=8.2, 1.9 Hz, 1H), 7.22 (d, J=1.9 Hz, 1H), 7.69 (d, J=8.9 Hz, 2H), 8.26 (t, J=5.2 Hz, 1H); MS (ES) m/z: 549.2 (MH$^+$); HRMS Calcd. for $C_{26}H_{37}N_4O_7S$(MH$^+$): 549.2377. Found: 549.2369.

EXAMPLE 194

(2S)-2-[(4-{4-[((2R)-2-Hydroxy-2-{4-hydroxy-3-[(methylsulfonyl)amino]phenyl}-ethyl)amino]-1-piperidineyl}benzoyl)amino]pentanedioic acid The title compound was prepared from (2S)-2-[4-(4-oxo-piperidine-1-yl)-benzoylamino]-pentanedioic acid dibenzyl ester (which was obtained in Example 156) and N-[5-((1R)-2-amino-1-hydroxy-ethyl)-2-hydroxy-phenyl]-methanesulfonamide (which was obtained in Example 10) according to the procedure of Example 179 as a white solid; mp >230° C. (decomposed); $^1$H NMR (300 MHz, DMSO-$d_6$) δ 1.40–1.60 (m, 2H), 1.90–2.10 (m, 4H), 2.31 (t, J=7.5 Hz, 2H), 2.65–3.20 (m, 7H), 3.00 (s, 3H), 3.85–4.00 (m, 2H), 4.25–4.35 (m, 1H), 4.65–4.80 (m, 1H), 6.88 (d, J=8.4 Hz, 1H), 6.95 (d, J=8.7 Hz, 2H), 7.08 (dd, J=8.4, 1.2 Hz, 1H), 7.25 (d, J=1.8 Hz, 1H), 7.74 (d, J=8.7 Hz, 2H), 8.14 (d, J=7.2 Hz, 1H); MS (ES) m/z: 579.1 (MH$^+$); HRMS Calcd. for $C_{26}H_{35}N_4O_9S$(MH$^+$): 579.1973. Found: 579.1955.

EXAMPLE 195

N-(4-{4-[((2R)-2-Hydroxy-2-{4-hydroxy-3-[(methylsulfonyl)amino]phenyl}ethyl)amino]-1-piperidineyl}benzoyl)-beta-alanine The title compound was prepared from 3-[4-(4-oxo-piperidine-1-yl)-benzoylamino]-propionic acid benzyl ester (which was obtained in Example 159) and N-[5-((1R)-2-amino-1-hydroxy-ethyl)-2-hydroxy-phenyl]-methanesulfonamide (which was obtained in Example 10) according to the procedure of Example 179 as a white solid; mp >170° C. (decomposed); $^1$H NMR (300 MHz, DMSO-$d_6$) δ 1.20–1.45 (m, 2H), 1.80–1.95 (m, 2H), 2.43 (t, J=7.0 Hz, 2H), 2.60–2.90 (m, 5H), 2.90 (s, 3H), 3.00–3.40 (m, 2H), 3.70–3.85 (m, 2H), 4.50 (dd, J=8.0, 4.2 Hz, 1H), 6.82 (d, J=8.3 Hz, 1H), 6.92 (d, J=8.9 Hz, 2H), 7.01 (dd, J=8.3, 1.9 Hz, 1H), 7.18 (d, J=1.9 Hz, 1H), 7.68 (d, J=8.9 Hz, 2H), 8.26 (t, J=5.2 Hz, 1H); MS (ES) m/z: 521.2 (MH$^+$); HRMS Calcd. for $C_{24}H_{33}N_4O_7S(MH^+)$: 521.2064. Found: 521.2056.

EXAMPLE 196

Ethyl[(4-{4-[((2R)-2-hydroxy-2-{4-hydroxy-3-[(methylsulfonyl)amino]phenyl}ethyl)amino]-1-piperidineyl}benzoyl)amino]acetate The title compound was prepared from ethyl {[4-(4-oxo-1-piperidinyl)benzoyl]amino}acetate (which was obtained in Example 161) and N-[5-((1R)-2-amino-1-hydroxy-ethyl)-2-hydroxy-phenyl]-methanesulfonamide (which was obtained in Example 10) according to the procedure of Example 180 as a white solid; mp >140° C. (decomposed); $^1$H NMR (300 MHz, DMSO-$d_6$) δ 1.20 (t, J=7.1 Hz, 3H), 1.20–1.35 (m, 2H), 1.75–1.90 (m, 2H), 2.50–2.90 (m, 5 H), 2.90 (s, 3H), 3.70–3.85 (m, 2H), 3.93 (d, J=5.8 Hz, 2H), 4.10 (q, J=7.1 Hz, 2H), 4.47 (dd, J=7.9, 4.4 Hz, 1H), 6.79 (d, J=8.3 Hz, 1H), 6.90–7.00 (m, 3H), 7.16 (d, J=2.0 Hz, 1H), 7.72 (d, J=8.9 Hz, 2H), 8.58 (t, J=5.8 Hz, 1H); MS (ES) m/z: 535.2 (MH$^+$); HRMS Calcd. for $C_{26}H_{37}N_4O_7S(MH^+)$: 535.2221. Found: 535.2216.

EXAMPLE 197

[(4-{4-[((2R)-2-Hydroxy-2-{4-hydroxy-3-[(methylsulfonyl)amino]phenyl]ethyl)amino]-1-piperidineyl}benzoyl)amino]acetic acid The title compound was prepared from ethyl [(4-{4-[((2R)-2-hydroxy-2-{4-hydroxy-3-[(methylsulfonyl)amino]phenyl}ethyl)amino]-1-piperidineyl}benzoyl)amino]acetate (which was obtained in Example 196) by sodium hydroxide hydrolysis as a white solid; mp >85° C. (decomposed); $^1$H NMR (300 MHz, DMSO-$d_6$) δ 1.20–1.40 (m, 2H), 1.75–1.90 (m, 2H), 2.55–2.90 (m, 5H), 2.80 (s, 3H), 3.49 (d, J=4.5 Hz, 2H), 3.70–3.80 (m, 2H), 4.43 (dd, J=7.9, 4.4 Hz, 1H), 6.70 (d, J=7.4 Hz, 1H), 6.81 (dd, J=7.4, 2.0 Hz, 1H), 6.92 (d, J=8.9 Hz, 2H), 7.12 (d, J=2.0 Hz, 1H), 7.54 (t, J=4.5 Hz, 1H), 7.64 (d, J=8.9 Hz, 2H); MS (ES) m/z: 507.2 (MH$^+$); HRMS Calcd. for $C_{23}H_{31}N_4O_7S(MH^+)$: 507.1908. Found: 507.1912.

EXAMPLE 198

(2S)-2-(4-{4-[(2R)-2-Hydroxy-2-(4-hydroxy-3-methanesulfonylamino-phenyl)-ethylamino]-piperidine-1-yl}-benzoylamino)-4-methyl-pentanoic acid ethyl ester The title compound was prepared from ethyl 4-methyl-2-[(2S)-4-(4-oxo-piperidine-1-yl)-benzoylamino]-pentanoic acid ethyl ester(which was obtained in Example 165) and N-[5-((1R)-2-amino-1-hydroxy-ethyl)-2-hydroxy-phenyl]-methanesulfonamide (which was obtained in Example 10) according to the procedure of Example 180 as an off-white solid; mp >85° C. (decomposed); $^1$H NMR (300 MHz, DMSO-$d_6$) δ 0.86 (d, J=6.3 Hz, 3H), 0.92 (d, J=6.3 Hz, 3H), 1.18 (t, J=7.1 Hz, 3H), 1.20–1.40 (m, 2H), 1.45–1.95 (m, 5H), 2.55–2.92 (m, 5H), 2.92 (s, 3H), 3.70–3.85 (m, 2H), 4.10 (q, J=7.1 Hz, 2H), 4.40–4.55 (m, 2H), 6.82 (d, J=8.3 Hz, 1H), 6.94 (d, J=8.9 Hz, 2H), 7.00 (dd, J=8.3, 2.0 Hz, 1H), 7.18 (d, J=2.0 Hz, 1H), 7.75 (d, J=8.9 Hz, 2H), 8.33 (d, J=7.7 Hz, 1H); MS (ES) m/z: 591.3 (MH$^+$); HRMS Calcd. for $C_{29}H_{43}N_4O_7S(MH^+)$: 591.2847. Found: 591.2840.

EXAMPLE 199

(2S)-2-(4-{4-[(2R)-2-Hydroxy-2-(4-hydroxy-3-methanesulfonylamino-phenyl)-ethylamino]-piperidine-1-yl}-benzoylamino)-4-methyl-pentanoic acid The title compound was prepared from 2-(4-{4-[2-hydroxy-2-(4-hydroxy-3-methanesulfonylamino-phenyl)-ethylamino]-piperidine-1-yl}-benzoylamino)-4-methyl-pentanoic acid ethyl ester (which was obtained in Example 198) by sodium hydroxide hydrolysis as a white solid; mp >177° C. (decomposed); $^1$H NMR (300 MHz, DMSO-$d_6$) δ 0.87 (d, J=6.3 Hz, 3H), 0.90 (d, J=6.3 Hz, 3H), 1.35–1.75 (m, 5H), 1.90–2.00 (m, 2H), 2.60–2.90 (m, 5H), 2.94 (s, 3H), 3.65–3.80 (m, 2H), 4.25–4.35 (m, 1H), 4.60–4.65 (m, 1H), 6.85 (d, J=8.3 Hz, 1H), 6.90 (d, J=8.9 Hz, 2H), 7.05 (dd, J=8.3,1.9 Hz, 1H), 7.21 (d, J=1.9 Hz, 1H), 7.73 (d, J=8.9 Hz, 2H), 7.98 (d, J=7.7 Hz, 1H); MS (ES) m/z: 561.3 (M-H)$^-$; HRMS Calcd. for $C_{27}H_{37}N_4O_7S(M-H)^-$: 561.2377. Found: 561.2381.

EXAMPLE 200

1-(4-{4-[(2R)-2-Hydroxy-2-(4-hydroxy-3-methanesulfonylamino-phenyl)-ethylamino]-piperidine-1-yl}-benzoyl)-pyrrolidine-(2S)-2-carboxylic acid methyl ester The title compound was prepared from 1-[4-(4-oxo-piperidine-1-yl)-benzoyl]-pyrrolidine-(2S)-2-carboxylic acid methyl ester (which was obtained in Example 160) and N-[5-((1R)-2-amino-1-hydroxy-ethyl)-2-hydroxy-phenyl]-methanesulfonamide (which was obtained in Example 10) according to the procedure of Example 180 as an off-white solid; mp >80° C. (decomposed); $^1$H NMR (300 MHz, DMSO-$d_6$) δ 1.20–1.40 (m, 2H), 1.75–1.95 (m, 4H), 2.15–2.30 (m, 2H), 2.50–2.90 (m, 5H), 2.90 (s, 3H), 3.55–3.80 (m, 7H), 4.40–4.55 (m, 2H), 6.81 (d, J=8.3 Hz, 1H), 6.92 (d, J=8.7 Hz, 2H), 6.98 (dd, J=8.3, 2.0 Hz, 1H), 7.17 (d, J=2.0 Hz, 1H), 7.43 (d, J=8.7 Hz, 2H); MS (ES) m/z: 561.3 (MH$^+$); HRMS Calcd. for $C_{27}H_{37}N_4O_7S(MH^+)$: 561.2377. Found: 561.2369.

EXAMPLE 201

1-(4-{4-(2R)-2-Hydroxy-2-(4-hydroxy-3-methanesulfonylamino-phenyl)-ethylamino]-piperidine-1-yl}-benzoyl)-pyrrolidine-(2S)-2-carboxylic acid The title compound was prepared from 1-(4-{4-[(2R)-2-hydroxy-2-(4-hydroxy-3-methanesulfonylamino-phenyl)-ethylamino]-piperidine-1-yl}-benzoyl)-pyrrolidine-(2S)-2-carboxylic acid methyl ester(which was obtained in Example 200) by sodium hydroxide hydrolysis as a white solid; mp >220° C. (decomposed); $^1$H NMR (300 MHz, DMSO-d$_6$) δ 1.20–1.40 (m, 2H), 1.75–1.95 (m, 4H), 2.50–2.90 (m, 7H), 2.62 (s, 3H), 3.50–4.00 (m, 5H), 4.35–4.45 (m, 1H), 6.60 (d, J=8.3 Hz, 1H), 6.79 (d, J=8.7 Hz, 2H), 6.90 (dd, J=8.2 Hz, 1H), 7.06 (d, J=1.4 Hz, 1H), 7.37 (d, J=8.6 Hz, 2H); MS (ES) m/z: 545.6 (M-H)$^-$; HRMS Calcd. for C$_{26}$H$_{33}$N$_4$O$_7$S (M-H)$^-$: 545.2075. Found: 545.2064.

EXAMPLE 202

(2S)-2-(4-{4-[(2R)-2-Hydroxy-2-(4-hydroxy-3-methanesulfonylamino-phenyl)-ethylamino]-piperidine-1-yl}-benzoylamino)-3-methyl-butyric acid ethyl ester The title compound was prepared from 3-methyl-(2S)-2-[4-(4-oxo-piperidine-1-yl)-benzoylamino]-butyric acid ethyl ester (which was obtained in Example 163) and N-[5-((1R)-2-amino-1-hydroxy-ethyl)-2-hydroxy-phenyl]-methanesulfonamide (which was obtained in Example 10) according to the procedure of Example 180 as an off-white solid; mp >85° C. (decomposed); $^1$H NMR (300 MHz, DMSO-d$_6$) δ 0.92 (d, J=6.8 Hz, 3H), 0.97 (d, J=6.8 Hz, 3H), 1.17 (t, J=7.1 Hz, 3H), 1.20–1.40 (m, 2H), 1.75–1.95 (m, 2H), 2.05–2.20 (m, 1H), 2.55–2.90 (m, 5H), 2.90 (s, 3H), 3.70–3.85 (m, 2H), 4.00–4.20 (m, 2H), 4.22 (t, J=7.7 Hz, 1H), 4.48 (dd, J=8.0, 4.4 Hz, 1H), 6.80 (d, J=8.2 Hz, 1H), 6.95 (d, J=8.9 Hz, 2H), 6.98 (dd, J=8.2, 2.0 Hz, 1H), 7.17 (d, J=2.0 Hz, 1H), 7.76 (d, J=8.9 Hz, 2H), 8.17 (d, J=7.9 Hz, 1H); MS (ES) m/z: 577.2 (MH$^+$); HRMS Calcd. for C$_{29}$H$_{43}$N$_4$O$_7$S(MH$^+$): 577.2690. Found: 577.2682.

EXAMPLE 203

(2S)-2-(4-{4-[(2R)-2-Hydroxy-2-(4-hydroxy-3-methanesulfonylamino-phenyl)-ethylamino]-piperidine-1-yl}-benzoylamino)-3-methyl-butyric acid The title compound was prepared from (2S)-2-(4-{4-[(2R)-2-hydroxy-2-(4-hydroxy-3-methanesulfonylamino-phenyl)-ethylamino]-piperidine-1-yl}-benzoylamino)-3-methyl-butyric acid ethyl ester (which was obtained in Example 202) by sodium hydroxide hydrolysis as a pale yellowish solid; mp >135° C. (decomposed); $^1$H NMR (300 MHz, DMSO-d$_6$) δ 0.90 (d, J=2.3 Hz, 3H), 0.92 (d, J=2.3 Hz, 3H), 1.45–1.55 (m, 2H), 1.90–2.05 (m, 2H), 2.05–2.20 (m, 1H), 2.60–2.94 (m, 5H), 2.94 (s, 3H), 3.70–3.85 (m, 2H), 4.11 (t, J=6.0 Hz, 1H), 4.65–4.75 (m, 1H), 6.86 (d, J=8.3 Hz, 1H), 6.91 (d, J=8.9 Hz, 2H), 7.06 (dd, J=8.3, 2.0 Hz, 1H), 7.22 (d, J=2.0 Hz, 1H), 7.65–7.75 (m, 3H); MS (ES) m/z: 549.3 (MH$^+$); HRMS Calcd. for C$_{26}$H$_{35}$N$_4$O$_7$S (M-H)$^-$: 547.2231. Found: 547.2229.

EXAMPLE 204

(2S)-2-(4-{4-[(2R)-2-Hydroxy-2-(4-hydroxy-3-methanesulfonylamino-phenyl)-ethylamino]-piperidine-1-yl}-benzoylamino)-3-phenyl-propionic acid methyl ester The title compound was prepared from (2S)-2-[4-(4-oxo-piperidine-1-yl)-benzoylamino]-3-phenyl-propionic acid methyl ester(which was obtained in Example 164) and N-[5-((1R)-2-amino-1-hydroxy-ethyl)-2-hydroxy-phenyl]-methanesulfonamide (which was obtained in Example 10) according to the procedure of Example 180 as an off-white solid; mp >98° C. (decomposed); $^1$H NMR (300 MHz, DMSO-d$_6$) δ 1.20–1.40 (m, 2H), 1.80–1.90 (m, 2H), 2.05–2.90 (m, 5H), 2.91 (s, 3H), 3.00–3.20 (m, 2H), 3.70–3.80 (m, 2H), 4.47 (dd, J=8.0, 4.3 Hz, 1H), 4.50–4.65 (m, 1H), 6.81 (d, J=8.2 Hz, 1H), 6.92 (d, J=8.9 Hz, 2H), 7.00 (dd, J=8.2, 2.0 Hz, 1H), 7.10–7.30 (m, 6H), 7.67 (d, J=8.9 Hz, 2H), 8.47 (d, J=7.8 Hz, 1H); MS (ES) m/z: 611.2 (MH$^+$); HRMS Calcd. for C$_{31}$H$_{39}$N$_4$O$_7$S(MH$^+$): 611.2534. Found: 611.2525.

EXAMPLE 205

(2S)-2-(4-{4-[(2R)-2-Hydroxy-2-(4-hydroxy-3-methanesulfonylamino-phenyl)-ethylamino]-piperidine-1-yl}-benzoylamino)-3-phenyl-propionic acid The title compound was prepared from (2S)-2-(4-{4-[(2R)-2-hydroxy-2-(4-hydroxy-3-methanesulfonylamino-phenyl)-ethylamino]-piperidine-1-yl}-benzoylamino)-3-phenyl-propionic acid methyl ester(which was obtained in Example 204) by sodium hydroxide hydrolysis as a pale yellowish solid; mp >160° C. (decomposed); $^1$H NMR (300 MHz, DMSO-d$_6$) δ 1.40–1.50 (m, 2H), 1.90–2.05 (m, 2H), 2.50–3.50 (m, 7H), 2.95 (s, 3H), 3.69–3.75 (m, 2H), 4.30–4.45 (m, 2H), 4.70–4.75 (m, 1H), 6.83 (d, J=8.8 Hz, 2H), 6.88 (d, J=8.3 Hz, 1H), 7.05–7.30 (m, 7H), 7.63 (d, J=8.8 Hz, 2H), 7.93 (br d, J=6.6 Hz, 1H); MS (ES) m/z: 597.1 (MH$^+$); HRMS Calcd. for C$_{30}$H$_{35}$N$_4$O$_7$S(M-H)$^-$: 595.2231. Found: 595.2232.

EXAMPLE 206

Methyl1-[(4-{4-[((2R)-2-hydroxy-2-{4-hydroxy-3-piperidineyl}benzoyl)amino] cyclopropanecarboxylate The title compound was prepared from methyl 1-[4-(4-oxo-piperidine-1-yl)-benzoylamino]-cyclopropanecarboxylate (which was obtained in Example 167) and N-[5-((1R)-2-amino-1-hydroxy-ethyl)-2-hydroxy-phenyl]-methanesulfonamide (which was obtained in Example 10) according to the procedure of Example 180 as a white solid; mp >110° C. (decomposed); $^1$H NMR (300 MHz, DMSO-d$_6$) δ 1.05–1.40 (m, 6H), 1.75–1.90 (m, 2H), 2.55–2.91 (m, 5H), 2.91 (s, 3H), 3.58 (s, 3H), 3.69–3.80 (m, 2H), 4.47 (dd, J=7.9, 4.4 Hz, 1H), 6.81 (d, J=8.5 Hz, 1H), 6.85 (d, J=8.9 Hz, 2H), 7.00 (dd, J=8.5, 2.0 Hz, 1H), 7.17 (d, J=2.0 Hz, 1H), 7.71 (d, J=8.9 Hz, 1H), 8.72 (s, 1H); MS (ES) m/z: 547.1 (MH$^+$); HRMS Calcd. for C$_{26}$H$_{35}$N$_4$O$_7$S(MH$^+$): 547.2221. Found: 547.2218.

EXAMPLE 207

[Butyl-(4-{4-[(2R)-2-hydroxy-2-(4-hydroxy-3-methanesulfonylamino-phenyl)-ethylamino]-piperidine-1-yl}-benzoyl)-amino]-acetic acid ethyl ester A mixture of 4-(4-oxo-piperidine-1-yl)-benzoic acid (which was obtained in Example 151) (0.30 g, 1.37 mmol), 1-[3-(dimethylamino)propyl-3-ethylcarbodiimide hydrochloride (0.53, 2.74 mmol) and N-butylglycine ethyl ester (0.44 g, 2.7 mmol) was stirred in methylene chloride (70 mL). N-methylmorpholine (0.28 g, 2.74 mol) was added dropwise and the mixture was stirred overnight. The mixture was then washed with 0.05 N hydrochloric acid and water. The resulting solution was dried with magnesium sulfate and concentrated to give a gum. The gum was dissolved in dimethylformamide (15 mL) and then treated with N-[5-((1R)-2-amino-1-hydroxy-ethyl)-2-hydroxy-phenyl]-methanesulfonamide (0.25 g, 1 mmol) (which was obtained in Example 10), sodium triacetoxyborohydride (0.85 g, 4 mmol) and acetic acid (0.3 mL). After stirring at room temperature under a nitrogen atmosphere for 2 hours the mixture was poured into a saturated aqueous sodium bicarbonate. The aqueous layer was extracted with n-butanol and the concentrated gum was purified by silica gel chromatography (methanol/methylene chloride) to give the title compound as a white solid; mp >60° C. (decomposed); $^1$H NMR (300 MHz, DMSO-d$_6$) δ 0.70–1.60 (m, 12H), 1.75–1.95 (m, 2H), 2.50–3.50 (m, 7H), 2.91 (s, 3H), 3.60–3.75 (m, 2H), 4.00–4.15 (m, 4H), 4.47 (dd, J=8.0, 4.3 Hz, 1H), 6.81 (d, J=8.5 Hz, 1H), 6.90–7.00 (m, 3H), 7.05–7.25 (m, 3H); MS (ES) m/z: 591.3 (MH$^+$); HRMS Calcd. for C$_{29}$H$_{43}$N$_4$O$_7$S (MH$^+$): 591.2847. Found: 591.2840.

EXAMPLE 208

Methyl[(4-{4-[((2R)-2-hydroxy-2-{4-hydroxy-3-[(methylsulfonyl)amino]phenyl}ethyl)amino]-1-piperidineyl}benzoyl)amino]acetate The title compound was prepared from methyl {[4-(4-oxo-1-piperidineyl)benzoyl]amino}acetate (which was obtained in Example 162) and N-[5-((1R)-2-amino-1-hydroxy- ethyl)-2-hydroxy-phenyl]-methanesulfonamide (which was obtained in Example 10) according to the procedure of Example 180 as a white solid; mp >75° C. (decomposed); $^1$H NMR (300 MHz, DMSO-d$_6$) δ 1.20–1.35 (m, 2H), 1.75–1.90 (m, 2H), 2.50–2.90 (m, 5H), 2.91 (s, 3H), 3.63 (s, 3H), 3.70–3.85 (m, 2H), 3.95 (d, J=5.7 Hz, 2H), 4.49 (dd, J=8.0, 4.3 Hz, 1H), 6.81 (d, J=8.2 Hz, 1H), 6.96 (d, J=8.9 Hz, 2H), 7.00 (dd, J=8.2, 2.0 Hz, 1H), 7.17 (d, J=2.0 Hz, 1H), 7.71 (d, J=8.9 Hz, 2H), 8.60 (t, J=5.8 Hz, 1H); MS (ES) m/z: 521.3 (MH$^+$); HRMS Calcd. for C$_{25}$H$_{37}$N$_4$O$_7$S (M$^+$): 520.2064. Found: 520.2054.

EXAMPLE 209

(2S)-2-(4-{4-[2-Hydroxy-2-(4-hydroxy-3-methanesulfonylamino-phenyl)-ethylamino]-piperidine-1-yl}-benzoylamino)-4-methyl-pentanoic acid methyl ester The title compound was prepared from methyl 4-methyl-2-[(2S)-4-(4-oxo-piperidine-1-yl)-benzoylamino]-pentanoic acid methyl ester(which was obtained in Example 166) and N-[5-((1R)-2-amino-1-hydroxy-ethyl)-2-hydroxy-phenyl]-methanesulfonamide (which was obtained in Example 10) according to the procedure of Example 180 as a white solid; mp >90° C. (decomposed); $^1$H NMR (300 MHz, DMSO-d$_6$) δ 0.86 (d, J=6.4 Hz, 3H), 0.92 (d, J=6.4 Hz, 3H), 1.20–1.40 (m, 2H), 1.50–1.95 (m, 5H), 2.55–2.92 (m, 5H), 2.91 (s, 3H), 3.62 (s, 3H), 3.70–3.85 (m, 2H), 4.40–4.55 (m, 2H), 6.82 (d, J=8.2 Hz, 1H), 6.93 (d, J=8.9 Hz, 2H), 7.00 (dd, J=8.2, 2.0 Hz, 2H), 7.18 (d, J=2.0 Hz, 1H), 7.75 (d, J=8.9 Hz, 2H), 8.34 (d, J=7.7 Hz, 1H); MS (ES) m/z: 577.3 (MH$^+$); HRMS Calcd. for C$_{28}$H$_{41}$N$_4$O$_7$S(MH$^+$): 577.2690. Found: 577.2682.

EXAMPLE 210

(2E)-3-(4-{4-[(2R)-2-Hydroxy-2-(4-hydroxy-3-methanesulfonylamino-phenyl)-ethylamino]-piperidine-1-yl}-phenyl)-acrylic acid A solution of 0.10 g (0.2 mmol) of (E)-3-(4-{4-[(2R)-2-hydroxy-2-(4-hydroxy-3-methanesulfonylamino-phenyl)-ethylamino]-piperidine-1-yl}-phenyl)-acrylic acid ethyl ester (which was obtained in Example 183) in ethanol (3 mL) was treated with 3 mL of 1 N NaOH. After 18 h at room temperature, the mixture was acidified with acetic acid. The resulting suspension was filtered and the precipitate was washed with water, and dried in vacuo to give 0.09 g of a tan solid; m.p. 220° C.; $^1$H NMR (DMSO-d$_6$) δ 1.20–1.40 (m, 2H), 1.80–1.95 (m, 2H), 2.57–2.95 (m, 5H), 2.92 (t, 3H), 3.74–3.82 (m, 2H), 4.48–4.52 (m, 1H), 6.22 (s, 1H), 6.27 (s, 1H), 6.81–7.03 (m, 4H), 7.18 (d, 1H), 7.42–7.49 (m, 3H)); MS (ES) m/z: 476.0 (MH$^+$).

EXAMPLE 211

4-{4-[((2R)-2-Hydroxy-2-{4-hydroxy-3-[(methylsulfonyl)amino]phenyl}ethyl)amino]-1-piperidinyl}-N-[(1S)-1-(hydroxymethyl)-3-methylbutyl]benzamide The title compound was prepared from N-[(1S)-1-(hydroxymethyl)-3-methylbutyl]-4-(4-oxo-1-piperidineyl)benzamide (which was obtained in Example 173) (0.13 g, 0.4 mmol) and N-[5-((1R)-2-amino-1-hydroxy-ethyl)-2-hydroxy-phenyl]-methanesulfonamide (0.12 g, 0.48 mmol) (which was obtained in Example 10) according to the prodedure shown for Example 180 to give 0.16 g of an off-white solid; m.p. 120–122° C.; MS (ES) m/z: 549.3 (MH$^+$); HRMS (ES) Calcd. for C$_{27}$H$_{41}$N$_4$O$_6$S(MH$^+$): 549.2741, Found: 549.2735.

EXAMPLE 212

4-{4-[((2R)-2-Hydroxy-2-{4-hydroxy-3-[(methylsulfonyl)amino]phenyl}ethyl)amino]-1-piperidineyl}-N-[(3S)-2-oxoazepanyl]benzamide The title compound was prepared from N-[(3S)-2-oxoazepanyl]-4-(4-oxo-1-piperidineyl)benzamide (which was obtained in Example 175) (0.13 g, 0.4 mmol) and N-[5-((1R)-2-amino-1-hydroxy-ethyl)-2-hydroxy-phenyl]-methanesulfonamide (which was obtained in Example 10) (0.12 g, 0.48 mmol) according to the prodedure shown for Example 180 to give 0.20 g of an off-white solid; m.p. 135–137° C.; MS (ES) m/z: 560.2 (MH$^+$); HRMS (ES) Calcd. for C$_{27}$H$_{38}$N$_5$O$_6$S(MH$^+$): 560.2537, Found: 560.2531.

EXAMPLE 213

N-Butyl-4-{4-[((2R)-2-hydroxy-2-{4-hydroxy-3-[(methylsulfonyl)amino]phenyl}-ethyl)amino]-1-piperidineyl}-N-(1H-tetraazol-5-ylmethyl)benzamide The title compound was prepared from N-butyl-4-(4-oxo-1-piperidineyl)-N-(1H-tetraazol-5-ylmethyl)benzamide (which was obtained in Example 178) (0.14 g, 0.4 mmol) and N-[5-((1R)-2-amino-1-hydroxy-ethyl)-2-hydroxy-phenyl]-methanesulfonamide (which was obtained in Example 10) (0.12 g, 0.48 mmol) according to the prodedure shown for Example 180 to give 0.22 g of an off-white solid; m.p. 168–170° C.; MS (ES) m/z: 587.5 (MH$^+$); HRMS (ES) Calcd. for C$_{27}$H$_{39}$N$_8$O$_5$S(MH$^+$): 587.2759, Found: 587.2751.

EXAMPLE 214

4-(1,4-Dioxa-8-aza-spiro[4.5]dec-8-yl)-phenylamine

A mixture of 8-(4-nitro-phenyl)-1,4-dioxa-8-aza-spiro[4.5]decane (Synthesis, 606, 1981) (3.5 g, 13.3 mmol) and 10% Pd/C (0.5 g) in 100 mL of ethanol/methylene chloride (2:1) was pressurized with 30 psi hydrogen and shaken over 1 hours. The catalyst was then removed by filtering through a short pad of silica gel to give the title compound (2.8g, 90%) as a grey solid; $^1$H NMR (300 MHz, DMSO-d$_6$) δ 1.85–2.00 (m, 4H), 3.00–3.10 (m, 4H), 3.93 (s, 4H), 6.60 (d, J=6.0 Hz, 2H), 6.80 (d, J=6.0 Hz, 2H); MS (ES) m/z: 235.2 (MH$^+$); HRMS Calcd. for C$_{13}$H$_{18}$N$_2$O$_2$: 234.1380. Found: 234.1371.

EXAMPLE 215

N-{4-[4-(1,4-Dioxa-8-aza-spiro[4.5]dec-8-yl)-phenylsulfamoyl]-phenyl}-acetamide

To a stirred solution of 4-(1,4-dioxa-8-aza-spiro[4.5]dec-8-yl)-phenylamine (which was obtained in Example 214) (2.8 g, 11.9mol) in 1.4-dioxane (150 mL) and triethylamine (7 mL) was added a solution of N-acetylsulfanilyl chloride (3.5 g, 15 mmol) in 75 mL of 1,4-dioxane at room temperature. The reaction was stirred for 18 hours. The reaction mixture was concentrated. The residue was dissolved in methylene chloride and washed with diluted hydrochloric acid. The white solid in water layer was collected and dried to give the title compound as a white solid (2.5 g, 43%); $^1$H NMR (300 MHz, DMSO-d$_6$) δ 1.92 (brs, 4H), 2.06 (s, 3H), 3.68 (brs, 4H), 3.93 (s, 4H), 7.06 (d, J=8.4 Hz, 2H), 7.33 (brs, 2H), 7.68 (d, J=9.0 Hz, 2H), 7.71 (d, J=9.0Hz, 2H), 10.24 (brs, 1H), 10.38 (s, 1H); MS (ES) m/z: 432.3 (MH$^+$); HRMS Calcd. for C$_{21}$H$_{25}$N$_3$O$_5$S(M$^+$): 431.1515. Found: 431.1530.

EXAMPLE 216

N-{4-[4-(4-Oxo-piperidine-1-yl)-phenylsulfamoyl]-phenyl}-acetamide

N-{4-[4-(1,4-Dioxa-8-aza-spiro[4.5]dec-8-yl)-phenylsulfamoyl]-phenyl}-acetamide (which was obtained in Example 215) (2.2 g, 5.1 mmol) was treated with concentrated hydrochloric acid (50 mL) at 0° C. and then allowed to warm to room temperature. After 30 min., 20 mL of 5 N NaOH was added dropwise and the precipitate was collected by filtration, and dried over P$_2$O$_5$ to give the title compound as a white solid (1.2 g); $^1$H NMR (300 MHz, DMSO-d$_6$) δ 2.06 (s, 3H), 2.43 (t, J=5.8 Hz, 4H), 3.53 (t, J=5.8 Hz, 4H), 6.85–7.05 (m, 4H), 7.62 (d, J=9.0 Hz, 2H), 7.71 (d, J=9.0 Hz, 2H), 9.81 (s, 1H), 10.35 (s, 1H); MS (ES) m/z: 388.3 (MH$^+$); HRMS Calcd. for C$_{19}$H$_{21}$N$_3$O$_4$S(M$^+$) :387.1253. Found: 387.1272.

EXAMPLE 217

N-[4-(1,4-Dioxa-8-aza-spiro[4.5]dec-8-yl)-phenyl]-4-methoxy-benzenesulfonamide

The title compound was prepared from 4-(1,4-dioxa-8-aza-spiro[4.5]dec-8-yl)-phenylamine (which was obtained in Example 214) and 4-methoxybenzenesulfonyl chloride according to the procedure of Example 215 as a crystalline solid; $^1$H NMR (300 MHz, DMSO-d$_6$) δ 1.65 (t, J=5.6 Hz, 4H), 3.15 (t, J=5.6 Hz, 4H), 3.79 (s, 3H), 3.88 (s, 4H), 6.79 (d, J=9.0 Hz, 2H), 6.88 (d, J=9.0 Hz, 2H), 7.02 (d, J=9.0Hz, 2H), 7.60 (d, J=9.0Hz, 2H), 9.63 (s, 1H); MS (ES) m/z: 405.3 (MH$^+$); HRMS Calcd. for C$_{20}$H$_{24}$N$_2$O$_5$S(M$^+$): 404.1406. Found: 404.1402. Anal. Calcd. for C$_{20}$H$_{24}$N$_2$O$_5$S: C, 59.39; H, 5.98; N, 6.93. Found: C, 59.48; H, 6.03; N, 6.85.

EXAMPLE 218

4-Methoxy-N-[4-(4-oxo-piperidine-1-yl)-phenyl]benzenesulfonamide

The title compound was prepared from N-[4-(1,4-dioxa-8-aza-spiro[4.5]dec-8-yl)-phenyl]-4-methoxy-benzenesulfonamide (which was obtained in Example 217) according to the procedure of Example 216 as a grey solid; $^1$H NMR (300 MHz, DMSO-d$_6$) δ 2.37 (t, J=6.0 Hz, 4H), 3.50 (t, J=6.0 Hz, 4H), 3.79 (s, 3H), 6.88 (d, J=9.0 Hz, 2H), 6.93 (d, J=9.0 Hz, 2H), 7.01 (d, J=9.0 Hz, 2H), 7.60 (d, J=9.0 Hz, 2H), 9.66 (s, 1H); MS (ES) m/z: 361.2 (MH$^+$); HRMS Calcd. for C$_{18}$H$_{20}$N$_2$O$_4$S(M$^+$): 360.1144. Found: 360.1146.

EXAMPLE 219

8-(2-Nitro-phenyl)-1,4-dioxa-8-aza-spiro[4.5]decane

A solution of 2-fluoronitrobenzene (10 g, 70.9 mmol) and 1,4-dioxa-8-aza-spiro[4.5]decane (10 g, 69.8 mmol) in pyridine (70 mL) was heated at 70° C. for 1 day, diluted with water, and extracted with ethyl acetate. The combined organic extracts were washed with brine, dried with sodium sulfate, and filtered. The solvent was removed under reduced pressure to give the title compound (15 g) as a red oil; $^1$H NMR (300 MHz, CDCl$_3$) δ 1.88 (t, J=5.6 Hz, 4H), 3.16 (t, J=5.6 Hz, 4H), 4.00 (s, 4H), 7.03 (dd, J=8.2, 8.2 Hz, 2H), 7.17 (d, J=8.2 Hz, 2H), 7.40 (ddd, J=8.2, 8.2, 1.7 Hz, 1H), 7.77 (dd, J=8.4, 1.7Hz, 1H); MS (ES) m/z: 265.1 (MH$^+$); HRMS Calcd. for C$_{13}$H$_{17}$N$_2$O$_4$ (MH$^+$): 265.1188. Found: 265.1164.

EXAMPLE 220

2-(1,4-Dioxa-8-aza-spiro[4.5]dec-8-yl)-phenylamine hydrochloride

A mixture of 8-(2-nitro-phenyl)-1,4-dioxa-8-aza-spiro [5.5]decane (which was obtained in Example 219) (14.1 g, 15.9 mmol) and 10% Pd/C (1 g) in 100 mL of ethanol was pressurized with 30 psi hydrogen and shaken over 2 hours. The catalyst was then removed by filtering through a short pad of silica gel. Hydrogen chloride (1.0 M solution in diethyl ether) was added and the solid that formed was collected by filtration to give the title compound as a white solid; $^1$H NMR (300 MHz, DMSO-d$_6$) δ 1.85–2.00 (m, 4H), 3.00–3.40 (m, 4H), 3.93 (s, 4H), 7.12–7.28 (m, 2H), 7.28–7.55 (m, 2H); MS (ES) m/z: 235.2 (MH$^+$); HRMS Calcd. for C$_{13}$H$_{19}$N$_2$O$_2$ (MH$^+$): 235.1447. Found: 235.1451.

EXAMPLE 221

N-{4-[2-(1,4-Dioxa-8-aza-spiro[4.5]dec-8-yl)-phenylsulfamoyl]-phenyl]-acetamide

The title compound was prepared from 2-(1,4-dioxa-8-aza-spiro[4.5]dec-8-yl)-phenylamine hydrochloride (which was obtained in Example 220) and N-acetylsulfanilyl chloride according to the procedure of Example 215 as a crystalline solid; $^1$H NMR (300 MHz, DMSO-d$_6$) δ 1.73 (t, J=5.4 Hz, 4H), 2.73 (t, J=5.4 Hz, 4H), 3.33 (s, 4H), 3.89 (s, 3H), 7.00–7.10 (m, 2H), 7.10–7.20 (m, 1H), 7.30–7.40 (m, 1H), 7.67 (d, J=9.3 Hz, 2H), 7.71 (d, J=9.3 Hz, 2H), 8.79 (s, 1H), 10.29 (s, 1H); MS (ES) m/z: 432.2 (MH$^+$); HRMS Calcd. for C$_{21}$H$_{26}$N$_3$O$_5$S (MH$^+$): 432.1593. Found: 432.1597. Anal. Calcd. for C$_{21}$N$_{25}$N$_3$O$_5$S: C, 58.45; H, 5.84; N, 9.74. Found: C, 58.41; H, 5.83; N, 9.72.

EXAMPLE 222

N-{4-[2-(4-Oxo-piperidine-1-yl)-phenylsulfamoyl]-phenyl}-acetamide

The title compound was prepared from N-{4-[2-(1,4-dioxa-8-aza-spiro[4.5]dec-8-yl)-phenylsulfamoyl]-phenyl}-acetamide (which was obtained in Example 221) according to the procedure of Example 216 as a white solid; $^1$H NMR (300 MHz, DMSO-$d_6$) δ 2.05 (s, 3H), 2.43 (t, J=5.9 Hz, 4H), 2.77 (t, J=5.9 Hz, 4H), 7.00–7.20 (m, 3H), 7.35–7.45 (m, 1H), 7.64 (d, J=6.9 Hz, 2H), 7.71 (d, J=6.9 Hz, 2H), 9.10 (s, 1H), 10.30 (s, 1H); MS (ES) m/z: 388.3 (MH$^+$); HRMS Calcd. for $C_{19}H_{22}N_3O_4S$(MH$^+$): 388.1331. Found: 388.1341.

EXAMPLE 223

N-[4-(1,4-Dioxa-8-aza-spiro[4.5]dec-8-yl)-phenyl]-4-(3-hexyl-ureido)-benzenesulfonamide The title compound was prepared from 4-(1,4-dioxa-8-aza-spiro[4.5]dec-8-yl)-phenylamine (which was obtained in Example 214) and 4-(3-hexyl-ureido)benzenesulfonyl chloride (U.S. Pat. No. 5,561,142/1996) according to the procedure of Example 215 as a white flake; $^1$H NMR (300 MHz, DMSO-$d_6$) δ 0.86 (t, J=6.5 Hz, 3H), 1.20–1.50 (m, 8H), 1.65 (t, J=5.7 Hz, 4H), 3.00–3.10 (m, 2H), 3.14 (t, J=5.7 Hz, 4H), 3.88 (s, 4H), 6.28 (t, J=5.6 Hz, 1H), 6.79 (d, J=9.0 Hz, 2H), 6.87 (d, J=9.0 Hz, 2H), 7.45 (d, J=9.1 Hz, 2H), 7.51 (d, J=9.1 Hz, 2H), 8.82 (s, 1H); MS (ES) m/z: 517.2 (MH$^+$); HRMS Calcd. for $C_{26}H_{37}N_4O_5S$(MH$^+$): 517.2485. Found: 517.2377. Anal. Calcd. for $C_{26}H_{36}N_4O_5S$: C, 60.44; H, 7.02; N, 10.84. Found: C, 60.29; H, 6.95; N, 10.91.

EXAMPLE 224

1-(4-Amino-phenyl)-piperidine-4-one hydrochloride

A mixture of 1-(4-nitro-phenyl)-piperidine-4-one (Synthesis 1981, 606) (4.0 g, 18 mmol) and 500 mg of 10% Pd/C in 75 mL of methylene chloride was hydrogenated under $H_2$ (5~10 psi) for 1 hour. The catalyst was then removed by filtering through a short pad of silica gel. The filtrate was treated with hydrogen chloride gas and the precipitate was collected to give 2 g of the title compound as a tan solid; $^1$H NMR (300 MHz, DMSO-$d_6$) δ 2.44 (t, J=6.0 Hz, 4H), 3.65 (t, J=6.0 Hz, 4H), 7.14 (d, J=9.0 Hz, 2H), 7.25 (d, J=9.0 Hz, 2H); MS (ES) m/z: 190.9 (MH$^+$); HRMS Calcd. for $C_{11}H_{15}N_2O$ (MH$^+$): 190.1106. Found: 190.1096.

EXAMPLE 225

4-(3-Hexyl-ureido)-N-[4-(4-oxo-piperidine-1-yl)-phenyl]benzenesulfonamide

Method A: The title compound was prepared from N-[4-(1,4-dioxa-8-aza-spiro[4.5]dec-8-yl)-phenyl]-4-(3-hexyl-ureido)-benzenesulfonamide (which was obtained in Example 223) according to the procedure of Example 216 a as a grey solid.

Method B: To a stirred solution of 1-(4-amino-phenyl)-piperidine-4-one hydrochloride (which was obtained in Example 224) (3.95 g, 15 mmol) in 250 mL of dioxane was added 13.7 mL of triethylamine followed by 4-(3-hexyl-ureido)benzenesulfonyl chloride (U.S. Pat. No. 5,561,142/1996)(6.36 g, 20 mmol). After being stirred over 1 day, the mixture was concentrated and the residue chromatographed on silica gel (0 to 10% methanol/methylene chloride) to afford 3.0 g of the title compound; $^1$H NMR (300 MHz, CDCl$_3$) δ 0.88 (t, J=7.0 Hz, 3H), 1.20–1.60 (m, 8H), 2.45–2.60 (m, 4H), 3.20–3.75 (m, 2H), 3.50–3.60 (m, 4H), 4.90 (brs, 1H), 6.50 (brs, 1H), 6.82 (d, J=8.5 Hz, 2H), 6.97 (d, J=8.5 Hz, 2H), 7.38 (d, J=8.7 Hz, 2H), 7.56 (d, J=8.7 Hz, 2H); MS (ES) m/z: 473.5 (MH$^+$); HRMS Calcd. for $C_{24}H_{25}N_4O_4S$(MH$^+$): 473.2233. Found: 473.2220.

EXAMPLE 226

4-[4-(3-Cyclopentyl-propyl)-5-oxo-4,5-dihydro-tetrazol-1-yl])-N-[4-(4-oxo-piperidine-1-yl)-phenyl]benzenesulfonamide The title compound was prepared from 1-(4-amino-phenyl)-piperidine-4-one (which was obtained in Example 224) and 4-[(3-cyclopentyl-propyl)-5-oxo-4,5-dihydro-tetrazol-1-yl]-phenylsulfonyl chloride (U.S. Pat. No. 5,561,142/1996) according to the Method B of Example 225 as a yellowish solid; $^1$H NMR (300 MHz, DMSO-$d_6$) δ 0.90–1.80 (m, 17H), 2.36 (t, J=6.0 Hz, 2H), 3.49 (t, J=6.0 Hz, 2H), 3.96 (t, J=7.0 Hz, 2H), 6.86 (d, J=6.7 Hz, 2H), 6.94 (d, J=6.7 Hz, 2H), 7.86 (d, J=8.8 Hz, 2H), 8.06 (d, J=8.8 Hz, 2H), 9.92 (s, 1H); MS (ES) m/z: 525.1 (MH$^+$); HRMS Calcd. for $C_{26}H_{32}N_6O_4S$(M$^+$): 524.2205. Found: 524.2193. Anal. Calcd. for $C_{26}H_{32}N_6O_4S$: C, 59.52; H, 6.15; N, 16.02. Found: C, 59.50; H, 6.28; N, 15.81.

EXAMPLE 227

5-Pyridin-2-yl-thiophene-2-sulfonic acid [4-(4-oxo-piperidine-1-yl)-phenyl]-amide The title compound was prepared from 5-pyridin-2-yl-thiophene-2-sulphonyl chloride and 1-(4-amino-phenyl)-piperidine-4-one (which was obtained in Example 224) according to the procedure B of Example 225 as a white solid; $^1$H NMR (300 MHz, DMSO-$d_6$) δ 2.37 (t, J=6.0 Hz, 4H), 3.52 (t, J=6.0 Hz, 4H), 6.89 (d, J=9.0 Hz, 2H), 7.02 (d, J=9.0 Hz, 2H), 7.39 (dd, J=4.2, 1.5 Hz, 1H), 7.42 (d, J=2.1 Hz, 1H), 7.76 (d, J=2.1 Hz, 1H), 7.90 (dd, J=7.8, 1.5 Hz, 1H), 8.00 (d, J=7.8 Hz, 1H), 8.53 (d, J=4.2 Hz, 1H), 10.05 (s, 1H); MS (ES) m/z: 413.9 (MH$^+$); HRMS Calcd. for $C_{20}H_{19}N_3O_3S_2$ (M$^+$): 413.0867. Found: 413.0877.

EXAMPLE 228

Butane-1-sulfonic acid [4-(4-oxo-piperidine-1-yl)-phenyl]-amide

The title compound was prepared from 1-butanesulfonyl chloride and 1-(4-amino-phenyl)-piperidine-4-one hydrochloride (which was obtained in Example 224) according to the procedure B of Example 225 as a crystalline solid; $^1$H NMR (300 MHz, DMSO-$d_6$) δ 0.83 (t, J=7.3 Hz, 3H), 1.25–1.40 (m, 2H), 1.55–1.70 (m, 2H), 2.40 (t, J=5.9 Hz, 4H), 2.94 (t, J=7.6 Hz, 2H), 3.54 (t, J=5.9 Hz, 4H), 7.00 (d, J=9.0 Hz, 2H), 7.09 (d, J=9.0 Hz, 2H), 9.34 (s, 1H); MS (ES) m/z: 311.0 (MH$^+$); HRMS Calcd. for $C_{15}H_{22}N_2O_2S$(M$^+$): 310.1351. Found: 310.1375. Anal. Calcd. for $C_{15}H_{22}N_2O_2S$: C, 58.04; H, 7.14; N, 9.02. Found: C, 57.78; H, 6.95; N, 8.83.

EXAMPLE 229

5-(5-Trifluoromethyl-pyridin-2-sulfonyl)-thiophene-2-sulfonic acid [4-(4-oxo-piperidine-1-yl)-phenyl]-amide The title compound was prepared from 5-(5-trifluoromethyl-pyridin-2-sulfonyl)-thiophene-2-sulphonyl chloride and 1-(4-amino-phenyl)-piperidine-4-one (which was obtained in Example 224) according to the procedure B of Example 225 as a white solid; $^1$H NMR (300 MHz, DMSO-$d_6$) δ 2.37 (t, J=4.5 Hz, 4H), 3.52 (t, J=4.5 Hz, 4H), 6.90–7.10 (m, 4H), 7.90 (d, J=1.2 Hz, 1H), 8.41 (d, J=6.3 Hz, 1H), 8.50 (d, J=1.2 Hz, 1H), 8.62 (dd, J=6.3, 1.5 Hz, 1H), 9.23 (s, 1H), 9.89 (s, 1H); MS (ES) m/z: 545.9 (MH$^+$);

HRMS Calcd. for $C_{21}H_{19}F_3N_3O_5S_3$ (MH$^+$): 546.0439. Found: 546.0466. Anal. Calcd. for $C_{21}H_{18}F_3N_3O_5S_3$: C, 46.23; H, 3.33; N, 7.70. Found: C, 46.46; H, 3.39; N, 7.35.

EXAMPLE 230

Octane-1-sulfonic acid [4-(4-oxo-1-piperidineyl)-phenyl]-amide

The title compound was prepared from 1-octanesulfonyl chloride and 1-(4-amino-phenyl)-piperidine-4-one hydrochloride (which was obtained in Example 224) according to the procedure B of Example 225 as a white solid; $^1$H NMR (300 MHz, DMSO-d$_6$) δ 0.84 (t, J=5.4 Hz, 3H), 1.15–1.40 (m, 10H), 1.60–1.75 (m, 2H), 2.40 (t, J=4.5 Hz, 4H), 2.94 (t, J=5.7 Hz, 2H), 3.54 (t, J=4.5 Hz, 4H), 6.99 (d, J=6.9 Hz, 2H), 7.09 (d, J=6.9 Hz, 2H), 9.31 (s, 1H); MS (ES) m/z: 367.0 (MH$^+$); HRMS Calcd. for $C_{19}H_{30}N_2O_2S$(M$^+$): 366.1977. Found: 366.1969. Anal. Calcd. for $C_{19}H_{30}N_2O_2S$: C, 62.26; H, 8.25; N, 7.64. Found: C, 62.40; H, 7.98; N, 7.59.

EXAMPLE 231

4-(2,4-Dioxo-thiazolidin-5-ylmethyl)-N-[4-(4-oxo-piperidine-1-yl)-phenyl]-benzenesulfonamide The title compound was prepared from 4-(2,4-dioxo-thiazolidin-5-ylmethyl)benzenesulfonylchloride (*J. Med. Chem.* 1992, 35, 1853) and 1-(4-amino-phenyl)-piperidine-4-one hydrochloride (which was obtained in Example 224) according to the procedure B of Example 225 as a yellowish solid; $^1$H NMR (300 MHz, DMSO-d$_6$) δ 2.37 (t, J=6.0 Hz, 4H), 3.10–3.60 (m, 2H), 3.44 (t, J=6.0 Hz, 4H), 4.95 (dd, J=12.3, 6.0 Hz, 1H), 6.80–7.00 (m, 4H), 7.27 (d, J=8.1 Hz, 2H), 7.63 (d, J=8.1 Hz, 2H), 9.77 (brs, 1H), 12.09 (brs, 1H); MS (ES) m/z: 459.9 (MH$^+$); HRMS Calcd. for $C_{21}H_{21}N_3O_5S_2$ M$^+$): 459.0923. Found: 459.0930.

EXAMPLE 232

{4-[4-(4-Oxo-piperidine-1-yl)-phenylsulfamoyl]-phenoxy}-acetic acid methyl ester The title compound was prepared from (4-chlorosulfonyl-phenoxy)-acetic acid methyl ester (*Chem. Pharm. Bull.* 1995, 43, 1132) and 1-(4-amino-phenyl)-piperidine-4-one hydrochloride (which was obtained in Example 224) according to the procedure B of Example 225 as a grey solid; MS (ES) m/z: 418.9 (MH$^+$); HRMS Calcd. for $C_{20}H_{23}N_2O_6S$ (MH$^+$): 419.1271. Found: 419.1271.

EXAMPLE 233

4-[4-(4-Oxo-piperidine-1-yl)-phenylsulfamoyl]-benzoic acid

The title compound was prepared from 4-(chlorosulfonyl) benzoic acid and 1-(4-amino-phenyl)-piperidine-4-one hydrochloride (which was obtained in Example 224) according to the procedure B of Example 225 as a pale grey solid; $^1$H NMR (300 MHz, DMSO-d$_6$) δ 2.36 (t, J=6.0 Hz, 4H), 3.49 (t, J=6.0 Hz, 4H), 6.87 (d, J=9.3 Hz, 2H), 6.91 (d, J=9.3 Hz, 2H), 7.77 (d, J=8.1 Hz, 2H), 8.04 (d, J=8.1 Hz, 2H), 9.97 (s, 1H), 13.10 (brs, 1H); MS (ES) m/z: 374.9 (MH$^+$); HRMS Calcd. for $C_{18}H_{19}N_2O_5S$(MH$^+$): 375.1009. Found: 375.1009.

EXAMPLE 234

3-[4-(4-Oxo-piperidine-1-yl)-phenylsulfamoyl]-thiophene-2-carboxylic acid methyl ester The title compound was prepared from 2-(methoxycarbonyl)thiophene-3-sulphonyl chloride and 1-(4-amino-phenyl)-piperidine-4-one hydrochloride (which was obtained in Example 224) according to the procedure B of Example 225 as a white solid; $^1$H NMR (300 MHz, DMSO-d$_6$) δ 2.37 (t, J=6.0 Hz, 4H), 3.50 (t, J=6.0 Hz, 4H), 3.89 (s, 3H), 6.90 (d, J=9.1 Hz, 2H), 6.96 (d, J=9.1 Hz, 2H), 7.33 (d, J=6.9 Hz, 1H), 7.90 (d, J=6.9 Hz, 1H), 9.50 (s, 1H); MS (ES) m/z: 395.0 (MH$^+$); HRMS Calcd. for $C_{17}H_{19}N_2O_5S_2$ (MH$^+$): 395.0736. Found: 395.0721.

EXAMPLE 235

4-[4-(4-Oxo-piperidine-1-yl)-phenylsulfamoyl]-benzoic acid ethyl ester

A stirred solution of 4-[4-(4-oxo-piperidine-1-yl)-phenylsulfamoyl]-benzoic acid (which was obtained in Example 234) (1.4 g, 3.74 mmol) in 50 mL of ethanol was treated with hydrochloride gas at room temperature. After four hours the solution was concentrated and the residue was dissolved in concentrated hydrochloric acid (200 mL) at room temperature. After another 3 hours the pH was adjusted to ~5 and the precipitate was collected by filtration, and dried over $P_2O_5$ to give the title compound as a yellowish solid (1.1 g, 70%); $^1$H NMR (300 MHz, CDCl$_3$) δ 1.40 (t, J=7.1 Hz, 3H), 2.36 (t, J=6.0 Hz, 4H), 3.56 (t, J=6.0 Hz, 4H), 4.41 (q, J=7.1 Hz, 2H), 6.82 (d, J=8.9 Hz, 2H), 6.97 (d, J=8.9 Hz, 2H), 7.78 (d, J=8.3 Hz, 2H), 8.07 (d, J=8.3 Hz, 2H); MS (ES) m/z: 403.2 (MH$^+$); HRMS Calcd. for $C_{20}H_{23}N_2O_5S$(MH$^+$): 403.1328. Found: 403.1330.

EXAMPLE 236

[4-(4-Oxo-piperidine-1-yl)-phenylsulfamoyl]-acetic acid benzyl ester

The title compound was prepared from benzyloxycarbonylmethylsulfonylchloride (*J. Antibiot.*, 1994, 47, 1041) and 1-(4-amino-phenyl)-piperidine-4-one (which was obtained in Example 224) according to the procedure B of Example 225 as a white solid; $^1$H NMR (300 MHz, DMSO-d$_6$) δ 2.42 (t, J=6.0 Hz, 4H), 3.55 (t, J=6.0 Hz, 4H), 4.16 (s, 2H), 5.16 (s, 2H), 6.99 (d, J=9.0 Hz, 2H), 7.10 (d, J=9.0 Hz, 2H), 9.73 (s, 1H); MS (ES) m/z: 403.2 (MH$^+$); HRMS Calcd. for $C_{20}H_{22}N_2O_5S$(M$^+$): 402.1250. Found: 402.1237.

EXAMPLE 237

Pyridine-3-sulfonic acid[4-(4-oxo piperidine-1-yl)-phenyl]amide

To a stirred solution of 1-(4-amino-phenyl)-piperidine-4-one hydrochloride (which was obtained in Example 224) (8.76 g, 0.32 mol) in methylene chloride (100 mL) at room temperature was added triethylamine (9 mL). To this mixture was added a mixture of 3-pyridinesulfonyl chloride (7.45 g, 0.035 mol) and triethylamine (9 mL). The reaction was stirred for 18 hours. The reaction mixture was concentrated. The product was flash silica gel chromatographed eluting with 7:3 ethyl acetate/hexanes and then flash silica gel chromatographed eluting with 3% methanol in methylene chloride to give the titled compound as a yellow solid (1.34 g, 13%); $^1$H NMR (300 MHz, CDCl$_3$) δ 2.54 (t, J=6 Hz, 4H), 3.56 (t, J=6 Hz, 4H), 6.79 (s, 1H), 6.85 (d, J=12 Hz, 2H), 6.98 (d, J=12 Hz, 2H), 7.40 (m, 1H), 7.97 (dd, J=3 Hz, 1H), 8.75 (dd, J=6 Hz, 1H), 8.90 (d, J=3 Hz, 1H); MS (ES) m/z: 331.9 (MH$^+$, 100%); HRMS Calcd. for $C_{16}H_{17}N_3O_3S$ (MH$^+$): 332.1063. Found: 332.1063.

EXAMPLE 238

5-Chloro-3-methyl-benzo[b]thiophene-2-sulfonic acid [4-(4-oxo-piperidine-1-yl)-phenyl]-amide The title compound was prepared according to the procedure of Example 225 as a light yellow solid; $^1$H NMR (300 MHz, CDCl$_3$) δ 2.53 (t, J=6.06 Hz, 4H), 2.81 (s, 3H), 3.56 (t, J=6.06 Hz, 4H), 6.39 (s, 1H), 6.82 (d, 1H), 7.02 (d, 1H), 7.57 (dd, J=2.01 Hz, 8.70 Hz, 1H), 7.70–7.71 (m, 1H), 7.80 (s, 1H), 7.83 (s, 1H), 7.90 (d, J=2.16 Hz, 1H); MS (ES) m/z: 434.8 (MH$^+$).

EXAMPLE 239

4-Cyano-N-[4-(4-oxo-piperidine-1-yl)-phenyl]-benzenesulfonamide

The title compound was prepared according to the procedure of Example 225 as a yellow solid; $^1$H NMR (300 MHz, CDCl$_3$) δ 2.56 (t, J=6.09 Hz, 2H), 3.58 (t, J=6.03 Hz, 2H), 6.42 (s, 1H), 6.80–6.88 (m, 2H), 6.93–6.98 (m, 2H), 7.69–7.75 (m, 1H), 7.79–7.89 (m, 2H), 8.06–8.10 (m, 1H); MS (ES) m/z: 355.9 (MH$^+$).

EXAMPLE 240

3-Bromo-5-chloro-thiophene-2-sulfonic acid [4-(4-oxo-piperidine-1-yl)-phenyl]-amide The title compound was prepared according to the procedure of Example 225 as an olive-green foam; $^1$H NMR (300 MHz, CDCl$_3$) δ 2.54 (t, J=6.06 Hz, 4H), 3.60 (t, J=6.03 Hz, 4H), 6.79 (s, 1H), 6.83–6.91 (m, 2H), 6.92–6.95 (m, 1H), 7.07–7.11 (m, 1H), 7.21–7.24 (m, 1H).

EXAMPLE 241

5-Isoxazol-3-yl-thiophene-2-sulfonic acid [4-(4-oxo-piperidine-1-yl)-phenyl]-amide The title compound was prepared according to the procedure of Example 225 as a yellow/brown solid; $^1$H NMR (300 MHz, CDCl$_3$) δ 2.55 (t, J=6.12 Hz, 4H), 3.58 (t, J=6.00 Hz, 4H), 6.46–6.49 (m, 2H), 6.86–6.91 (m, 2H), 7.02–7.09 (m, 2H), 7.12 (s, 1H), 7.36–7.41 (m, 2H); MS (ES) m/z: 403.9 (MH$^+$).

EXAMPLE 242

3,4-Dimethoxy-N-[4-(4-oxo-piperidine-1-yl)-phenyl]-benzenesulfonamide

The title compound was prepared according to the procedure of Example 225 as a dull yellow solid; $^1$H NMR (300 MHz, CDCl$_3$) δ 2.54 (t, J=4.5 Hz, 4H), 3.55 (t, J=4.5 Hz, 4H), 3.83 (s, 3H), 3.91 (s, 3H), 6.21 (brs, 1H), 6.83–6.87 (m, 3H), 6.94–7.03 (m, 2H), 7.12 (d, J=1.5 Hz, 2H); MS (ES) m/z: 391.0 (MH$^+$); HRMS found for C$_{18}$H$_{17}$N$_3$O$_4$S$_2$: 391.1333.

EXAMPLE 243

3,4-Dichloro-N-[4-(4-oxo-piperidine-1-yl)-phenyl]-benzenesulfonamide

To a stirred solution of 0.5 g (1.9 mmol) of the hydrochloride salt of 1-(4-amino-phenyl)-piperidine-4-one (which was obtained in Example 224) in 10 mL of anhydrous methylene chloride was added 0.99 mL (5.7 mmol) of diisopropylethyl amine. After 10 minutes of stirring, 0.51 g (2.1 mmol) of 3,4-dichlorobenzene sulfonyl chloride was added and the mixture was allowed to stir overnight. The reaction mixture was quenched with water and the solvent was removed in vacuo. The residue was dissolved in ethyl acetate and washed twice with water, twice with brine, dried over sodium sulfate and then concentrated in vacuo. The residue was then purified by flash chromatography (10% EtOAc in hexanes to 50% EtOAc in hexanes) and the title compound was collected as 0.25 g of a yellow solid; $^1$H NMR (300 MHz, CDCl$_3$) δ 2.55 (t, J=6.09 Hz, 4H), 3.58 (t, J=6.03 Hz, 4H), 6.33 (s, 1H), 6.60–6.88 (m, 2H), 6.95–7.00 (m, 2H), 7.50 (d, J=1.47 Hz, 2H), 7.78–7.79 (m, 1H); MS (ES) m/z: 398.8 (MH$^+$); HRMS found for C$_{17}$H$_{16}$Cl$_2$N$_2$O$_3$S: 398.0227.

EXAMPLE 244

N-[4-(4-Oxo-piperidine-1-yl)-phenyl]-4-trifluoromethyl-benzenesulfonamide

The title compound was prepared from 4-(trifluoromethyl)benzene sulfonyl chloride according to the procedure of Example 243 as a yellow solid; $^1$H NMR (300 MHz, CDCl$_3$) δ 2.55 (t, J=6.12 Hz, 4H), 3.57 (t, J=6.0 Hz, 4H), 6.41 (s, 1H), 6.81–6.89 (m, 2H), 6.95–7.00 (m, 2H), 7.71 (d, J=8.37 Hz, 2H), 7.83 (d, J=8.31 Hz, 2H); MS (ES) m/z: 398.9 (MH$^+$); HRMS found for C$_{18}$H$_{17}$F$_3$N$_2$O$_3$S: 398.0910.

EXAMPLE 245

N-[4-(4-Oxo-piperidine-1-yl)-phenyl]-4-trifluoromethoxy-benzenesulfonamide

The title compound was prepared from 4-(trifluoromethoxy)benzene sulfonyl chloride according to the procedure of Example 243 as a yellow solid; $^1$H NMR (300 MHz, CDCl$_3$) δ 2.54 (t, J=6.06 Hz, 4H), 3.56 (t, J=6.03 Hz, 4H), 6.45 (s, 1H), 6.81–6.89 (m, 2H), 6.95–7.00 (m, 2H), 7.24–7.27 (m, 2H), 7.74–7.79 (m, 2H); MS (ES) m/z: 414.9 (MH$^+$); HRMS found for C$_{18}$H$_{17}$F$_3$N$_2$O$_4$S: 414.0854.

EXAMPLE 246

4-Chloro-N-[4-(4-oxo-piperidine-1-yl)-phenyl]-benzenesulfonamide

The title compound was prepared from 4-chlorobenzene sulfonyl chloride according to the procedure of Example 243 as a yellow solid; $^1$H NMR (300 MHz, CDCl$_3$) δ 2.54 (t, J=6.09 Hz, 4H), 3.56 (t, J=6.03 Hz, 4H), 6.51 (s, 1H), 6.80–6.88 (m, 2H), 6.94–7.00 (m, 2H), 7.38–7.43 (m, 2H), 7.61–7.67 (m, 2H); MS (ES) m/z: 364.9 (MH$^+$); HRMS found for C$_{17}$H$_{17}$ClN$_2$O$_3$S: 364.0652.

EXAMPLE 247

4-Butyl-N-[4-(4-oxo-piperidine-1-yl)-phenyl]-benzenesulfonamide

The title compound was prepared from 4-n-butylbenzene sulfonyl chloride according to the procedure of Example 243 as a light grey solid; $^1$H NMR (300 MHz, CDCl$_3$) δ 0.91 (t, J=7.26 Hz, 3H), 1.23–1.39 (m, 2H), 1.53–1.64 (m, 2H), 2.53 (t, J=6.12 Hz, 4H), 2.64 (t, J=7.62 Hz, 2H), 3.55 (t, J=6.0 Hz, 4H), 6.21 (s, 1H), 6.80–6.85 (m, 2H), 6.94–6.99 (m, 2H), 7.21–7.24 (m, 2H), 7.59–7.62 (m, 2H); HRMS found for C$_{21}$H$_{26}$N$_2$O$_3$S: 386.1660.

EXAMPLE 248

2,5-Dimethoxy-N-[4-(4-oxo-piperidine-1-yl)-phenyl]-benzenesulfonamide

The title compound was prepared from 2,5-dimethoxybenzene sulfonyl chloride according to the procedure of Example 243 as a yellow solid; ¹H NMR (300 MHz, CDCl₃) δ 2.63 (t, J=6.15 Hz, 4H), 3.72 (s, 3H), 3.82 (t, J=6.15 Hz, 4H), 4.03 (s, 3H), 6.77–6.91 (m, 2H), 6.96–7.02 (m, 2H), 7.27–7.32 (m, 2H), 8.13–8.21 (m, 2H); MS (ES) m/z: 391.0 (MH⁺); HRMS found for $C_{19}H_{22}N_2O_5S$: 390.9799.

EXAMPLE 249

3,5-Dichloro-N-[4-(4-oxo-piperidine-1-yl)-phenyl]-benzenesulfonamide

The title compound was prepared from 3,5-dichlorobenzene sulfonyl chloride according to the procedure of Example 243 as a pale yellow solid; ¹H NMR (300 MHz, CDCl₃) δ 2.5 (t, 4H), 3.55 (t, 4H), 6.41 (s, 1H), 6.84–6.91 (m, 2H), 6.96–7.02 (m, 2H), 7.52 (t, J=1.86 Hz, 1H), 7.56 (d, J=1.86 Hz, 2H); MS (ES) m/z: 398.8 (MH⁺); HRMS found for $C_{17}H_{16}Cl_2N_2O_3S$: 398.1622.

EXAMPLE 250

5-Bromo-2-methoxy-N-[4-(4-oxo-piperidine-1-yl)-phenyl]-benzenesulfonamide

The title compound was prepared from 5-bromo-2-methoxybenzene sulfonyl chloride according to the procedure of Example 243 as a yellow solid; ¹H NMR (300 MHz, CDCl₃) δ 2.51 (t, J=6.03 Hz, 4H), 3.52 (t, J=6.03 Hz, 4H), 4.06 (s, 3H), 6.77–6.82 (m, 2H), 6.89–7.00 (m, 2H), 7.59 (dd, J=2.55 Hz, 8.79 Hz, 2H), 7.86 (d, J=2.49 Hz, 2H); HRMS found for $C_{18}H_{19}Br N_2O_4S$: 438.0215.

EXAMPLE 251

{(4-Butyl-benzenesulfonyl)-[4-(4-oxo-piperidine-1-yl)-phenyl]-amino}-acetic acid ethyl ester A solution of 0.12 g of 4-butyl-N-[4-(4-oxo-piperidine-1-yl)-phenyl]-benzenesulfonamide (which was obtained in Example 247), 0.038 mL of ethyl bromoacetate and 0.047 g of potassium carbonate in 10 mL acetonitrile was refluxed overnight. The solvent was removed in vacuo and the residue was purified by flash chromatography (8:1 Hexanes: EtOAc-1:1 Hexanes: EtOAc) to give 0.107 g of the title compound as a yellow gum; ¹H NMR (300 MHz, CDCl₃) δ 0.93 (t, J=7.26 Hz, 3H), 1.19–1.26 (m, 3H), 1.31–1.43 (m, 2H), 1.57–1.66 (m, 2H), 2.52 (t, J=6.03 Hz, 4H), 2.67 (t, J-7.56 Hz, 2H), 3.60 (t, J=6.00 Hz, 4H), 4.14 (q, J=7.14 Hz, 2H), 4.35 (s, 2H), 6.80–6.85 (m, 2H), 7.06–7.12 (m, 2H), 7.24 (m, 2H), 7.59 (d, J=8.28 Hz, 2H); MS (ES) m/z: 473.0 (MH⁺); HRMS found for $C_{25}H_{32}N_2O_5S$: 472.2028.

EXAMPLE 252

{(3,4-Dimethoxy-benzenesulfonyl)-[4-(4-oxo-piperidine-1-yl)-phenyl]-amino}-acetic acid ethyl ester The title compound was prepared from 3,4-dimethoxy-N-[4-(4-oxo-piperidine-1-yl)-phenyl]-benzenesulfonamide (which was obtained in Example 242) according to the procedure of Example 251 as a yellow gum; ¹H NMR (300 MHz, CDCl₃) 67 1.26 (t, J=7.59 Hz, 3H), 2.53 (t, J=6.09 Hz, 4H), 3.59 (t, J=6.00 Hz, 4H), 3.83 (s, 3H), 3.94 (s, 3H), 4.11–4.19 (M, 2H), 4.36 (s, 1H), 6.80–6.91 (m, 2H), 7.09–7.14 (m, 2H), 7.17 (d, J=2.16 Hz, 1H), 7.33 (d, J=2.16 Hz, 1H), 7.36 (d, J=2.07 Hz, 1H); MS (ES) m/z: 477.0 (MH⁺); HRMS found for $C_{23}H_{28}N_2O_7S$: 477.1687.

EXAMPLE 253

{(Butane-1-sulfonyl)-[4-(4-oxo-piperidine-1-yl)-phenyl]-amino}-acetic acid benzyl ester The title compound was prepared from butane-1-sulfonic acid [4-(4-oxo-piperidine-1-yl)-phenyl]-amide (which was obtained in Example 228) and benzyl-2-bromoacetate according to the procedure of Example 251 as an orange oil; ¹H NMR (300 MHz, CDCl₃) δ 0.91 (t, J=7.29 Hz, 3H), 1.34–1.47 (m, 2H), 1.75–1.86 (m, 2H), 2.55 (t, J=6.09 Hz, 4H), 3.17–3.23 (m, 2H), 3.62 (t, J=6.00 Hz, 4H), 4.45 (s, 2H), 5.18 (s, 2H), 6.87–6.92 (m, 2H), 7.30–7.40 (m, 7H); MS (ES) m/z: 459.0 (MH⁺); HRMS found for $C_{24}H_{30}N_2O_5S$: 459.1944.

EXAMPLE 254

{(3,4-Dimethoxy-benzenesulfonyl)-[4-(4-oxo-piperidine-1-yl)-phenyl]-amino]-acetic acid benzyl ester The title compound was prepared from 3,4-dimethoxy-N-[4-(4-oxo-piperidine-1-yl)-phenyl]-benzenesulfonamide (which was obtained in Example 242) and benzyl-2-bromoacetate according to the procedure of Example 251 as an orange gum; ¹H NMR (300 MHz, CDCl₃) δ 2.53 (t, J=6.06 Hz, 4H), 3.59 (t, J=6.00 Hz, 4H), 3.79 (s, 3H), 3.93 (s, 3H), 4.50 (s, 2H), 5.13 (s, 2H), 6.78–6.87 (m, 2H), 7.07–7.10 (m, 2H), 7.15 (d, J=2.1 Hz, 1H), 7.27–7.37 (m, 7H); MS (ES) m/z: 539.0 (MH⁺); HRMS found for $C_{28}H_{30}N_2O_7S(MH^+)$: 539.1842.

EXAMPLE 255

N-{4-[4-(2-Hydroxy-2-phenyl-ethylamino)-piperidine-1-yl]-phenyl}-4-methoxy-benzenesulfonamide A mixture of 4-methoxy-N-[4-(4-oxo-piperidine-1-yl)-phenyl]-benzenesulfonamide (which was obtained in Example 218) (0.16 g, 0.44 mmol) and 2-amino-1-phenylethanol (0.18 g, 1.3 mmol) in 75 mL of methanol was hydrogenated in the presence of 100 mg of 10% Pd/C under H₂ (5~20 psi) for overnight. The catalyst was then removed by filtering through a short pad of silica gel. The filtrate was concentrated and purified by silica gel chromatography using 5–10% MeOH/CH₂Cl₂ as eluent to give 0.13 g (61%) of the title compound as a white solid; ¹H NMR (300 MHz, DMSO-d₆) δ 1.20–1.40 (m, 2H), 1.78–1.92 (m, 2H), 2.50–2.80 (m, 5H), 3.60–3.70 (m, 2H), 3.79 (s, 3H), 4.56–4.60 (m, 1H), 5.26 (brs, 1H), 6.76 (d, J=9.0 Hz, 2H), 6.86 (d, J=9.0 Hz, 2H), 7.04 (d, J=9.0 Hz, 2H), 7.20–7.25 (m, 1H), 7.25–7.36 (m, 4H), 7.58 (d, J=9.0 Hz, 2H); MS (ES) m/z: 482.4 (MH⁺); HRMS Calcd. for $C_{26}H_{31}N_3O_4S$ (M⁺): 481.2035. Found: 481.2028.

EXAMPLE 256

N-(4-{4-[2-Hydroxy-2-(3-hydroxy-phenyl)-ethylamino]-piperidine-1-yl}-phenyl)-4-methoxy-benzenesulfonamide The title compound was prepared from 4-methoxy-N-[4-(4-oxo-piperidine-1-yl)-phenyl]-benzenesulfonamide (which was obtained in Example 218) and DL-norphenylephrine according to the procedure of Example 255 as a white solid; ¹H NMR (300 MHz, DMSO-d₆) δ 1.25–1.60 (m, 2H), 2.00–2.15 (m, 2H), 2.50–3.10 (m, 5H), 3.60–3.70 (m, 2H), 3.79 (s, 3H), 4.80–4.90 (m, 1H), 6.05 (brs, 1H), 6.70–6.80 (m, 1H), 6.80–6.85 (m, 4H), 6.90 (d, J=9.0 Hz, 2H), 7.02 (d, J=9.0 Hz, 2H), 7.16 (t, J=7.7 Hz, 1H), 7.60 (d, J=9.0 Hz, 2H), 9.45 (s, 1H), 9.70 (s, 1H); MS (ES) m/z: 498.5 (MH⁺); HRMS Calcd. for $C_{26}H_{31}N_3O_5S$ (M⁺): 497.1984. Found: 497.1961.

EXAMPLE 257

N-[4-(4-{4-[2-Hydroxy-2-(3-hydroxy-phenyl)-ethylamino]-piperidine-1-yl}-Phenylsulfamovl)-phenyl]-acetamide The title compound was prepared from N-{4-[4-(4-oxo-piperidine-1-yl)-phenylsulfamoyl]-phenyl}-acetamide (which was obtained in Example 216) and DL-norphenylephrine according to the procedure of Example 255 as a white solid; $^1$H NMR (300 MHz, DMSO-$d_6$) δ 1.35–1.50 (m, 2H), 1.80–2.00 (m, 2H), 2.06 (s, 3H), 2.50–2.90 (m, 5H), 3.45–3.60 (m, 2H), 4.55–4.65 (m, 1H), 5.55 (brs, 1H), 6.60–6.70 (m, 1H), 6.70–6.85 (m, 4H), 6.86 (d, J=9.3 Hz, 2H), 7.11 (t, J=7.8 Hz, 1H), 7.58 (d, J=8.7 Hz, 2H), 7.68 (d, J=8.7 Hz, 2H), 9.35 (s, 1H), 10.33 (s, 1H); MS (ES) m/z: 525.4 (MH$^+$); HRMS Calcd. for $C_{27}H_{33}N_4O_5S$ (MH$^+$): 525.2172. Found: 525.2177.

EXAMPLE 258

N-(4-{4-[4-((2R)-2-Hydroxy-2-phenyl-ethylamino)-piperidine-1-yl]-phenylsulfamoyl}-phenyl)-acetamide The title compound was prepared from N-{4-[4-(4-oxo-piperidine-1-yl)-phenylsulfamoyl]-phenyl}-acetamide (which was obtained in Example 216) and (1R)-2-amino-1-(3-chloro-phenyl)-ethanol (which was obtained in Example 1) according to the procedure of Example 255 as a white solid; $^1$H NMR (300 MHz, DMSO-$d_6$) δ 1.55–1.75 (m, 2H), 2.06 (s, 3H), 2.00–2.15 (m, 2H), 2.50–3.20 (m, 5H), 3.55–3.70 (m, 2H), 4.90–5.00 (m, 1H), 6.00–6.20 (brs, 1H), 6.80 (d, J=9.0 Hz, 2H), 6.89 (d, J=9.0 Hz, 2H), 7.25–7.52 (m, 5H), 7.59 (d, J=8.7 Hz, 2H), 7.70 (d, J=8.7 Hz, 2H), 10.41 (s, 1H); MS (ES) m/z: 509.2 (MH$^+$); HRMS Calcd. for $C_{27}H_{33}N_4O_4S$(MH$^+$): 509.2223. Found: 509.2194.

EXAMPLE 259

N-(4-{[4-(4-{[2-Hydroxy-2-(4-hydroxyphenyl)ethyl]amino}-1-piperidineyl)-anilino]sulfonyl}phenyl)acetamide The title compound was prepared from N-{4-[4-(4-oxo-piperidine-1-yl)-phenylsulfamoyl]-phenyl}-acetamide (which was obtained in Example 216) and DL-octopamine according to the procedure of Example 255 as a white solid; $^1$H NMR (300 MHz, DMSO-$d_6$) δ 1.55–1.75 (m, 2H), 2.00–2.15 (m, 2H), 2.06 (s, 3H), 2.50–3.20 (m, 5H), 3.60–3.70 (m, 2H), 4.80–4.90 (m, 1H), 6.00 (brs, 1H), 6.76 (d, J=9.7 Hz, 2H), 6.80 (d, J=9.7 Hz, 2H), 6.88 (d, J=9.0 Hz, 2H), 7.19 (d, J=8.7 Hz, 2H), 7.59 (d, J=9.0 Hz, 2H), 7.70 (d, J=8.7 Hz, 2H), 9.47 (s, 1H), 10.43 (s, 1H); MS (ES) m/z: 525.3 (MH$^+$); HRMS Calcd. for $C_{27}H_{33}N_4O_5S$(MH$^+$): 525.2172. Found: 525.2178.

EXAMPLE 260

N-[4-(4-{[(2R)-2-(3-Chlorophenyl)-2-hydroxyethyl]amino}-1-piperidineyl)phenyl]-4-methoxybenzenesulfonamide A mixture of 4-methoxy-N-[4-(4-oxo-piperidine-1-yl)-phenyl]-benzenesulfonamide (which was obtained in Example 218) (0.288 g, 0.8 mmol) and (1R)-2-amino-1-(3-chloro-phenyl)-ethanol hydrochloride (which was obtained in Example 1) (0.832 g, 4.0 mmol) was dissolved in 50 mL of methanol and the pH was adjusted to 5 with triethylamine. After stirred at room temperature for one day acetic acid (1 mL) and NaCNBH$_3$ (50 mg, 0.8 mmol) were then added. The reaction was stirred for another day, the solvent was removed, and the residue was purified by thin layer chromatography (10% methanol/CH$_2$Cl$_2$) to give the title compound as a white solid; $^1$H NMR (300 MHz, DMSO-$d_6$) δ 1.40–1.60 (m, 2H), 1.95–2.10 (m, 2H), 2.50–3.10 (m, 5H), 3.50–3.70 (m, 2H), 3.79 (s, 3H), 4.80–4.90 (m, 1H), 6.79 (d, J=9.0 Hz, 2H), 6.89 (d, J=9.0 Hz, 2H), 7.05 (d, J=9.0 Hz, 2H), 7.30–7.50 (m, 4H), 7.60 (d, J=9.0 Hz, 2H), 9.60 (brs, 1H); MS (ES) m/z: 516.2 (MH$^+$); HRMS Calcd. for $C_{26}H_{31}ClN_3O_4S$(MH$^+$); 516.1724. Found: 516.1713.

EXAMPLE 261

N-[4-(4-{[(2R)-2-Hydroxy-2-phenylethyl]amino}-1-piperidineyl)phenyl]-4-methoxybenzenesulfonamide The title compound was prepared from 4-methoxy-N-[4-(4-oxo-piperidine-1-yl)-phenyl]-benzenesulfonamide (which was obtained in Example 218) and (1R)-2-amino-1-(3-chloro-phenyl)-ethanol hydrochloride (which was obtained in Example 1) according to the procedure of Example 255 as a white solid; $^1$H NMR (300 MHz, DMSO-$d_6$) δ 1.55–1.75 (m, 2H), 2.05–2.15 (m, 2H), 2.50–3.10 (m, 5H), 3.50–3.70 (m, 2H), 3.79 (s, 3H), 4.90–5.05 (m, 1H), 6.10–6.20 (m, 1H), 6.79 (d, J=9.0 Hz, 2H), 6.89 (d, J=9.0 Hz, 2H), 7.05 (d, J=11.8 Hz, 2H), 7.25–7.50 (m, 5H), 7.60 (d, J=11.8 Hz, 2H), 9.70 (brs, 1H); MS (ES) m/z: 482.2 (MH$^+$); HRMS Calcd. for $C_{26}H_{32}N_3O_4S$(MH$^+$): 482.2114. Found: 482.2120.

EXAMPLE 262

N-(4-{[4-(4-{[2-Hydroxy-3-(4-methoxyphenoxy)propyl]amino}-1-piperidineyl)anilino]-sulfonyl}phenyl)acetamide The title compound was prepared from N-{4-[4-(4-oxo-piperidine-1-yl)-phenylsulfamoyl]-phenyl}-acetamide (which was obtained in Example 216) and 1-amino-3-(4-methoxy-phenoxy)-propan-2-ol according to the procedure of Example 255 as a white solid; $^1$H NMR (300 MHz, DMSO-$d_6$) δ 1.55–1.75 (m, 2H), 1.95–2.15 (m, 2H), 2.06 (s, 3H), 2.50–3.20 (m, 5H), 3.85–3.95 (m, 2H), 4.10–4.20 (m, 1H), 5.70 (brs, 1H), 6.80 (d, J=9.0 Hz, 2H), 6.80–6.95 (m, 6H), 7.59 (d, J=9.0 Hz, 2H), 7.69 (d, J=9.0 Hz, 2H), 10.38 (s, 1H); MS (ES) m/z: 569.6 (MH$^+$); HRMS Calcd. for $C_{29}H_{37}N_4O_6S$(MH$^+$): 569.2434. Found: 569.2418.

EXAMPLE 263

N-(4-{[4-(4-{[(2R)-2-(3,4-Dihydroxyphenyl)-2-hydroxyethyl]amino-1-piperidineyl)anilino]sulfonyl}phenyl)acetamide The title compound was prepared from N-{4-[4-(4-oxo-piperidine-1-yl)-phenylsulfamoyl]-phenyl}-acetamide (which was obtained in Example 216) and L-norepinephrine according to the procedure of Example 255 as a grey solid; $^1$H NMR (300 MHz, DMSO-$d_6$) δ 1.50–1.72 (m, 2H), 1.95–2.10 (m, 2H), 2.06 (s, 3H), 2.50–3.20 (m, 5H), 3.55–3.70 (m, 2H), 4.05–4.20 (brs, 1H), 4.60–4.75 (m, 1H), 5.75–5.90 (brs, 1H), 6.60–6.90 (m, 7H), 7.59 (d, J=9.0 Hz, 2H), 7.70 (d, J=9.0 Hz, 2H), 8.93 (brs, 1H), 10.42 (s, 1H); MS (ES) m/z: 541.6 (MH$^+$); HRMS Calcd. for $C_{27}H_{33}N_4O_6S$(MH$^+$): 541.2121. Found: 541.2133.

EXAMPLE 264

N-(4-{[2-(4-{[2-Hydroxy-2-(3-hydroxyphenyl)ethyl]amino}-1-piperidineyl)anilino]-sulfonyl}phenyl)acetamide The title compound was prepared from N-{4-[2-(4-oxo-piperidine-1-yl)-phenylsulfamoyl]-phenyl}-acetamide (which was obtained in Example 222) and DL-norphenylephrine according to the procedure of Example 255 as a white solid; $^1$H NMR (300 MHz, DMSO-$d_6$) δ 1.70–1.90 (m, 2H), 1.90–2.10 (m, 2H), 2.06 (s, 3H), 2.50–3.20 (m, 7H), 4.75–4.95 (m, 1H), 6.10 (brs, 1H), 6.50–7.40 (m, 8H), 7.65–7.80 (m, 4H), 9.48 (s, 1H), 10.42 (s, 1H); MS (ES) m/z: 525.6 (MH$^+$); HRMS Calcd. for $C_{27}H_{33}N_4O_5S$(MH$^+$): 525.2172. Found: 525.2164.

EXAMPLE 265

N-(4-{[2-(4-{[(2R)-2-(3,4-Dihydroxyphenyl)-2-hydroxyethyl]amino}-1-piperdinyl)-anilino]sulfonyl}phenyl)acetamide The title compound was prepared from N-{4-[2-(4-oxo-piperidine-1-yl)-phenylsulfamoyl]-phenyl}-acetamide (which was obtained in Example 222) and L-norepinephrine according to the procedure of Example 255 as a grey solid; $^1$H NMR (300 MHz, DMSO-$d_6$) δ 1.30–1.52 (m, 2H), 1.70–1.90 (m, 2H), 1.89 (s, 3H), 2.50–3.50 (m, 7H), 4.40–4.55 (m, 1H), 6.00 (brs, 1H), 6.50–6.80 (m, 3H), 6.95–7.15 (m, 2H), 7.25–7.40 (m, 2H), 7.60–7.75 (m, 4H), 10.30 (s, 1H); MS (ES) m/z: 541.4 (MH$^+$); HRMS Calcd. for $C_{27}H_{33}N_4O_6S$(MH$^+$): 541.2121. Found: 541.2110.

EXAMPLE 266

N-[4-(4-{[(2R)-2-(3,4-Dihydroxyphenyl)-2-hydroxyethyl]amino}-1-piperidineyl)phenyl]-4-methoxybenzenesulfonamide The title compound was prepared from 4-methoxy-N-[4-(4-oxo-piperidine-1-yl)-phenyl]-benzenesulfonamide (which was obtained in Example 218) and L-norepinephrine according to the procedure of Example 255 as a white solid; 1 H NMR (300 MHz, DMSO-$d_6$) δ 1.40–1.55 (m, 2H), 1.90–2.05 (m, 2H), 2.50–3.00 (m, 5H), 3.50–3.75 (m, 2H), 3.79 (s, 3H), 4.50–4.65 (m, 1H), 6.60 (d, J=8.0 Hz, 1H), 6.68 (d, J=8.0 Hz, 1H), 6.76–6.80 (m, 3H), 6.88 (d, J=9.0 Hz, 2H), 7.04 (d, J=7.8 Hz, 2H), 7.61 (d, J=7.8 Hz, 2H), 8.85 (s, 1H); MS (ES) m/z: 513.9 (MH$^+$); HRMS Calcd. for $C_{26}H_{32}N_3O_6S$(MH$^+$): 514.2011. Found: 514.2000.

EXAMPLE 267

N-(4-{[4-(4-{[2-Hydroxy-2-(4-hydroxy-3-methoxyphenyl)ethyl]amino}-1-piperidineyl)anilino]sulfonyl}phenyl)acetamide The title compound was prepared from N-{4-[4-(4-oxo-piperidine-1-yl)-phenylsulfamoyl]-phenyl}-acetamide (which was obtained in Example 216) and DL-normetanephrine according to the procedure of Example 255 as a white solid; $^1$H NMR (300 MHz, DMSO-$d_6$) δ 1.40–1.60 (m, 2H), 1.90–2.06 (m, 2H), 2.06 (s, 3H), 2.50–3.50 (m, 5H), 3.55–3.65 (m, 2H), 3.77 (s, 3H), 4.70–4.80 (m, 1H), 5.70–5.85 (brs, 1H), 6.70–6.90 (m, 7H), 7.59 (d, J=8.7 Hz, 2H), 7.69 (d, J=8.7 Hz, 2H), 8.95 (brs, 1H), 10.37 (s, 1H); MS (ES) m/z: 555.2 (MH$^+$); HRMS Calcd. for $C_{28}H_{35}N_4O_6S$(MH$^+$): 555.2277. Found: 555.2265.

EXAMPLE 268

N-(4-{[4-(4-{[2-(2,4-Dihydroxyphenyl)-2-hydroxyethyl]amino}-1-piperidineyl)-anilino]sulfonyl}phenyl)acetamide The title compound was prepared from N-{4-[4-(4-oxo-piperidine-1-yl)-phenylsulfamoyl]-phenyl}-acetamide (which was obtained in Example 216) and 2-amino-1-(2,4-dihydroxy-phenyl)-ethanol according to the procedure of Example 255 as a pale yellowish solid; $^1$H NMR (300 MHz, DMSO-$d_6$) δ 1.55–1.75 (m, 2H), 1.95–2.15 (m, 2H), 2.08 (s, 3H), 2.50–3.20 (m, 5H), 3.60–3.70 (m, 2H), 5.04–5.10 (m, 1H), 6.65–6.75 (m, 1H), 6.24 (dd, J=8.1, 2.1 Hz, 1H), 6.32 (d, J=2.1 Hz, 1H), 6.80 (d, J=9.0 Hz, 2H), 6.88 (d, J=9.0 Hz, 2H), 7.12 (d, J=8.1 Hz, 1H), 7.59 (d, J=9.0 Hz, 2H), 7.70 (d, J=9.0 Hz, 2H), 9.26 (s, 1H), 9.71 (brs, 1H), 10.44 (s, 1H); MS (ES) m/z: 541.4 (MH$^+$); HRMS Calcd. for $C_{27}H_{33}N_4O_6S$(MH$^+$): 541.2121. Found: 541.2084.

EXAMPLE 269

N-(4-{[4-(4-{[(2S)-2-Hydroxy-3-(4-hydroxyphenoxy)propyl]amino}-1-piperidineyl)anilino]sulfonyl}phenyl)acetamide The title compound was prepared from N-{4-[4-(4-oxo-piperidine-1-yl)-phenylsulfamoyl]-phenyl}-acetamide (which was obtained in Example 216) and (2S)-1-amino-3-(4-hydroxy-phenoxy)-propan-2-ol (which was obtained in Example 5) according to the procedure of Example 255 as a grey solid; $^1$H NMR (300 MHz, DMSO-$d_6$) δ 1.40–1.65 (m, 2H), 1.95–2.15 (m, 2H), 2.06 (s, 3H), 2.50–3.20 (m, 5H), 3.55–3.70 (m, 2H), 3.80–3.90 (m, 1H), 4.05–4.20 (m, 1H), 5.70 (brs, 1H), 6.67 (d, J=9.0 Hz, 2H), 6.76 (d, J=9.0 Hz, 2H), 6.78 (d, J=9.0 Hz, 2H), 6.88 (d, J=9.0 Hz, 2H), 7.58 (d, J=9.0 Hz, 2H), 7.69 (d, J=9.0 Hz, 2H), 8.97 (s, 1H), 10.37 (s, 1H); MS (ES) m/z: 555.1 (MH$^+$); HRMS Calcd. for $C_{28}H_{35}N_4O_6S$(MH$^+$): 555.2277. Found: 555.2267.

EXAMPLE 270

N-{4-[(4-{4-{[(2-Hydroxy-2-{4-hydroxy-3-[(methylsulfonyl)amino]phenyl}ethyl)amino]-1-piperidineyl}anilino)sulfonyl]phenyl}acetamide The title compound was prepared from N-{4-[4-(4-oxo-piperidine-1-yl)-phenylsulfamoyl]-phenyl}-acetamide (which was obtained in Example 216) and N-[2-benzyloxy-5-(2-dibenzylamino-1-hydroxy-ethyl)-phenyl]-methanesulfonamide (which was obtained in Example 7) according to the procedure of Example 255 as a yellowish solid; $^1$H NMR (300 MHz, DMSO-$d_6$) δ 1.35–1.60 (m, 2H), 1.90–2.10 (m, 2H), 2.06 (s, 3H), 2.50–3.00 (m, 5H), 3.16 (s, 3H), 3.55–3.70 (m, 2H), 4.65–4.80 (m, 1H), 6.00 (brs, 1H), 6.70–7.25 (m, 7H), 7.58 (d, J=9.0 Hz, 2H), 7.68 (d, J=9.0 Hz, 2H), 10.39 (s, 1H); MS (ES) m/z: 618.1 (MH$^+$); HRMS Calcd. for $C_{28}H_{36}N_5O_7S_2$ (MH$^+$): 618.2056. Found: 618.2036.

EXAMPLE 271

4-{[(Hexylamino)carbonyl]amino}-N-[4-(4-{[2-hydroxy-2-(6-methyl-3-pyridinyl)ethyl]amino}-1-piperidineyl)phenyl]benzenesulfonamide The title compound was prepared from 4-(3-hexyl-ureido)-N-[4-(4-oxo-piperidine-1-yl)-phenyl]-benzenesulfonamide (which was obtained in Example 225) and 2-amino-1-(6-methyl-pyridin-3-yl)ethanol according to the procedure of Example 255 as a grey solid; $^1$H NMR (300 MHz, DMSO-$d_6$) δ 0.86 (t, J=6.8 Hz, 3H), 1.20–3.30 (m, 19H), 2.45 (s, 3H), 3.50–3.75 (m, 2H), 4.70–4.80 (m, 1H), 6.41 (t, J=5.5 Hz, 1H), 6.78 (d, J=9.1 Hz, 2H), 6.87 (d, J=9.1 Hz, 2H), 7.21 (d, J=8.0 Hz, 1H), 7.46 (d, J=9.2 Hz, 2H), 7.48 (d, J=9.2 Hz, 2H), 7.64 (dd, J=8.0, 2.0 Hz, 1H), 8.43 (d, J=2.0 Hz, 1H), 9.00 (s, 1H), 9.50 (brs, 1H), 11.10 (s, 1H); MS (ES) m/z: 609.3 (MH$^+$); HRMS Calcd. for $C_{32}H_{45}N_6O_4S$(MH$^+$): 609.3223. Found: 609.3235.

EXAMPLE 272

N-(4-{[4-(4-{[(2S)-2-Hydroxy-3-phenoxypropyl]amino}-1-piperidineyl)anilino]-sulfonyl}phenyl)acetamide The title compound was prepared from N-{4-[4-(4-oxo-piperidine-1-yl)-phenylsulfamoyl]-phenyl}-acetamide (which was obtained in Example 216) and (2S)-1-amino-3-phenoxy-propan-2-ol (which was obtained in Example 3) according to the procedure of Example 255 as a white solid; $^1$H NMR (300 MHz, DMSO-d$_6$) δ 1.40–1.65 (m, 2H), 1.95–2.10 (m, 2H), 2.06 (s, 3H), 2.50–3.20 (m, 5H), 3.55–3.75 (m, 2H), 3.96 (d, J=5.2 Hz, 2H), 4.15–4.25 (m, 1H), 5.70 (brs, 1H), 6.80 (d, J=9.0 Hz, 2H), 6.88 (d, J=9.0 Hz, 2H), 6.90–7.00 (m, 3H), 7.25–7.35 (m, 2H), 7.59 (d, J=9.0 Hz, 2H), 7.69 (d, J=9.0 Hz, 2H), 9.70 (s, 1H), 10.37 (s, 1H); MS (ES) m/z: 539.1 (MH$^+$); HRMS Calcd. for C$_{28}$H$_{35}$N$_4$O$_5$S(MH$^+$): 539.2328. Found: 539.2357.

EXAMPLE 273

5-[2-({1-[4-({[4-(Acetylamino)phenyl]sulfonyl}amino)phenyl]-4-piperidineyl}amino)-1-hydroxethyl]-1H-indole-7-carboxamide The title compound was prepared from N-{4-[4-(4-oxo-piperidine-1-yl)-phenylsulfamoyl]-phenyl}-acetamide (which was obtained in Example 216) and 5-(2-amino-1-hydroxy-ethyl)-1H-indole-7-carboxamide according to the procedure of Example 255 as a pale grey solid; $^1$H NMR (300 MHz, DMSO-d$_6$) δ 1.60–1.80 (m, 2H), 2.00–2.15 (m, 2H), 2.06 (s, 3H), 2.50–2.70 (m, 2H), 3.10–3.20 (m, 3H), 3.60–3.75 (m, 2H), 4.95–5.05 (m, 1H), 6.13 (brs, 1H), 6.49 (t, J=2.7 Hz, 1H), 6.81 (d, J=9.0 Hz, 2H), 6.88 (d, J=9.0 Hz, 2H), 7.35 (t, J=2.7 Hz, 1H), 7.42 (brs, 1H), 7.59 (d, J=9.0 Hz, 2H), 7.69 (d, J=9.0 Hz, 2H), 7.77 (s, 1H), 8.11 (s, 1H), 9.72 (s, 1H), 10.40 (s, 1H); MS (ES) m/z: 591.1 (MH$^+$); HRMS Calcd. for C$_{30}$H$_{35}$N$_6$O$_5$S(MH$^+$): 591.2390. Found: 591.2392.

EXAMPLE 274

N-[4-({4-[4-({(2S)-2-Hydroxy-3-[(2-oxo-2,3-dihydro-1H-benzimidazol-4-yl)oxy]propyl}amino)-1-piperidineyl]anilino}sulfonyl)phenyl]acetamide The title compound was prepared from N-{4-[4-(4-oxo-piperidine-1-yl)-phenylsulfamoyl]-phenyl}-acetamide (which was obtained in Example 216) and (S)-4-[2-hydroxy-3-aminopropoxy]-1,3-dihydro-2H-benzimidazol-2-one (U.S. Pat. No. 5,786,356/1998) according to the procedure of Example 255 as a white solid; $^1$H NMR (300 MHz, DMSO-d$_6$) δ 1.60–1.80 (m, 2H), 2.00–2.15 (m, 2H), 2.06 (s, 3H), 2.50–2.70 (m, 2H), 2.90–3.20 (m, 3H), 3.60–3.75 (m, 2H), 4.15–4.25 (m, 1H), 5.70 (brs, 1H), 6.61 (t, J=8.7 Hz, 1H), 6.80–6.92 (m, 5H), 7.60 (d, J=9.0 Hz, 2H), 7.70 (d, J=9.0 Hz, 2H), 9.72 (brs, 1H), 10.42 (s, 1H), 10.65 (s, 1H), 10.80 (s, 1); MS (ES) m/z: 595.2 (MH$^+$); HRMS Calcd. for C$_{29}$H$_{35}$N$_6$O$_6$S(MH$^+$): 595.2339. Found: 595.2332.

EXAMPLE 275

4-{[(Hexylamino)carbonyl]amino}-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide The title compound was prepared from 4-(3-hexyl-ureido)-N-[4-(4-oxo-piperidine-1-yl)-phenyl]-benzenesulfonamide (which was obtained in Example 225) and (S)-4-[2-hydroxy-3-aminopropoxy]-1,3-dihydro-2H-benzimidazol-2-one (U.S. Pat. No. 5,786,356/1998) according to the procedure of Example 255 as a white solid; $^1$H NMR (300 MHz, DMSO-d$_6$) δ 0.86 (t, J=6.8 Hz, 3H), 1.20–1.60 (m, 10H), 1.90–2.05 (m, 2H), 2.50–3.50 (m, 9H), 3.50–3.65 (m, 1H), 3.95–4.05 (m, 2H), 6.43 (t, J=5.6 Hz, 1H), 6.58 (d, J=7.8 Hz, 1H), 6.61 (d, J=8.2 Hz, 1H), 6.70–6.89 (m, 5H), 7.46 (d, J=9.0 Hz, 2H), 7.51 (d, J=9.0 Hz, 2H), 9.06 (s, 1H), 9.60 (brs, 1H), 10.60 (s, 1H), 10.75 (s, 1H); MS (ES) m/z: 680.3 (MH$^+$); HRMS Calcd. for C$_{34}$H$_{46}$N$_7$O$_6$S(MH$^+$): 680.3230. Found: 680.3221.

EXAMPLE 276

4-{[(Hexylamino)carbonyl]amino}-N-(4-{4-[((2R)-2-hydroxy-2-{4-hydroxy-3-[(methylsulfonyl)amino]phenyl}ethyl)amino]-1-piperidineyl}phenyl)benzenesulfonamide The title compound was prepared from 4-(3-hexyl-ureido)-N-[4-(4-oxo-piperidine-1-yl)-phenyl]-benzenesulfonamide (which was obtained in Example 225) and N-[2-benzyloxy-5-(2-amino-(1R)-1-hydroxy-ethyl)-phenyl]-methanesulfonamide (which was obtained in Example 8) according to the procedure of Example 255 as a grey solid; $^1$H NMR (300 MHz, DMSO-d$_6$) δ 0.86 (t, J=6.9 Hz, 3H), 1.20–1.80 (m, 10H), 1.95–2.15 (m, 2H), 2.50–3.30 (m, 7H), 2.97 (s, 3H), 3.55–3.70 (m, 2H), 4.70–4.85 (m, 1H), 5.90–6.10 (m, 1H), 6.48 (t, J=5.6 Hz, 1H), 6.83 (d, J=9.2 Hz, 2H), 6.90 (d, J=9.2 Hz, 2H), 6.91 (d, J=8.4 Hz, 1H), 7.07 (dd, J=8.4, 2.0 Hz, 1H), 7.24 (d, J=2.0 Hz, 1H), 7.46 (d, J=9.2 Hz, 2H), 7.51 (d, J=9.2 Hz, 1H), 8.50–8.90 (brs, 1H), 9.39 (s, 1H), 9.61 (s, 1H); MS (ES) m/z: 703.4 (MH$^+$); HRMS Calcd. for C$_{33}$H$_{47}$N$_6$O$_7$S$_2$ (MH$^+$): 703.2948. Found: 703.2946.

EXAMPLE 277

4-[4-(3-Cyclopentylpropyl)-5-oxo-4,5-dihydro-1H-tetraazol-1-yl]-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide The title compound was prepared from 4-[4-(3-cyclopentyl-propyl)-5-oxo-4,5-dihydro-tetrazol-1-yl]-N-[4-(4-oxo-piperidine-1-yl)-phenyl]-benzenesulfonamide (which was obtained in Example 226) and (S)-4-[2-hydroxy-3-aminopropoxy]-1,3-dihydro-2H-benzimidazol-2-one (U.S. Pat. No. 5,786,356/1998) according to the procedure of Example 255 as a white solid; $^1$H NMR (300 MHz, DMSO-d$_6$) δ 0.90–4.00 (m, 29H), 5.10–5.30 (m, 1H), 6.58 (d, J=7.9 Hz, 1H), 6.61 (d, J=7.9 Hz, 1H), 6.81 (d, J=8.9 Hz, 2H), 6.89 (d, J=8.9 Hz, 2H), 6.90 (dd, J=7.9, 7.9 Hz, 1H), 7.86 (d, J=8.5 Hz, 2H), 8.07 (d, J=8.5 Hz, 2H), 10.70 (s, 1H), 10.80 (s, 1H); MS (ES) m/z: 732.3 (MH$^+$); HRMS Calcd. for C$_{36}$H$_{46}$N$_9$O$_6$S(MH$^+$): 732.3292. Found: 732.3294.

EXAMPLE 278

N-{4-[4-({(2S)-2-Hydroxy-3-[(2-oxo-2,3-dihydro-1H-benzimidazol-4-yl)oxy]propyl}-amino)-1-piperidineyl]phenyl}-5-(2-pyridinyl)-2-thiophenesulfonamide 5-Pyridin-2-yl-thiophene-2-sulfonic acid [4-(4-oxo-piperidine-1-yl)-phenyl]-amide (which was obtained in Example 227) (0.21 g, 0.5 mmol) and (S)-4-[2-hydroxy-3- aminopropoxy]-1,3-dihydro-2H-benzimidazol-2-one (U.S. Pat. No. 5,786,356/1998) (0.11 g, 0.5 mmol) were mixed in dimethylformamide (10 mL) and then treated with sodium triacetoxyborohydride (0.16 g, 0.75 mmol) and acetic acid (0.045 g, 0.75 mmol). After stirring at room temperature under a nitrogen atmosphere for one day the mixture was quenched with 1N NaOH and then poured into a saturated aqueous NaHCO$_3$. The precipitate which formed was collected and purified by preparative thin layer chromatography (16% MeOH/CH$_2$CH$_2$) to give the titled compound as a pale yellowish solid; $^1$H NMR (300 MHz, DMSO-d$_6$) δ 1.25–1.40 (m, 2H), 1.80–1.90 (m, 2H), 2.50–2.90 (m, 5H), 3.53 (brd, J=9.0 Hz, 2H), 3.85–4.00 (m, 2H), 4.00–4.10 (m, 1H), 4.91 (brs, 1H), 6.56 (d, J=5.7 Hz, 1H), 6.61 (d, J=5.7 Hz, 1H), 6.80–6.90 (m, 3H), 6.96 (d, J=6.6Hz, 2H), 7.36 (dd, J=3.3, 1.2Hz, 1H), 7.41 (d, J=3.0Hz, 1H), 7.75 (d, J=3.0 Hz, 1H), 7.88 (dd, J=6.0, 1.2 Hz, 1H), 7.98 (d, J=6.0 Hz, 1H), 8.54 (d, J=3.3 Hz, 1H), 10.60 (s, 1H), 10.70 (s, 1H); MS (ES) m/z: 621.0 (MH$^+$); HRMS Calcd. for C$_{30}$H$_{33}$N$_6$O$_5$S$_2$ (MH$^+$): 621.1954. Found: 621.1952.

EXAMPLE 279

N-[4-(4-{(2S)-2-Hydroxy-3-(4-hydroxyphenoxy) propl]amino}-1-piperidineyl)phenyl]-3,4-dimethoxybenzenesulfonamide The title compound was prepared according to the procedure of Example 278 as an off-white solid; $^1$H NMR (300 MHz, DMSO-d$_6$) δ 1.20–1.25 (m, 2H), 1.75 (m, 2H), 2.27 (m, 2H), 2.52–2.61 (m, 2H), 2.65 (m, 1H), 2.73 (m, 1H), 3.15–3.17 (m, 2H), 3.54–3.58 (m, 2H), 3.72 (s, 3H), 3.78 (s, 3H), 3.81–3.83 (m, 1H) 3.86–3.89 (m, 2H), 6.54–6.69 (m, 1H), 6.72–6.81 (m, 6H), 6.89 (d, 1H, J=9.0 Hz), 7.03 (d, 2H, J=8.52 Hz), 7.16 (d, 1H, J=2.07 Hz), 7.20–7.24 (dd, 1H, J=2.04 Hz, 8.37 Hz), 8.92 (s, 1H), 9.61 (brs, 1H); MS (ES) m/z: 558.0 (MH$^+$); HRMS found for C$_{34}$H$_{38}$N$_4$O$_6$S: 558.2271.

EXAMPLE 280

N-(4-{4-[(2-Hydroxy-2-{4-hydroxy-3-[(methylsulfonyl)amino]phenyl}ethyl)amino]-1-piperidineyl}phenyl)-3,4-dimethoxybenzenesulfonamide The title compound was prepared according to the procedure of Example 278 as a brown solid; $^1$H NMR (300 MHz, DMSO-d$_6$) δ 1.50–1.59 (m, 2H), 1.95–2.05 (m, 2H), 2.54–2.62 (m, 2H), 2.72 (m, 2H), 2.94 (s, 3H), 3.00–3.04 (m, 2H), 3.56 (brd, 2H, J=12.00 Hz), 3.72 (s, 3H), 3.78 (s, 3H), 4.10 (brs, 1H), 4.70 (brd, 1H, J=7.8 Hz), 5.95 (brs, 1H), 6.81 (d, 1H, J=9.09 Hz), 6.86–6.92 (m, 2H), 7.01–7.04 (m, 2H), 7.17–7.24 (m, 5H), 8.45 (brs, 1H), 9.16 (s, 1H); MS (ES) m/z: 621.0 (MH$^+$); HRMS found for C$_{28}$H$_{36}$N$_4$O$_8$S$_2$: 621.2079.

EXAMPLE 281

4-Butoxy-N-(4-{4-[2-hydroxy-2-(4-hydroxy-3-methanesulfonylamino-phenyl)-ethylamino]-piperidine-1-yl}-phenyl)-benzenesulfonamide The title compound was prepared according to the procedure of Example 278 as an off-white solid; $^1$H NMR (300 MHz, DMSO-d$_6$) δ 0.915 (t, J=7.32 Hz, 3H), 1.07–1.14 (m, 2H), 1.34–1.47 (m, 2H), 1.63–1.73 (m, 2H), 1.91 (m, 3H), 2.27 (m, 2H), 2.55–2.63 (m, 2H), 2.73 (m, 2H), 2.8 (m, 2H), 2.93 (s, 3H), 3.16 (m, 2H), 3.53–3.58 (m, 2H), 3.99 (t, J=6.39 Hz, 2H), 4.58 (brs, 1H), 6.78 (d, J=9.09 Hz, 2H), 6.83–6.89 (m, 3H), 7.00–7.05 (m, 3H), 7.20 (s, 2H), 7.57 (d, J=8.82 Hz, 2H), 9.64 (brs, 1H); MS (ES) m/z: 633.1 (MH$^+$); HRMS found for C$_{30}$H$_{40}$N$_4$O$_7$S$_2$: 633.2401.

EXAMPLE 282

N-(4-{[4-(4-{[(2S)-3-(9H-Carbazol-4-yloxy)-2-hydroxypropyl]amino}-1-piperidineyl)-anilino]sulfonyl}phenyl)acetamide The title compound was prepared from N-{4-[4-(4-oxo-piperidine-1-yl)-phenylsulfamoyl]-phenyl}-acetamide (which was obtained in Example 216) and (2S)-3-(9H-carbazol-4-yloxy)-2-hydroxy-propylamine (Berridge et al., Int. J. Radial. Appl. Instrum., 1992, 563) according to the procedure of Example 255 as a yellowish solid; $^1$H NMR (300 MHz, DMSO-d$_6$) δ 1.55–1.75 (m, 2H), 2.00–2.15 (m, 2H), 2.06 (s, 3H), 2.50–2.70 (m, 2H), 3.00–3.50 (m, 3H), 3.60–3.70 (m, 2H), 4.10–4.25 (m, 2H), 4.35–4.50 (m, 1H), 5.97 (brs, 1H), 6.72 (d, J=8.0 Hz, 1H), 6.80 (d, J=8.0 Hz, 2H), 6.88 (d, J=8.0 Hz, 2H), 7.10–7.50 (m, 5H), 7.59 (d, J=8.7 Hz, 2H), 7.69 (d, J=8.7 Hz, 2H), 8.22 (d, J=7.8 Hz, 1H), 9.71 (s, 1H), 10.40 (s, 1H), 11.32 (s, 1H); MS (ES) m/z: 627.9 (MH$^+$); HRMS Calcd. for C$_{34}$H$_{38}$N$_5$O$_5$S(MH$^+$): 628.2594. Found: 628.2593.

EXAMPLE 283

5-Chloro-N-{4-[4-({(2S)-2-hydroxy-3-[(2-oxo-2,3-dihydro-1H-benzimidazol-4-yl)oxy]propyl}amino)-1-piperidineyl]phenyl}-3-methyl-1-benzothiophene-2-sulfonamide The title compound was prepared according to the procedure of Example 278 as a yellow solid; $^1$H NMR (300 MHz, DMSO-d$_6$) δ 1.33–1.36 (m, 2H), 1.79–1.91 (m, 2H), 2.21–2.27 (m, 2H), 2.40 (s, 3H), 2.58–2.66 (m, 2H), 2.73 (m, 2H), 2.84–2.88 (m, 2H), 3.46–3.56 (m, 2H), 3.92–4.03 (m, 2H), 5.03 (brs, 1H), 6.55–6.63 (m, 2H), 6.81 (t, J=9.3 Hz, 3H), 6.86–7.00 (m, 2H), 7.55 (dd, J=1.8 Hz, 8.7 Hz, 1H), 7.98 (d, J=1.8 Hz, 1H), 8.04 (d, J=8.7 Hz, 1H), 10.54 (s, 1H), 10.7 (s, 1H); MS (ES) m/z: 642.0 (MH$^+$); HRMS found for C$_{30}$H$_{32}$ClN$_5$O$_5$S$_2$: 642.1598.

EXAMPLE 284

4-Cyano-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide The title compound was prepared according to the procedure of Example 278 as a yellow solid; $^1$H NMR (300 MHz, DMSO-d$_6$) δ 1.27–1.37 (m, 2H), 1.85–1.90 (m, 2H), 2.56–2.75 (m, 2H), 2.79–2.80 (m, 2H), 2.82–2.84 (m, 2H), 3.50–3.51 (m, 2H), 3.87–3.96 (m, 2H), 3.99–4.03 (m, 2H), 4.90 (brs, 1H), 6.56–6.63 (m, 2H), 6.67–6.87 (m, 5H), 7.81 (d, 2H), 8.02 (d, 2H), 10.58 (s, 1H), 10.92 (brs, 1H); MS (ES) m/z: 563.0 (MH$^+$); HRMS found for C$_{30}$H$_{32}$N$_5$O$_5$S$_2$: 563.2090.

EXAMPLE 285

4-Cyano-N-[(4-cyanophenyl)sulfonyl]-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide The title compound was prepared according to the procedure of Example 278 as a pale yellow solid; $^1$H NMR (300

MHz, DMSO-$d_6$) δ 1.23–1.34 (m, 2H), 1.90 (m, 2H), 2.26–2.28 (m, 2H), 2.63–2.75 (m, 2H), 2.79–2.87 (m, 2H), 3.72–3.76 (m, 2H), 3.89–3.97 (m, 2H), 4.01–4.05 (m, 2H), 4.92 (brs, 1H), 6.57 (d, J=7.59 Hz, 1H), 6.62 (d, J=8.19 Hz, 1H), 6.79–6.84 (m, 4H), 6.87–6.92 (m, 4H), 7.99 (d, 2H), 8.21 (d, 2H), 10.55 (s, 1H), 10.7 (brs, 1H); MS (ES) m/z: 728.0 (MH$^+$); HRMS found for $C_{30}H_{32}N_5O_5S_2$: 728.1970.

EXAMPLE 286

3-Bromo-5-chloro-N-{4-[4-({(2S)-2-hydroxy-3-[(2-oxo-2,3-dihydro-1H-benzimidazol-4-yl)oxy]propyl}amino)-1-piperidineyl]phenyl}-2-thiophenesulfonamide The title compound was prepared according to the procedure of Example 278 as an orange-yellow solid; $^1$H NMR (300 MHz, DMSO-$d_6$) δ 1.35–1.44 (m, 2H), 1.84–2.05 (m, 2H), 2.60–2.67 (m, 2H), 2.72–2.77 (m, 2H), 2.92–2.96 (m, 2H), 3.15–3.17 (m, 2H), 3.55–3.59 (m, 2H), 3.95–4.02 (m, 2H), 5.12 (brs, 1H), 6.56–6.64 (m, 1H), 6.82 (m, 1H), 6.88 (s, 2H), 6.92 (d, J=8.97 Hz, 4H), 7.38 (s, 1H), 10.6 (s, 1H), 10.7 (s, 1H); MS (ES) m/z: 657.8 (MH$^+$); HRMS found for $C_{25}H_{27}BrClN_5O_5S_2$: 656.0444.

EXAMPLE 287

N-{4-[4-({(2S)-2-Hydroxy-3-[(2-oxo-2,3-dihydro-1H-benzimidazol-4-yl)oxy]propyl}-amino)-1-piperidineyl]phenyl}-5-(3-isoxazolyl)-2-thiophenesulfonamide The title compound was prepared according to the procedure of Example 278 as a red-brown solid; $^1$H NMR (300 MHz, DMSO-$d_6$) δ 1.36–1.40 (m, 2H), 1.90 (m, 2H), 2.27 (m, 1H), 2.61–2.69 (m, 2H), 2.72–2.76 (m, 2H), 2.87–2.91 (m, 2H), 3.55–3.60 (m, 2H), 3.93–4.02 (m, 2H), 5.07 (brs, 1H), 6.59 (q, 2H), 6.81–6.89 (m, 4H), 6.94 (d, J=9.03 Hz, 2H), 7.06 (d, J=1.92 Hz, 5 1H), 7.47 (d, J=4.02 Hz, 1H), 7.66 (d, J=3.93 Hz, 1H), 8.71 (d, J=1.98 Hz, 1H), 10.55 (s, 1H), 10.7 (brs, 1H); MS (ES) m/z: 611.0 (MH$^+$).

EXAMPLE 288

4-[4-(3-Cyclopentyl-propyl)-5-oxo-4,5-dihydro-tetrazol-1-yl]-N-(4-{4-[2-hydroxy-2-(4-hydroxy-3-methanesulfonylamino-phenyl)-ethaylamino]-piperidine-1-yl}-phenyl)-benzenesulfonamide The title compound was prepared from 4-[4-(cyclopentyl-propyl)-5-oxo-4,5-dihydro-tetrazol-1-yl]-N-[4-(4-oxo-piperidine-1-yl)-phenyl]-benzenesulfonamide (which was obtained in Example 226) and N-[2-benzyloxy-5-(2-dibenzylamino-1-hydroxy-ethyl)-phenyl]-methanesulfonamide (which was obtained in Example 7) according to the procedure of Example 255 as a grey solid; MS (ES) m/z: 754.9 (MH$^+$); HRMS Calcd. for $C_{35}H_{47}N_8O_7S_2$ (MH$^+$): 755.3009. Found: 755.2997.

EXAMPLE 289

4-Butoxy-N-(4-{4-[3-(9H-carbazol-4-yloxy)-2-hydroxy-propylamino]-piperidine-1-yl}-phenyl)-benzenesulfonamide The title compound was prepared according to the procedure of Example 278 as an off-white solid; $^1$H NMR (300 MHz, DMSO-$d_6$) δ 0.91 (t, J=7.32 Hz, 3H), 1.34–1.46 (m, 2H), 1.62–1.72 (m, 2H), 1.90 (m, 2H), 2.57–2.65 (m, 2H), 2.83–2.85 (m, 2H), 2.96–2.99 (m, 2H), 3.17 (d, J=5.13 Hz, 2H), 3.49–3.54 (m, 2H), 3.99 (t, J=6.45 Hz, 2H), 4.11–4.16 (m, 2H), 5.25 (brs, 1H), 5.76 (s, 1H), 6.68 (d, J=7.8 Hz, 1H), 6.76 (d, J=9.3 Hz, 2H), 6.87 (d, J=9.0 Hz, 2H), 7.00–7.15 (m, 4H), 7.25–7.36 (m, 2H), 7.44 (d, J=8.1 Hz, 1H), 7.57 (d, J=8.7 Hz, 2H), 8.20 (d, J=7.8 Hz, 1H), 9.63 (brs, 1H), 11.25 (s, 1H); MS (ES) m/z: 643.2 (MH$^+$); HRMS found for $C_{36}H_{42}N_4O_5S$: 643.2961.

EXAMPLE 290

N-[4-(4-{4-[(2S)-3-(9H-Carbazol-4-yloxy)-2-hydroxy-propylamino]-piperidine-1-yl}-phenyl)-4-(3-hexyl-ureido)-benzenesulfonamide The title compound was prepared from 4-(3-hexyl-ureido)-N-[4-(4-oxo-piperidine-1-yl)-phenyl]-benzensulfonamide (which was obtained in Example 225) and (2S)-3-(9H-carbazol-4-yloxy)-2-hydroxy-propylamine (Berridge et al., Int. J. RadiaL. AppL. Instrum., 1992, 563) according to the procedure of Example 255 as an off-white solid; $^1$H NMR (300 MHz, DMSO-$d_6$) δ 0.86 (t, J=6.8 Hz, 3H), 1.20–1.45 (m, 8H), 1.40–1.55 (m, 2H), 1.90–2.05 (m, 2H), 2.50–2.75 (m, 2H), 2.90–3.50 (m, 7H), 3.60–3.70 (m, 2H), 4.10–4.35 (m, 3H), 6.40 (t, J=5.6 Hz, 1H), 6.68 (d, J=8.0 Hz, 1H), 6.78 (d, J=9.0 Hz, 2H), 6.88 (d, J=9.0 Hz, 2H), 7.08 (d, J=8.0 Hz, 1H), 7.14 (t, J=7.2 Hz, 1H), 7.21 (d, J=8.0 Hz, 1H), 7.33 (t, J=5.2 Hz, 1H), 7.40–7.60 (m, 5H), 8.21 (d, J=7.7 Hz, 1H), 9.01 (s, 1H), 9.59 (brs, 1H), 11.30 (s, 1H); MS (ES) m/z: 713.1 (MH$^+$); HRMS Calcd. for $C_{39}H_{49}N_6O_5S$(MH$^+$): 713.3485. Found: 713.3501.

EXAMPLE 291

N-{4-[(4-{4-[((2R)-2-Hydroxy-2-{4-hydroxy-3-[(methylsulfonyl)amino]-phenyl}ethyl)amino]-1-piperidineyl}anilino)sulfonyl]phenyl}acetamide The title compound was prepared from N-{4-[4-(4-oxo-piperidine-1-yl)-phenylsulfamoyl]-phenyl}-acetamide (which was obtained in Example 216) and N-[5-((1R)-2-amino-1-hydroxy-ethyl)-2-benzyloxy-phenyl]-methanesulfonamide (which was obtained in Example 8) according to the procedure of Example 255 as an off-white solid; $^1$H NMR (300 MHz, DMSO-$d_6$) δ 1.40–1.70 (m, 2H), 1.90–2.10 (m, 2H), 2.06 (s, 3H), 2.50–2.65 (m, 2H), 2.90–3.15 (m, 3H), 2.94 (s, 3H), 3.55–3.70 (m, 2H), 4.65–4.80 (m, 1H), 6.79 (d, J=9.0 Hz, 2H), 6.97 (d, J=9.0 Hz, 2H), 7.00 (d, J=8.0 Hz, 1H), 7.06 (dd, J=8.0, 1.2 Hz, 1H), 7.22 (d, J=1.2 Hz, 1H), 7.40 (d, J=8.7 Hz, 2H), 7.69 (d, J=8.7 Hz, 2H), 10.42 (s, 1H), 10.44 (s, 1H); MS (ES) m/z: 618.0 (MH$^+$); HRMS Calcd. for $C_{28}H_{36}N_5O_7S_2$ (MH$^+$): 618.2056. Found: 618.2056.

EXAMPLE 292

N-[4-(4-{[(2S)-3-(9H-Carbazol-4-yloxy)-2-hydroxypropyl]amino}-1-piperidineyl)phenyl]-3,4-dimethoxybenzenesulfonamide The title compound was prepared according to the procedure of Example 278 as a tan solid; $^1$H NMR (300 MHz, DMSO-$d_6$) δ 1.38 (m, 2H), 1.90 (m, 2H), 2.59–2.65 (m, 2H), 2.84 (m, 2H), 2.97 (m, 2H), 3.50–3.54 (m, 2H), 3.71 (s, 3H), 3.78 (s, 3H), 4.10–4.14 (m, 2H), 4.16–4.17 (m, 2H), 5.2 (brs, 1H), 6.68 (d, J=6.0 Hz, 1H), 6.77 (d, J=6.9 Hz, 2H), 6.88 (d, J=6.9 Hz, 2H), 7.01–7.07 (q, 2H), 7.10–7.17 (m, 2H), 7.21–7.23 (dd, J=1.8 Hz, 6.3 Hz, 1H), 7.26–7.35 (m, 2H), 7.44 (d, J=6.0 Hz, 1H), 8.20 (d, J=5.7 Hz, 1H), 11.2 (s, 1H); MS (ES) m/z: 631.2 (MH$^+$); HRMS found for $C_{34}H_{38}N_4O_6S$: 631.2596.

EXAMPLE 293

N-[4-(4-{[(2S)-2-Hydroxy-3-(4-hydroxyphenoxy)propyl]amino}-1-piperidinyl)phenyl]-5-(2-pyridinyl)-2-thiophenesulfonamide The title compound was prepared from 5-pyridin-2-yl-thiophene-2-sulfonic acid [4-(4-oxo-piperidine-1-yl)-phenyl]-amide (which was obtained in Example 227) and 4-((2S)-3-amino-2-hydroxy-propoxy)-phenol (which was obtained in Example 5) according to the procedure of Example 278 as an off-white solid; $^1$H NMR (300 MHz, DMSO-$d_6$) δ 1.20–1.40 (m, 2H), 1.80–1.90 (m, 2H), 2.40–2.80 (m, 5H), 3.50–3.60 (m, 2H), 3.70–3.90 (m, 3H), 4.99 (brs, 1H), 6.66 (d, J=8.0 Hz, 2H), 6.75 (d, J=8.0 Hz, 2H), 6.83 (d, J=9.0 Hz, 2H), 6.96 (d, J=9.0 Hz, 1H), 7.36 (dd, J=4.4, 1.7 Hz, 1H), 7.41 (d, J=4.0 Hz, 1H), 7.76 (d, J=4.0 Hz, 1H), 7.88 (dd, J=8.0, 1.7 Hz, 1H), 8.00 (d, J=8.0 Hz, 1H), 8.54 (d, J=4.4 Hz, 1H), 8.89 (s, 1H); MS (ES) m/z: 580.9 (MH$^+$); HRMS Calcd. for $C_{29}H_{33}N_4O_5S_2$ (MH$^+$): 581.1892. Found: 581.1910.

EXAMPLE 294

N-(4-{4-[(2-Hydroxy-2-{4-hydroxy-3-[(methylsulfonyl)amino]phenyl}ethyl)amino]-1-piperidineyl}phenyl)-5-(2-pyridinyl)-2-thiophenesulfonamide The title compound was prepared from 5-pyridin-2-yl-thiophene-2-sulfonic acid [4-(4-oxo-piperidine-1-yl)-phenyl]-amide (which was obtained in Example 227) and N-[5-(2-amino-1-hydroxy-ethyl)-2-hydroxy-phenyl]-methanesulfonamide (which was obtained in Example 9) according to the procedure of Example 278 as an off-white solid; $^1$H NMR (300 MHz, DMSO-$d_6$) δ 1.20–1.40 (m, 2H), 1.80–1.90 (m, 2H), 2.45–2.75 (m, 5H), 2.91 (s, 3H), 3.40–3.60 (m, 2H), 4.47 (dd, J=8.0, 4.1 Hz, 1H), 6.80 (d, J=8.3 Hz, 1H), 6.82 (d, J=8.0 Hz, 2H), 6.95 (d, J=8.0 Hz, 2H), 7.00 (dd, J=8.3, 2.0 Hz, 1H), 7.17 (d, J=2.0 Hz, 1H), 7.37 (dd, J=4.8, 1.7 Hz, 1H), 7.40 (d, J=3.9 Hz, 1H), 7.75 (d, J=3.9 Hz, 1H), 7.88 (dd, J=8.0, 1.7 Hz, 1H), 7.98 (d, J=8.0 Hz, 1H), 8.54 (brd, J=4.8 Hz, 1H); MS (ES) m/z: 644.1 (MH$^+$); HRMS Calcd. for $C_{29}H_{34}N_5O_6S_3$ (MH$^+$): 644.1671. Found: 644.1663.

EXAMPLE 295

N-(4-{4-[(2-Hydroxy-2-{4-hydroxy-3-[(methylsulfonyl)amino]phenyl}ethyl)amino]-1-piperidineyl}phenyl)-1-butanesulfonamide The title compound was prepared from butane-1-sulfonic acid [4-(4-oxo-piperidine-1-yl)-phenyl]-amide (which was obtained in Example 228) and N-[2-benzyloxy-5-(2-dibenzylamino-1-hydroxy-ethyl)-phenyl]-methanesulfonamide (which was obtained in Example 7) according to the procedure of Example 255 as an off-white solid; $^1$H NMR (300 MHz, DMSO-$d_6$) δ 0.83 (t, J=7.2 Hz, 3H), 1.20–1.40 (m, 2H), 1.50–1.70 (m, 4H), 1.95–2.10 (m, 2H), 2.40–2.60 (m, 2H), 2.94 (s, 3H), 2.90–3.20 (m, 5H), 3.62–3.75 (m, 2H), 4.70–4.80 (m, 1H), 5.95 (brs, 1H), 6.85–6.95 (m, 3H), 7.00–7.10 (m, 3H), 7.24 (d, J=2.0 Hz, 1H), 8.70 (brs, 1H), 9.33 (brs, 1H); MS (ES) m/z: 541.0 (MH$^+$); HRMS Calcd. for $C_{24}H_{37}N_4O_6S_2$ (MH$^+$): 541.2155. Found: 541.2161.

EXAMPLE 296

N-{4-[4-({(2S)-2-Hydroxy-3-[(2-oxo-2,3-dihydro-1H-benzimidazol-4-yl)oxy]propyl}amino)-1-piperidineyl]phenyl}-1-butanesulfonamide The title compound was prepared from butane-1-sulfonic acid [4-(4-oxo-piperidine-1-yl)-phenyl]-amide (which was obtained in Example 228) and (S)-4-[2-hydroxy-3-aminopropoxy]-1,3-dihydro-2H-benzimidazol-2-one (U.S. Pat. No. 5,786,356/1998) according to the procedure of Example 255 as an off-white solid; $^1$H NMR (300 MHz, DMSO-$d_6$) δ 0.83 (t, J=7.2 Hz, 3H), 1.20–1.70 (m, 6H), 1.95–2.10 (m, 2H), 2.67 (brt, J=11.7 Hz, 2H), 2.70–3.20 (m, 7H), 3.62–3.75 (m, 2H), 3.95–4.10 (m, 3H), 6.59 (d, J=7.5 Hz, 1H), 6.63 (d, J=8.0 Hz, 1H), 6.80–7.00 (m, 3H), 7.06 (d, J=9.0 Hz, 2H), 9.32 (brs, 1H), 10.61 (brs, 1H), 10.73 (brs, 1H); MS (ES) m/z: 518.1 (MH$^+$); HRMS Calcd. for $C_{25}H_{36}N_5O_5S$(MH$^+$): 518.2437. Found: 518.2452.

EXAMPLE 297

N-(4-{4-[(2-Hydroxy-2-{4-hydroxy-3-[(methylsulfonyl)amino]phenyl}ethyl)amino]-1-piperidineyl}phenyl)-1-octanesulfonamide The title compound was prepared from octane-1-sulfonic acid [4-(4-oxo-piperidine-1-yl)-phenyl]-amide (which was obtained in Example 230) and N-[2-benzyloxy-5-(2-dibenzylamino-1-hydroxy-ethyl)-phenyl]-methanesulfonamide (which was obtained in Example 7) according to the procedure of Example 255 as an off-white solid; $^1$H NMR (300 MHz, DMSO-$d_6$) δ 0.84 (t, J=7.0 Hz, 3H), 1.15–1.40 (m, 12H), 1.50–1.70 (m, 2H), 1.80–1.95 (m, 2H), 2.50–2.92 (m, 7H), 3.50–3.65 (m, 2H), 4.49 (dd, J=8.0, 4.1 Hz, 1H), 6.82 (d, J=8.3 Hz, 1H), 6.88 (d, J=8.0 Hz, 2H), 7.00 (dd, J=8.3, 2.0 Hz, 1H), 7.04 (d, J=8.0 Hz, 2H), 7.17 (d, J=2.0 Hz, 1H); MS (ES) m/z: 597.1 (MH$^+$); HRMS Calcd. for $C_{28}H_{45}N_4O_6S_2$ (MH$^+$): 597.2781. Found: 597.2776.

EXAMPLE 298

N-{4-[4-({(2S)-2-Hydroxy-3-[(2-oxo-2,3-dihydro-1H-benzimidazol-4-yl)oxy]propyl}amino)-1-piperidineyl]phenyl}-1-octanesulfonamide The title compound was prepared from octane-1-sulfonic acid [4-(4-oxo-piperidine-1-yl)-phenyl]-amide (which was obtained in Example 230) and (S)-4-[2-hydroxy-3-aminopropoxy]-1,3-dihydro-2H-benzimidazol-2-one (U.S. Pat. No. 5,786,356/1998) according to the procedure of Example 255 as an off-white solid; $^1$H NMR (300 MHz, DMSO-$d_6$) δ 0.85 (t, J=7.0 Hz, 3H), 1.10–1.40 (m, 10H), 1.50–1.70 (m, 4H), 1.95–2.16 (m, 2H), 2.67 (brt, J=11.1 Hz, 2H), 2.93 (brt, J=7.9 Hz, 2H), 2.95–3.20 (m, 3H), 3.62–3.75 (m, 2H), 4.00–4.12 (m, 2H), 4.12–4.30 (m, 1H), 6.59 (d, J=7.8 Hz, 1H), 6.63 (d, J=8.3 Hz, 1H), 6.80–7.00 (m, 3H), 7.07 (d, J=9.0 Hz, 2H), 9.33 (brs, 1H), 10.60 (brs, 1H), 10.75 (brs, 1H); MS (ES) m/z: 574.1 (MH$^+$); HRMS Calcd. for $C_{29}H_{44}N_5O_5S$(MH$^+$): 574.3063. Found: 574.3084.

EXAMPLE 299

N-{4-[4-({(2S)-2-Hydroxy-3-[(2-oxo-2,3-dihydro-1H-benzimidazol-4-yl)oxy]propyl-amino)-1-piperidineyl]phenyl}-5-{[5-(trifluoromethyl)-2-pyridinyl]sulfonyl}-2-thiophenesulfonamide The title compound was prepared from 5-(5-trifluoromethyl-pyridine-2-sulfonyl)-thiophene-2-sulfonic acid [4-(4-oxo-piperidine-1-yl)-phenyl]-amide (which was obtained in Example 229) and (S)-4-[2-hydroxy-3-aminopropoxy]-1,3-dihydro-2H-benzimidazol-2-one (U.S. Pat. No. 5,786,356/1998) according to the procedure of Example 278 as a yellowish solid; $^1$H NMR (300 MHz, DMSO-$d_6$) δ 1.30–1.50 (m, 2H), 1.80–2.00 (m, 2H), 2.50–3.00 (m, 5H), 3.54 (brd, J=9.3 Hz, 2H), 3.90–4.10 (m, 3H), 6.57 (d, J=6.0 Hz, 1H), 6.62 (d, J=6.0 Hz, 1H), 6.62–6.90 (m, 5H), 7.92 (d, J=2.0 Hz, 1H), 8.39 (d, J=9.0 Hz, 1H), 8.48 (d, J=2.0 Hz, 1H), 8.62 (dd, J=9.0, 2.0 Hz, 1H), 9.23 (s, 1H), 10.56 (s, 1H), 10.69 (s, 1H); MS (ES) m/z: 752.9 (MH$^+$); HRMS Calcd. for $C_{31}H_{32}F_3N_6O_7S_3$ (MH$^+$): 753.1447. Found: 753.1468.

EXAMPLE 300

N-[4-(4-{[(2S)-2-Hydroxy-3-(4-hydroxyphenoxy) propyl]amino}-1-piperidineyl)phenyl]-5-{[5-(trifluoromethyl)-2-pyridinyl]sulfonyl}-2-thiophenesulfonamide The title compound was prepared from 5-(5-trifluoromethyl-pyridine-2-sulfonyl)-thiophene-2-sulfonic acid [4-(4-oxo-piperidine-1-yl)-phenyl]-amide (which was obtained in Example 229) and 4-((2S)-3-amino-2-hydroxy-propoxyl)-phenol (which was obtained in Example 5) according to the procedure of Example 278 as a grey solid; $^1$H NMR (300 MHz, DMSO-d$_6$) δ 1.25–1.45 (m, 2H), 1.70–1.95 (m, 2H), 2.50–2.85 (m, 5H), 3.54 (brd, J=12.4 Hz, 2H), 3.65–3.95 (m, 3H), 6.60–6.90 (m, 8H), 7.92 (d, J=1.6 Hz, 1H), 8.41 (d, J=8.3 Hz, 1H), 8.48 (d, J=1.6 Hz, 1H), 8.61 (dd, J=8.3, 2.0 Hz, 1H), 8.89 (s, 1H), 9.23 (s, 1H); MS (ES) m/z: 713.1 (MH$^+$); HRMS Calcd. for $C_{30}H_{32}F_3N_4O_7S_3$ (MH$^+$): 713.1385. Found: 713.1407.

EXAMPLE 301

4-[(2,4-Dioxo-1,3-thiazolidin-5-yl)methyl]-N-{4-[4-({(2S)-2-hydroxy-3-[(2-oxo-2,3-dihydro-1H-benzimidazol-4-yl)oxy]propyl}amino)-1-piperidineyl]phenyl}-benzenesulfonamide The title compound was prepared from 4-(2,4-dioxo-thiazolidin-5-ylmethyl)-N-[4-(4-oxo-piperidine-1-yl)-phenyl]-benzenesulfonamide (which was obtained in Example 231) and (S)-4-[2-hydroxy-3-aminopropoxy]-1,3-dihydro-2H-benzimidazol-2-one (U.S. Pat. No. 5,786,356/1998) according to the procedure of Example 278 as an off-white solid; $^1$H NMR (300 MHz, DMSO-d$_6$) δ 1.40–1.60 (m, 2H), 1.90–2.10 (m, 2H), 2.50–2.70 (m, 2H), 2.70–3.50 (m, 5H), 3.60 (brd, J=11.6 Hz, 2H), 4.00 (brs, 3H), 4.60 (dd, J=9.4, 4.2 Hz, 1H), 6.58 (d, J=7.8 Hz, 1H), 6.62 (d, J=8.1 Hz, 1H), 6.70–6.90 (m, 5H), 7.35 (d, J=8.4 Hz, 2H), 7.55 (d, J 8.4 Hz, 2H), 9.70 (brs, 1H), 10.61 (brs, 1H), 10.72 (brs, 1H); MS (ES) m/z: 667.0 (MH$^+$); HRMS Calcd. for $C_{31}H_{35}N_6O_7S_2$ (MH$^+$): 677.2009. Found: 677.1999.

EXAMPLE 302

4-[(2,4-Dioxo-1,3-thiazolidin-5-yl)methyl]-N-(4-{4-[(2-hydroxy-2-{4-hydroxy-3-[(methylsulfonyl)amino]phenyl}ethyl)amino]-1-piperidineyl}phenyl)benzenesulfonamide The title compound was prepared from 4-(2,4-dioxo-thiazolidin-5-ylmethyl)-N-[4-(4-oxo-piperidine-1-yl)-phenyl]-benzenesulfonamide (which was obtained in Example 231) and N-[5-(2-amino-1-hydroxy-ethyl)-2-hydroxy-phenyl]-methanesulfonamide (which was obtained in Example 9) according to the procedure of Example 278 as an off-white solid; $^1$H NMR (300 MHz, DMSO-d$_6$) δ 1.45–1.60 (m, 2H), 1.85–2.05 (m, 2H), 2.50–3.50 (m, 7H), 2.93 (s, 3H), 3.59 (brd, J=11.9 Hz, 2H), 4.28 (dd, J=7.0, 3.8 Hz, 1H), 4.60–4.65 (m, 1H), 6.70–6.90 (m, 5H), 7.05 (dd, J=8.3, 1.9 Hz, 1H), 7.21 (d, J=1.9 Hz, 1H), 7.33 (d, J=8.3 Hz, 2H), 7.55 (d, J=8.3 Hz, 2H); MS (ES) m/z: 690.0 (MH$^+$); HRMS Calcd. for $C_{30}H_{36}N_5O_8S_3$ (MH$^+$): 690.1726. Found: 690.1714.

EXAMPLE 303

N-{4-[4-({(2S)-2-Hydroxy-3-[(8-hydroxy-2-oxo-1,2,3,4-tetrahydro-5-quinolinyl)oxy]-propyl}amino)-1-piperidineyl]phenyl}-3,4-dimethoxybenzenesulfonamide The title compound was prepared from 3,4-dimethoxy-N-[4-(4-oxo-piperidine-1-yl)-phenyl]-benzenesulfonamide (which was obtained in Example 242) and 5-(3-amino-(2S)-2-hydroxy-propoxy)-8-hydroxy-3,4-dihydro-1H-quinolin-2-one (which was obtained in Example 12) according to the procedure of Example 278 as a white solid; $^1$H NMR (300 MHz, DMSO-d$_6$) δ 1.20–1.40 (m, 2H), 1.80–1.95 (m, 2H), 2.39 (t, J=7.2 Hz, 2H), 2.50–2.75 (m, 5H), 2.82 (t, J=7.2 Hz, 2H), 3.45–3.55 (m, 2H), 3.63 (s, 3H), 3.72 (s, 3H), 3.70–3.85 (m, 3H), 4.91 (brs, 1H), 6.44 (d, J=8.8 Hz, 1H), 6.60 (d, J=8.8 Hz, 1H), 6.78 (d, J=9.1 Hz, 1H), 6.88 (d, J=9.1 Hz, 1H), 7.02 (d, J=8.5 Hz, 1H), 7.18 (dd, J=8.5, 2.1 Hz, 1H), 7.36 (d, J=2.1 Hz, 1H),8.72 (s, 1H), 9.17 (brs, 1H); MS (ES) m/z: 627.1 (MH$^+$); HRMS Calcd. for $C_{31}H_{39}N_4O_8S$ (MH$^+$): 627.2489. Found: 627.2458.

EXAMPLE 304

N-[4-(4-{[(2S)-2-Hydroxy-3-(4-hydroxyphenoxy) propyl]amino}-1-piperidineyl)phenyl]-1-octanesulfonamide The title compound was prepared from octane-1-sulfonic acid (4-(4-oxo-piperidine-1-yl)-phenyl]-amide (which was obtained in Example 230) and 4-((2S)-3-amino-2-hydroxy-propoxyl)-phenol (which was obtained in Example 5) according to the procedure of Example 278 as an off-white solid; $^1$H NMR (300 MHz, DMSO-d$_6$) δ 0.85 (t, J=7.0 Hz, 3H), 1.15–1.45 (m, 12H), 1.50–1.70 (m, 2H), 1.80–1.95 (m, 2H), 2.50–2.80 (m, 5H), 2.92 (brt, J=6.7 Hz, 2H), 3.54 (brd, J=12.3 Hz, 2H), 3.70–3.90 (m, 3H), 6.66 (d, J=6.7 Hz, 2H), 6.75 (d, J=8.3 Hz, 1H), 6.88 (d, J=9.0 Hz, 2H), 7.04 (d, J=9.0 Hz, 2H), 8.89 (brs, 1H), 9.28 (brs, 1H); MS (ES) m/z: 534.1 (MH$^+$); HRMS Calcd. for $C_{28}H_{44}N_3O_5S$(MH$^+$): 534.3002. Found: 534.3017.

EXAMPLE 305

4-{[(Hexylamino)carbonyl]amino}-N-{4-[4-({(2S)-2-hydroxy-3-[(8-hydroxy-2-oxo-1,2,3,4-tetrahydro-5-quinolinyl)oxy]propyl}amino)-1-piperidineyl]phenyl}benzenesulfonamide The title compound was prepared from 4-(3-hexyl-ureido)-N-[4-(4-oxo-piperidine-1-yl)-phenyl]-benzensulfonamide (which was obtained in Example 225) and 5-(3-amino-(2S)-2-hydroxy-propoxy)-8-hydroxy-3,4-dihydro-1H-quinolin-2-one (which was obtained in Example 12) according to the procedure of Example 278 as a white solid; $^1$H NMR (300 MHz, DMSO-d$_6$) δ 0.86 (t, J=5.1 Hz, 3H), 1.20–1.35 (m, 8H), 1.35–1.50 (m, 2H), 1.75–1.90 (m, 2H), 2.39 (t, J=5.1 Hz, 2H), 2.50–2.75 (m, 5H), 2.82 (t, J=5.1 Hz, 2H), 3.05 (q, J=5.1 Hz, 2H), 3.40–3.55 (m, 2H), 3.75–3.85 (m, 3H), 4.90 (brs, 1H), 6.30 (t, J=5.1 Hz, 1H), 6.44 (d, J=6.6 Hz, 1H), 6.59 (d, J=6.6 Hz, 1H), 6.76 (d, J=6.9 Hz, 1H), 6.85 (d, J=6.9 Hz, 1H), 7.46 (d, J=6.9 Hz, 2H), 7.50 (d, J=6.9 Hz, 2H), 8.67 (s, 1H), 8.84 (s, 1H), 9.10 (brs, 1H), 9.50 (brs, 1H); MS (ES) m/z: 709.2 (MH$^+$); HRMS Calcd. for $C_{36}H_{49}N_6O_7S$(MH$^+$): 709.3383. Found: 709.3391.

EXAMPLE 306

N-{4-[4-({(2S)-2-Hydroxy-3-[(8-hydroxy-2-oxo-1,2,3,4-tetrahydro-5-quinolinyl)oxy]-propyl}amino)-1-piperidineyl]phenyl}-1-butanesulfonamide The title compound was prepared from butane-1-sulfonic acid ]4-(4-oxo-piperidine-1-yl)-phenyl]-amide (which was obtained in Example 228) and 5-(3-amino-(2S)-2-hydroxy-propoxy)-8-hydroxy-3,4-dihydro-1H-quinolin-2-one (which was obtained in Example 12) according to the procedure of Example 278 as a white solid; $^1$H NMR (300 MHz, DMSO-d$_6$) δ 0.82 (t, J=7.3 Hz, 3H), 1.20–1.40 (m, 4H), 1.50–1.70 (m, 2H), 1.80–1.95 (m, 2H), 2.39 (t, J=7.3 Hz, 2H), 2.50–2.80 (m, 5H), 2.85 (t, J=7.3 Hz, 2H), 2.85–3.00 (m, 2H), 3.45–3.60 (m, 2H), 3.75–3.85 (m, 3H), 6.44 (d, J=8.7 Hz, 1H), 6.60 (d, J=8.7 Hz, 1H), 6.89 (d, J=9.0 Hz, 2H), 7.04 (d, J=9.0 Hz, 2H), 8.74 (s, 1H); MS (ES) m/z: 546.9 (MH$^+$); HRMS Calcd. for C$_{27}$H$_{39}$N$_4$O$_6$S(MH$^+$): 547.2590. Found: 547.2583.

EXAMPLE 307

N-[4-({4-[4-({(2S)-2-Hydroxy-3-[(8-hydroxy-2-oxo-1,2,3,4-tetrahydro-5-quinolinyl)oxy]propyl}amino)-1-piperidineyl]anilino}sulfonyl)phenyl]acetamide The title compound was prepared from N-{4-[4-(4-oxo-piperidine-1-yl)-phenylsulfamoyl]-phenyl}-acetamide (which was obtained in Example 216) and 5-(3-amino-(2S)-2-hydroxy-propoxy)-8-hydroxy-3,4-dihydro-1H-quinolin-2-one (which was obtained in Example 12) according to the procedure of Example 278 as a white solid; $^1$H NMR (300 MHz, DMSO-d$_6$) δ 1.20–1.40 (m, 2H), 1.75–1.90 (m, 2H), 2.05 (s, 3H), 2.39 (t, J=7.5 Hz, 2H), 2.50–2.80 (m, 5H), 2.83 (t, J=7.5 Hz, 2H), 3.40–3.55 (m, 2H), 3.70–3.85 (m, 3H), 6.44 (d, J=8.7 Hz, 1H), 6.60 (d, J=8.7 Hz, 1H), 6.76 (d, J=9.0 Hz, 2H), 6.85 (d, J=9.0 Hz, 2H), 7.58 (d, J=9.0 Hz, 2H), 7.67 (d, J=9.0 Hz, 2H), 8.72 (s, 1H), 10.27 (s, 1H); MS (ES) m/z: 623.9 (MH$^+$); HRMS Calcd. for C$_{31}$H$_{38}$N$_5$O$_7$S(MH$^+$): 624.2492. Found: 624.2469.

EXAMPLE 308

N-(4-{4-[((2S)-2-Hydroxy-3-{4-hydroxy-3-[(methylsulfonyl)amino]phenoxy}propyl)-amino]-1-piperidineyl}phenyl)-,4-dimethoxybenzenesulfonamide The title compound was prepared from 3,4-dimethoxy-N-[4-(4-oxo-piperidine-1-yl)-phenyl]-benzenesulfonamide (which was obtained in Example 242) and N-[5-((2S)-3-amino-2-hydroxy-propoxy)-2-hydroxy-phenyl]-methanesulfonamide (which was obtained in Example 14) according to the procedure of Example 278 as a white solid; $^1$H NMR (300 MHz, DMSO-d$_6$) δ 1.20–1.40 (m, 2H), 1.75–1.90 (m, 2H), 2.50–2.80 (m, 5H), 2.92 (s, 3H), 3.40–3.55 (m, 2H), 3.71 (s, 3H), 3.78 (s, 3H), 3.70–3.85 (m, 3H), 6.60 (dd, J=8.8, 2.9 Hz, 1H), 6.70–6.85 (m, 5H), 6.88 (d, J=9.0 Hz, 2H), 7.02 (d, J=8.6 Hz, 2H), 7.16 (d, J=2.1 Hz, 1H), 7.23 (dd, J=8.4, 2.1 Hz, 1H); MS (ES) m/z: 650.9 (MH$^+$); HRMS Calcd. for C$_{29}$H$_{39}$N$_4$O$_9$S$_2$ (MH$^+$): 651.2158. Found: 651.2117.

EXAMPLE 309

N-(4-{4-[((2S)-2-Hydroxy-3-{4-hydroxy-3-[(methylsulfonyl)amino]phenoxy}-propyl)amino]-1-piperidineyl}phenyl)-1-butanesulfonamide The title compound was prepared from butane-1-sulfonic acid [4-(4-oxo-piperidine-1-yl)-phenyl]-amide (which was obtained in Example 228) and N-[5-((2S)-3-amino-2-hydroxy-propoxy)-2-hydroxy-phenyl]-methanesulfonamide (which was obtained in Example 14) according to the procedure of Example 278 as an off-white solid; $^1$H NMR (300 MHz, DMSO-d$_6$) δ 0.83 (t, J=7.3 Hz, 3H), 1.25–1.40 (m, 2H), 1.55–1.70 (m, 2H), 1.80–1.95 (m, 2H), 2.50–2.80 (m, 5H), 2.92 (s, 3H), 2.85–3.30 (m, 2H), 3.50–3.65 (m, 2H), 3.70–3.90 (m, 3H), 6.61 (dd, J=8.8, 2.9 Hz, 1H), 6.70–6.80 (m, 2H), 6.88 (d, J=8.9 Hz, 2H), 7.05 (d, J=8.9 Hz, 2H); MS (ES) m/z: 571.0 (MH$^+$); HRMS Calcd. for C$_{25}$H$_{39}$N$_4$O$_7$S$_2$ (MH$^+$): 571.2261. Found: 571.2279.

EXAMPLE 310

4-{[(Hexylamino)carbonyl]amino}-N-4-{4-[((2S)-2-hydroxy-3-{4-hydroxy-3-[(methylsulfonyl)amino]phenoxy}propyl)amino]-1-piperidineyl}phenyl)benzenesulfonamide The title compound was prepared from 4-(3-hexyl-ureido)-N-[4-(4-oxo-piperidine-1-yl)-phenyl]-benzensulfonamide (which was obtained in Example 225) and N-[5-((2S)-3-amino-2-hydroxy-propoxy)-2-hydroxy-phenyl]-methanesulfonamide (which was obtained in Example 14) according to the procedure of Example 278 as an off-white solid; $^1$H NMR (300 MHz, DMSO-d$_6$) δ 0.86 (t, J=6.9 Hz, 3H), 1.25–1.40 (m, 8H), 1.30–1.45 (m, 2H), 1.75–1.90 (m, 2H), 2.50–2.75 (m, 5H), 2.92 (s, 3H), 3.00–3.15 (m, 2H), 3.45–3.55 (m, 2H), 3.70–3.90 (m, 3H), 6.32 (t, J=5.6 Hz, 1H), 6.60 (dd, J=8.8, 2.9 Hz, 1H), 6.70–6.80 (m, 4H), 6.85 (d, J=9.1 Hz, 2H), 7.45 (d, J=6.8 Hz, 2H), 7.50 (d, J=6.8 Hz, 2H), 8.64 (brs, 1H); MS (ES) m/z: 733.1 (MH$^+$); HRMS Calcd. for C$_{34}$H$_{49}$N$_6$O$_8$S$_2$ (MH$^+$): 733.3053. Found: 733.3049.

EXAMPLE 311

N-[4-(4-{[((2R)-2-(3-Chlorophenyl)-2-hydroxyethyl]amino}-1-piperidineyl)phenyl]-4-{[(hexylamino)carbonyl]amino}benzenesulfonamide The title compound was prepared from 4-(3-hexyl-ureido)-N-[4-(4-oxo-piperidine-1-yl)-phenyl]-benzensulfonamide (which was obtained in Example 225) and (1R)-2-amino-1-(3-chloro-phenyl)-ethanol (which was obtained in Example 1) according to the procedure of Example 278 as a brown solid; $^1$H NMR (300 MHz, DMSO-d$_6$) δ 0.84 (t, J=6.9 Hz, 3H), 1.20–1.50 (m, 10H), 1.75–1.90 (m, 2H), 2.50–2.80 (m, 5H), 3.00–3.15 (m, 2H), 3.40–3.50 (m, 2H), 4.60 (dd, J=8.1, 3.8 Hz, 1H), 6.29 (t, J=5.7 Hz, 1H), 6.77 (d, J=9.1 Hz, 2H), 6.85 (d, J=9.1 Hz, 2H), 7.25–7.50 (m, 8H), 8.94 (s, 1H), 9.55 (brs, 1H); MS (ES) m/z: 628.1 (MH$^+$); HRMS Calcd. for C$_{32}$H$_{43}$ClN$_5$O$_4$S (MH$^+$): 628.2748. Found: 628.2718.

EXAMPLE 312

Ethyl{4-[(4-{4-[((2S)-2-hydroxy-3-{4-hydroxy-3-[(methylsulfonyl)amino]-phenoxy}propyl)amino]-1-piperidineyl}anilino)sulfonyl]phenyl}acetate The title compound was prepared from {4-[4-(4-oxo-piperidine-1-yl)-phenylsulfamoyl]-phenyl}-acetic acid methyl ester (which was prepared according to the procedure of Example 225) and N-[5-((2S)-3-amino-2-hydroxy-propoxy)-2-hydroxy-phenyl]-methanesulfonamide (which was obtained in Example 14) according to the procedure of Example 278 as a brown solid; $^1$H NMR (300 MHz, DMSO-d$_6$) δ 1.16 (t, J=7.1 Hz, 3H), 1.20–1.40 (m, 2H), 1.75–1.90 (m, 2H), 2.50–2.80 (m, 5H), 2.91 (s, 3H), 3.40–3.55 (m, 2H), 3.74 (s, 2H), 3.70–3.85 (m, 3H), 4.07 (q, J=7.1 Hz, 2H), 6.59 (dd, J=8.8, 3.0 Hz, 1H), 6.70–6.80 (m, 4H), 6.87 (d, J=9.1 Hz, 2H), 7.41 (d, J=8.4 Hz, 2H), 7.63 (d, J=8.4 Hz, 2H); MS (ES) m/z: 677.0 (MH$^+$); HRMS Calcd. for C$_{31}$H$_{41}$N$_4$O$_9$S$_2$ (MH$^+$): 677.2315. Found: 677.2289.

EXAMPLE 313

Methyl{4-[(4-{4-[((2R)-2-hydroxy-2-{4-hydroxy-3-[(methylsulfonyl)amino]-phenyl]ethyl)amino]-1-piperidineyl}anilino)sulfonyl]phenoxy}acetate The title compound was prepared from {4-[4-(4-oxo-piperidine-1-yl)-phenylsulfamoyl]-phenoxy}-acetic acid methyl ester (which was obtained in Example 232) and N-[5-((1R)-2-amino-1-hydroxy-ethyl)-2-hydroxy-phenyl]-methanesulfonamide (which was obtained in Example 10) according to the procedure of Example 278 as an off-white solid; $^1$H NMR (300 MHz, DMSO-d$_6$) δ 1.20–1.40 (m, 2H), 1.75–1.90 (m, 2H), 2.50–2.80 (m, 5H), 2.92 (s, 3H), 3.65–3.75 (m, 2H), 3.67 (s, 3H), 4.47 (dd, J=8.0, 4.1 Hz, 1H), 4.87 (s, 2H), 6.50–6.90 (m, 8H), 7.17 (d, J=1.8 Hz, 1H), 7.59 (d, J=8.9 Hz, 2H); MS (ES) m/z: 649.0 (MH$^+$); HRMS Calcd. for C$_{29}$H$_{37}$N$_4$O$_9$S$_2$ (MH$^+$): 649.2004. Found: 649.2014.

EXAMPLE 314

Methyl[4-({4-[4-({(2S)-2-hydroxy-3-[(2-oxo-2,3-dihydro-1H-benzimidazol-4-yl)oxy]propyl}amino)-1-piperidineyl]anilino}sulfonyl)phenoxy]acetate The title compound was prepared from {4-[4-(4-oxo-piperidine-1-yl)-phenylsulfamoyl]-phenoxy}-acetic acid methyl ester (which was obtained in Example 232) and (S)-4-[2-hydroxy-3-aminopropoxy]-1,3-dihydro-2H-benzimidazol-2-one (U.S. Pat. No. 5,786,356/1998) according to the procedure of Example 278 as a pale yellowish solid; $^1$H NMR (300 MHz, DMSO-d$_6$) δ 1.20–1.40 (m, 2H), 1.75–1.90 (m, 2H), 2.50–2.85 (m, 5H), 3.30–3.50 (m, 2H), 3.69 (s, 3H), 3.80–4.05 (m, 3H), 4.87 (s, 2H), 6.56 (d, J=7.8 Hz, 1H), 6.61 (d, J=8.1 Hz, 1H), 6.65–6.90 (m, 5H), 7.02 (d, J=9.0 Hz, 2H), 7.59 (d, J=9.0 Hz, 2H), 10.60 (s, 1H), 10.75 (brs, 1H); MS (ES) m/z: 626.1 (MH$^+$); HRMS Calcd. for C$_{30}$H$_{36}$N$_5$O$_8$S(MH$^+$): 626.2285. Found: 626.2298.

EXAMPLE 315

N-[5-({(2S)-3-[(1-{4-[(Butylsulfonyl)amino]phenyl}-4-piperidineyl)amino]-2-hydroxypropyl}oxy)-2-hydroxyphenyl]benzenesulfonamide The title compound was prepared from butane-1-sulfonic acid [4-(4-oxo-piperidine-1-yl)-phenyl]-amide (which was obtained in Example 228) and N-[5-((2S)-3-amino-2-hydroxy-propoxy)-2-hydroxy-phenyl]-benzenesulfonamide (which was obtained in Example 21) according to the procedure of Example 278 as an off-white solid; $^1$H NMR (300 MHz, DMSO-d$_6$) δ 0.83 (t, J=7.3 Hz, 3H), 1.20–1.40 (m, 4H), 1.55–1.70 (m, 2H), 1.80–1.95 (m, 2H), 2.50–2.80 (m, 5H), 2.92 (t, J=7.6 Hz, 2H), 3.50–3.90 (m, 5H), 6.39 (d, J=8.7, 2.9 Hz, 1H), 6.57 (d, J=8.7 Hz, 1H), 6.72 (d, J=2.9 Hz, 1H), 6.90 (d, J=9.0 Hz, 2H), 7.05 (d, J=9.0 Hz, 2H), 7.40–7.60 (m, 3H), 7.74 (d, J=7.7 Hz, 2H); MS (ES) m/z: 633.1 (MH$^+$); HRMS Calcd. for C$_{30}$H$_{41}$N$_4$O$_7$S$_2$ (MH$^+$): 633.2411. Found: 633.2409.

EXAMPLE 316

N-(4-{4-[((2R)-2-Hydroxy-2-{4-hydroxy-3-[(isopropylsulfonyl)amino]phenyl}-ethyl)amino]-1-piperidineyl}phenyl)-1-butanesulfonamide The title compound was prepared from butane-1-sulfonic acid [4-(4-oxo-piperidine-1-yl)-phenyl]-amide (which was obtained in Example 228) and propane-2-sulfonic acid [5-((1R)-2-amino-1-hydroxy-ethyl)-2-hydroxy-phenyl]-amide (which was obtained in Example 27) according to the procedure of Example 278 as an off-white solid; $^1$H NMR (300 MHz, DMSO-d$_6$) δ 0.83 (t, J=7.3 Hz, 3H), 1.20–1.40 (m, 4H), 1.25 (d, J=6.8 Hz, 6H), 1.55–1.75 (m, 2H), 1.75–1.90 (m, 2H), 2.50–2.75 (m, 5H), 2.92 (t, J=7.7 Hz, 2H), 3.05–3.15 (m, 1H), 3.45–3.60 (m, 2H), 4.46 (dd, J=7.8, 4.5 Hz, 1H), 6.78 (d, J=8.2 Hz, 1H), 6.88 (d, J=9.0 Hz, 2H), 6.96 (dd, J=8.2, 2.0 Hz, 1H), 7.04 (d, J=9.0 Hz, 2H), 7.23 (d, J=2.0 Hz, 1H); MS (ES) m/z: 569.0 (MH$^+$); HRMS Calcd. for C$_{26}$H$_{41}$N$_4$O$_6$S$_2$ (MH$^+$): 569.2462. Found: 569.2458.

EXAMPLE 317

4-[(4-{4-[((2R)-2-Hydroxy-2-{4-hydroxy-3-[(methylsulfonyl)amino]phenyl}amino]-1-piperidineyl}anilino)sulfonyl]benzoic acid The title compound was prepared from 4-[4-(4-oxo-piperidine-1-yl)-phenylsulfamoyl]-benzoic acid (which was obtained in Example 233) and N-[ 5-((1R)-2-amino-1-hydroxy-ethyl)-2-hydroxy-phenyl]-methanesulfonamide (which was obtained in Example 10) according to the procedure of Example 278 as a white solid; $^1$H NMR (300 MHz, DMSO-d$_6$) δ 1.35–1.50 (m, 2H), 1.75–2.00 (m, 2H), 2.50–2.95 (m, 5H), 2.92 (s, 3H), 3.45–3.60 (m, 2H), 4.60–4.70 (m, 1H), 6.77 (d, J=9.3 Hz, 2H), 6.80–6.90 (m, 3H), 7.02 (dd, J=8.4,1.8 Hz, 1H), 7.20 (d, J=1.8 Hz, 1H), 7.60 (d, J=8.4 Hz, 2H), 7.93 (d, J=8.4 Hz, 2H); MS (ES) m/z: 603.2 (M–H)$^-$; HRMS Calcd. for C$_{27}$H$_{31}$N$_4$O$_8$S$_2$ (M–H)$^-$: 603.1588. Found: 603.1572.

EXAMPLE 318

Ethyl4-[(4-4-{((2R)-2-hydroxy-2-{4-hydroxy-3-[(methylsulfonyl)amino]phenyl}ethyl)-amino]-1-piperidineyl}anilino)sulfonyl]benzoate The title compound was prepared from 4-[4-(4-oxo-piperidine-1-yl)-phenylsulfamoyl]-benzoic acid ethyl ester (which was obtained in Example 235) and N-[5-((1R)-2-amino-1-hydroxy-ethyl)-2-hydroxy-phenyl]-methanesulfonamide (which was obtained in Example 10) according to the procedure of Example 278 as a pale yellowish solid; $^1$H NMR (300 MHz, DMSO-d$_6$) δ 1.20–1.40 (m, 2H), 1.32 (t, J=7.1 Hz, 3H), 1.75–1.90 (m, 2H), 2.50–2.70 (m, 5H), 2.91 (s, 3H), 3.40–3.55 (m, 2H), 4.32 (q, J=7.1 Hz, 2H), 4.47 (dd, J=8.1, 4.2 Hz, 1H), 6.70–6.90 (m, 5H), 6.99 (dd, J=8.3, 2.0 Hz, 1H), 7.17 (d, J=2.0 Hz, 1H), 7.79 (d, J=8.5 Hz, 2H), 8.07 (d, J=8.5 Hz, 2H); MS (ES) m/z: 633.3 (MH$^+$); HRMS Calcd. for C$_{29}$H$_{37}$N$_4$O$_8$S$_2$ (MH$^+$): 633.2047. Found: 633.2013.

EXAMPLE 319

Methyl{4-[(4-{4-[((2R)-2-{4-chloro-3-[(methylsulfonyl)amino]phenyl}-2-hydroxyethyl)amino]-1-piperidineyl}anilino)sulfonyl]phenoxy}acetate The title compound was prepared from {4-[4-(4-oxo-piperidine-1-yl)-phenylsulfamoyl]-phenoxy}-acetic acid methyl ester (which was obtained in Example 232) and N-[5-((1R)-2-azido-1-hydroxy-ethyl)-2-chloro-phenyl]-methanesulfonamide (which was obtained in Example 25) according to the procedure of Example 95 as a pale grey solid; $^1$H NMR (300 MHz, DMSO-d$_6$) δ 1.20–1.40 (m, 2H), 1.75–1.90 (m, 2H), 2.50–2.80 (m, 5H), 2.97 (s, 3H), 3.40–3.55 (m, 2H), 3.69 (s, 3H), 4.63 (dd, J=8.0, 3.8 Hz, 1H), 4.87 (s, 2H), 6.77 (d, J=9.0 Hz, 2H), 6.87 (d, J=9.0Hz, 2H), 7.03 (d, J=9.0Hz, 2H), 7.17 (dd, J=8.3, 1.7 Hz, 1H), 7.43 (d, J=8.3 Hz, 1H), 7.43 (d, J=1.7 Hz, 1H), 7.62 (d, J=9.0 Hz, 2H); MS (ES) m/z: 667.0 (MH$^+$); HRMS Calcd. for $C_{29}H36ClN_4O_8S_2$ (MH$^+$): 667.1657. Found: 667.1651.

EXAMPLE 320

Methyl3-[(4-{4-[((2R)-2-hydroxy-2-{4-hydroxy-3-[(methylsulfonyl)amino]-phenyl}ethyl)amino]-1-piperidineyl}anilino)sulfonyl]-2-thiophenecarboxylate The title compound was prepared from 3-[4-(4-oxo-piperidine-1-yl)-phenylsulfamoyl]-thiophene-2-carboxylic acid methyl ester (which was obtained in Example 234) and N-[5-((1R)-2-amino-1-hydroxy-ethyl)-2-hydroxy-phenyl]-methanesulfonamide (which was obtained in Example 10) according to the procedure of Example 278 as a pale yellowish solid; $^1$H NMR (300 MHz, DMSO-d$_6$) δ 1.20–1.40 (m, 2H), 1.70–1.90 (m, 2H), 2.50–2.75 (m, 5H), 3.40–3.55 (m, 2H), 3.89 (s, 2H), 4.46 (dd, J=8.0, 4.2 Hz, 1H), 6.75–6.85 (m, 3H), 6.90 (d, J=9.0 Hz, 2H), 7.00 (dd, J=8.3, 2.0 Hz, 1H), 7.16 (d, J=2.0 Hz, 1H), 7.32 (d, J=3.3 Hz, 1H), 7.89 (d, J=3.3 Hz, 1H); MS (ES) m/z: 624.9 (MH$^+$); HRMS Calcd. for $C_{26}H_{34}N_4O_8S_3$ (MH$^+$): 625.1455. Found: 625.1441.

EXAMPLE 321

3-[(4-{4-[((2R)-2-Hydroxy-2-{4-hydroxy-3-[(methylsulfonyl)amino]phenyl}ethyl)amino]-1-piperidineyl}anilino)sulfonyl]-2-thiophenecarboxylic acid The title compound was prepared from methyl 3-[(4-{4-[((2R)-2-hydroxy-2-{4-hydroxy-3-[(methylsulfonyl)amino]phenyl}ethyl)amino]-1-piperidineyl}anilino)sulfonyl]-2-thiophenecarboxylate (which was obtained in Example 320) by NaOH hydrolysis as a pale grey solid; $^1$H NMR (300 MHz, DMSO-d$_6$) δ 1.50–1.70 (m, 2H), 1.95–2.10 (m, 2H), 2.50–2.70 (m, 2H), 2.95 (s, 3H), 3.00–3.30 (m, 3H), 3.60–3.70 (m, 2H), 4.75–4.85 (m, 1H), 6.10 (brs, 1H), 6.80 (d, J=9.0 Hz, 2H), 6.85–6.95 (m, 3H), 7.04 (d, J=5.4 Hz, 1H), 7.08 (dd, J=8.4,1.8 Hz, 1H), 7.26 (d, J=1.8 Hz, 1H), 7.39 (d, J=5.4 Hz, 1H), 8.73 (brs, 1H), 9.96 (brs, 1H); MS (ES) m/z: 610.7 (MH$^+$); HRMS Calcd. for $C_{25}H_{31}N_4O_8S_3$ (MH$^+$): 611.1299. Found: 611.1284.

EXAMPLE 322

Benzyl[(4-{4-[((2R)-2-hydroxy-2-{4-hydroxy-3-[(methylsulfonyl)amino]phenyl}-ethyl)amino]-1-piperidineyl}anilino)sulfonyl]acetate The title compound was prepared from [4-(4-oxo-piperidine-1-yl)-phenylsulfamoyl]-acetic acid benzyl ester (which was obtained in Example 236) and N-[5-((1R)-2-amino-1-hydroxy-ethyl)-2-hydroxy-phenyl]-methanesulfonamide (which was obtained in Example 10) according to the procedure of Example 278 as a white solid; $^1$H NMR (300 MHz, DMSO-d$_6$) δ 1.20–1.40 (m, 2H), 1.70–1.95 (m, 2H), 2.50–2.75 (m, 2H), 2.92 (s, 3H), 3.50–3.60 (m, 3H), 4.13 (s, 2H), 4.48 (dd, J=8.0, 4.3 Hz, 1H), 5.15 (s, 2H), 6.82 (d, J=8.3 Hz, 1H), 6.86 (d, J=9.0 Hz, 2H), 7.00 (dd, J=8.3, 2.0 Hz, 1H), 7.06 (d, J=9.0 Hz, 2H), 7.18 (d, J=2.0 Hz, 1H), 7.30–7.40 (m, 5H); MS (ES) m/z: 633.3 (MH$^+$); HRMS Calcd. for $C_{29}H_{37}N_4O_8S_2$ (MH$^+$): 633.2047. Found: 633.2031.

EXAMPLE 323

[(4-{4-[((2R)-2-Hydroxy-2-{4-hydroxy-3-[(methylsulfonyl)amino]phenyl}ethyl)amino]-1-piperidineyl}anilino)sulfonyl]acetic acid The title compound was prepared from [4-(4-oxo-piperidine-1-yl)-phenylsulfamoyl]-acetic acid benzyl ester (which was obtained in Example 236) and N-[5-((1R)-2-amino-1-hydroxy-ethyl)-2-hydroxy-phenyl]-methanesulfonamide (which was obtained in Example 10) according to the procedure of Example 255 as an off-white solid; $^1$H NMR (300 MHz, DMSO-d$_6$) δ 1.40–1.60 (m, 2H), 1.90–2.05 (m, 2H), 2.50–2.90 (m, 5H), 2.94 (s, 3H), 3.50–3.65 (m, 2H), 4.65–4.75 (m, 1H), 6.80–6.90 (m, 3H), 7.00–7.10 (m, 3H), 7.23 (d, J=2.0 Hz, 1H); MS (ES) m/z: 543.3 (MH$^+$); HRMS Calcd. for $C_{29}H_{37}N_4O_8S_2$ (MH$^+$): 543.1578. Found: 543.1572.

EXAMPLE 324

Benzyl[(butyl-4-{4-[((2R)-2-hydroxy-2-{4-hydroxy-3-[(methylsulfonyl)amino]phenyl}-ethyl)amino]-1-piperidineyl}anilino)sulfonyl]acetate The title compound was prepared from benzyl {[butyl-4-(4-oxo-1-piperidineyl)anilino]sulfonyl}acetate (which was obtained in Example 253) and N-[5-((1R)-2-amino-1-hydroxy-ethyl)-2-hydroxy-phenyl]-methanesulfonamide (which was obtained in Example 10) according to the procedure of Example 278 as an off-white solid; $^1$H NMR (300 MHz, DMSO-d$_6$) δ 0.79 (t, J=7.2 Hz, 3H), 1.10–1.40 (m, 6H), 1.80–1.95 (m, 2H), 2.55–2.80 (m, 5H), 2.92 (s, 3H), 3.45 (t, J=7.1 Hz, 2H), 4.24 (s, 2H), 4.49 (dd, J=7.9, 4.2 Hz, 1H), 5.20 (s, 2H), 6.82 (d, J=8.2 Hz, 1H), 6.92 (d, J=9.0 Hz, 2H), 7.00 (dd, J=8.2, 2.0 Hz, 1H), 7.10–7.20 (m, 3H), 7.30–7.45 (m, 5H); MS (ES) m/z: 689.1 (MH$^+$); HRMS Calcd. for $C_{33}H_{45}N_4O_8S_2$ (MH$^+$): 689.2673. Found: 689.2679.

EXAMPLE 325

[(Butyl-4-{4-[((2R)-2-hydroxy-2-{4-hydroxy-3-[(methylsulfonyl)amino]phenyl}-ethyl)amino]-1-piperidineyl}anilino)sulfonyl]acetic acid The title compound was prepared from benzyl {[butyl-4-(4-oxo-1-piperidineyl)anilino]sulfonyl}acetate (which was obtained in Example 253) and N-[5-((1R)-2-amino-1-hydroxy-ethyl)-2-hydroxy-phenyl]-methanesulfonamide (which was obtained in Example 10) according to the procedure of Example 255 as a pale grey solid; $^1$H NMR (300 MHz, DMSO-d$_6$) δ 0.79 (t, J=7.1 Hz, 3H), 1.10–1.35 (m, 4H), 1.50–1.70 (m, 2H), 2.00–2.10 (m, 2H), 2.55–3.10 (m, 5H), 2.92 (s, 3H), 3.55–3.70 (m, 2H), 3.70–3.85 (m, 2H), 4.75–4.85 (m, 1H), 6.88 (d, J=8.3 Hz, 1H), 6.92 (d, J=9.0 Hz, 2H), 7.08 (dd, J=8.3, 2.0 Hz, 1H), 7.20–7.35 (m, 3H); MS (ES) m/z: 597.1 (M$^-$H)$^-$; HRMS Calcd. for $C_{26}H_{39}N_4O_8S_2$ (MH$^+$): 599.2204. Found: 599.2218.

EXAMPLE 326

N-(4-{4-[((2R)-2-Hydroxy-2-{4-hydroxy-3-[(methylsulfonyl)amino]phenyl}ethyl)amino]-1-piperidineyl}phenyl)-3-pyridinesulfonamide To a stirred mixture of pyridine-3-sulfonic acid-[4-(4-oxo piperidine-1-yl)-phenyl]amide (which was obtained in Example 237) (0.94 g, 2.8 mmol), N-[5-((1R)-2-amino-1-hydroxy-ethyl)-2-hydroxy-phenyl]-methanesulfonamide (which was obtained in Example 10) (0.70 g, 2.8 mmol) in dimethylformamide (10 mL) at room temperature was added sodium triacetoxyborohydride (0.72 g, 3.4 mmol) and glacial acid (0.18 mL, 3.1 mmol). The reaction was stirred under $N_2$ atmosphere for 18 hours. The reaction mixture was poured onto 1:1 water/saturated sodium bicarbonate, extracted with ethyl acetate three times, dried over sodium sulfate and concentrated. The product was purified by flash silica gel chromatography eluting with 10% methanol in methylene chloride and finally with 20% methanol in methylene chloride to give the titled compound as a yellow solid (0.23 g, 15%); $^1$H NMR (300 MHz, DMSO-$d_6$) δ 1.25–1.45 (m, 2H), 1.80–1.95 (m, 2H), 2.50–2.80 (m, 5H), 2.92 (s, 3H), 3.40–3.55 (m, 2H), 4.45–4.60 (m, 1H), 6.85–6.90 (m, 5H), 7.02 (dd, J=8.3, 2.0 Hz, 1H), 7.18 (d, J=2.0 Hz, 1H), 7.59 (dd, J=7.4, 4.4 Hz, 1H), 7.95–8.05 (m, 2H), 8.70–8.80 (m, 2H); MS (ES) m/z: 561.95 (MH+, 100%); HRMS Calcd. for $C_{25}H_{32}N_5O_6S_2$ (MH$^+$): 562.1788. Found: 562.1774.

EXAMPLE 327

3,4-Dichloro-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide The title compound was prepared according to the procedure of Example 326 as a yellow solid; $^1$H NMR (300 MHz, DMSO-$d_6$) δ 1.29–1.41 (m, 2H), 1.87–1.91 (m, 2H), 2.60–2.75 (m, 5H), 2.82–2.93 (m, 1H), 3.53–3.57 (m, 2H), 3.88–4.04 (m, 4H), 4.99 (brs, 1H), 6.55–6.63 (m, 2H), 6.79–6.89 (m, 5H), 7.55–7.60 (m, 1H), 7.81–7.95 (m, 2H), 10.58 (s, 1H), 10.70 (brs, 1H); MS (ES) m/z: 605.9 (MH$^+$); HRMS found for $C_{27}H_{29}Cl_2N_5O_5S$: 606.1323.

EXAMPLE 328

N-{4-[4-({(2S)-2-Hydroxy-3-[(2-oxo-2,3-dihydro-1H-benzimidazol-4-yl)oxy]propyl}-amino)-1-piperidineyl]phenyl}-4-(trifluoromethyl)benzenesulfonamide The title compound was prepared according to the procedure of Example 326 as a yellow solid; $^1$H NMR (300 MHz, DMSO-$d_6$) δ 1.33–1.37 (m, 2H), 1.87–1.90 (m, 2H), 2.59–2.69 (m, 4H), 2.72–2.76 (m, 1H), 2.84–2.96 (m, 1H), 3.47–3.56 (m, 2H), 3.92–4.04 (m, 4H), 5.01 (brs, 1H), 6.55–6.63 (m, 2H), 6.78–6.94 (m, 5H), 7.87 (d, J=8.4 Hz, 2H), 7.94 (d, J=8.4 Hz, 2H), 10.5 (s, 1H), 10.7 (brs, 1H); MS (ES) m/z: 606.1 (MH$^+$); HRMS found for $C_{28}H_{30}F_3N_5O_5S$: 606.1989.

EXAMPLE 329

N-{4-[4-({(2S)-2-Hydroxy-3-[(2-oxo-2,3-dihydro-1H-benzimidazol-4-yl)oxy]propyl}-amino)-1-piperidineyl]phenyl}-4-(trifluoromethoxy)benzenesulfonamide The title compound was prepared according to the procedure of Example 326 as a yellow solid; $^1$H NMR (300 MHz, DMSO-$d_6$) δ 1.32–1.36 (m, 2H), 1.86–1.90 (m, 2H), 2.58–2.73 (m, 6H), 2.81–2.89 (m, 1H), 3.51–3.55 (m, 2H), 3.91–3.96 (m, 2H), 3.99–4.04 (m, 1H), 4.95 (brs, 1H), 6.55–6.63 (m, 2H), 6.78–6.89 (m, 5H), 7.54 (d, J=8.1 Hz, 2H), 7.76–7.82 (m, 2H), 10.5 (s, 1H), 10.65 (brs, 1H); MS (ES) m/z: 622.0 (MH$^+$); HRMS found for $C_{28}H_{30}F_3N_5O_6S$: 622.1961.

EXAMPLE 330

N-{4-[4-({(2S)-2-Hydroxy-3-[(2-oxo-2,3-dihydro-1H-benzimidazol-4-yl)oxy]propyl}-amino)-1-piperidineyl]phenyl}-4-methoxybenzenesulfonamide The title compound was prepared according to the procedure of Example 326 as a grey solid; $^1$H NMR (300 MHz, DMSO-$d_6$) δ 1.23–1.36 (m, 2H), 1.84–1.88 (m, 2H), 2.57–2.73 (m, 6H), 2.76–2.82 (m, 1H), 3.48–3.52 (m, 2H), 3.79 (s, 3H), 3.87–3.95 (m, 2H), 3.99–4.04 (m, 1H), 4.90 (brs, 1H), 6.55–6.63 (m, 2H), 6.75–6.88 (m, 5H), 7.00–7.05 (m, 2H), 7.57–7.68 (m, 2H), 10.65 (s, 1H), 10.8 (brs, 1H); MS (ES) m/z: 568.1 (MH$^+$); HRMS found for $C_{28}H_{33}N_5O_6S$: 568.220.

EXAMPLE 331

4-Chloro-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide The title compound was prepared according to the procedure of Example 326 as a grey solid; $^1$H NMR (300 MHz, DMSO-$d_6$) δ 1.23–1.39 (m, 2H), 1.90–1.99 (m, 2H), 2.59–2.73 (m, 6H), 2.81–2.86 (m, 1H), 3.46–3.55 (m, 2H), 3.99–4.04 (m, 2H), 4.07–4.13 (m, 1H), 4.95 (brs, 1H), 6.55–6.62 (m, 2H), 6.67–6.92 (m, 5H), 7.59–7.68 (m, 4H), 10.6 (s, 1H), 10.7 (brs, 1H); MS (ES) m/z: 571.9 (MH$^+$); HRMS found for $C_{27}H_{30}ClN_5O_5S$: 572.1750.

EXAMPLE 332

4-Butyl-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide The title compound was prepared according to the procedure of Example 326 as an off-white solid; $^1$H NMR (300 MHz, DMSO-$d_6$) δ 0.87 (t, J=7.23 Hz, 3H), 1.22–1.35 (m, 4H), 1.47–1.58 (m, 2H), 1.86–1.90 (m, 2H), 2.60–2.65 (m, 6H), 2.71–2.72 (m, 2H), 2.73–2.85 (m, 1H), 3.49–3.53 (m, 2H), 3.91–3.99 (m, 1H), 4.01–4.12 (m, 2H), 4.95 (brs, 1H), 6.55–6.63 (m, 2H), 6.75–6.89 (m, 5H), 7.33 (d, J=8.4 Hz, 2H), 7.57 (d, J=8.4 Hz, 2H), 10.58 (s, 1H), 10.7 (brs, 1H); MS (ES) m/z: 594.1 (MH$^+$); HRMS found for $C_{31}H_{39}N_5O_5S$: 594.2674.

EXAMPLE 333

3,5-Dichloro-N-{4-[4-({(2S)-2-hydroxy-3-[(2-oxo-2,3-dihydro-1H-benzimidazol-4-yl)oxy]propyl}amino)-1-piperidineyl]phenyl}benzenesulfonamide The title compound was prepared according to the procedure of Example 326 as a tan solid; $^1$H NMR (300 MHz, DMSO-$d_6$) δ 1.29–1.40 (m, 2H), 1.87–1.91 (m, 2H), 2.61–2.75 (m, 4H), 2.84–2.88 (m, 2H), 3.46–3.58 (m, 2H), 3.92–3.97 (m, 2H), 3.99–4.04 (m, 2H), 4.99 (brs, 1H), 6.55–6.63 (m, 2H), 6.80–6.94 (m, 5H), 7.6 (d, J=1.8 Hz, 2H), 7.93 (t, J=1.8 Hz, 1H), 10.58 (s, 1H), 10.7 (brs, 1H); MS (ES) m/z: 606.0 (MH$^+$); HRMS found for $C_{27}H_{29}Cl_2N_5O_5S$: 606.1291.

EXAMPLE 334

N-{4-[4-({(2S)-2-Hydroxy-3-[(2-oxo-2,3-dihydro-1H-benzimidazol-4-yl)oxy]propyl}-amino)-1-piperidineyl]phenyl}-2,5-dimethoxybenzenesulfonamide The title compound was prepared according to the procedure of Example 326 as a yellow solid; $^1$H NMR (300 MHz, DMSO-$d_6$) δ 1.23–1.40 (m, 2H), 1.91 (m, 2H), 2.55–2.63 (m, 4H), 2.72–2.73 (m, 1H), 2.82 (m, 1H), 3.44–3.52 (m, 2H), 3.68 (s, 3H), 3.85 (s, 3H), 3.91–4.04 (m, 4H), 4.87 (brs, 1H), 6.55–6.62 (m, 2H), 6.67–6.92 (m, 5H), 7.12–7.13 (m, 3H), 10.57 (s, 1H), 10.69 (brs, 1H); MS (ES) m/z: 598.1 (MH$^+$); HRMS found for $C_{29}H_{35}N_5O_7S$: 598.2343.

EXAMPLE 335

N-(4-{4-[((2R)-2-Hydroxy-2-{4-hydroxy-3-[(methylsulfonyl)amino]phenyl}ethyl)amino]-1-piperidineyl}phenyl)-2,5-dimethoxybenzenesulfonamide The title compound was prepared according to the procedure of Example 326 as a yellow solid; $^1$H NMR (300 MHz, DMSO-d$_6$) δ 1.34–1.37 (m, 2H), 1.84–1.90 (m, 2H), 2.53–2.66 (m, 2H), 2.69–2.75 (m, 3H), 2.92 (s, 3H), 3.01–3.08 (m, 2H), 3.49–3.53 (m, 2H), 3.68 (s, 3H), 3.85 (s, 3H), 4.55–4.57 (m, 2H), 5.4 (brs, 1H), 6.53 (d, J=7.8 Hz, 2H), 6.70–6.92 (m, 3H), 6.99–7.04 (m, 2H), 7.12 (d, J=2.61 Hz, 2H), 7.19 (d, J=1.92 Hz, 1H), 9.44 (brs, 1H); MS (ES) m/z: 621.0 (MH$^+$); HRMS found for $C_{28}H_{36}N_4O_8S_2$: 621.2049.

EXAMPLE 336

Ethyl{[(4-butylphenyl)sulfonyl]-4-[4-({(2S)-2-hydroxy-3-[(2-oxo-2,3-dihydro-1H-benzimidazol-4-yl)oxy]propyl}amino)-1-piperidineyl]anilino}acetate The title compound was prepared according to the procedure of Example 326 as an off-white solid; $^1$H NMR (300 MHz, DMSO-d$_6$) δ 0.89 (1, J=7.26 Hz, 3H), 1.13 (t, J=7.11 Hz, 3H), 1.23–1.36 (m, 4H), 1.48–1.62 (m, 2H), 1.86–1.90 (m, 2H), 2.26–2.28 (m, 4H), 2.58 (m,1H), 2.63–2.71 (m, 4H), 2.74–2.79 (m, 1H), 3.60–3.71 (m, 2H), 3.88–3.96 (m, 2H), 4.00–4.13 (m, 3H), 4.39 (s, 2H), 4.90 (brs, 1H), 6.59 (q, J=7.59 Hz, 2H), 6.79–6.93 (m, 5H), 7.38 (d, J=8.31 Hz, 2H), 7.54 (d, J=8.31 Hz, 2H), 10.6 (s, 1H), 10.7 (brs, 1H); MS (ES) m/z: 680.2 (MH$^+$); HRMS found for $C_{35}H_{45}N_5O_7S$: 680.3112.

EXAMPLE 337

5-Bromo-N-[(5-bromo-2-methoxyphenyl)sulfony]-N-{4-[4-({(2S)-2-hydroxy-3-[(2-oxo-2,3-dihydro-1H-benzimidazol-4-yl)oxy]propyl}amino)-1-piperidineyl]phenyl}-2-methoxybenzenesulfonamide The title compound was prepared according to the procedure of Example 326 as a dull yellow solid; $^1$H NMR (300 MHz, DMSO-d$_6$) δ 1.23–1.35 (m, 2H), 1.90 (m, 2H), 2.27–2.28 (m, 2H), 2.57–2.73 (m, 2H), 2.79–2.86 (m, 2H), 3.49 (s, 3H), 3.71 (s, 3H), 3.91–3.96 (m, 2H), 4.01–4.06 (m, 2H), 4.13–4.15 (m, 1H), 4.91 (brs, 1H), 6.55–6.64 (m, 2H), 6.82–7.00 (m, 8H), 7.20 (d, J=9.09 Hz, 1H), 7.60 (d, J=2.55 Hz, 1H), 7.88 (dd, J=2.52 Hz, 6.39 Hz, 1H), 10.6 (s, 1H), 10.7 (brs, 1H); MS (ES) m/z: 896.0 (MH$^+$); HRMS found for $C_{35}H_{37}Br_2N_5O_9S_2$: 896.0486.

EXAMPLE 338

5-Bromo-N-{4-[4-({(2S)-2-hydroxy-3-[(2-oxo-2,3-dihydro-1H-benzimidazol-4-yl)oxy]propyl}amino)-1-piperidineyl]phenyl}-2-methoxybenzenesulfonamide The title compound was prepared according to the procedure of Example 326 as a moss green solid; $^1$H NMR (300 MHz, DMSO-d$_6$) δ 1.23–1.37 (m, 2H), 1.84–1.90 (m, 2H), 2.57–2.65 (m, 2H), 2.69–2.73 (m, 2H), 2.80–2.83 (m, 1H), 3.49–3.53 (m, 2H), 3.91 (s, 3H), 3.86–3.96 (m, 2H), 3.99–4.04 (m, 2H), 4.09–4.15 (m, 1H), 4.95 (brs, 1H), 6.55–6.63 (m, 2H), 6.75–6.91 (m, 5H), 7.17 (d, J=8.94 Hz, 1H), 7.66 (d, J=2.58 Hz, 1H), 7.73 (dd, J=2.55 Hz, 6.24 Hz, 1H), 10.55 (s, 1H), 10.65 (brs, 1H); MS (ES) m/z: 647.9 (MH$^+$); HRMS found for $C_{28}H_{32}BrN_5O_6S$: 646.1331.

EXAMPLE 339

Ethyl([(3,4-dimethoxyphenyl)sulfonyl]-4-{4-[((2R)-2-hydroxy-2-{4-hydroxy-3-[(methylsulfonyl)amino]phenyl}ethyl)amino]-1-piperidineyl}anilino)acetate The title compound was prepared according to the procedure of Example 326 as an off-white solid; $^1$H NMR (300 MHz, DMSO-d$_6$) δ 1.14 (t, J=7.08 Hz, 3H), 1.24–1.33 (m, 2H), 1.81–1.91 (m, 2H), 2.26–2.28 (m, 2H), 2.60–2.73 (m, 4H), 2.92 (s, 1H), 3.17 (s, 1H), 3.61–3.65 (m, 3H), 3.72 (s, 3H), 3.83 (m, 3H), 4.06 (q, J=7.11 Hz, 2H), 4.38 (s, 3H), 4.48–4.52 (m, 2H), 5.76 (s, 1H), 6.81–6.85 (m, 2H), 6.91–6.95 (m, 2H), 7.00 (d, J=2.01 Hz, 1H), 7.03 (d, J=2.01 Hz, 2H), 7.07 (s, 1H), 7.10 (s, 1H), 7.18 (d, J=2.01 Hz, 1H), 7.21 (d, J=2.1 Hz, 1H); MS (ES) m/z: 707.0 (MH$^+$); HRMS found for $C_{32}H_{42}N_4O_{10}S_2$: 707.2418.

EXAMPLE 340

Ethyl5-[((2S)-3-{[1-(4-{[(3,4-dimethoxyphenyl)sulfonyl]amino}phenyl)-4-piperidineyl]amino}-2-hydroxypropyl)oxy]-2-methyl-1H-indole-3-carboxylate The title compound was prepared according to the procedure of Example 326 as an off-white solid; $^1$H NMR (300 MHz, DMSO-d$_6$) δ 1.23 (m, 2H), 1.33 (t, J=7.08 Hz, 3H), 1.84–1.91 (m, 2H), 2.58–2.66 (m, 3H), 2.61 (s, 3H), 2.72–2.89 (m, 2H), 3.47–3.53 (m, 2H), 3.71 (s, 3H), 3.78 (m, 3H), 3.87–3.96 (m, 4H), 4.22 (q, J=7.08 Hz, 2H), 5.12 (brs, 3H), 6.74–6.82 (m, 3H), 6.88 (d, J=9.0 Hz, 2H), 7.02 (d, J=8.7 Hz, 1H), 7.16 (d, J=2.1 Hz, 1H), 7.20–7.27 (m, 2H), 7.43 (d, J=2.4 Hz, 1H), 9.62 (brs, 1H), 11.67 (s, 1H); MS (ES) m/z: 667.1 (MH$^+$); HRMS found for $C_{34}H_{42}N_4O_8S$: 667.2797.

EXAMPLE 341

Ethyl 4-[((2S)-3-{[1-(4-{[(3,4-dimethoxyphenyl)sulfonyl]amino}phenyl)-4-piperidineyl]amino}-2-hydroxypropyl)oxy]-2-methyl-5-phenyl-1H-pyrrole-3-carboxylate The title compound was prepared according to the procedure of Example 326 as a light grey solid; $^1$H NMR (300 MHz, DMSO-d$_6$) δ 1.27 (t, J=7.11 Hz, 3H), 1.34–1.39 (m, 2H), 1.83–1.91 (m, 2H), 2.42 (s, 3H), 2.57–2.69 (m, 4H), 2.72–2.76 (m, 1H), 2.75–2.86 (m, 2H), 3.52–3.63 (m, 2H), 3.72 (s, 3H), 3.78 (m, 3H), 3.85–3.91 (m, 2H), 4.18 (q, J=7.11 Hz, 2H), 5.76 (s, 1H), 6.79 (d, J=9.09 Hz, 2H), 6.89 (d, J=9.03 Hz, 2H), 7.03 (d, J=8.52 Hz, 1H), 7.13–7.24 (m, 3H), 7.29–7.38 (m, 2H), 7.76 (d, J=7.47 Hz, 2H), 9.59 (brs, 1H), 11.3 (s, 1H); MS (ES) m/z: 693.1 (MH$^+$); HRMS found for $C_{36}H_{44}N_4O_8S$: 693.2953.

EXAMPLE 342

Benzyl((butylsulfonyl)-4-{4-[((2R)-2-hydroxy-2-{4-hydroxy-3-[(methylsulfonyl)-[amino]phenyl}ethyl)amino]-1-piperidineyl}anilino)acetate The title compound was prepared according to the procedure of Example 326 as an off-white solid; $^1$H NMR (300

MHz, DMSO-d$_6$) δ 0.85 (t, J=7.35 Hz, 3H), 1.14–1.40 (m, 4H), 1.58–1.69 (m, 4H), 1.83–1.91 (m, 2H), 2.60–2.78 (m, 8H), 2.92 (s, 3H), 3.05–3.17 (m, 2H), 3.63–3.67 (m, 2H), 4.49 (s, 3H), 5.12 (s, 2H), 5.25 (brs, 1H), 6.83 (d, J=8.22 Hz, 1H), 6.90 (d, J=9.06 Hz, 2H), 7.01 (dd, J=1.95 Hz, 8.31 Hz, 2H), 7.18 (d, J=1.95 Hz, 1H), 7.23 (d, J=8.97 Hz, 2H), 7.22–7.39 (m, 4H); MS (ES) m/z: 689.1 (MH$^+$); HRMS found for C$_{33}$H$_{44}$N$_4$O$_8$S$_2$: 689.2669.

EXAMPLE 343

((Butvlsulfonyl)-4-{4-[((2R)-2-hydroxy-2-{4-hydroxy-3-[(methylsulfonyl)-amino]phenyl}ethyl)amino]-1-piperidineyl}anilino)acetic acid A mixture of 0.18 g of [(butane-1-sulfonyl)-(4-{4-[(2R)-2-hydroxy-2-(4-hydroxy-3-methanesulfonylamino-phenyl)-ethylamino]-piperidine-1-yl}-phenyl)-amino]-acetic acid benzyl ester (which was obtained in Example 342) and 0.05 g of 10% palladium on carbon in 15 mL of methanol was shaken on a Parr hydrogenator at 25 psi overnight. The mixture was filtered through a pad of celite and the filtrate was concentrated in vacuo, which afforded a beige solid; $^1$H NMR (300 MHz, DMSO-d$_6$) δ 0.86 (t, J=7.23 Hz, 3H), 1.29–1.41 (m, 2H), 1.48–1.51 (m, 2H), 1.54–1.73 (m, 2H), 1.92–2.09 (m, 2H), 2.57–2.64 (m, 2H), 2.79–2.87 (m, 2H), 2.94 (s, 3H), 3.00–3.07 (m, 4H), 3.16 (s, 2H), 3.20–3.26 (m, 2H), 3.64–3.75 (m, 2H), 4.02–4.04 (m, 2H), 4.77–4.81 (m,1H), 6.84–6.91 (m, 3H), 7.06 (dd, J=2.1 Hz, 8.4 Hz, 2H), 7.23 (d, J=1.8 Hz,1H), 7.34 (d, J=9.00 Hz, 2H); MS (ES) m/z: 599.0 (MH$^+$); HRMS found for C$_{26}$H$_{38}$N$_4$O$_8$S$_2$: 599.2202.

EXAMPLE 344

([(3,4-Dimethoxyphenyl)sulfonyl]-4-{4-[((2R)-2-hydroxy-2-{4-hydroxy-3-[(methylsulfonyl)amino]phenyl}ethyl)amino]-1-piperidineyl}anilino)acetic acid The title compound was prepared according to the procedure of Example 255 as a grey solid; $^1$H NMR (300 MHz, DMSO-d$_6$) δ 1.48–1.70 (m, 4H), 2.02–2.10 (m, 2H), 2.61–2.73 (s, 2H), 2.95 (s, 3H), 3.05–3.09 (m, 1H), 3.17 (s, 2H), 3.73 (s, 3H), 3.79 (m, 2H), 3.83 (s, 3H), 4.11 (brs, 1H), 4.26 (s, 1H), 4.81–4.84 (m, 1H), 6.19 (brs, 1H), 6.84–6.87 (m, 3H), 6.89 (s, 1H), 6.97 (d, J=9.0 Hz, 2H), 7.04–7.10 (m, 2H), 7.20 (dd, J=2.1 Hz, 8.4 Hz, 1H), 7.25 (d, J=2.1 Hz, 1H), 8.79 (brs, 1H), 10.17 (brs, 1H); MS (ES) m/z: 679.0 (MH$^+$); HRMS found for C$_{30}$H$_{38}$N$_4$O$_{10}$S$_2$: 679.2126.

EXAMPLE 345

Ethyl ((butylsulfonyl)-4-{4-[((2R)-2-hydroxy-2-{4-hydroxy-3-[(methylsulfonyl)amino]-phenyl}ethyl)amino]-1-piperidineyl}anilino)acetate The title compound was prepared according to the procedure of Example 326 as a yellow solid; $^1$H NMR (300 MHz, DMSO-d$_6$) δ 0.87 (t, J=7.29 Hz, 3H), 1.14–1.20 (m, 4H), 1.30–1.43 (m, 4H), 1.60–1.70 (m, 2H), 1.84–1.91 (m, 2H), 2.60–2.78 (m, 6H), 3.11–3.16 (m, 2H), 3.32 (brs, 4H), 3.63–3.68 (m, 2H), 3.95–4.14 (m, 2H), 4.38 (s, 2H), 4.48–4.53 (m, 1H), 5.3 (brs, 1H), 6.82 (d, J=8.4Hz, 1H), 6.91 (d, J=9.3 Hz, 2H), 7.01 (dd, J=1.8 Hz, 8.1 Hz, 1H), 7.18 (d, J=2.1 Hz, 1H), 7.25 (d, J=9.0 Hz, 2H); MS (ES) m/z: 627.3 (MH$^+$); HRMS found for C$_{28}$H$_{42}$N$_4$O$_8$S$_2$: 627.2503.

EXAMPLE 346

4-{[3-Chloro-5-(trifluoromethyl)-2-pyridinyl]oxy]-N-[4-(4-{[(2S)-2-hydroxy-3-phenoxypropyl]amino}-1-piperidineyl)phenyl]benzenesulfonamide Example 346 illustrated a solution phase combinatorial methodology for preparing compounds of the present invention in matrix fashion. A 3×3 grid of 20 mL Teflon lined screw cap vials was arranged. To each vial was added the amino ketone, the solvents, and the base, then one sulfonyl chloride per row, one arylethanolamine or aryloxypropanolamine per column, was added according to the following detailed procedure: To a suspension of 1-(4-aminophenyl)-4-piperidone hydrochloride (which was obtained in Example 224) (79 mg, 0.3 mmol) in 10 mL of THF/CH$_2$Cl$_2$ (1:1) was added 4-(3-chloro-5-trifluoromethyl-2-pyridyloxy)benzenesulfonyl chloride (167 mg,0.45 mmol), triethylamine (0.1 mL), and (piperidineomethyl)polystyrene (462 mg, 2.6 mmol/g). The mixture was shaken for 1 day. Aminomethylated polystyrene resin (95 mg, 2.6 mmol/g) was added to the reaction along with 1 mL of CH$_2$Cl$_2$ and the reaction was continued for another day. The resins were removed by filtration and washed with CH$_2$Cl$_2$ (3×1 mL). The filtrate and washings were combined and concentrated to give 4-(3-chloro-5-trifluoromethyl-2-pyridyloxy)-N-[4-(4-oxo-piperidine-1-yl)-phenyl]-benzenesulfonamide which was redissolved in 10 mL of trimethyl orthoformate/methanol (1:1). To the solution was added (2S)-1-amino-3-phenoxy-propan-2-ol (75 mg, 0.45 mmol). The mixture was shaken for 18 hours and then Amberlite IRA-400 borohydride resin (360 mg, 2.5 mmol/g) was added to the mixture and reaction was continued for 5 hours. To the mixture was then added formylpolystyrene (1 g, 0.5 mmol/g) and 1 mL of CH$_2$Cl$_2$. The reaction was continued for 18 hours. The resins were removed by filtration and washing extensively with methanol and CH$_2$Cl$_2$. The filtrate and washings were combined and concentrated. The residue was purified by thin layer chromatography (12% MeOH/CH$_2$Cl$_2$) to give the title compound as a white solid; $^1$H NMR (300 MHz, DMSO-d$_6$) δ 1.20–1.40 (m, 2H), 1.70–1.90 (m, 2H), 2.50–2.80 (m, 5H), 3.45–3.60 (m, 2H), 3.80–4.00 (m, 3H), 4.95 (brs, 1H), 5.24 (brs, 1H), 6.81 (d, J=9.0 Hz, 2H), 6.88 (d, J=9.0 Hz, 2H), 6.85–7.00 (m, 3H), 7.25–7.35 (m, 2H), 7.41 (d, J=9.0 Hz, 2H), 7.75 (d, J=9.0 Hz, 2H), 8.53 (d, J=2.0 Hz, 1H), 8.62 (d, J=2.0 Hz, 1H); MS (ES) m/z: 677.0 (MH$^+$); HRMS Calcd. for C$_{32}$H$_{33}$F$_3$N$_4$O$_5$SCl (MH$^+$): 677.1812. Found: 677.1816. Anal. Calcd. for C$_{32}$H$_{32}$F$_3$N$_4$O$_5$SCl: C, 56.70; H, 4.76; N, 8.27. Found: C, 56.58; H, 4.90; N, 8.03.

EXAMPLE 347

N-{[5-({4-[4-({(2S)-2-Hydroxy-3-[(2-oxo-2,3-dihydro-1H-benzimidazol-4-yl)oxy]propyl}amino)-1-piperidineyl]anilino}sulfonyl)-2-thienyl]methyl}benzamide The title compound was prepared from 1-(4-aminophenyl)-4-piperidone hydrochloride (which was obtained in Example 224), (2-benzoylaminomethyl)thiophene-5-sulphonyl chloride, and (S)-4-[2-hydroxy-3-aminopropoxy]-1,3-dihydro-2H-benzimidazol-2-one (U.S. Pat. No. 5,786,356/1998) according to the procedure of Example 346; MS (ES) m/z: 677.4 (MH$^+$).

EXAMPLE 348

N-[(5-{[4-(4-[(2S)-2-Hydroxy-3-phenoxypropyl]amino}-1-piperidineyl)anilino]sulfonyl}-2-thienyl)methyl]benzamide The title compound was prepared from 1-(4-aminophenyl)-4-piperidone hydrochloride (which was obtained in Example 224), (2-benzoylaminomethyl)thiophene-5-sulphonyl chloride, and (2S)-1-amino-3-phenoxy-propan-2-ol according to the procedure of Example 346; MS (ES) m/z: 621.4 (MH$^+$).

EXAMPLE 349

N-[(5-{[4-(4-{[2-Hydroxy-2-(3-hydroxyphenyl)ethyl]amino}-1-piperidineyl)-anilino]sulfonyl}-2-thienyl)methyl]benzamide The title compound was prepared from 1-(4-aminophenyl)-4-piperidone hydrochloride (which was obtained in Example 224), (2-benzoylaminomethyl)thiophene-5-sulphonyl chloride, and DL-norphenylephrine according to the procedure of Example 346; MS (ES) m/z: 607.4 (MH$^+$).

EXAMPLE 350

4-{[3-Chloro-5-(trifluoromethyl)-2-pyridinyl]oxy}-N-{4-[4-({(2S)-2-hydroxy-3-[(2-oxo-2,3-dihydro-1H-benzimidazol-4-yl)oxy]propyl}amino)-1-piperidineyl]phenyl}-benzenesulfonamide The title compound was prepared from 1-(4-aminophenyl)-4-piperidone hydrochloride (which was obtained in Example 224), 4-(3-chloro-5-trifluoromethyl-2-pyridyloxy)benzenesulfonyl chloride, and (S)-4-[2-hydroxy-3-aminopropoxy]-1,3-dihydro-2H-benzimidazol-2-one (U.S. Pat. No. 5,786,356/1998) according to the procedure of Example 346; MS (ES) m/z: 733.3 (MH$^+$).

EXAMPLE 351

4-{[3-Chloro-5-(trifluoromethyl)-2-pyridinyl]oxy}-N-[4-(4-{[2-hydroxy-2-(3-hydroxyphenyl)ethyl]amino}-1-piperidineyl)phenyl]benzenesulfonamide The title compound was prepared from 1-(4-aminophenyl)-4-piperidone hydrochloride (which was obtained in Example 224), 4-(3-chloro-5-trifluoromethyl-2-pyridyloxy)benzenesulfonyl chloride, and DL-norphenylephrine according to the procedure of Example 346; MS (ES) m/z: 663.2 (MH$^+$).

EXAMPLE 352

3,5-Dichloro-4-(2-chloro-4-nitrophenoxy)-N-{4-[4-({(2S)-2-hydroxy-3-[(2-oxo-2,3-dihydro-1H-benzimidazol-4-yl)oxy]propyl}amino)-1-piperidineyl]phenyl}-benzenesulfonamide The title compound was prepared from 1-(4-aminophenyl)-4-piperidone hydrochloride (which was obtained in Example 224), 4-(2-chloro-4-nitrophenoxy)-3,5-dichlorobenzenesulfonyl chloride, and (S)-4-[2-hydroxy-3-aminopropoxy]-1,3-dihydro-2H-benzimidazol-2-one (U.S. Pat. No. 5,786,356/1998) according to the procedure of Example 346; MS (ES) m/z: 777.2, 779.2 (MH$^+$).

EXAMPLE 353

3,5-Dichloro-4-(2-chloro-4-nitrophenoxy)-N-[4-(4-{[(2S)-2-hydroxy-3-phenoxypropyl]amino}-1-piperidineyl)phenyl]benzenesultonamide The title compound was prepared from 1-(4-aminophenyl)-4-piperidone hydrochloride (which was obtained in Example 224), 4-(2-chloro-4-nitrophenoxy)-3,5-dichlorobenzenesulfonyl chloride, and (2S)-1-amino-3-phenoxy-propan-2-ol according to the procedure of Example 346; MS (ES) m/z: 723.2, 725.2 (MH$^+$).

EXAMPLE 354

3,5-Dichloro-4-(2-chloro-4-nitrophenoxy)-N-[4-(4-{[2-hydroxy-2-(3-hydroxyphenyl)-ethyl]amino}-1-piperidineyl)phenyl]benzenesulfonamide The title compound was prepared from 1-(4-aminophenyl)-4-piperidone hydrochloride (which was obtained in Example 224), 4-(2-chloro-4-nitrophenoxy)-3,5-dichlorobenzenesulfonyl chloride, and DL-norphenylephrine according to the procedure of Example 346; MS (ES) m/z: 709.1, 711.1 (MH$^+$).

EXAMPLE 355

N-[4-(4-{[(2S)-2-Hydroxy-3-phenoxypropyl]amino}-1-piperidineyl)phenyl]-2-thiophenesulfonamide The title compound was prepared according to the procedure of Example 346 as an off-white solid; $^1$H NMR (300 MHz, DMSO-d$_6$) δ 0.81–0.83 (m, 1H), 1.23–1.36 (m, 3H), 1.84–1.88 (m, 2H), 2.61–2.73 (m, 4H), 3.53 (d, J=12.03 Hz, 3H), 3.95–4.04 (m, 2H), 5.02 (brs, 1H), 6.80 (d, J=9.09 Hz, 1H), 6.89–6.94 (m, 6H), 7.08–7.11 (m, 2H), 7.24–7.30 (m, 1H), 7.40 (dd, J=1.29 Hz, 5.01 Hz, 1H), 7.86 (dd, J=1.29 Hz, 3.69 Hz, 1H); MS (ES) m/z: 488.0 (MH$^+$); HRMS found for C$_{24}$H$_{29}$N$_3$O$_4$S$_2$: 488.1691.

EXAMPLE 356

4-Butoxy-N-[4-(4-{[(2S)-2-hydroxy-3-phenoxypropyl]amino}-1-piperidineyl)-phenyl]benzenesulfonamide The title compound was prepared according to the procedure of Example 346 as an off-white solid; $^1$H NMR (300 MHz, DMSO-d$_6$) δ 0.91 (t, J=7.32 Hz, 3H), 1.24–1.35 (m, 2H), 1.39–1.50 (m, 2H), 1.63–1.72 (m, 2H), 1.82–1.91 (m, 2H), 2.57–2.65 (m, 4H), 2.69–2.72 (m, 2H), 3.13–3.19 (m, 1H), 3.46–3.52 (m, 2H), 3.83–3.90 (m, 2H), 3.92–4.01 (m, 2H), 4.98 (brs, 1H), 5.21–5.25 (m, 1H), 6.76 (d, J=9.09 Hz, 2H), 6.85–6.95 (m, 2H), 7.01 (d, J=8.94 Hz, 2H), 7.24–7.31 (m, 4H), 7.57 (d, J=8.88 Hz, 2H), 8.04 (s, 1H); MS (ES) m/z: 554.5 (MH$^+$); HRMS found for C$_{30}$H$_{39}$N$_3$O$_5$S: 554.2685.

EXAMPLE 357

N-4-(4-{[(2S)-2-Hydroxy-2-(3-hydroxyphenyl)ethyl]amino}-1-piperidineyl)phenyl]-2-thiophenesulfonamide The title compound was prepared according to the procedure of Example 346 as a light green solid; $^1$H NMR (300 MHz, DMSO-d$_6$) δ 0.81–0.90 (m, 1H), 1.24–1.35 (m, 2H), 1.87–1.91 (m, 2H), 2.59–2.73 (m, 4H), 3.40–3.47 (m, 2H), 3.53–3.57 (m, 2H), 4.53 (brs, 2H), 5.31 (brs, 1H), 6.62 (d, J=7.68 Hz, 1H), 6.75 (d, J=8.64 Hz, 1H), 6.82 (d, J=9.09 Hz, 3H), 6.92 (d, J=8.97 Hz, 1H), 7.07–7.12 (m, 2H), 7.41 (dd, J=1.26 Hz, 3.75 Hz, 1H), 7.86 (dd, J=1.14 Hz, 4.92 Hz, 1H), 9.29 (s, 1H); MS (ES) m/z: 474.0 (MH$^+$); HRMS found for C$_{23}$H$_{27}$N$_3$O$_4$S$_2$: 474.1522.

EXAMPLE 358

4-Butoxy-N-{4-[4-({(2S)-2-hydroxy-3-[(2-oxo-2,3-dihVdro-1H-benzimidazol-4-yl)oxy]propyl}amino)-1-piperidineyl]phenyl}benzenesulfonamide The title compound was prepared according to the procedure of Example 346 as a brownish solid; $^1$H NMR (300 MHz, DMSO-d$_6$) δ 0.89–0.95 (m, 3H), 1.35–1.49 (m, 2H), 1.64–1.73 (m, 2H), 1.90–2.02 (m, 1H), 2.58–2.62 (m, 1H), 2.90–3.05 (m, 1H), 3.13–3.16 (m, 1H), 3.62–3.66 (brd, 1H), 3.89–4.06 (m, 2H), 5.06–5.08 (d, J=4.86 Hz, 1H), 5.48 (brs, 1H), 6.56–6.70 (m, 3H), 6.79–6.91 (m, 8H), 7.01–7.04 (d, J=8.91 Hz, 2H), 7.46–7.54 (m, 2H), 7.57–7.60 (dd, J=1.83 Hz, 8.88 Hz, 2H) 8.04 (s, 1H), 8.16 (s, 1H), 9.66 (brs, 1H), 10.55–10.65 (m, 2H), 10.7 (s, 1H); MS (ES) m/z: 610.4 (MH$^+$); HRMS found for $C_{31}H_{39}N_5O_6S$: 610.2707.

EXAMPLE 359

N-{4-[4-({(2S)-2-Hydroxy-3-[(2-oxo-2,3-dihydro-1H-benzimidazol-4-yl)oxy]-propyl}amino)-1-piperidinyl]phenyl}-3,4-dimethoxybenzenesulfonamide The title compound was prepared according to the procedure of Example 346 as a gray solid; $^1$H NMR (300 MHz, DMSO-d$_6$) δ 1.49–1.55 (m, 2H), 1.99–2.17 (m, 2H), 2.58–2.65 (m, 2H), 2.85–2.98 (m, 2H), 3.07–3.09 (m, 2H), 3.59–3.63 (m, 2H), 3.72 (s, 3H), 3.78 (s, 3H), 4.01 (s, 3H), 5.35 (brs, 1H), 6.57–6.64 (m, 2H), 6.79–6.92 (m, 5H), 7.018–7.046 (d, J=8.4 Hz, 1H), 7.18–7.25 (m, 2H), 8.18 (s, 1H), 9.62 (brs, 1H), 10.61 (s, 1H), 10.72 (s, 1H); MS (ES) m/z: 598.1 (MH$^+$); HRMS found for $C_{29}H_{35}N_5O_7S$: 598.2348.

EXAMPLE 360

N-[4-(4-{[(2S)-2-Hydroxy-3-phenoxypropyl]amino}-1-piperidinyl)phenyl]-3,4-dimethoxybenzenesulfonamide The title compound was prepared according to the procedure of Example 346 as an off-white solid; $^1$H NMR (300 MHz, DMSO-d$_6$) δ 0.85–0.90 (m, 1H), 1.24–1.51 (m, 2H), 1.82–1.90 (m, 2H), 2.58–2.70 (m, 4H), 3.48–3.52 (m, 2H), 3.71 (s, 3H), 3.78 (s, 3H), 3.84–3.92 (m, 2H), 4.99 (brs, 1H), 5.23–5.25 (m, 1H), 6.76 (s, 1H), 6.79 (s, 1H), 6.86–6.94 (m, 2H), 7.01 (s, 1H), 7.04 (s, 1H), 7.16 (d, J=2.13 Hz, 2H), 7.20–7.21 (d, J=2.1 Hz, 1H), 7.23–7.24 (m, 1H), 7.26–7.29 (m, 2H), 7.66–7.72 (m, 1H), 8.08 (s, 1H), 9.56 (brs, 1H); MS (ES) m/z: 542.1 (MH$^+$); HRMS found for $C_{28}H_{35}N_3O_6S$: 542.2330.

EXAMPLE 361

N-[4-(4-{[2-Hydroxy-2-(3-hydroxyphenyl)ethyl]amino}-1-piperidinyl)phenyl]-3,4-dimethoxybenzenesulfonamide The title compound was prepared according to the procedure of Example 346 as an off-white solid; $^1$H NMR (300 MHz, DMSO-d$_6$) δ 1.35–1.40 (m, 2H), 1.64 (m, 1H), 1.85–1.95 (m, 2H), 2.72–2.73 (m, 2H), 2.80 (m, 2H), 3.52–3.57 (m, 2H), 3.71 (s, 3H), 3.78 (s, 3H), 4.58 (m, 1H), 5.55 (brs, 1H), 6.62–6.65 (m, 1H), 6.74–6.81 (m, 3H), 6.89 (d, J=9.0 Hz, 1H), 7.01 (s, 1H), 7.04 (s, 1H), 7.08–7.14 (m, 1H), 7.17 (d, J=8.01 Hz, 1H), 7.21 (d, J=2.13 Hz, 1H), 7.24 (d, J=2.07 Hz, 1H), 9.34 (s, 1H), 9.55 (brs, 1H); MS (ES) m/z: 528.1 (MH$^+$); HRMS found for $C_{27}H_{33}N_3O_6S$: 528.2160.

EXAMPLE 362

N-{4-[4-({(2S)-2-Hydroxy-3-[(2-oxo-2,3-dihydro-1H-benzimidazol-4-yl)oxy]propyl}-amino)-1-piperidinyl]phenyl}-2-thiophenesulfonamide The title compound was prepared according to the procedure of Example 346 as a greenish solid; $^1$H NMR (300 MHz, DMSO-d$_6$) δ 1.38 (m, 2H), 1.91 (m, 2H), 2.64 (t, 2H), 2.75 (m, 2H), 2.85 (m, 2H), 3.15 (d, 1H), 3.55 (m, 2H), 3.93–3.96 (m, 2H), 5.05 (brs, 1H), 6.57 (d, J=5.7 Hz, 1H), 6.61 (d, J=6.3 Hz, 1H), 6.81–6.87 (m, 2H), 6.92 (d, J=6.9 Hz, 1H), 7.10 (t, J=3.6 Hz, 1H), 7.41 (d, J=2.1 Hz, 1H), 7.86 (d, J=3.6 Hz, 1H), 10.6 (s, 1H), 10.7 (s, 1H); MS (ES) m/z: 544.0 (MH$^+$); HRMS found for $C_{25}H_{29}N_5O_5S_2$: 544.1709.

EXAMPLE 363

Ethyl 3-oxo-3-[4-(4-oxo-1-piperidinyl)anilino]propanoate

To a stirred solution, under N$_2$ atmosphere, of 1-(4-amino-phenyl)-piperidine-4-one hydrochloride (which was obtained in Example 224) (10.0 g, 38 mmol), and triethylamine (15.35 g, 150 mmol) in methylene chloride (100 mL) was added ethyl 3-chloro-3-oxopropionate (6.32 g, 42 mmol). The reaction was stirred for 18 hours. The reaction mixture was concentrated down in vaco and purified by flash silica gel chromatography eluting with 1:1 ethyl acetate / hexanes to give an orange solid (0.86 g, 7%); $^1$H NMR (300 MHz, CDCl$_3$) δ 1.32 (t, J=7.2 Hz, 3H), 2.55 (t, J=6 Hz, 4H), 3.46 (s, 2H), 3.56 (t, J=6 Hz, 4H), 4.22 (q, J=7.2 Hz, 2H), 6.93 (d, J=9.0 Hz, 2H), 7.47 (d, J=9.0 Hz, 2H), 9.09 (s, 1H); MS (ES) m/z: 305.3 (MH$^+$, 100%).

EXAMPLE 364

Ethyl 3-[butyl-4-(4-oxo-1-piperidinyl)anilino]-3-oxopropanoate

A solution of 8-(4-nitro-phenyl)-1,4-dioxa-8-aza-spiro[4.5]decane (13.01 g, 49 mmol) was hydrogenated under 45 psi for one hour using 10% palladium on carbon (2.5 g) as catalyst. The reaction mixture was filtered through celite pad and the filtrate was concentrated down to give a white solid (11.46 g, 100%). This material was taken onto next step immediately. To a stirred mixture, under N$_2$ atmosphere, of the aniline (11.46 g, 49 mmol), butryaldehyde (4.43 mL, 49 mmol) in tetrahydrofuran (250 mL) was added sodium triacetoxyborohydride (14.62 g, 68.6 mmol), and glacial acetic acid (2.82 mL, 49 mmol). The reaction was stirred for two hours. The reaction was quenched with 1N NaOH (50 mL), diluted with water, extracted with ether 3 times and dried over sodium sulfate. The product was purified by flash silica gel chromatography eluting with 1:1 ethyl acetate/hexanes to give an oil (5.80 g, 41%). This material was immediately taken onto next step. A solution of the N-butyl aniline (5.80 g, 19.9 mmol) in a 1:1 mixture of perchloric acid and hydrochloric acid (100 mL) was stirred at room temperature for three days. The reaction mixture was poured onto ice and made basic with concentracted ammonium hydroxide, extracted with ether four times, dried over sodium sulfate and concentrated to give a yellow oil. The yellowish oil was purified by flash silica gel chromatography eluting with 1:1 ethyl acetate/hexanes to give 1-[4-(butylamino)phenyl]-4-piperidineone as an oil (3.84 g, 82%). To a stirred mixture of 1-[4-(butylamino)phenyl]-4-piperidineone (2.46 g, 10 mmol), triethylamine (1.81 mL, 13 mmol), and 4-(dimethylamino)pyridine (DMAP) (catalytic amount) was added ethyl 3-chloro-3-oxopropionate (2.18 g, 13 mmol) dropwise. The reaction was stirred for 18 hours. The reaction mixture was filtered, concentrated in vacuo, taken up in methylene chloride, and washed with saturated sodium bicarbonate two times and dried over sodium sulfate. The product was purified by flash silica gel chromatography eluting with 1:1 ethyl acetate/hexanes to give a yellow oil (3.84 g, 68%); MS (ES) m/z: 361.3 (MH$^+$, 100%).

EXAMPLE 365

3-[Cyclohexyl-4-(4-oxo-1-piperidinyl)anilino]-3-oxopropanoic acid

A solution of 8-(4-nitro-phenyl)-1,4-dioxa-8-aza-spiro[4.5]decane (13.01 g, 49 mmol) was hydrogenated under 45 psi for one hour using 10% palladium on carbon (2.5 g) as catalyst. The reaction mixture was filtered through celite pad and the filtrate was concentrated down to give a white solid (11.46 g, 100%). This material was taken onto next step immediately. To a stirred mixture, under $N_2$ atmosphere, of the aniline (10.99 g, 47 mmol), cyclohexanone (4.90 mL, 47 mmol) in tetrahydrofuran (250 mL) was added sodium triacetoxyborohydride (14.05 g, 66 mmol), and glacial acetic acid (2.71 mL, 47 mmol). The reaction was stirred for one hour. The reaction was quenched with 1N NaOH (50 mL), diluted with water, extracted with ether 3 times and dried over sodium sulfate. The product was isolated as an oil (14.85 g, 100%). This material was immediately taken onto next step without further purification. A solution of N-cyclohexyl aniline (14.85 g, 47 mmol) in hydrochloric acid (100 mL) was stirred at room temperature for 18 hours. The reaction mixture was poured onto ice and made basic with concentrated ammonium hydroxide, extracted with ether four times, dried over sodium sulfate and concentrated to give a yellow oil. The product was used without further purification (12.78 g, 100%). To a stirred mixture of the ketone (12.78 g, 47 mmol), triethylamine (8.49 mL, 61 mmol), and DMAP (catalytic amount) was added ethyl 3-chloro-3-oxopropionate (9.19 g, 61 mmol) dropwise. The reaction was stirred for 18 hours. The reaction mixture was filtered and concentrated in vacuo to give an oil (3.48 g, 19%).

To a stirred solution of 1N sodium hydroxide (6 mL) was added the oil (3.11 g, 8.1 mmol). The reaction was stirred for 18 hours. The reaction mixture was brought to a pH of 6 with acetic acid, extracted with ethyl acetate, and dried over sodium sulfate. The product was purified by flash chromatography on reverse phase silica gel eluting 70:30 methanol/water to give a yellow solid (1.36 g, 47%). MS (ES) m/z: 359.2 (MH+, 100%); HRMS Calcd. for $C_{20}H_{26}N_2O_4$ (2M−H)$^-$: 715.3711. Found: 715.3707.

EXAMPLE 366

{3-[4-(4-Oxo-piperidine-1-yl)-phenyl]-ureido}-acetic acid ethyl ester

Isocyanatoacetate (1.76 g, 13.6 mmol) in 10 mL of methylene chloride was added dropwise to a stirred solution of 1-(4-amino-phenyl)-piperidine-4-one (2,60 g, 13.6 mmol) (which was obtained in Example 224) in 100 mL of methylene chloride at room temperature. After stirring for 3 hours the solvent was removed and the residue was washed with hexanes to give the title compound as a pale brown solid (2.0 g, 46%); $^1$H NMR (300 MHz, DMSO-d$_6$) δ 1.20 (t, J=7.1 Hz, 3H), 2.41 (t, J=6.0 Hz, 4H), 3.48 (t, J=6.0 Hz, 4H), 3.83 (d, J=5.8 Hz, 2H); 4.10 (q, J=7.1 Hz, 2H), 6.31 (t, J=5.8 Hz, 2H), 6.94 (d, J=9.0 Hz, 2H), 7.26 (d, J=9.0 Hz, 1H), 8.52 (s, 1H); MS (ES) m/z: 320.5 (MH$^+$); HRMS Calcd. for $C_{20}H_{28}N_2O_4$ (M$^+$): 319.1532. Found: 319.1540.

EXAMPLE 367

Ethyl ({[butyl-4-(4-oxo-1-piperidineyl)anilino]carbonyl}amino)acetate

The title compound was prepared from ethyl isocyanatoacetate and 1-[4-(butylamino)phenyl]-4-piperidineone (which was obtained in Example 364) according to the procedure of Example 366 as a pale brown solid; MS (ES) m/z: 376.5 (MH$^+$).

EXAMPLE 368

N-[4-(4-Oxo-piperidine-1-yl)-phenyl]-butyramide

Butyryl chloride (0.3 lmL, 2.94 mmol) was added to a solution of N-[4-(4-oxo-piperidine-1-yl)-phenyl]amine (which was obtained in Example 224) (0.70 g, 2.77 mmol) and triethylamine (1.9 mL, 13.9 mmol) in anhydrous methylene chloride (10 mL). The reaction was stirred overnight. The reaction was quenched with water (50 mL) and washed with methylene chloride (3×20 mL). The organic extracts were combined, dried (sodium sulfate) and concentrated. The desired product was isolated using silica gel flash chromatography to give the title compound as a yellow solid (0.41 g); $^1$H NMR (300 MHz, CDCl$_3$) δ 1.01 (t, 3H, J=7.38 Hz), 1.72 (m, 2H), 2.29 (t, 2H, J=7.62 Hz), 2.55 (t, 4H, J=6.03 Hz), 3.55 (t, 4H, J=5.97 Hz), 6.95 (d, 2H, J=7.91), 7.42 (d, 2H, J=8.97 Hz). MS (ES) m/z: 260.9 (MH$^+$); HRMS found for $C_{15}H_{20}N_2O_2$: 260.1511. Anal. Calcd. for C, 69.20; H, 7.74, N, 10.76. Found: C, 69.03; H, 7.94; N, 10.59.

EXAMPLE 369

3,4-Dimethoxy-N-[4-(4-oxo-piperidine-1-yl)-phenyl]-benzamide

The title compound was prepared according to the procedure of Example 368 as an off-white solid; $^1$H NMR (300 MHz, CDCl$_3$) δ 2.42 (t, 4H, J=5.94 Hz), 3.56 (t, 4H, J=6.03 Hz), 3.81 (s, 3H), 3.84 (s, 3H), 7.05 (m, 3H), 7.52 (d, 1H, 2.10 Hz), 7.62 (m, 3H), 9.97 (s, 1H). MS (ES) m/z: 355.0 (MH$^+$); HRMS found for $C_{20}H_{22}N_2O_4$: 354.1577.

EXAMPLE 370

2-Chloro-N-[4-(4-oxo-piperidine-1-yl)-phenyl]-acetamide

The title compound was prepared according to the procedure of Example 368 as a dark blue solid; $^1$H NMR (300 MHz, CDCl$_3$) δ 2.55 (t, 4H, J=5.88 Hz), 3.58 (t, 4H, J=5.91 Hz), 4.19 (s, 2H), 6.97 (d, 2H, J=8.67 Hz), 7.47 (d, 2H, 8.94 Hz), 8.17 (brs, 1H). MS (ES) m/z: 266.8 (MH$^+$); HRMS found for $C_{13}H_{15}N_2O_2$: 266.0805.

EXAMPLE 371

Ethyl 3-(4-{4-[((2R)-2-hydroxy-2-{4-hydroxy-3-[(methylsulfonyl)amino]phenyl}-ethyl)-amino]-1-piperidineyl}anilino)-3-oxopropanoate To a stirred solution of N-[5-((1R)-2-amino-1-hydroxy-ethyl)-2-hydroxy-phenyl]-methanessulfonamide (which was obtained in Example 10) (0.3 g, 1.2 mmol) and ethyl 3-oxo-3-[4-(4-oxo-1-piperidineyl)anilino]propanoate (which was obtained in Example 363) (0.39 g, 1.28 mmol) in dimethylformamide (8 mL) under nitrogen atmosphere was added sodium triacetoxyborohydride (0.34 g, 1.59 mmol) and glacial acetic acid (0.08 g, 1.3 mmol). The mixture was stirred at room temperature for 3 days. The reaction was quenched with saturated sodium bicarbonate, extracted with ethyl acetate three times, dried over sodium sulfate, and concentrated. The product was purified by flash silica gel chromotagraphy eluting with 20% methanol in methylene chloride to give the title compound as a yellow solid (0.23 g, 36%); $^1$H NMR (300 MHz, DMSO-d$_6$) δ 1.19 (t, J=7.0 Hz, 3H), 1.25–1.45 (m, 2H), 1.75–1.95 (m, 2H), 2.50–2.70 (m, 5H), 2.92 (s, 3H), 3.33(s, 2H), 3.45–3.60 (m, 2H), 4.09 (q, J=7.0 Hz, 2H), 4.48 (dd, J=8.1, 4.2 Hz, 1H), 6.80 (d, J=8.3 Hz, 1H), 6.90 (d, J=9.0 Hz, 2H), 7.00 (dd, J=8.3, 2.0 Hz, 1H), 7.18 (d, J=2.0 Hz, 1H), 7.39 (d, J=9.0 Hz, 2H), 9.92 (s, 1H); MS (ES) m/z: 535.3 (MH$^+$); HRMS Calcd. for $C_{25}H_{35}N_4O_7S$(MH$^+$): 535.2221. Found: 535.2208.

EXAMPLE 372

3-(4-{4-[((2R)-2-Hydroxy-2-{4-hydroxy-3-[(methylsulfonyl)amino]phenyl}ethyl)amino]-1-piperidineyl}anilino)-3-oxopropanoic acid To a stirred solution of ethyl 3-(4-{4-[((2R)-2-hydroxy-2-{4-hydroxy-3-[(methylsulfonyl)amino]phenyl}ethyl)

amino]-1-piperidineyl}anilino)-3-oxopropanoate (which was obtained in Example 371) (0.23 g, 0.43 mmol) in distilled water (3 mL) and ethanol (2 mL) was added 1 N sodium hydroxide (2 mL). The reaction was stirred at room temperature for 1 hr. The reaction mixture was made acidic (pH 6) with glacial acetic acid, concentrated, triturated with water, ether, ethyl acetate to give the title compound as a light yellow solid (0.13 g, 59%); $^1$H NMR (300 MHz, DMSO-$d_6$) δ 1.30–1.45(m, 2H), 1.80–1.95 (m, 2H), 2.50–2.80 (m, 5H), 2.90 (s, 2H), 2.91(s, 3H), 3.45–3.60 (m, 2H), 4.48–4.53(m, 1H), 6.80–6.90(m, 3H), 7.00(d, J=8.3 Hz, 1H), 7.18 (d, J=1.6 Hz, 1H), 7.38(d, J=9.0 Hz, 2H), 11.50–11.60(m, 1H); MS (ES) m/z: 505.3 (M–H)$^-$; HRMS Calcd. for $C_{23}H_{31}N_4O_7S(MH^+)$: 507.1908. Found: 507.1895.

EXAMPLE 373

Ethyl 3-(butyl-4-{4-[((2R)-2-hydroxy-2-{4-hydroxy-3-[(methylsulfonyl)amino]phenyl}-ethyl)amino]-1-piperidineyl}anilino)-3-oxopropanoate To a stirred solution, under nitrogen atmosphere, of N-[5-((1R)-2-amino-1-hydroxy-ethyl)-2-hydroxy-phenyl]-methanessulfonamide (which was obtained in Example 10) (0.85 g, 3.5 mmol) and ethyl 3-[butyl-4-(4-oxo-1-piperidineyl)anilino]-3-oxopropanoate (which was obtained in Example 364) (1.47 g, 3.7 mmol) in methylene chloride (15 mL), dimethylformamide (5 mL) was added trimethyl orthoformate (1.53 mL, 14.0 mmol). The mixture was stirred for 2 hours before sodium triacetoxyborohydride (1.04 g, 4.9 mmol) and glacial acetic acid (0.2 mL, 3.5 mmol) was added. The reaction was stirred for 18 hours at room temperature. The reaction mixture was poured onto 1:1 water/saturated sodium bicarbonate, extracted with 10% methanol in methylene chloride, dried over sodium sulfate, and concentrated. The product was purified by flash chromatography on normal phase silica gel eluting with 10% methanol in methylene chloride, then with 15% methanol in methylene chloride, and then flash chromatograph on reverse phase silica gel eluting with methanol to give the titled compound as a tan solid (0.6 g, 29%); $^1$H NMR (300 MHz, DMSO-$d_6$) δ 0.81 (t, J=7.0 Hz, 3H), 1.11 (t, J=7.0 Hz, 3H), 1.20–1.50 (m, 6H), 1.80–2.00 (m, 2H), 2.65–2.90 (m, 5H), 2.93 (s, 3H), 3.09 (s, 2H), 3.56 (t, J=6.8 Hz, 2H), 3.65–3.80 (m, 2H), 3.97 (q, J=7.0 Hz, 2H), 4.55–4.65 (m, 1H), 6.85 (d, J=8.3 Hz, 1H), 6.96 (d, J=9.0 Hz, 2H), 7.00–7.10 (m, 3H), 7.20 (d, J=2.0 Hz, 1H); MS (ES) m/z: 591.2 (MH$^+$); HRMS Calcd. for $C_{29}H_{42}N_4O_7S(M^+)$: 590.2774. Found: 590.2847.

EXAMPLE 374

3-(Butyl-4-{4-[((2R)-2-hydroxy-2-{4-hydroxy-3-[(methylsulfonyl)amino]phenyl}-ethyl)amino]-1-piperidineyl}anilino)-3-oxopropanoic acid To a stirred solution of ethyl 3-(butyl-4-{4-[((2R)-2-hydroxy-2-{4-hydroxy-3-1}ethyl)amino]-1-piperidineyl}anilino)-3-oxopropanoate (which was obtained in Example 373) (0.23 g, 0.39 mmol) in distilled water (3 mL) and ethanol (2 mL) was added 1 N sodium hydroxide (2 mL). The reaction was stirred at room temperature for 1 hour. The mixture was acidified (pH 6) with glacial acetic acid, concentrated, triturated with water, ethyl acetate, ether, and dried under vacuum to give the titled compound as a tan solid (0.04 g, 19%); $^1$H NMR (300 MHz, DMSO-$d_6$) δ 1.20–1.50 (m, 6H), 1.70–1.95 (m, 2H), 2.60–2.80 (m, 5H), 2.83 (s, 2H), 2.91 (s, 3H), 3.45–3.70 (m, 4H), 4.55–4.65 (m, 1H), 6.81 (d, J=8.0 Hz, 1H), 6.90 (d, J=8.7 Hz, 2H), 7.09 (d, J=8.7 Hz, 2H), 7.07 (s, 1H); MS (ES) m/z: 563.2 (MH$^+$); HRMS Calcd. for $C_{27}H_{39}N_4O_7S(MH^+)$: 563.2461. Found: 563.2526.

EXAMPLE 375

Ethyl 3-(cyclohexyl-4-{4-[((2R)-2-hydroxy-2-{4-hydroxy-3-[(methylsulfonyl)amino]-phenyl}ethyl)amino]-1-piperidineyl}anilino)-3-oxopropanoate A solution of 8-(4-nitro-phenyl)-1,4-dioxa-8-aza-spiro [4.5]decane (13.01 g, 49 mmol) was hydrogenated under 45 psi for one hour using 10% palladium on carbon (2.5 g) as catalyst. The reaction mixture was filtered through celite pad and the filtrate was concentrated down to give a white solid (11.46 g, 100%). This material was taken onto next step immediately. To a stirred mixture, under $N_2$ atmosphere, of the aniline (10.99 g, 47 mmol), cyclohexanone (4.90 mL, 47 mmol) in tetrahydrofuran (250 mL) was added sodium triacetoxyborohydride (14.05 g, 66 mmol), and glacial acetic acid (2.71 mL, 47 mmol). The reaction was stirred for one hour. The reaction was quenched with 1 N NaOH (50 mL), diluted with water, extracted with ether 3 times and dried over sodium sulfate. The product was isolated as an oil (14.85 g, 100%). This material was immediately taken onto next step without further purification. A solution of the N-cyclohexyl aniline (14.85 g, 47 mmol) in hydrochloric acid (100 mL) was stirred at room temperature for 18 hours. The reaction mixture was poured onto ice and made basic with concentrated ammonium hydroxide, extracted with ether four times, dried over sodium sulfate and concentrated to give a yellow oil. The product was used without further purification (12.78 g, 100%). To a stirred mixture of the ketone (12.78 g, 47 mmol), triethylamine (8.49 mL, 61 mmol), and DMAP (catalytic amount) was added ethyl 3-chloro-3-oxopropionate (9.19 g, 61 mmol) dropwise. The reaction was stirred for 18 hours. The reaction mixture was filtered and concentrated in vacuo to give an oil (3.48 g, 19%).

To a stirred solution, under nitrogen atmosphere, of N-[5-((1 R)-2-amino-1-hydroxy-ethyl)-2-hydroxy-phenyl]-methanessulfonamide (which was obtained in Example 10) (0.20 g, 0.81 mmol) and the oil (0.37 g, 0.81 mmol) in methylene chloride (10 mL), dimethylformamide (2 mL) was added trimethyl orthoformate (0.35 mL, 3.2 mmol). The mixture was stirred for 18 hours before sodium triacetoxyborohydride (0.24 g, 1.1 mmol) and glacial acetic acid (0.047 mL, 0.81 mmol) were added. The mixture was stirred an additional 24 hours. The mixture was poured onto 1:1 water/saturated sodium bicarbonate, extracted with 10% methanol in methylene chloride, dried over sodium sulfate, and concentrated. The product was purified by flash chromatography on normal phase silica gel eluting with 15% methanol in methylene chloride, and then flash chromatographed on reverse phase silica gel eluting with methanol to give the title compound as a tan solid (0.12 g, 24%); $^1$H NMR (300 MHz, DMSO-$d_6$) δ 0.60–1.00 (m, 4H), 1.11 (t, J=7.0 Hz, 3H), 1.15–1.80 (m, 8H), 1.80–2.00 (m, 2H), 2.65–2.80 (m, 5H), 2.93 (s, 3H), 2.97 (s, 2H), 3.65–3.80 (m, 2H), 3.97 (q, J=7.0 Hz, 2H), 4.25–4.40 (m, 1H), 4.50–4.60 (m, 1H), 6.85 (d, J=8.3 Hz, 1H), 6.90–7.00 (m, 4H), 7.03 (dd, J=8.3, 2.0 Hz, 1H), 7.20 (d, J=2.0 Hz, 1H); MS (ES) m/z: 617.2 (MH$^+$); HRMS Calcd. for $C_{31}H_{44}N_4O_7S(M^+)$: 616.2932. Found: 617.3001.

EXAMPLE 376

3-(Cyclohexyl-4-{4-[((2R)-2-hydroxy-2-{4-hydroxy-3-[(methylsulfonyl)amino]phenyl}-ethyl)amino]-1-piperidineyl}anilino)-3-oxopropanoic acid A mixture of N-[5-((1R)-2-amino-1-hydroxy-ethyl)-2-hydroxy-phenyl]-methanessulfonamide (which was obtained in Example 10) (0.28 g, 1.1 mmol), 3-[cyclohexyl-4-(4-oxo-1-piperidineyl)anilino]-3-oxopropanoic acid (which was obtained in Example 365) (0.41 g, 1.1 mmol), glacial acetic acid (1 mL), and 10% palladium on carbon in anhydrous methanol (75 mL) was hydrogenated under 20 psi for 18 hours. The mixture was filtered through celite. The filtrate was concentrated. The product was triturated with hot ether, and then with methanol to give the title compound as a tan solid (0.03 g, 4.6%); $^1$H NMR (300 MHz, DMSO-d$_6$) δ 0.80–1.05 (m, 4H), 1.15–1.60 (m, 4H), 1.60–1.75 (m, 4H), 1.90–2.05 (m, 2H), 2.65–2.90 (m, 5H), 2.83 (s, 2H), 2.93 (s, 3H), 3.65–3.80 (m, 2H), 4.30–4.45 (m, 1H), 4.60–4.70 (m, 1H), 6.85 (d, J=8.3 Hz, 1H), 6.95 (d, J=9.1 Hz, 2H), 7.02 (d, J=9.1 Hz, 2H), 7.05 (d, J=8.3 Hz, 1H), 7.22 (s, 1H); MS (ES) m/z: 587.3 (M–H)$^-$; HRMS Calcd. for C$_{29}$H$_{41}$N$_4$O$_7$S(M$^+$+H): 589.2690. Found: 589.2690.

EXAMPLE 377

Ethyl {[(4-{4-[((2R)-2-hydroxy-2-{4-hydroxy-3-[(methylsulfonyl)amino]phenyl}-ethyl)amino]-1-piperidineyl}anilino)carbonyl]amino}acetate The title compound was prepared from {3-[4-(4-oxo-piperidine-1-yl)-phenyl]-ureido}-acetic acid ethyl ester (which was obtained in Example 366) and N-[5-((1R)-2-amino-1-hydroxy-ethyl)-2-hydroxy-phenyl]-methanesulfonamide (which was obtained in Example 10) according to the procedure of Example 278 as a white solid; $^1$H NMR (300 MHz, DMSO-d$_6$) δ 1.20 (t, J=7.1 Hz, 3H), 1.20–1.40 (m, 2H), 1.80–1.95 (m, 2H), 2.50–2.70 (m, 5H), 2.92 (s, 3H), 3.40–3.50 (m, 2H), 3.83 (d, J=5.9 Hz, 2H), 4.10 (q, J=7.1 Hz, 2H), 4.47 (dd, J=8.0, 4.3 Hz, 1H), 6.28 (t, J=5.9 Hz, 1H), 6.75–6.85 (m, 3H), 7.00 (dd, J=8.3, 2.0 Hz, 1H), 7.15–7.25 (m, 3H), 8.45 (s, 1H); MS (ES) m/z: 550.5 (MH$^+$); HRMS Calcd. for C$_{25}$H$_{36}$N$_5$O$_7$S(MH$^+$): 550.2330. Found: 550.2319.

EXAMPLE 378

{[(4-{4-[((2R)-2-Hydroxy-2-{4-hydroxy-3-[(methylsulfonyl)amino]phenyl}ethyl)amino]-1-piperidineyl}anilino)carbonyl]amino}acetic acid The title compound was prepared from ethyl {[(4-{4-[((2R)-2-hydroxy-2-{4-hydroxy-3-[(methylsulfonyl)amino]phenyl}ethyl)amino]-1-piperidineyl}anilino)carbonyl]amino}acetate (which was obtained in Example 377) by NaOH hydrolysis as a white solid; $^1$H NMR (300 MHz, DMSO-d$_6$) δ 1.35–1.55 (m, 2H), 1.80–2.00 (m, 2H), 2.50–2.90 (m, 5H), 2.92 (s, 3H), 3.30–3.50 (m, 2H), 3.59 (d, J=5.9 Hz, 2H), 4.60 (dd, J=8.8, 3.5 Hz, 1H), 6.14 (t, J=5.0 Hz, 1H), 6.80 (d, J=9.1 Hz, 2H), 6.84 (d, J=8.3 Hz, 1H), 7.03 (dd, J=8.3, 2.0 Hz, 1H), 7.15–7.25 (m, 3H), 8.54 (s, 1H); MS (ES) m/z: 520.3 (M–H)$^-$; HRMS Calcd. for C$_{23}$H$_{32}$N$_5$O$_7$S (MH$^+$): 522.2017. Found: 522.2000.

EXAMPLE 379

Ethyl {[(butyl-4-{4-[((2R)-2-hydroxy-2-{4-hydroxy-3-[(methylsulfonyl)amino]phenyl}-ethyl)amino]-1-piperidineyl}anilino)carbonyl]amino}acetate The title compound was prepared from ethyl ({[butyl-4-(4-oxo-1-piperidineyl)anilino]carbonyl}amino)acetate (which was obtained in Example 367) and N-[5-((1R)-2-amino-1-hydroxy-ethyl)-2-hydroxy-phenyl]-methanesulfonamide (which was obtained in Example 10) according to the procedure of Example 278 as a white solid; $^1$H NMR (300 MHz, DMSO-d$_6$) δ 0.83 (t, J=7.1 Hz, 3H), 1.17 (t, J=7.1 Hz, 3H), 1.15–1.40 (m, 6H), 1.80–1.95 (m, 2H), 2.50–2.80 (m, 5H), 2.90 (s, 3H), 3.49 (t, J=6.9 Hz, 2H), 3.55–3.60 (m, 2H), 3.65 (d, J=5.9 Hz, 2H), 4.04 (q, J=7.1 Hz, 2H), 4.48 (dd, J=7.9, 4.4 Hz, 1H), 5.60 (t, J=5.9 Hz, 1H), 6.80 (d, J=8.2 Hz, 1H), 6.90–7.10 (m, 5H), 7.17 (d, J=2.0 Hz, 1H); MS (ES) m/z: 606.3 (MH$^+$); HRMS Calcd. for C$_{29}$H$_{44}$N$_5$O$_7$S(MH$^+$): 606.2956. Found: 606.2955.

EXAMPLE 380

{[(Butyl-4-{4-[((2R)-2-hydroxy-2-{4-hydroxy-3-[(methylsulfonyl)amino]phenyl}ethyl)-amino]-1-piperidineyl}anilino)carbonyl]amino}acetic acid The title compound was prepared from ethyl {[(butyl-4-{4-[((2R)-2-hydroxy-2-{4-hydroxy-3-[(methylsulfonyl)amino]phenyl}ethyl)amino]-1-piperidineyl}anilino)carbonyl]amino}acetate (which was obtained in Example 379) by NaOH hydrolysis as a white solid; $^1$H NMR (300 MHz, DMSO-d$_6$) δ 0.83 (t, J=7.1 Hz, 3H), 1.15–1.60 (m, 6H), 1.85–2.00 (m, 2H), 2.65–2.95 (m, 5H), 2.92 (s, 3H), 3.42 (d, J=4.0 Hz, 2H), 3.45–3.55 (m, 2H), 3.65–3.80 (m, 2H), 4.65–4.75 (m, 1H), 5.16 (t, J=4.0 Hz, 1H), 6.83 (d, J=8.3 Hz, 1H), 6.95–7.15 (m, 5H), 7.20 (d, J=2.0 Hz, 1H); MS (ES) m/z: 576.3 (M–H)$^-$; HRMS Calcd. for C$_{27}$H$_{38}$N$_5$O$_7$S(M–H)$^-$: 576.2497. Found: 576.2502.

EXAMPLE 381

N-{4-[4-({(2S)-2-Hydroxy-3-[(2-oxo-2,3-dihydro-1H-benzimidazol-4-yl)oxy]propyl}-amino)-1-piperidineyl]phenyl}-3,4-dimethoxybenzamide Sodium triacetoxyborohydride (0.044 g, 2.1 mmol) was added to a solution of 4-((2S)-3-amino-2-hydroxy-propoxy)-1,3-dihydro-benzoimidazol-2-one (U.S. Pat. No. 5,786,356) (0.23 g, 1.05 mmol), 3,4-dimethoxy-N-[4-(4-oxo-piperidine-1-yl)-phenyl]-benzamide (which was obtained in Example 369) (0.41 g, 1.16 mmol), and acetic acid (0.07 mL, 1.16 mmol) in anhydrous dimethylforamide (8 mL). The reaction was stirred for 2 hours. The reaction was quenched with 50% water/saturated aqueous NaHCO$_3$ (20 mL). The solids were captured on a filter and washed with ethyl acetate, diethyl ether, and hexanes to afford 0.31 g of the desired product as a brown solid; $^1$H NMR (300 MHz, DMSO-d$_6$) δ 1.32 (m, 2H), 1.89 (m, 2H), 2.54 (m, 1H), 2.65 (m, 2H), 2.84 (m, 2H), 3.56 (m, 2H), 3.83 (s, 3H), 3.84 (s, 3H), 3.95 (m, 2H), 4.02 (s, 1H), 5.06 (brs, 1H), 6.52 (d, 1H, J=7.1), 6.51 (d, 1H, J=8.1Hz), 6.88 (m, 2H), 7.08 (d, 1H, J=8.7 Hz), 7.58 (m, 5H), 8.87 (s, 1H), 10.59 (brs, 1H), 10.72 (brs, 1H); MS (ES) m/z: 561.2 (MH$^+$).

EXAMPLE 382

2-Chloro-N-{4-[4-({(2S)-2-hydroxy-3-[(2-oxo-2,3-dihydro-1H-benzimidazol-4-yl)oxy]propyl}amino)-1-piperidineyl]phenyl]acetamide The title compound was prepared according to the procedure of Example 381 as a tan solid; $^1$H NMR (300 MHz, DMSO-d$_6$) δ 1.31 (m, 2H), 1.88 (m, 2H), 2.56 (m, 1H), 2.67 (m, 2H), 2.79 (m, 2H), 3.54 (m, 2H), 3.95 (s, 2H), 4.06 (m, 1H), 4.19 (s, 2H), 4.91 (brs, 1H), 6.56 (d, 1H, J=7.8), 6.64 (d, 1H, J=8.1 Hz), 6.88 (m, 3H), 7.39 (d, 2H, J=9.0 Hz), 10.06 (s, 1H); MS (ES) m/z: 474.0 (MH$^+$); HRMS found for C$_{23}$H$_{28}$ClN$_5$O$_4$: 474.1934.

EXAMPLE 383

N-{4-[4-({(2S)-2-Hydroxy-3-[(2-oxo-2,3-dihydro-1H-benzimidazol-4-yl)oxy]propyl}-amino)-1-piperidineyl]phenyl}-2-(4-morpholinyl)acetamide The title compound was prepared according to the procedure of Example 381 as a yellow solid; $^1$H NMR (300

MHz, DMSO-d$_6$) δ 1.35 (m, 2H), 1.88 (m, 2H), 2.61 (m, 2H), 2.69 (m, 2H), 2.79 (m, 2H), 3.07 (s, 2H), 3.48 (m, 4H), 3.64 (t, 4H, J=4.23), 3.96 (m, 3H), 5.11 (brs, 1H), 6.58 (d, 1H, J=7.8), 6.64 (d, 1H, J=8.4 Hz), 6.85 (m, 3H), 7.46 (d, 2H, J=8.7 Hz), 9.47 (s, 1H); MS (ES) m/z: 525.1 (MH$^+$); HRMS found for C$_{27}$H$_{36}$N$_6$O$_5$: 524.2719.

EXAMPLE 384

2-(Dimethylamino)-N-{4-[4-({(2S)-2-hydroxy-3-[(2-oxo-2,3-dihydro-1H-benzimidazol-4-yl)oxy]propyl}amino)-1-piperidineyl]phenyl}acetamide The title compound was prepared according to the procedure of Example 381 as a dark brown solid; $^1$H NMR (300 MHz, DMSO-d$_6$) δ 1.36 (m, 2H), 1.89 (m, 2H), 2.27 (s, 6H), 2.61 (m, 2H), 2.79 (m, 2H), 3.00 (s, 2H), 3.36 (m, 1H), 3.54 (m, 2H), 3.96 (m, 3H), 4.98 (brs, 1H), 6.58 (d, 1H, J=7.8), 6.64 (d, 1H, J=8.4 Hz), 6.85 (m, 3H), 7.46 (d, 2H, J=9.0 Hz), 10.59 (brs, 1H), 10.71 (brs, 1H); MS (ES) m/z: 483.1 (MH$^+$); HRMS found for C$_{25}$H$_{34}$N$_6$O$_4$: 483.2769.

EXAMPLE 385

N-(4-{4-[(2-Hydroxy-2-{4-hydroxy-3-[(methylsulfonyl)amino]phenyl}ethyl)amino]-1-piperidineyl}phenyl)-3,4-dimethoxybenzamide The title compound was prepared according to the procedure of Example 381 as a dark brown solid; $^1$H NMR (300 MHz, DMSO-d$_6$) δ 1.35 (m, 2H), 1.89 (m, 2H), 2.70 (m, 3H), 2.85 (m, 2H), 3.60 (m, 3H), 3.82 (s, 3H), 3.83 (s, 3H), 4.50 (m, 1H), 6.93 (m, 2H), 7.03 (m, 2H), 7.19 (d, 1H, J=1.74 Hz), 7.57 (m, 4H), 7.86 (dd, 1H, J=6.39 Hz), 8.03 (d, 1H, J=2.13 Hz), 9.11 '(s, 1H), 9.86 (s, 1H); MS (ES)m/z: 585.1 (MH$^+$).

EXAMPLE 386

N-{4-[4-({(2S)-2-Hydroxy-3-[(2-oxo-2,3-dihydro-1H-benzimidazol-4-yl)oxy]propyl}-amino)-1-piperidineyl]phenyl}butanamide The title compound was prepared according to the procedure of Example 381 as a grey solid; mp 190–201° C.; $^1$H NMR (300 MHz, DMSO-d$_6$) δ 0.89 (t, 3H), 1.50–1.80 (m, 4H), 2.10–2.40 (m, 4H), 2.50–2.80 (m, 3H), 3.10–3.30 (m, 2H), 3.60–3.80 (m, 2H), 3.90–4.10 (m, 2H), 4.20–4.35 (m, 1H), 5.80 (d, 1H), 6.59 (t, 2H), 6.80–7.00 (m, 2H), 7.40–7.60 (m, 3H), 8.80 (brs, 1H), 9.20 (brs, 1H), 9.70 (s, 1H), 10.65 (s, 1H), 10.80 (s, 1H); MS (ES) m/z: 468.0 (MH$^+$); HRMS Calcd. for C$_{25}$H$_{34}$N$_4$O$_4$ (MH$^+$): 468.2611. Found: 468.2574.

EXAMPLE 387

N-[4-(4-{[(2S)-3-(9H-Carbazol-4-yloxy)-2-hydroxypropyl]amino}-1-piperidineyl)phenyl]butanamide The title compound was prepared according to the procedure of Example 381 as an off-white solid; mp 194–199° C.; $^1$H NMR (300 MHz, DMSO-d$_6$) δ 0.89 (t, 3H), 1.30–1.45 (m, 2H), 1.50–1.70 (m, 2H), 1.80–2.00 (m, 2H), 2.25 (t, 2H), 2.50–3.00 (m, 5H), 3.40–3.60 (m, 2H), 4.00–4.20 (m, 3H), 5.10 (brs, 1H), 6.70 (d, 1H), 6.82 (d, 2H), 7.00–7.50 (m, 7H), 8.22 (d, 1H), 9.60 (s, 1H), 11.20 (s, 1H); MS (ES) m/z: 501.0 (MH$^+$).

EXAMPLE 388

N-[4-(4-{[(2S)-2-Hydroxy-3-(4-hydroxyphenoxy)propyl]amino}-1-piperidineyl)phenyl]-3,4-dimethoxybenzamide The title compound was prepared according to the procedure of Example 381 as a yellowish solid; mp 77–84° C.; $^1$H NMR (300 MHz, DMSO-d$_6$) δ 1.20–1.40 (m, 2H), 1.80–1.95 (m, 2H), 2.50–2.80 (m, 4H), 3.10–3.40 (m, 1H), 3.50–3.70 (m, 2H), 3.82 (s, 3H), 3.83 (s, 3H), 3.75–3.90 (m, 3H), 6.58 (d, 1H), 6.75 (d, 1H), 6.91 (d, 2H), 7.06 (d, 1H), 7.40–7.70 (m, 4H), 8.89 (brs, 1H), 9.86 (s, 1H); MS (ES) m/z: 522.0 (MH$^+$); HRMS Calcd. for C$_{29}$H$_{36}$N$_3$O$_6$ (MH$^+$): 522.2604. Found: 522.2602.

EXAMPLE 389

N-[4-(4-{[(2S)-3-(9H-Carbazol-4-yloxy)-2-hydroxypropyl]amino}-1-piperidineyl)phenyl]-3,4-dimethoxybenzamide The title compound was prepared according to the procedure of Example 381 as a yellowish solid; mp 183–191° C.; $^1$H NMR (300 MHz, DMSO-d$_6$) δ 1.20–1.45 (m, 2H), 1.80–2.00 (m, 2H), 2.50–3.40 (m, 5H), 3.50–3.65 (m, 2H), 3.73 (s, 3H), 3.74 (s, 3H), 4.00–4.20 (m, 3H), 5.10 (brs, 1H), 6.70 (d, 1H), 6.90 (d, 1H), 6.90–7.60 (m, 11H), 8.25 (d, 1H), 9.87 (s, 1H), 11.30 (s, 1H); MS (ES) m/z: 595.1 (MH$^+$); HRMS Calcd. for C$_{35}$H$_{38}$N$_4$O$_5$ (MH$^+$): 595.2920. Found: 595.2907.

EXAMPLE 390

N-{4-[4-({(2S)-2-Hydroxy-3-[(2-oxo-2,3-dihydro-1H-benzimidazol-4-yl)oxy]propyl}-amino)-1-piperidineyl]phenyl}-1,3-benzodioxole-5-carboxamide The title compound was prepared according to the procedure of Example 381 as a grey solid; mp 160–169° C.; $^1$H NMR (300 MHz, DMSO-d$_6$) δ 1.30–1.45 (m, 2H), 1.80–1.95 (m, 2H), 2.50–2.90 (m, 5H), 3.50–3.70 (m, 2H), 3.80–4.10 (m, 3H), 6.25 (s, 2H), 6.58 (d, 1H), 6.64 (d, 1H), 6.80–7.00 (m, 5H), 7.05 (d, 2H), 7.40–7.60 (m, 5H), 9.85 (s, 1H), 10.50–10.70 (m, 2H); MS (ES) m/z: 546.1 (MH$^+$); HRMS Calcd. for C$_{29}$H$_{31}$N$_5$O$_6$ (MH$^+$): 546.2353. Found: 546.2343.

EXAMPLE 391

N-[4-(4-{[(2S)-3-(9H-Carbazol-4-yloxy)-2-hydroxypropyl]amino}-1-piperidineyl)phenyl]-1,3-benzodioxole-5-carboxamide The title compound was prepared according to the procedure of Example 381 as an off-white solid; mp 217–223° C.; $^1$H NMR (300 MHz, DMSO-d$_6$) δ 1.30–1.45 (m, 2H), 1.75–2.00 (m, 2H), 2.50–2.90 (m, 5H), 3.50–4.30 (m, 5H), 6.12 (s, 2H), 6.70 (d, 1H), 6.80–7.60 (m, 17H), 9.87 (s, 1H), 11.30 (s, 1H); MS (ES) m/z: 579.1 (MH$^+$); HRMS Calcd. for C$_{34}$H$_{35}$N$_4$O$_5$ (MH$^+$): 579.2607. Found: 279.2595.

EXAMPLE 392

3-Cyclopentyl-N-{4-[4-({(2S)-2-hydroxy-3-[(2-oxo-2,3-dihydro-1H-benzimidazol-4-yl)oxy]propyl}amino)-1-piperidineyl]phenyl}propanamide The title compound was prepared according to the procedure of Example 381 as a grey solid; mp 140–144° C.; $^1$H NMR (300 MHz, DMSO-d$_6$) δ 1.00–2.00 (m, 15H), 2.50 (t, 2H), 2.50–2.90 (m, 5H), 3.55 (d, 2H), 3.80–4.05 (m, 3H), 4.90 (brs, 1H), 6.55 (d, 1H), 6.63 (d, 1H), 6.80–6.90 (m, 3H), 7.40 (d, 2H), 9.60 (s, 1H), 10.60 (brs, 1H), 10.70 (brs, 1H); MS (ES) m/z: 522.2 (MH$^+$); HRMS Calcd. for C$_{29}$H$_{39}$N$_5$O$_4$ (MH$^+$): 522.3080. Found: 522.3091.

EXAMPLE 393

3-Cyclopentyl-N-(4-{4-[((2R)-2-hydroxy-2-{4-hydroxy-3-[(methylsulfonyl)amino]phenyl}-ethyl)amino]-1-piperidineyl}phenyl)propanamide The title compound was prepared according to the procedure of Example 381 as a red solid; mp 82–90° C.; $^1$H NMR (300 MHz, DMSO-d$_6$) δ 1.00–2.00 (m, 15H), 2.30 (t, 2H), 2.50–2.70 (m, 5H), 3.45 (brd, 2H), 4.48 (dd, 1H), 6.70–6.90 (m, 3H), 6.98 (dd, 1H), 7.17 (d, 1H), 7.40 (d, 2H), 9.61 (s, 1H); MS (ES) m/z: 545.1 (MH$^+$); HRMS Calcd. for C$_{28}$H$_{41}$N$_4$O$_5$S(MH$^+$): 545.2798. Found: 545.2788.

EXAMPLE 394

N-(4-{4-[((2R)-2-Hydroxy-2-{4-hydroxy-3-[(methylsulfonyl)amino]phenyl}ethyl)amino]-1-piperidineyl}phenyl)-1,3-benzodioxole-5-carboxamide The title compound was prepared according to the procedure of Example 381 as an off-white solid; mp 104–113° C.; $^1$H NMR (300 MHz, DMSO-d$_6$) δ 1.30–1.45 (m, 2H), 1.80–1.95 (m, 2H), 2.50–2.80 (m, 5H), 2.92 (s, 3H), 3.55 (d, 2H), 4.49 (dd, 1H), 6.15 (s, 2H), 6.80 (d, 1H), 6.90 (d, 1H), 6.90–7.10 (m, 3H), 7.15 (d, 1H), 7.40–7.60 (m, 4H), 9.80 (s, 1H); MS (ES) m/z: 569.0 (MH$^+$).

EXAMPLE 395

1-Benzhydryl-3-(tert-butyl-dimethyl-silanyloxy)-azetidine

Tert-butyidimethylsiyl chloride (10.12 g, 42.3 mmol) was added to a solution of 1-(diphenylmethyl)-3-hydroxyazetidine (7.65 g, 50.8mmol) and imidazole (7.2 g, 106 mmol) in anhydrous dimethylforamide (20 mL). The reaction was stirred at room temperature for 24 hours and then treated with water (200 mL). The resultant precipitate was captured on a filter and washed with hot water. The solid was dried under reduced pressure to give 14.1 g of the desired product as a white solid; $^1$H NMR (300 MHz, CDCl$_3$) δ 0.06 (s, 6H), 0.84(s, 9H), 2.83 (t, 2H, J=6.42 Hz), 3.52 (t, 2H, J=6.09 Hz), 4.21 (s, 1H), 4.44 (m, 1H), 7.18 (m, 2H), 7.23 (m, 4H), 7.37 (d, 4H, J=8.49 Hz); MS (ES) m/z: 354.5 (MH$^+$); Anal. Calcd. for C$_{22}$H$_{31}$NOSi: C, 74.73; H, 8.84; N, 3.96. Found: C, 74.55; H, 8.75; N, 3.88.

EXAMPLE 396

1-(4-Nitro-phenyl)-azetidin-3-ol

Ammonium formate (15.1 g, 246 mmol) was added to a solution of 1-benzhydryl-3-(tert-butyl-dimethyl-silanyloxy)-azetidine (which was obtained in Example 395) (8.7 g, 24.6 mmol) and 10%Pd/C (1 g) in methanol (100 mL). The reaction was stirred for 3 hours at room temperature. The solution was passed through celite and concentrated to afford a crude solid. The crude solid was taken up in pyridine (75 mL) and the salts were removed by filtration. 4-Fluoronitrobenzene (2.9 mL, 27.1 mmol) was added to the above solution and the reaction was stirred at reflux overnight. Pyridine was removed by vacuum distillation and the resultant crude was treated with water (100 mL), followed by extraction with ethyl acetate (3×25 mL). The organic layers were combined, dried (Na$_2$SO$_4$), filtered, and passed through a plug of silica. The solvent was evaporated and triturated with hexanes to give 3.91 g of the desired product as red solid; $^1$H NMR (300 MHz, CDCl$_3$) δ 1.62 (s, 1H), 3.89(m, 2H), 4.31 (m, 2H), 4.87 (m, 1H), 6.31 (d, 2H, J=7.14), 8.09 (d, 2H, J=7.14 Hz); MS (ES) m/z: 194.8 (MH$^+$); Anal. Calcd. for C$_9$H$_{10}$N$_2$O$_3$: C, 55.67; H, 5.19; N, 14.43. Found: C, 55.67; H, 5.05; N, 14.59.

EXAMPLE 397

Methanesulfonic acid 1-(4-nitro-phenyl)-azetidin-3-yl ester 1-(4-Nitro-phenyl)-azetidin-3-ol (which was obtained in Example 396) (5.0 g, 25.8 mmol) was added to a solution of methanesulfonyl chloride (2.2 mL, 28.3 mmol) in dry pyridine (35 mL) and stirred at room temperature overnight. Water was added and the resultant precipitate was captured on a filter, washed with water, methanol, and hexanes to give 3.72 g of the desired product as an orange solid; $^1$H NMR (DMSO-d$_6$) δ3.35 (s, 3H), 4.15 (m, 3H), 4.45 (m, 2H), 5.48 (m, 1H), 6.53 (d, 2H, J=9.12 Hz), 8.09 (d, 2H, J=9.12 Hz); MS (ES) m/z: 273.5 (MH$^+$); Anal. Calcd. for C$_{10}$H$_{12}$N$_2$O$_5$S: C, 44.1 1; H, 4.44; N, 10.29. Found: C, 44.50; H, 4.48; N, 10.64.

EXAMPLE 398

Benzyl-[1-(4-nitro-phenyl)-azetidin-3-yl]-amine

Methanesulfonic acid 1-(4-nitro-phenyl)-azetidin-3-yl ester (which was obtained in Example 397) (14.32 g, 52.6 mmol) was added to neat benzyl amine (56 mL, 526 mmol) and stirred at 100° C. for 2 days. Water (200 mL) was added and the resultant precipitate was collected and partitioned between ethyl acetate and saturated aqueous NaHCO$_3$. The aqueous layer was washed with ethyl acetate (2×50 mL). The organic extract was dried over anhydrous sodium sulfate, filtered, and concentrated. The solid was washed with diethyl ether and dried to give 12.1 g of the desired product as an orange solid; $^1$H NMR (300 MHz, CDCl$_3$) δ1.66 (brs, 1H), 3.72 (m, 2H), 3.82 (s, 2H), 3.89 (m, 1H), 4.19 (t, 2H, J=7.77 Hz), 6.29 (d, 2H, J=9.12 Hz), 7.34 (m, 5H), 8.07 (d, 2H, J=9.18 Hz); MS (ES) m/z: 283.8 (MH$^+$); Anal. Calcd. for C$_{16}$H$_{17}$N$_3$O$_2$: C, 67.83; H, 6.05; N, 14.83. Found: C, 67.59; H, 6.04; N, 14.79.

EXAMPLE 399

(2S)-1-{Benzyl-[1-(4-nitro-phenyl)-azetidin-3-yl]-amino}-3-(9H-carbazol-4-yloxy)-propan-2-ol Benzyl-[1-(4-nitro-phenyl)-azetidin-3-yl]-amine (which was obtained in Example 398) (1.95 g, 6.87 mmol) and (2S)-3-(9H-carbazol-4-yloxy)-methyl oxirane (Berridge et al., *Int. J. RadiaL Appl. Instrum.*, 1992, 563) (1.64 g, 6.87 mmol) was stirred at reflux in anhydrous methanol for 24 hours. Methanol was removed in vacuo and the desired product was isolated using silica gel flash chromatography to give 3.01 g of product as a yellow solid; $^1$H NMR (300 MHz, CDCl$_3$) δ2.90 (m, 2H), 3.04 (s, 1H), 3.85 (m, 3H), 3.98 (m, 3H), 4.23 (m, 3H), 6.01 (d, 2H, J=7.26Hz), 6.61 (d, 1H, J=8.10 Hz), 7.06 (d, 1H, J=8.04 Hz), 7.17 (t, 1H, J=2.14 Hz), 7.34 (m, 7H), 7.97 (d, 2H, J=9.12 Hz), 8.14 (t, 2H, J=8.79 Hz); MS (ES) m/z: 522.9 (MH$^+$); Anal. Calcd. for C$_{31}$H$_{30}$N$_4$O$_4$: C, 71.25; H, 5.79; N, 10.72. Found: C, 70.77; H, 6.17; N, 9.61.

EXAMPLE 400

(2S)-1-{Benzyl-[1-(4-nitro-phenyl-azetidin-3-yl]-amino}-3-(4-benzyloxy-phenoxy)-propan-2-ol Benzyl-[1-(4-nitro-phenyl)-azetidin-3-yl]-amine (which was obtained in Example 398) (2.07 g, 7.34 mmol) and (2S)-2-(4-benzyloxy-phenoxymethyl-oxirane (EP 0 714 883) (2.07 g, 6.99 mmol) were stirred at reflux in anhydrous methanol for 24 hours. Methanol was removed in vacuo and the desired product was isolated using silica gel flash chromatography to give 3.01 g of product as a yellow solid; $^1$H NMR (300 MHz, CDCl$_3$) δ2.74 (m, 2H), 2.95 (brs, 2H), 3.90 (m, 2H), 3.94 (m, 4H), 4.01 (m, 2H), 4.05 (q, 2H, J=7.11 Hz), 5.01 (s, 2H), 6.28 (d, 2H, J=5.28 Hz), 6.82 (d, 2H, J=4.35 Hz), 6.89 (d, 2H, J=4.35 Hz), 7.34 (m, 10H), 8.08 (d, 2H, J=5.34 Hz); MS (ES) m/z: 540.0 (MH$^+$); Anal. Calcd. for $C_{32}H_{33}N_3O_5$: C, 71.23; H, 6.16; N, 7.79. Found: C, 70.68; H, 6.34; N, 7.61.

EXAMPLE 401

(2S)-1-{[1-(4-Amino-phenyl)-azetidin-3-yl]-benzyl-amino}-3-(4-benzyloxy-phenoxy)-propan-2-ol Sodium hydrosulfite (3.0 g, 17.2 mmol) was added to a heterogeneous solution of (2S)-1-{benzyl-[1-(4-nitro-phenyl-azetidin-3-yl]-amino}-3-(4-benzyloxy-phenoxy)-propan-2-ol (which was obtained in Example 400) (1.0 g, 1.72 mmol), sodium bicarbonate(1.5 g, 1.72mmol) in acetonitrile (15 mL), methanol (35 mL) and water (10 mL). This reaction was stirred at 60° C. overnight. Solids were removed by filtration. The mother liquor was concentrated and the resultant crude was taken up in water followed by extraction with ethyl acetate (3×20 mL). The organic extract was dried over anhydrous sodium sulfate, passed through a plug of silica, and concentrated to give 0.89 g of the desired product as a brown gum; $^1$H NMR (300 MHz, CDCl$_3$) δ2.66 (m, 2H), 3.13 (brs, 2H), 3.56 (m, 4H), 3.77 (m, 2H), 3.90 (m, 4H), 4.99 (s, 2H), 6.33 (d, 2H, J=4.80 Hz), 6.59 (d, 2H, J=6.78 Hz), 6.81 (d, 2H, J=9.21 Hz), 6.86 (d, 2H, J=6.75), 7.36 (m, 10H); MS (ES) m/z: 510.0 (MH$^+$).

EXAMPLE 402

N-Acetyl-N-[4-(3-{benzyl-[(2S)-3-(4-benzyloxy-phenoxy)-2-hydroxy-propyl]-amino}-azetidin-1-yl)-phenyl]-acetamide Acetic anhydride (0.09 mL, 0.93 mmol) was added to a solution of (2S)-1-{[1-(4-amino-phenyl)-azetidin-3-yl]-benzyl-amino}-3-(4-benzyloxy-phenoxy)-propan-2-ol (which was obtained in Example 401) (0.37 g, 0.727 mmol) and N,N-dimethylaminopyridine (catalytic amount) in anhydrous methylene chloride (7 mL). The reaction was stirred at room temperature overnight. The solution was then treated with water (30 mL) followed by extraction with ethyl acetate (3×30 mL). The organic extract was dried with anhydrous sodium sulfate, filtered and concentrated to afford a crude solid. The desired product was isolated using silica gel flash chromatography to give 0.41 g of an off-white solid; $^1$H NMR (300 MHz, CDCl$_3$) δ 2.05 (s, 3H), 2.12 (s, 3H), 2.75 (m, 1H), 2.93 (m, 1H), 3.49 (m, 2H), 3.65 (d, 2H, J=14 Hz), 3.75 (m, 1H), 3.88 (m, 2H), 4.01 (d, 2H, J=4.23 Hz), 5.01 (s, 2H), 5.18 (m, 1H), 6.36 (d, 2H, J=8.4 Hz), 6.79 (d, 2H, J=6.78 Hz), 6.89 (d, 2H, J=6.78 Hz), 7.32 (m, 8H), 7.38 (m, 4H). MS (ES) m/z: 594.1 (MH$^+$).

EXAMPLE 403

N-[4-(3-{Benzyl-[(2S)-3-(4-benzyloxy-phenoxy)-2-hydroxy-propyl]-amino}-azetidin-1-yl)-phenyl]-4-butoxy-benzenesulfonamide 4-Butoxybenzenesulfonyl chloride (0.20 g, 0.79 mmol) was added to a solution of (2S)-1-{[1-(4-amino-phenyl)-azetidin-3-yl]-benzyl-amino}-3-(4-benzyloxy-phenoxy)-propan-2-ol (which was obtained in Example 401) (0.37 g, 0.727 mmol) and triethylamine (0.56 mL, 3.99 mmol) in anhydrous methylene chloride (7 mL). The reaction was stirred at room temperature overnight. The solution was then treated with water (30 mL) followed by extraction with ethyl acetate (3×30 mL). The organic extract was dried with anhydrous sodium sulfate, filtered and concentrated to afford a crude solid. The desired product was isolated using silica gel flash chromatography to give 90 mg of an off-white solid; $^1$H NMR (300 MHz, CDCl$_3$) δ 0.99 (t, 3H, J=5.04 Hz), 1.47 (m, 2H), 1.78 (m, 2H), 2.69 (m, 2H), 3.08 (brs, 1H), 3.65 (m, 3H), 3.78 (m, 2H), 3.87 (m, 4H), 3.95 (t, 2H, J=6.45 Hz), 5.01 (s, 2H), 6.01 (s, 1H), 6.29 (d, 2H, J=8.73Hz), 6.86 (m, 10H), 7.35 (m, 8H), 7.56 (d, 2H, J=8.94 Hz). MS (ES) m/z: 722.1 (MH$^+$); Anal. Calcd. for $C_{42}H_{47}N_3O_6S$: C, 69.88; H, 6.56; N, 5.82. Found: C, 68.91; H, 6.38; N, 5.55.

EXAMPLE 404

N-[4-(3-{Benzyl-[3-(9H-carbazol-4-yloxy)-2-hydroxy-propyl]-amino}-azetidin-1-yl)-phenyl}-acetamide The title compound was prepared according to the procedure of Example 403 as an off-white solid; $^1$H NMR (DMSO-d$_6$) δ 1.95 (s, 3H), 2.64 (m, 1H), 2.82 (m, 1H), 3.32 (s, 2H), 3.47 (m, 2H), 3.67 (m, 4H), 4.12 (m, 2H), 5.07 (d, 1H, J=4.5 Hz), 6.15 (d, 2H, J=8.7 Hz), 6.09 (d, 1H, J=8.79 Hz), 6.65 (d, 1H, J=7.95 Hz), 7.07 (m, 2H), 7.26 (m, 10H), 7.46 (d, 1H, J=7.71 Hz), 8.18 (d, 1H, J=7.71 Hz), 9.57 (s, 1H), 11.25 (s, 1H); MS (ES) m/z: 535.1; (MH$^+$); HRMS found for $C_{33}H_{34}N_4O_3$: 534.2643

EXAMPLE 405

N-[4-(3-{Benzyl-[(2S)-3-(9H-carbazol-4-yloxy)-2-hydroxy-propyl]-amino}-azetidin-1-yl)-phenyl]-4-butoxy-benzenesulfonamide The title compound was prepared according to the procedure of Example 403 as an off-white solid; $^1$H NMR (300 MHz, CDCl$_3$) δ 0.95 (t, 3H, J=4.95 Hz), 1.45 (m, 2H), 1.74 (m, 2H), 2.83 (m, 2H), 3.22 (brs, 1H), 3.61 (m, 3H), 3.79 (s, 1H), 3.84 (m, 3H), 3.93 (t, 2H, J=7.29 Hz), 4.15 (m, 2H), 6.15 (d, 2H, J=8.7 Hz), 6.24 (s, 1H), 6.59 (d, 2H, J=6.99 Hz), 6.84 (m, 4H), 7.04 (d, 1H, J=8.01 Hz), 7.18 (m, 2H), 7.37 (m, 2H), 7.54 (d, 2H, J=7.02 Hz), 8.17 (s, 1H), 8.18 (s, 1H); MS (ES) m/z: 705.1 (MH$^+$).

EXAMPLE 406

N-[4-(3-{Benzyl-[3-(9H-carbazol-4-yloxy)-2-hydroxy-propyl]-amino}-azetidin-1-yl)-phenyl]-3,4-dimethoxy-benzenesulfonamide The title compound was prepared according to the procedure of Example 403; $^1$H NMR (300 MHz, CDCl$_3$) δ 2.82 (m, 2H), 3.18 (brs, 1H), 3.61 (m, 3H), 3.75 (s, 3H), 3.79 (m, 1H), 3.89 (s, 3H), 3.93 (m, 2H), 4.17 (m, 3H), 6.12 (s, 1H), 6.21 (d, 2H, J=8.7 Hz), 6.63 (d, 1H, J=7.95 Hz), 6.83 (m, 3H), 7.06 (m, 3H), 7.25 (m, 1H), 7.28 (m, 2H), 7.39 (m, 1H), 8.15 (s, 1H), 8.21 (d, 1H, J=7.8 Hz); MS (ES) m/z: 693.1 (MH$^+$); HRMS found for $C_{39}H_{40}N_4O_6$ S: 693.2731

EXAMPLE 407

N-{4-[4-(3-{Benzyl-[3-(9H-carbazol-4-yloxy)-2-hydroxy-propyl]-amino}-azetidin-1-yl)-phenylsulfamoyl]-phenyl}-acetamide The title compound was prepared according to the procedure of Example 403; $^1$H NMR (300 MHz, CDCl$_3$) δ 2.17 (s, 3H), 2.85 (m, 2H), 3.59 (m, 3H), 3.68 (m, 1H), 3.80 (m, 3H), 4.19 (m, 3H), 6.13 (d, 2H, J=8.67 Hz), 6.06 (d, 1H, J=7.95 Hz), 6.86 (d, 2H, J=8.64 Hz), 7.08 (d, 1H, J=8.07 Hz), 7.14 (t, 1H, J=7.5 Hz), 7.31 (m, 8H), 7.59 (q, 4H, J=7.71 Hz), 8.22 (d, 1H, J=7.71 Hz), 8.51 (s, 1H), 9.50 (s, 1H), 79 (s, 1H); MS (ES) m/z: 690.1 (MH⁺); HRMS found for $C_{39}H_{39}NO_5S$: 690.2777.

EXAMPLE 408

N-[4-(3-{Benzyl-[3-(4-benzyloxy-phenoxy)-2-hydroxy-propyl]-amino}-azetidin-1-yl)-phenyl-3,4-dimethoxy-benzenesulfonamide

The title compound was prepared according to the procedure of Example 403; ¹H NMR (300 MHz, CDCl₃) δ 2.69 (m, 2H), 3.06 (brs, 1H), 3.63 (m, 3H), 3.78 (s, 3H), 3.87 (m, 3H), 3.91 (s, 3H), 3.93 (m, 3H), 5.01 (s, 2H), 6.05 (s, 1H), 6.29 (d, 2H, J=9.81 Hz), 6.82 (m, 10 H), 7.06 (d, 1H), 7.56 (d, 2H, J=6.94 Hz), 7.34 (m, 10 H). MS (ES) m/z: 710.1 (MH⁺); HRMS found for $C_{40}H_{43}N_3O_7S$: 710.2899.

EXAMPLE 409

N-{4-[4-(3-{Benzyl-[3-(4-benzyloxy-phenoxy)-2-hydroxy-propyl]-amino}-azetidin-1-yl)-phenylsulfamoyl]-phenyl}-acetamide

The title compound was prepared according to the procedure of Example 403; ¹H NMR (300 MHz, CDCl₃) δ 2.17 (s, 3H), 2.67 (m, 2H), 3.15 (brs, 1H), 3.62 (m, 3H), 3.78 (m, 2H), 3.88 (m, 4H), 5.01 (s, 2H), 6.26 (m, 3H), 6.87 (m, 6H), 7.34 (m, 5H), 7.40 (m, 3H), 7.52 (d 5H). MS (ES) m/z: 707.1 (MH⁺); HRMS found for $C_{40}H_{42}N_4O_6S$: 707.2901.

EXAMPLE 410

N-Acetyl-N-[4-(3-{[(2S)-2-hydroxy-3-(4-hydroxyphenoxy)propyl]amino}- 1-azetidinyl)phenyl]acetamide

Ammonium formate (0.57 g, 9.1 mmol) was added to a solution of N-acetyl-N-[4-(3-{benzyl-[(2S)-3-(4-benzyloxy-phenoxy)-2-hydroxy-propyl]-amino}-azetidin-1-yl)-phenyl]-acetamide (which was obtained in Example 402) (0.25 g, 0.45 mmol) and 10% Pd/C (0.05 g) in dry methanol (7 mL). The reaction was stirred at room temperature overnight. The solution was passed through a pad of celite and then was concentrated. The crude solid was treated with saturated aqueous NaHCO₃ (30 mL) followed by extraction with ethyl acetate (3×20 mL). The organic extract was dried over anhydrous sodium sulfate, filtered, and evaporated to afford 0.18 g of the desired product as a white solid; ¹H NMR (300 MHz, CDCl₃) δ 2.05 (s, 6H), 2.61 (s, 1H), 2.75 (m, 2H), 3.49 (m, 2H), 3.75 (m, 1H), 3.85 (d, 2H, J=7.13 Hz), 4.02 (t, 2H, J=5.3 Hz), 4.12 (q, 1H), 6.32 (d, 2H, J=11.12 Hz), 6.90 (d, 2H, J=11.32 Hz), 6.55 (q, 4H, J=4.6 Hz), 7.53 (d, 2H, J=7.02 Hz), 7.61 (brs, 1H); MS (ES) m/z: 414.0 (MH⁺).

EXAMPLE 411

4-Butoxy-N-[4-(3-{[(2S)-2-hydroxy-3-(4-hydroxyphenoxy)propyl]amino}-1-azetidinyl)phenyl]benzenesulfonamide

The title compound was prepared according to the procedure of Example 410 as a dark blue solid; ¹H NMR (300 MHz, DMSO-d₆/CDCl₃) δ 0.97 (t, 3H, J=7.41 Hz), 1.48 (m, 2H), 1.78 (m, 2H), 2.58 (m, 1H), 2.75 (m, 2H), 3.49 (m, 2H), 3.75 (m, 1H), 3.85 (d, 2H), 3.97 (t, 2H, J=5.7 Hz), 4.02 (t, 2H, J=7.41 Hz), 4.12 (q, 1H), 6.26 (d, 2H, J=11.67), 6.75 (s, 4H), 6.84, (d, 2H, J=5.1 Hz), 6.90 (d, 2H, J=11.76 Hz), 7.53 (d, 2H, J=6.99 Hz), 8.35 (brs, 1H), 8.60 (brs, 1H); MS (ES) m/z: 542.0 (MH⁺); HRMS found for $C_{28}H_{35}N_3O_6S$: 542.2362.

EXAMPLE 412

N-[4-(3-{[(2S)-2-Hydroxy-3-(4-hydroxyphenoxy)propyl]amino}-1-azetidinyl)phenyl]-3,4-dimethoxybenzenesulfonamide

The title compound was prepared according to the procedure of Example 410 as a blue solid; ¹H NMR (300 MHz, DMSO-d₆/CDCl₃) δ 2.58 (m, 1H), 2.76 (m, 2H), 3.41 (s, 1H), 3.49 (m, 2H), 3.71 (m, 1H), 3.80 (s, 3H), 3.89 (s, 3H), 3.90 (d, 2H, J=3.39 Hz), 4.12 (q, 1H), 6.26 (d, 2H, J=5.01 Hz), 6.75 (s, 4H). 6.83 (d, 1H, J=8.49 Hz), 6.90 (d, 1H, J=8.73 Hz), 7.16 (d, 1H, J=2.07 Hz), 7.29 (dd, 1H), 8.35 (brs, 1H), 8.60 (brs, 1H); MS (ES) m/z: 530.0 (MH⁺); HRMS found for $C_{26}H_{31}N_3O_7S$: 530.1991.

EXAMPLE 413

N-(4-{[4-(3-{[(2S)-2-Hydroxy-3-(4-hydroxyphenoxy)propyl]amino}-1-azetidinyl)anilino]-sulfonyl}phenyl)acetamide

The title compound was prepared according to the procedure of Example 410 as a white solid; ¹H NMR (300 MHz, DMSO-d₆) δ 2.06, (s 3H), 2.53 (m, 1H), 2.61 (m, 2H), 3.35 (m, 2H), 3.58 (m, 1H), 3.78 (m, 3H), 3.85 (t, 2H), 4.89 (brs, 1H), 6.26 (d, 2H, J=8.7 Hz), 6.65 (d, 2H, J=6.6 Hz), 6.72 (d, 2H, J=2.4 Hz), 6.93 (d, 2H, J=1.8 Hz), 7.54 (d, 2H, J=9.0 Hz), 7.83 (d, 2H, J=8.8 Hz) 8.87 (s, 1H), 8.45 (brs, 1H), 10.26 (s, 1H); MS (ES) m/z: 527.1 (MH⁺); HRMS found for $C_{26}H_{30}N_4O_6S$: 527.1975.

EXAMPLE 414

4-Butoxy-N-[4-(3-{[(2S)-3-(9H-carbazol-4-yloxy)-2-hydroxypropyl]amino}-1-azetidinyl)phenyl]benzenesulfonamide

The title compound was prepared according to the procedure of Example 410 as an off-white solid; ¹H NMR (300 MHz, CDCl₃) δ 0.97 (t, 3H, J=7.47 Hz), 1.48 (m, 2H), 1.78 (m, 2H), 3.01 (m, 2H), 3.47 (m, 2H), 3.95 (t, 2H, J=5.94 Hz), 4.04 (d, 2H, J=6.66), 4.29 (m, 2H), 4.32 (m, 1H), 6.15 (brs, 1H), 6.26 (d, 2H, J=8.73 Hz), 6.67 (d, 1H, J=7.95 Hz), 6.83, (d, 2H, J=2.7 Hz), 7.07 (d, 1H, J=8.01 Hz), 7.22 (m, 2H), 7.32 (t, 2H, J=8.04 Hz), 7.41 (m, 2H), 7.57 (d, 2H, J=5.04 Hz), 8.13 (brs, 1H), 8.25 (d, 1H, J=7.77 Hz); MS (ES) m/z: 615.1 (MH⁺); HRMS found for $C_{34}H_{38}N_4O_5S$: 615.2656.

EXAMPLE 415

N-[4-(3-{[(2S)-3-(9H-Carbazol-4-yloxy)-2-hydroxypropyl]amino}-1-azetidinyl)phenyl]acetamide

The title compound was prepared according to the procedure of Example 410 as a dark brown solid; ¹H NMR (300 MHz, CDCl₃) δ 2.05 (s, 3H), 3.01 (m, 2H), 3.47 (m, 2H), 3.95 (m, 2H), 4.04 (m, 2H), 4.29 (m, 2H), 6.35 (d, 1H, J=6.3 Hz), 6.69 (d, 1H, J=6.9 Hz), 7.04, (brs, 1H), 7.21 (m, 1H), 7.29 (m, 2H), 7.32 (m, 2H), 7.41 (m, 2H), 7.30 (m, 2H), 8.10 (brs, 1H), 8.27 (m, 1H); MS (ES) m/z: 445.1 (MH⁺).

EXAMPLE 416

N-[4-(3-{[(2S)-3-(9H-Carbazol-4-yloxy)-2-hydroxypropyl]amino}-1-azetidinyl)phenyl[-3,4-dimethoxybenzenesulfonamide

The title compound was prepared according to the procedure of Example 410 as an off-white solid; ¹H NMR (300

MHz, DMSO-$d_6$) δ 2.76 (m, 2H), 3.18 (d, 2H, J=5.22 Hz), 3.72 (s, 3H), 3.78 (s, 3H), 3.93 (t, 2H, J=6.96 Hz), 4.02 (m, 1H), 4.14 (m, 2H), 4.19 (m, 1H), 5.11 (d, 1H, J=4.92 Hz), 6.2 (d, 2H, J=9.0 Hz), 6.69 (d, 2H, J=8.1 Hz), 6.85 (d, 2H, J=8.7 Hz), 7.13 (m, 2H), 7.17 (m, 2H), 7.33 (m, 2H), 7.43 (d, 2H, J=8.1 Hz), 8.21 (d, 1H, J=7.8 Hz), 9.45 (brs, 1H); MS (ES) m/z: 603.0 (MH$^+$); HRMS found for $C_{32}H_{34}N_4O_6S$: 603.2296.

EXAMPLE 417

N-(4-{[4-(3-{[(2S)-3-(9H-Carbazol-4-yloxy)-2-hydroxypropyl]amino}-1-azetidinyl)anilino]sulfonyl}phenyl)acetamide The title compound was prepared according to the procedure of Example 410 as an off-white solid; $^1$H NMR (300 MHz, DMSO-$d_6$) δ 2.06 (s, 3H), 2.71 (m, 2H), 3.40 (m, 2H), 3.68 (m, 1H), 3.93 (t, 2H, J=6.93 Hz), 4.02 (m, 2H), 4.13 (m, 1H), 5.09 (d, 1H, J=4.95 Hz), 6.25 (d, 2H, J=8.7 Hz), 6.47 (d, 1H, J=8.7 Hz), 6.81 (d, 2H, J=8.7 Hz), 7.13 (m, 2H), 7.27 (m, 2H), 7.46 (d, 2H, J=8.1 Hz), 7.68 (d, 2H, J=9.0 Hz), 8.21 (d, 1H, J=7.8 Hz), 9.50 (brs, 1H), 10.27 (brs, 1H), 11.24 (s, 1H); MS (ES) m/z: 600.0 (MH$^+$); HRMS found for $C_{32}H_{33}N_5O_5S$: 600.2280.

What is claimed is:

1. A compound of formula I having the structure

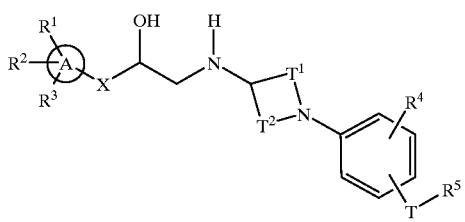

wherein

A is Ar;

X is a bond;

$T^1$ is $(CH_2)_m$;

$T^2$ is $(CH_2)_n$;

T is a bond;

$R^1$, $R^2$, and $R^3$ are each, independently, hydrogen, alkyl of 1–6 carbon atoms, cycloalkyl of 3–8 carbon atoms, hydroxy, halogen, trifluoromethyl, alkoxy of 1–6 carbon atoms, benzyloxy, allyloxy, propargyloxy, acyloxy of 2–7 carbon atoms, cyano, nitro, amino, aminocarbonyl, alkylamino of 1–6 carbon atoms, dialkylamino of 1–6 carbon atoms per alkyl group, formamido, ureido, acylamino of 2–7 carbon atoms, alkylsulfonylamino of 1–6 carbon atoms, arylsulfonylamino, dialkyloxyphosphorylamino of 1–6 carbon atoms per alkyl group, dihydroxyphosphorylamino, —$CO_2$-alkyl of 1–6 carbon atoms, or Ar optionally substituted with $R^{11}$;

$R^4$ is hydrogen, alkyl of 1–6 carbon atoms, halogen, hydroxy, alkyoxy of 1–6 carbon atoms, alkylthio of 1–6 carbon atoms, amino, alkylamino of 1–6 carbon atoms, carboxy, acyl of 2–7 carbon atoms, ArCO—, alkoxycarbonyl of 2–7 carbon atoms, aminocarbonyl, alkylaminocarbonyl of 2–7 carbon atoms, alkylsulfonyl of 1–6 carbon atoms, or alkylsulfonylamino of 1–6 carbon atoms, $R^5$ is

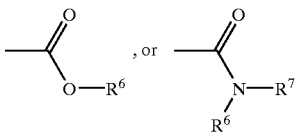

Aa is (i) an amino acid, wherein the nitrogen of amino acid attached to the adjacent carbonyl of $R^5$; or (ii) an alkyl ester of an amino acid, wherein the nitrogen of amino acid attached to the adjacent carbonyl of $R^5$, and the alkyl moiety of the alkyl ester contains 1–6 carbon atoms;

Y and Z are each, independently, $NR^7$, O, or S;

$X^1$ and $X^2$ are each, independently, CO or $SO_2$;

a dotted line represents and optional double bond;

$R^6$, and $R^7$ are each, independently, hydrogen; alkyl of 1–6 carbon atoms optionally substituted by $R^{11}$, $R^{12}$, and $R^{13}$; alkenyl of 2–7 carbon atoms optionally substituted by $R^{11}$, $R^{12}$, and $R^{13}$; alkynyl of 2–7 carbon atoms optionally substituted with $R^{11}$; cycloalkyl of 3–8 carbon atoms optionally substituted by $R^{11}$, $R^{12}$, and $R^{13}$; bicycloalkyl of 7–11 carbon atoms optionally substituted by $R^{11}$, $R^{12}$, and $R^{13}$; —$CO_2$-alkyl of 1–6 carbon atoms; or Ar optionally substituted by $R^{11}$, $R^{12}$, and $R^{13}$;

$R^{11}$, $R^{12}$, or $R^{13}$ are each, independently, alkyl of 1–6 carbon atoms, halogen, alkenyl of 2–7 carbon atoms, alkynyl of 2–7 carbon atoms, cycloalkyl of 3–8 carbon atoms, Ar-alkyl having 1–6 carbon atoms in the alkyl moiety, Ar optionally substituted with $R^{14}$, hydroxy, alkoxy of 1–6 carbon atoms, Ar-oxy, oxo, —CN, —CHO, —$CO_2$H, —$OCO_2$-alkyl of 1–6 carbon atoms, —$CO_2$-alkyl of 1–6 carbon atoms, —$CO_2$—Ar, —$CO_2$-alkyl-Ar wherein the alkyl moiety has 1–6 carbon atoms, —$OCO_2$—Ar, —$CONH_2$, —CONHOH, amino, alkylamino of 1–6 carbon atoms, dialkylamino of 1–6 carbon atoms per alkyl moiety, —NHCONH-alkyl of 1–6 carbon atoms, -$NHSO_2$-alkyl of 1–6 carbon atoms, —$NHSO_2$-Ar, or when $R^{11}$ and $R^{12}$ are contained on a common carbon atom of an alkyl moiety, they may be taken together to form a spiro cycloalkyl ring of 3–8 carbon atoms;

$R^{14}$ is halogen, alkoxy of 1–6 carbon atoms, alkyl of 1–6 carbon atoms, alkenyl of 2–7 carbon atoms, alkynyl of 2–7 carbon atoms, hydroxy, acyl of 2–7 carbon atoms, —$SO_2$-alkyl of 1–6 carbon atoms, $CO_2$-alkyl of 1–6 carbon atoms, or alkoxycarbonylalkyl of 3–13 carbon atoms;

Ar is an aromatic ring system containing 1–2 carbocyclic aromatic rings having 6–10 carbon atoms;

m=2;

n=2;

or a pharmaceutically acceptable salt thereof.

2. The compound according to claim 1, wherein

A is Ar;

X is a bond;

$T^1$ is $(CH_2)_m$;

$T^2$ is $(CH_2)_n$;

T is a bond;

$R^1$, $R^2$, and $R^3$ are each, independently, hydrogen, alkyl of 1–6 carbon atoms, hydroxy, halogen, trifluoromethyl, alkoxy of 1–6 carbon atoms, benzyloxy, acyloxy of 2–7 carbon atoms, cyano, nitro, amino, aminocarbonyl, alkylamino of 1–6 carbon ato ms, dialkylamino of 1–6 carbon atoms per alkyl group, acylamino of 2–7 carbon atoms, alkylsulfonylamino of 1–6 carbon atoms, arylsulfonylamino, —CO$_2$-alkyl of 1–6 carbon atoms, or Ar optionally substituted with R$^{11}$;

R$^4$ is hydrogen or halogen;

R$^5$ is

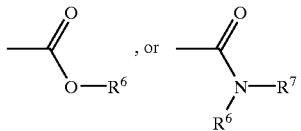

Aa is (i) an amino acid, wherein the nitrogen of amino acid attached to the adjacent carbonyl of R$^5$; or (ii) an alkyl ester of an amino acid, wherein the nitrogen of amino acid attached to the adjacent carbonyl of R$^5$, and the alkyl moiety of the alkyl ester contains 1–6 carbon atoms;

Y and Z are each, independently, NR$^7$, O, or S;

X$^1$ and X$^2$ are each, independently, CO or SO$_2$;

a dotted line represents and optional double bond;

R$^6$, and R$^7$ are each, independently, hydrogen; alkyl of 1–6 carbon atoms optionally substituted by R$^{11}$, R$^{12}$, and R$^{13}$; cycloalkyl of 3–8 carbon atoms optionally substituted by R$^{11}$, R$^{12}$, and R$^{13}$; bicycloalkyl of 7–11 carbon atoms optionally substituted by R$^{11}$, R$^{12}$, and R$^{13}$; —CO$_2$-alkyl of 1–6 carbon atoms; or Ar optionally substituted by R$^{11}$, R$^{12}$, and R$^{13}$;

R$^{11}$, R$^{12}$, or R$^{13}$ are each, independently, alkyl of 1–6 carbon atoms, halogen, alkenyl of 2–7 carbon atoms, alkynyl of 2–7 carbon atoms, cycloalkyl of 3–8 carbon atoms, Ar-alkyl having 1–6 carbon atoms in the alkyl moiety, Ar optionally substituted with R$^{14}$, hydroxy, alkoxy of 1–6 carbon atoms, Ar-oxy, oxo, —CN, —CHO, —CO$_2$H, —OCO$_2$-alkyl of 1–6 carbon atoms, —CO$_2$-alkyl of 1–6 carbon atoms, —CO$_2$—Ar, —CO$_2$-alkyl-Ar wherein the alkyl moiety has 1–6 carbon atoms, —OCO$_2$—Ar, —CONH$_2$, —CONHOH, amino, alkylamino of 1–6 carbon atoms, dialkylamino of 1–6 carbon atoms per alkyl moiety, —NHCONH-alkyl of 1–6 carbon atoms, —NHSO$_2$-alkyl of 1–6 carbon atoms, —NHSO$_2$—Ar, or when R$^{11}$ and R$^{12}$ are contained on a common carbon atom of an alkyl moiety, they may be taken together to form a spiro cycloalkyl ring of 3–8 carbon atoms;

R$^{14}$ is halogen, alkoxy of 1–6 carbon atoms, alkyl of 1–6 carbon atoms, hydroxy, acyl of 2–7 carbon atoms, —SO$_2$-alkyl of 1–6 carbon atoms, —CO$_2$-alkyl of 1–6 carbon atoms, or alkoxycarbonylalkyl of 3–13 carbon atoms;

Ar is an aromatic ring system containing 1–2 carbocyclic aromatic rings having 6–10 carbon atoms;

m=2;

n=2;

or a pharmaceutically acceptable salt thereof.

3. The compound of claim 1, which is zz) {4-[(2R)-2-hydroxy-2-(4-hydroxy-3-methane-sulfonylamino-phenyl)-ethylamino]-piperidine-1-yl}-benzoic acid ethyl ester;

aaa) {4-[(2R)-2-(3-chloro-phenyl)-2-hydroxy-ethylamino]-piperidine-1-yl}-benzoic acid ethyl ester hydrochloride;

fff) 4-{4-[(2R)-2-hydroxy-2-(4-hydroxy-3-methanesulfonylamino-phenyl)-ethylamino]-piperidine-1-yl}-benzoic acid;

jjj) 4-{4-[(2R)-2-hydroxy-2-(4-hydroxy-3-methane-sulfonylamino-phenyl)-ethylamino]-piperidine-1-yl}-benzamide;

lll) diethyl (2S)-2-[(4-{4-[((2R)-2-hydroxy-2-{4-hydroxy-3-[(methylsulfonyl)amino]phenyl}ethyl)amino]-1-piperidinyl}benzoyl)amino]pentanedioate;

mmm) ethyl 3-[(4-{4-[((2R)-2-hydroxy-2-{4-hydroxy-3-[(methylsulfonyl)amino]phenyl}ethyl)amino]-1-piperidinyl}benzoyl)amino]propanoate;

nnn) (2S)-2-[(4-{4-[((2R)-2-hydroxy-2-{4-hydroxy-3-[(methylsulfonyl)amino]phenyl}ethyl)amino]-1-piperidinyl}benzoyl)amino]pentanedioic acid;

ooo) N-(4-{4-[((2R)-2-hydroxy-2-{4-hydroxy-3-[(methylsulfonyl)amino]phenyl}ethyl)amino]-1-piperidinyl}benzoyl)-beta-alanine;

ppp) ethyl [(4-{4-[((2R)-2-hydroxy-2-{4-hydroxy-3-[(methylsulfonyl)amino]phenyl}ethyl)amino]-1-piperidinyl}benzoyl)amino]acetate;

qqq) [(4-{4-[((2R)-2-hydroxy-2-{4-hydroxy-3-[(methylsulfonyl)amino]phenyl}ethyl)amino]-1-piperidinyl}benzoyl)amino]acetic acid;

rrr) (2S)-2-(4-{4-[(2R)-2-hydroxy-2-(4-hydroxy-3-methanesulfonylamino-phenyl)-ethylamino]-piperidine-1-yl}-benzoylamino)-4-methyl-pentanoic acid ethyl ester;

sss) (2S)-2-(4-{4-[(2R)-2-hydroxy-2-(4-hydroxy-3-methanesulfonylamino-phenyl)-ethylamino]-piperidine-1-yl}-benzoylamino)-4-methyl-pentanoic acid;

vvv) (2S)-2-(4-{4-[(2R)-2-hydroxy-2-(4-hydroxy-3-methanesulfonylamino-phenyl)-ethylamino]-piperidine-1-yl}-benzoylamino)-3-methyl-butyric acid ethyl ester;

www) (2S)-2-(4-{4-[(2R)-2-hydroxy-2-(4-hydroxy-3-methanesulfonylamino-phenyl)-ethylamino]-piperidine-1-yl}-benzoylamino)-3-methyl-butyric acid;

xxx) (2S)-2-(4-{4-[(2R)-2-hydroxy-2-(4-hydroxy-3-methanesulfonylamino-phenyl)-ethylamino]-piperidine-1-yl}-benzoylamino)-3-phenyl-propionic acid methyl ester;

yyy) (2S)-2-(4-{4-[(2R)-2-hydroxy-2-(4-hydroxy-3-methanesulfonylamino-phenyl)-ethylamino]-piperidine-1-yl}-benzoylamino)-3-phenyl-propionic acid;

zzz) methyl 1-[(4-{4-[((2R)-2-hydroxy-2-{4-hydroxy-3-piperidinyl}benzoyl)amino]cyclopropanecarboxylate;

aaaa) [butyl-(4-{4-[(2R)-2-hydroxy-2-(4-hydroxy-3-methanesulfonylamino-phenyl)-ethylamino]-piperidine-1-yl}-benzoyl)-amino]-acetic acid ethyl ester;

bbbb) methyl [(4-{4-[((2R)-2-hydroxy-2-{4-hydroxy-3-[(methylsulfonyl)amino]phenyl}ethyl)amino]-1-piperidinyl}benzoyl)amino]acetate;

cccc) (2S)-2-(4-{4-[2-hydroxy-2-(4-hydroxy-3-methanesulfonylamino-phenyl)-ethylamino]-piperidine-1-yl}-benzoylamino)-4-methyl-pentanoic acid methyl ester;

eeee) 4-{4-[((2R)-2-hydroxy-2-{4-hydroxy-3-[(methylsulfonyl)amino]phenyl}ethyl)amino]-1-piperidinyl}-N-[(1S)-1-(hydroxymethyl)-3-methylbutyl]benzamide;

or a pharmaceutically acceptable salt thereof.

* * * * *